US009181337B2

(12) United States Patent
Subramanian et al.

(10) Patent No.: US 9,181,337 B2
(45) Date of Patent: *Nov. 10, 2015

(54) MODULATED LYSINE VARIANT SPECIES COMPOSITIONS AND METHODS FOR PRODUCING AND USING THE SAME

(71) Applicant: AbbVie, Inc., North Chicago, IL (US)

(72) Inventors: Kartik Subramanian, Northborough, MA (US); Mayda Perez Thiele, Vega Alta, PR (US); Xiaobei Zeng, Carolina, PR (US); Chee Furng Wong, Singapore (SG); Zehra Kaymakcalan, Westborough, MA (US); Ying Jing, Wellesley, MA (US); Christopher Chumsae, North Andover, MA (US)

(73) Assignee: AbbVie, Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/077,988

(22) Filed: Nov. 12, 2013

(65) Prior Publication Data

US 2015/0110775 A1 Apr. 23, 2015

Related U.S. Application Data

(60) Provisional application No. 61/893,088, filed on Oct. 18, 2013.

(51) Int. Cl.
*A61K 39/395* (2006.01)
*C07K 16/24* (2006.01)
(52) U.S. Cl.
CPC ........... *C07K 16/241* (2013.01); *C07K 2317/14* (2013.01)
(58) Field of Classification Search
None
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,096,816 A | 3/1992 | Maiorella |
| 5,110,913 A | 5/1992 | Coan et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |

(Continued)

FOREIGN PATENT DOCUMENTS

| | | |
|---|---|---|
| CN | 1299370 A | 6/2001 |
| CN | 1563090 A | 1/2005 |

(Continued)

OTHER PUBLICATIONS

Humira (adalimumab) prescribing information, Dec. 20, 2002, pp. 1-16.*
Abbott laboratories press release dated Dec. 31, 2002, pp. 1-4.*
Byun et al., Archives of Biochemistry and Biophysics 532 (2013), pp. 15-22.*
Muller-Spath et al. (Biotechnology and Bioengineering, vol. 100, No. 6, Aug. 15, 2008, pp. 1166-1177).*
Sargent (pp. 1-3, Internet Archive captured Aug. 28, 2103, http://cellculturedish.com/2012/01/cho-cells-the-top-expression-system-of-best-selling-biologic-drugs/).*
Daugherty et al. (Advanced Drug Delivery Reviews 58 (2006) 686-706).*
"Genentech unveils production capacity hikes," in-Pharma Technologist.com Jun. 28, 2005, pp. 1-2.

(Continued)

*Primary Examiner* — Zachary Skelding
(74) *Attorney, Agent, or Firm* — McCarter & English, LLP; Maria Laccotripe Zacharakis; Deborah L. Nagle

(57) ABSTRACT

The instant invention relates to modulated lysine variant species compositions comprising a protein, e.g., an antibody, or antigen-binding portion thereof, and methods, e.g., cell culture and/or protein purification methods, for producing such modulated lysine variant species compositions. Methods for using such compositions to treat a disorder, e.g., a disorder in which TNFα is detrimental, are also provided.

30 Claims, 61 Drawing Sheets

(56) References Cited

U.S. PATENT DOCUMENTS

| | | | |
|---|---|---|---|
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,976,833 A | 11/1999 | Furukawa et al. |
| 5,994,510 A | 11/1999 | Adair et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,974,681 B1 | 12/2005 | McGrew |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,323,553 B2 | 1/2008 | Fahrner et al. |
| 7,332,303 B2 | 2/2008 | Schilling et al. |
| 7,390,660 B2 | 6/2008 | Behrendt et al. |
| 7,429,491 B2 | 9/2008 | Luan et al. |
| 7,504,485 B2 | 3/2009 | Salfeld et al. |
| 7,521,206 B2 | 4/2009 | Heavner et al. |
| 7,521,210 B2 | 4/2009 | Knudsen |
| 7,541,031 B2 | 6/2009 | Salfeld et al. |
| 7,588,761 B2 | 9/2009 | Salfeld et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,231,876 B2 | 7/2012 | Wan et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,552 B2 | 6/2013 | Croughan et al. |
| 8,663,945 B2 | 3/2014 | Pla et al. |
| 8,753,633 B2 | 6/2014 | Salfeld et al. |
| 8,821,865 B2 | 9/2014 | Neu et al. |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 9,017,687 B1 | 4/2015 | Wang et al. |
| 2002/0045207 A1 | 4/2002 | Krummen et al. |
| 2002/0132299 A1 | 9/2002 | Field |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0175884 A1 | 9/2003 | Umana et al. |
| 2003/0178368 A1 | 9/2003 | van Reis |
| 2003/0206898 A1 | 11/2003 | Fischkoff et al. |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0101939 A1* | 5/2004 | Santora et al. ............... 435/183 |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1* | 8/2004 | Santora et al. ........... 530/388.23 |
| 2004/0166111 A1 | 8/2004 | Kaymakcalan et al. |
| 2004/0171152 A1 | 9/2004 | Price et al. |
| 2004/0191243 A1 | 9/2004 | Chen et al. |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0083741 A1 | 4/2006 | Hoffman et al. |
| 2006/0149042 A1 | 7/2006 | Konstantinov et al. |
| 2006/0153846 A1 | 7/2006 | Krause et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0041905 A1 | 2/2007 | Hoffman et al. |
| 2007/0060741 A1 | 3/2007 | Kelley et al. |

(56) References Cited

U.S. PATENT DOCUMENTS

| | | |
|---|---|---|
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0025976 A1 | 1/2008 | Le et al. |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0219952 A1 | 9/2008 | Fischer et al. |
| 2008/0227136 A1 | 9/2008 | Pla et al. |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0110679 A1 | 4/2009 | Li et al. |
| 2009/0123378 A1 | 5/2009 | Wong et al. |
| 2009/0142828 A1 | 6/2009 | Bucciarelli et al. |
| 2009/0148513 A1 | 6/2009 | Fraunhofer et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0135987 A1 | 6/2010 | Hickman et al. |
| 2010/0136025 A1 | 6/2010 | Hickman et al. |
| 2010/0160894 A1 | 6/2010 | Julian et al. |
| 2010/0221823 A1 | 9/2010 | McCoy et al. |
| 2010/0256336 A1 | 10/2010 | Yuk et al. |
| 2010/0278822 A1 | 11/2010 | Fraunhofer et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086798 A1 | 4/2011 | Sethuraman et al. |
| 2011/0097336 A1 | 4/2011 | Wu et al. |
| 2011/0123544 A1 | 5/2011 | Salfeld et al. |
| 2011/0130544 A1 | 6/2011 | Ram et al. |
| 2011/0171227 A1 | 7/2011 | Okun et al. |
| 2011/0207676 A1 | 8/2011 | Callewaert et al. |
| 2011/0300151 A1 | 12/2011 | Okun et al. |
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0107783 A1 | 5/2012 | Julian et al. |
| 2012/0123688 A1 | 5/2012 | Ramasubramanyan et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0201831 A1 | 8/2012 | Salfeld et al. |
| 2012/0213792 A1 | 8/2012 | Salfeld et al. |
| 2012/0219564 A1 | 8/2012 | Salfeld et al. |
| 2012/0238730 A1 | 9/2012 | Dong et al. |
| 2012/0244168 A1 | 9/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Fraunhofer et al. |
| 2012/0264920 A1 | 10/2012 | Wang et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0308514 A1 | 12/2012 | Salfeld et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0156760 A1 | 6/2013 | Fraunhofer et al. |
| 2013/0195888 A1 | 8/2013 | Wang et al. |
| 2013/0205604 A1 | 8/2013 | Esenwein et al. |
| 2013/0243786 A1 | 9/2013 | Banerjee et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0065710 A1 | 3/2014 | Rives et al. |
| 2014/0072585 A1 | 3/2014 | Herigstad et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0275494 A1 | 9/2014 | Wang et al. |
| 2014/0288278 A1 | 9/2014 | Nti-gyabaah et al. |
| 2014/0314745 A1 | 10/2014 | Rives et al. |
| 2014/0377275 A1 | 12/2014 | Neu et al. |

(56) References Cited

U.S. PATENT DOCUMENTS

| | | |
|---|---|---|
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |

FOREIGN PATENT DOCUMENTS

| | | |
|---|---|---|
| DE | 3631229 A1 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 0351789 A2 | 1/1990 |
| EP | 0366043 A1 | 5/1990 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2357250 A2 | 8/2011 |
| EP | 2495307 A1 | 9/2012 |
| EP | 2528002 A2 | 11/2012 |
| EP | 2574677 A1 | 4/2013 |
| GB | 2160530 A | 12/1985 |
| GB | 2279077 A | 12/1994 |
| IN | 2285/MUM/2013 A1 | 1/2015 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/09967 A1 | 7/1991 |
| WO | WO-92/01047 A1 | 1/1992 |
| WO | WO-92/11383 A1 | 7/1992 |
| WO | WO-92/16553 A1 | 10/1992 |
| WO | WO-93/06213 A1 | 4/1993 |
| WO | WO-94/02602 A1 | 2/1994 |
| WO | WO-94/08619 A1 | 4/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-9704801 A1 | 2/1997 |
| WO | WO-97/13852 A1 | 4/1997 |
| WO | WO-97/29131 A1 | 8/1997 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-9823645 A1 | 6/1998 |
| WO | WO-98/50433 A2 | 11/1998 |
| WO | WO-9856418 A1 | 12/1998 |
| WO | WO-99/32605 A1 | 7/1999 |
| WO | WO-99/57134 A1 | 11/1999 |
| WO | WO-9957246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-03045995 A2 | 6/2003 |
| WO | WO-03/059935 A2 | 7/2003 |
| WO | WO-03/066662 A2 | 8/2003 |
| WO | WO-2004008100 A2 | 1/2004 |
| WO | WO-2004/058944 A2 | 7/2004 |
| WO | WO-2004058800 A1 | 7/2004 |
| WO | WO-2004/097006 A1 | 11/2004 |
| WO | WO-2005042569 A1 | 5/2005 |
| WO | WO-2005/082483 A1 | 9/2005 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007/087384 A2 | 8/2007 |
| WO | WO-2007/117490 A2 | 10/2007 |
| WO | WO-2008/033517 A2 | 3/2008 |
| WO | WO-2008-057240 A2 | 5/2008 |
| WO | WO-2008068879 A1 | 6/2008 |
| WO | WO-2008087184 A2 | 7/2008 |
| WO | WO-2008121616 A2 | 10/2008 |
| WO | WO-2008135498 A2 | 11/2008 |
| WO | WO-2009/017491 A1 | 2/2009 |
| WO | WO-2009023562 A2 | 2/2009 |
| WO | WO-2009/027041 A1 | 3/2009 |
| WO | WO-2009058769 A1 | 5/2009 |
| WO | WO-2009/073569 A2 | 6/2009 |
| WO | WO-2009135656 A1 | 11/2009 |
| WO | WO-2010036443 A1 | 4/2010 |
| WO | WO-2010043703 A1 | 4/2010 |
| WO | WO-2010122460 A1 | 10/2010 |
| WO | WO-2010/129469 A1 | 11/2010 |
| WO | WO-2010127069 A1 | 11/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011134919 A2 | 11/2011 |
| WO | WO-2011134920 A1 | 11/2011 |
| WO | WO-2012019160 A1 | 2/2012 |
| WO | WO-2012030512 A1 | 3/2012 |
| WO | WO-2012050175 A1 | 4/2012 |
| WO | WO-2012051147 A1 | 4/2012 |
| WO | WO-2012/065072 A1 | 5/2012 |
| WO | WO-2012062810 A2 | 5/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013/011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-176754 A1 | 11/2013 |

(56) References Cited

FOREIGN PATENT DOCUMENTS

| WO | WO-2013-177115 A2 | 11/2013 |
|---|---|---|
| WO | WO-2013-177118 A2 | 11/2013 |
| WO | WO-2013-181585 A2 | 12/2013 |
| WO | WO-2014/207763 A1 | 12/2014 |
| WO | WO-2015/004679 A1 | 1/2015 |

OTHER PUBLICATIONS

Abraham, E., et al., "Efficacy and Safety of Monoclonal Antibody to Human Tumor Necrosis Factor α in Patients with Sepsis Syndrome," *JAMA*, vol. 273(12):934-941 (1995).
Adams. et al. J. Am. Acad. Dermatol 2004;51:660-2.
Altamirano, C., et al., "Strategies for fed batch cultivation of t-PA producing CHO cells: substitution of glucose and glutamine and rational design of culture medium", *J. Biotechn.* 110:171-179, 2004.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Avgerinos et al. (GAb '04 Abstracts—GE Healthcare Life Sciences, France Oct 3-5, 2004, pp. 15-16 published 2005).
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Barbuto, J. et al. "Production of Neutralizing Antibodies to Tumor Necrosis Factor by Human Tumor-Infiltrating B Lymphocytes" *Proc. Am. Assoc. Cancer Res*,. 34:487, Abstr. 2904 (1993).
Biblia, T.A. et al., "In Pursuit of the Optimal Fed-Batch Process for Monoclonal Antibody Production", Biotechnol. Prog 11(1):1-13, Jan.-Feb. 1995.
Birch, Jr. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boyle, P. et aL "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. *;455-458 (1997).

Bruggemann, M., Neuberger, M.S., "Strategies for expressing human antibody repertoires in transgenic mice," *Immunol. Today* 17:391-397 (1996).
Cai B, et al. "C-Terminal Lysine Processing of Human; Immunoglobulin G2 Heavy Chain in Vivo" Biotechnol. Bioeng. 2011;108: 404-412.
Carter et al., "Humanization of an anti-p185HER2 antibody for human cancer therapy," *Proc. Nat. Acad. Sci* 89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Choo et al. "High-level production of a monoclonal antibody in murine myeloma cells by perfusion culture using a gravity settler" Biotechnology Progress, vol. 23, No. 1, Jan. 1, 2007, 225-231.
Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).
Chua, FKF et al., "Hyper-stimulation of monoclonal antibody production by high osmolarity stress in eRDF medium", J. Biotechnology 37(3):265-275, Nov. 15, 1994.
Chung et al., "Utilization of Lysozyme Charge Ladders to Examine the Effects of Protein Surface; Charge Distribution on Binding Affinity in Ion Exchange Systems," Langmuir 26(2): 759-768 (2010).
Chung et al., "Cetuximab-Induced Anaphylaxis and IgE Specific for Galactose-α-1, 3-Galactose", *N. Engl. J. Med.*, 358:11, pp. 1109-1117 (2008).
Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).
Cohen, J., et al., "Intersept: an international, multicenter, placebo-controlled trial of monoclonal anitbody to human tumor necrosis factor-α in patients with sepsis," *Crit Care Med*, vol. 24(9):1431-1440 (1996).
Cox, J. et al. "A directory of human germ-line Vκ segments reveals a strong bias in their usage" *Eur. J. Immunol.*, 24(2):827-36 (1994).
Cromwell (GAB'04 Abstracts—GE Healthcare Life Sciences, Franc Oct. 3-5, 2004, pp. 17-18 published 2005).
Daugherty, et al. Formulation and Delivery Issues for Monoclonal Antibody Therapeutics. Advanced Drug Delivery Reviews, 2006. vol. 58, pp. 686-706.
Davies et al., "Antibody VH domains as small recognition units." *Biotechnology*, 13:475-479 (1995).
Department of Surgery, University of Toronto, Annual Report (1998-1999)(348 pages).
DePhillips et al., "Determinants of protein retention characteristics on cation-exchange adsorbents,"; Journal of Chromatograph A, 933:57-72 (2001).
deZongotita et al., "Phosphate feeding improves high-cell-concentration NS0 myeloma cell culture performance for monoclonal antibody production" Biotechnology and Bioengineering. 2000, 69: 566-576.
Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.
Dolezal, et al., "*Escherichia coli* Expression of a Bifunctional Fab-peptide Epitope Reagent for the Rapid Diagnosis of HIV-1 and HIV-2", *lmmunotechnology*, 1:197-209 (1995).
Doring, E., "Identification and Characterization of a TNFa Antagonist Derived from a Monoclonal Antibody" (1994) *Mol. Immunol* .31(14): 1059-1067.
Elliot et al., "Repeated therapy with monoclonal antibody to tumour necrosis factor α (cA2) in patients with rheumatoid arthritis" (1994) *Lancet*, 344:1125-1127.
Elliot, "Treatment of rheumatoid arthritis with chimeric monoclonal antibodies to tumor necrosis factor α" (1993) *Arthritis & Rheumatism*, 36(12):1681-1690.
Emery, P. "Adalimumab therapy: Clinical findings and implications for integration into clinical guidelines for rheumatoid arthritis." *Drugs of Today*, 41(3): p. 155-153. (2005).
Ewert et al., "Biophysical Properties of Human Antibody Variable Domains," J. Mol. Biol. 324: 531-; 553 (2003).

(56) References Cited

OTHER PUBLICATIONS

FDA Package insert for Adalimumab, Sep. 26, 2003, pp. 1-18.
Feldmann, "Anti-TNF-alpha Therapy of Rheumatoid Arthritis: What Have We Learned?" (2001) *Annu. Rev. Immunol.*, 19:163-196.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gatto, B. "Biologics targeted at TNF: design, production and challenges", Reumatismo 58(2):94-103, 2006.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grunberg, J. et al., "High-Yield Production of Recombinant Antibody Fragments in HEK-293 Cells Using Sodium Butyrate", BioTechniques 34(5):968-972, May 2003.
Han, Kyu Oh et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.
Harlow and Lane, Antibodies A Laboratory Manual, Purification of Antibodies by using a; Deae-matrix (Batch), Storing and Purifying Antibodies; Chapter 8: 302-303 (1988).
Harris et al. "Processing of C-terminal lysine and argnine residues of proteins isolated from mammalian cell culture" Journal of Chromatography, (1995) 705; 129-123.
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.

Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).
Hiatt et al., "Production of Antibodies in Transgenic Plants", *Nature*, 342:76-78 (1989).
Hillgren, A. et al., "Protection mechanism of Tween 80 during freeze-thawing of a model protein LDH," *International Journal of Pharmaceutics*, vol. 237:57-69 (2002).
Hokke et al., "Sialylated Carbohydrate Chains of Recombinant Human Glycoproteins Expressed in Chinese Hamster Ovary Cells Contain Traces of N-glycolylneuraminic acid", *FEBS*, 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood*, 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.*, 227:381388.
Hoogenboom, "Converting rodent into human antibodies by guided selection" (1996) *Antibody Engineering*, Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Huang et al. "Effects of anti-TNF monoclonal antibody infusion in patients with hairy cell leukaemia" (1992) *Br. J. Haematol.*, 81(2):231-234.
Hui et al., "Recovery and purification process development for monoclonal antibody production," MABS (2010) 2(5):480-499.
Huse, "Generation of a large combinatorial library of the immunoglobulin repertoire in phage lambda" (1989)*Science*, 246:1275-81.
Jakobovits, A., "Production of fully human antibodies by transgenic mice" (1995) *Curr. Op. Biotechnol.*, 6:561-566.
Jespers, "Guiding the Selection of Human Antibodies from Phage Display Repertoires to a Single Epitope of an Antigen" (1994) *Bio/Technology*, 12:899-903.
Johnson et al. (Archives of Biochemistry and Biophysics 444 (2005) 7-14).
Kalyanpur, M., "Downstream Processing in the Biotechnology Industry" Molecular Biotechnology, vol. 22:87-98 (2002).
Karampetsou et al. (Q J Med 2010; 103:917-928).
Kaschak et al: "Characterization of the basic charge variants of a human IgGI: Effect of copper concentration in cell culture media", MABS, vol. 3, No. 6, Nov. 1, 2011, pp. 577-583.
Kazuaki, F. et al., "Enhancement of productivity of recombinant α-amidating enzyme by low temperature culture", Cytotechnology 31:85-94, 1999.
Kempeni, "Update on D2E7: a fully human anti-tumour necrosis factor-alpha monoclonal antibody" (2000) *Ann. Rheum. Dis.*, 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." *Transfusion* 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.

(56) References Cited

OTHER PUBLICATIONS

Knight et al., "Construction and initial characterization of a mouse-human chimeric anti-TNF antibody" (1993) *Mol. Immunol.*, 30(16):1443-1453.

Kopaciewicz et al., "Retention Model for High-Performance Ion-Exchange Chromatography,"; Journal of Chromatography, 266:3-21 (1983).

Lerner, "Antibodies without immunization" (1992) *Science*, 258:1313-1314.

Leusch, "Failure to demonstrate TNFα-specific autoantibodies in human sera by ELISA and Western blot" (1991) *J. Immunol. Methods*, 139:145-47.

Lewis, "Use of alanine scanning mutagenesis to improve the affinity of an anti gp120 (HIV) antibody" (1994) *J. Cell. Biochem.*, 18D:215.

Li, F. et al., "Current Therapeutic Antibody Production and Process Optimization" BioProcessing Journal, vol. 4(5):23-30 (2005).

Lifely et al., "Glycosylation and Biological Activity of CAMPATH-1H Expressed in Different Cell Lines and Grown Under Different Culture Conditions", *Glycobiology*, 5(8):813-822 (1995).

Logan, John S. "Transgenic Animals: Beyond 'Funny Milk'", Current Opinion in Biotechnology, 4:591-595 (1993).

Lonberg et al., "Antigen-specific human antibodies from mice comprising four distinct genetic modifications" (1994) *Nature*, 368:856-859.

Lonberg et al., "Human Antibodies from Transgenic Mice" (1995) *Int. Rev. Immunol.*, 13:65-93.

Low, "Mimicking Somatic Hypermutation: Affinity Maturation of Antibodies Displayed on Bacteriophage Using a Bacterial Mutator Strain" (1996) *J. Mol. Biol.*, 260:359-368.

Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.

Ma, et al., "Generation and Assembly of Secretory Antibodies in Plants", *Science*, 268:716-719 (1995).

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".

Marks et al., "Human antibody fragments specific for human blood group antigens from a phage display library" (1993) *Bio/Technology*, 11:1145-1150.

Marks et al., "Molecular evolution of proteins on filamentous phage. Mimicking the strategy of the immune system" (1992) *J. Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." in *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies By Chain Shuffling" (1992) *Biotechnology*, 10:779-783.

Martin, A.C.R. "Accessing the Kabat antibody sequence database by computer" (1996)*Proteins: Structure, Function and Genetics*, 25:130-133.

Medynski, "Phage Display: All Dressed Up and Ready to Role" (1994) *Bio/Technology*, 12:1134-1136.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al. "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Moore, A., et al., "Effects of temperature shift on cell cycle, apoptosis and nucleotide pools in CHO cell batch cultures", Cytotechnology, 23:47-54, 1997.

Möller, Monoclonal antibodies to human tumor necrosis factor α: in vitro and vivo application (1990) *Cytokine*, 2(3):162-69.

Neuberger M. et al., "Mice perform a human repertoire" (1997) *Nature*, 386:25-26.

Ngo et al., "Kosmotropes enhance the yield of antibody purified by affinity chromatography using immobilized bacterial immunoglobulin binding proteins," Journal of Immunoassay & Immunochemistry, (2008) 29(1):105-115.

Nilsson, "Antibody engineering" (1995) *Current Opinion in Structural Biology*, 5:450-456.

Nogal, B., Chhiba, K. And Emery, J. C. (2012), Select host cell proteins coelute with monoclonal antibodies in protein a chromatography. Biotechnol Progress, 28: 454-458.

Noguchi et al., "Failure of Human Immunoresponse to N-Glycolylneuraminic Acid Epitope Contained in Recombinant Human Erythropoietin", *Nephron*, 72:599-603 (1996).

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

Oh, D-K. et al., "Increased erythritol production in fed-batch cultures of Torula sp. by controlling glucose concentration", J. Industrial Microb. & Biotechn. 26(4): 248-252, 2001.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Perchiacca et al., "Aggregation-resistance domain antibodies engineered with charged mutations; near the edges of the complementarity-determining regions," Protein Engineering Design & Selection, 25: 10 (591-601) 2012.

Pietersz et al., "In vitro and in vivo Antitumor Activity of a Chimeric anti-CD19 Antibody", *Cancer Immunol. Immunother.*, 41:53-60 (1995).

Potter et al., "Antibody Production in the Baculovirus Expression System", *Intern. Rev. Immunol.*, 10:103-112 (1993).

Poul et al., "Design of Cassette Baculovirus Vectors for the Production of Therapeutic Antibodies in Insect Cells", *Immunotechnology*, 1:189-196 (1995).

Queen, C., "A humanized antibody that binds to the interleukin 2 receptor" (1989) *Proc. Natl. Acad. Sci. USA*, 86(24):10029-10033.

Rader et al. "A phage display approach to rapid antibody humanization: Designed combinatorial V gene libraries" (1998) *Proc Natl Acad Sci USA*, 95:8910-8915.

Raju, Ts. "Glycosylation Variations with Expression Systems and Their Impact on Biological Activity of Therapeutic Immunoglobulins", *BioProcess International.*, 44-53 (2003).

Reichert JM., et al., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) *Crit. Care Med.*, 24(5):733-742.

Rheinwald JG, et al., "Growth of Cultured Mammalian Cells on Secondary Glucose Sources", Cell, 287-293, 1974.

Ridder et al., "Generation of Rabbit Monoclonal Antibody Fragments from a Combinatorial Phage Display Library and Their Production in Yeast *Pichia pastoris*", *Biotechnology*, 13:255-260 (1995).

Riechmann, "Phage display and selection of a site-directed randomized single-chain antibody Fv fragment for its affinity improvement" (1993) *Biochemistry*, 32(34):8848-8855.

Rube et al. (Int. J. Radiation Oncology Biol. Phys., vol. 56, No. 5, pp. 1414-1425,2003).

(56) References Cited

OTHER PUBLICATIONS

Rudikoff et al., "Single amino acid substitution altering antigen-binding specificity" (1982) *Proc. Natl. Acad. Sci. USA*, 70:1979-1983.

Salfeld, "Development of a Fully Human Antibody to TNF by Phage Display Technology," IBC Conference, *Antibody Engineering*, San Diego (Dec. 1996), pp. 1-36.

Sandadi, S. et al., "Heuristic Optimization of Antibody Production by Chinese Hamster Ovary Cells", Biotech. Progress, American Institute of Chem. Engineers: 21(5): 1537-1542, 2005.

Sandhu, J. "Protein engineering of antibodies" (1992) *Critical Reviews in Biotechnology*, 12:437-462.

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) *Analytical Biochemistry*, 299:119-129.

Sato et al, "Stimulation of monoclonal antibody production by human-human hybridoma cells with an elevated concentration of potassium or sodium phosphate in serum-free medium," Cytotechnology 2:63-67, 1989.

Seresht et al., "The impact of phosphate scarcity on pharmaceutical protein production in *S. cerevisiae*: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", *Anal. Biochem.*, 247(1):102-110 (1997).

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shih, "Effects of Anions on the Deamidation of Soy Protein". Journal of Food Science. 1991, 56: 452-454.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sioud et al., "Characterization of naturally occurring autoantibodies against tumour necrosis factor-alpha (TNF-α): in vitro function and precise epitope mapping by phage epitope library" (1994) *Clin. Exp. Immunol.*, 98:520-525.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," *J. Immun.* (2000) 164:1432-1441.

Tan et al. (Biotechnol. Appl. Biochem. (1999) 30, 59-64).

Taylor et al.,"Human immunoglobulin transgenes undergo rearrangement, somatic mutation and class switching in mice that lack endogenous IgM" (1994) *Int. Immunol.*, 6:579-591.

Thompson, "Affinity maturation of a high-affinity human monoclonal antibody against the third hypervariable loop of human immunodeficiency virus: use of phage display to improve affinity and broaden strain reactivity" (1996) *J. Mol. Biol.*, 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) *Cytokine*, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) *J. Mol. Biol.*, 227:776-98.

Tomlinson, "The structural repertoire of the human Vk domain" (1995) *The EMBO J.*, 14(18):4628-38.

Tracey, "Tumor necrosis factor: A pleiotropic cytokine and therapeutic target" (1994) *Annu. Rev. Med.*, 45:491-503.

Tsuchiyama et al., "Comparison of anti-TNF alpha autoantibodies in plasma and from EBV transformed lymphocytes of autoimmune and normal individuals" (1995) *Hum. Antibod. Hybridomas*, 6(2):73-76.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", *J. Biol. Chem.*, 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) *Clin. Exp. Immunol.*, 100:21-25.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vaughan, "Human antibodies by design" (1998) *Nature Biotechnology*, 16:535-539.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Ward, "Binding activities of a repertoire of single immunoglobulin variable domains secreted from *Escherichia coli*" (1989) *Nature*, 341:544-546.

Wedemayer et al., "Structural insights into the evolution of an antibody combining site" (1997) *Science*, 276:1665-1669.

Wiendl et al. (BioDrugs. 2002;16(3):183-200).

Williams et al., "Kinetic analysis by stopped-flow radiationless energy transfer studies: effect of anions on the activity of carboxypeptidase A". Biochemistry. 1986, 25, 94-100.

Winter, "Humanized antibodies" (1993) *Immunol. Today*, 14(6):243-246.

Winter, "Making antibodies by phage display technology" (1994) *Annu. Rev. Immunol.*, 12:433-455.

Wurm, FM, "Production of recombinant protein therapeutics in cultivated mammalian cells", Nature Biotechnology 22(11):1393-1398, 2004.

Yigzaw et al., "Exploitation of the adsorptive properties of depth filters for host cell protein removal during monoclonal antibody purification," Biotechnology Progress, (2006) 22(1):288-296.

Yumioka et al., "Screening of effective col. rinse solvent for Protein-A chromatography," Protein Expression and Purification, (2010) 70(2): 218-223.

Zatarain-Rios E and Mannik M, "Charge-charge interactions between articular cartilage and cationic antibodies, antigens, and immune complexes," Arthritis Rheum. Nov. 1987;30(11):1265-73.

Zhang et al., "Isolation and characterization of charge variants using cation exchange displacement chromatography," 1218(31): 5079-5086, 2011.

Zou et al., "Dominant expression of a 1.3 Mb human Ig kappa locus replacing mouse light chain production" (1996) *FASEB J.*, 10:1227-1232.

Boswell at al. "Effects of Charge on Antibody Tissue Distribution and Pharmacokinetics" Bioconjugate Chem.(21) 2153-2163 (2010).

Schiestl at al. "Acceptable changes in quality attributes of glycosylated biopharmaceuticals" Nature Biotechnology, 29(4), 310-312 (2011).

(56) References Cited

OTHER PUBLICATIONS

Senczuk at al. "Hydrophobic interaction chromatography in dual salt system increases protein binding capacity" Biotechnology and Bioengineering, 103(5), 930-935 (2009).
Anonymous, "SACHEM Displacement Chromatography," Aug. 29, 2012, Retrieved from the internet: www.displacementchromatography.com, retrieved on Jul. 30, 2014, 12 pages.
Barnes et al., "Stability of Protein Production from Recombinant Mammalian Cells," Biotechnology and Bioengineering, 81:6, Mar. 20, 2003, pp. 631-639.
Canghai, Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007, pp. 15-29.
Chumsae, Chris et al.: "Arginine modifications by methylglyoxal: discovery in a recombinant monoclonal antibody and contribution to acidic species.", Analytical Chemistry Dec 3, 2013, vol. 85, No. 23, Dec. 3, 2013, pp. 11401-11409.
Clincke, M. et al., "Effect of surfactant pluronic F-68 on CHO cell growth, metabolism, production, and glycosylation of human recombinant IFN-γ in mild operating conditions," Biotechnol. Prog. 27(1): pp. 181-190, 2011.
Du et al., "Chromatographic analysis of the acidic and basic species of recombinant monoclonal antibodies" MAbs, Sep.-Oct. 2012; 4(5): pp. 578-85.
Feng et al., "Cell Culture Processes for Monoclonal Antibody Production," mAbs, 2:5, pp. 466-477, Sep./Oct. 2010.
Folk et al., "Carboxypeptidase B, Purification and Characterization of the Porcine Enzyme," J. Biological Chem, 1960, 235: pp. 2272-2277.
Gramer M Jet Al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Hossler et al.; "Improvement of mammalian cell culture performance through surfactant enabled concentrated feed media"; Biotechnology Progress; 29(4): pp. 1023-1033 (2013).
ICH Topic Q6B "Specifications:Test Procedures and Acceptance Criteria for Biotechnological/Biological Products," Sep. 1999, pp. 1-17.
International Search Report and Written Opinion from PCT/US2014/024151 dated Aug. 7, 2014, 16 pages.
International Search Report from PCT/US2014/024256 dated Jul. 30, 2014, pp. 1-15.
Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jayme et al.; "Media formulation options and manufacturing process controls to safeguard against introduction of animal origin contaminants in animal cell culture"; Cytotechnology; 33: pp. 27-36 (2000).
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012, pp. 1061-1068.
Martinelle, K. et al., Cells and Culture, Proceedings of the 20th ESACT Meeting v4, pp. 819-822, Jun. 17-20, 2007.
McAtee et al., "Isolation of monoclonal antibody charge variants by displacement chromatography," Current Protocols in Protein Science, 14 pages. Aug. 2012.
Patel, T. P. et al.: "Different culture methods lead to differences in glycosylation of a murine IgG monoclonal antibody", Biochemical journal, The Biochemical Society, London, GB, vol. 285, No. 3, Jan. 1, 1992, pp. 839-845.
Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996, pp. 189-200.
Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011, pp. 317-323.
Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997, pp. 201-207.
Sakai et al.; "Use of nonionic surfactants for effective supply of phosphatidic acid in serum-free culture of Chinese hamster ovary cells"; Journal of Bioscience and Bioengineering; 92(3): pp. 256-261 (2001).
Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006, pp. 1161-1173.
Sundaram et al., "An innovative approach for the characterization of the isoforms of a monoclonal antibody product," Mabs, 3(6): pp. 505-512, 2011.
Sung, Hyun Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009, pp. 639-648.
Tharmalingam et al.; "Pluronic Enhances the Robustness and Reduces the Cell Attachment of Mammalian Cells"; Molecular Biotechnology; 39(2):pp. 167-177 (2008).
Wolff et al., "The Kinetics of Carboxypeptidase B Activity," J. Biological Chem, 1962, 237: pp. 3094-3099.
Wong N.S.C. et al: "An investigation of intracellular glycosylation activities in CHO cells: Effects of nucleotide sugar precursor feeding" Biotechnology and Bioengineering, vol. 187, No. 2, Oct. 1, 2010, pp. 321-336.
Worthington Biochemical Corporation, porcine pancreas carboxypeptidase B, 1 page, Feb. 25, 2012.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.
"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS, 21 pages.
"Memorandum in Support of Centocor's Motion No. 3 for Summary Judgment that the 394 and 031 Patents Are Invalid for Under 35 U.S.C. §102(f) for Failing to Name the Proper Inventors", dated Aug. 1, 2013 and submitted by defendant in Civil Action No. 09-40089-FDS, 13 pages.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.
"Plaintiffs' Memorandum in Support of Their Motion for Partial Summary Judgment", dated Aug. 1, 2013 and submitted by plaintiff in Civil Action No. 09-40089-FDS, 49 pages.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.
Cambridge Antibody Technology, advertisement of phage display services, Science vol. 253, No. 5018 (1991), 2 pages.
Charter, Edward A., "A New Process for the Separation and Purification of Egg Yolk; Antibodies," BASc., The University of British Columbia; A Thesis; Apr. 1993, 163 pages.

(56) References Cited

OTHER PUBLICATIONS

ERBITUX (cetuximab) label, Revised Aug. 2013, 8 pages.
Exhibit dated Aug. 1, 2013 and cited by defendant in Civil Action No. 09-40089-FDS providing the Jun. 23, 2009 trial transcript of the PM session in the matter of *Centocor, et al. v. Abbott Laboratories*, 50 pages.
Exhibit dated Aug. 1, 2013 and cited by defendant in Civil Action No. 09-40089-FDS providing the trial transcript in the matter of *Abbott Laboratories, et al, v. The Mathilda and Terrance Kennedy Institute*, S.D.N.Y, 90 pages.
Exhibit dated Aug. 1, 2013 and cited by plaintiff in Civil Action No. 09-40089-FDS providing excerpts from the File History of U.S. Appl. No. 12/578,487, 5 pages.
Exhibit dated Aug. 1, 2013 and cited by defendant in Civil Action No. 09-40089-FDS providing the Jun. 24, 2009 trial transcript of the AM session in the matter of *Centocor, et al. v. Abbott Laboratories*, E.D. TX, 42 pages.
Exhibit dated Aug. 1, 2013 and cited by defendant in Civil Action No. 09-40089-FDS providing the Sep. 20, 2012 Day 8 trial transcript in the matter of *Abbott v. Centocor Ortho Biotech Inc.*, D. MA, 71 pages.
Exhibit dated Aug. 1, 2013 and cited by plaintiff in Civil Action No. 09-40089-FDS providing Declaration by Jochen Salfeld, dated Jan. 17, 2013, 40 pages.
www.cygnustechnologies.com/product_detail/host-cell-protein-antibodies/anti-cho-h . . . CYGNUS Technologies, Anti-CHO HCP (Apr. 18, 2012), 1 page.
International Preliminary Report on Patentability for Application No. PCT/US07/08359, dated Dec. 12, 2011, 5 pages.
International Preliminary Report on Patentability for Application No. PCT/US2011/060388, dated May 30, 2012, 9 pages.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
Invitation to Pay Additional Fees for International Application No. PCT/US2013/031380, Dated Nov. 28, 2013, 5 pages.
Low, Nigel: thesis extract (1996) *Cambridge University*, 11 pages.
Luo et al., "Understanding of C-terminal lysine variants in antibody production using mammalian cells"Abstract of papers, ACS, Anaheim, CA, US, Mar. 2011, 1 page.
Schwieterman, "Immunosuppression in Combination with Monoclonal Antibodies" in Biologic Agents in Autoimmune Disease (Mar. 2-4, 1995), 9 page.
Teichmann, S. Declaration dated Dec. 7, 2010 from opposition proceedings in EP 0929578, 6 pages.

The Kennedy Institute of Rheumatology, 1995 Annual Scientific Report, "Anti-TNF trials and studies of mechanisms of action" 4 pages.
The MW Calculator available at the Sequence Manipulation Suite (see http://bioinformatics.org/sms2/index.html), downloaded Feb. 25, 2014, 2 pages.
The pI Calculator available at the Sequence Manipulation Suite (see <http://bioinformatics.org/sms2/index.html>), downloaded Feb. 25, 2014, 2 pages.
The Statement on a Nonproprietary Name Adopted by the USAN Council for Adalimumab, p. 1, downloaded on May 19, 2011 from www.ama-assn.org/resources/doc/usan/adalimumab.doc, 1 page.
International Search Report from PCT/US2014/065749 dated Jul. 29, 2014, pp. 1-18.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N. Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Andersen DC, the effect of cell-culture conditions on the oligosaccharide structures of secreted glycoproteins. Curr Opin Biotechnol. Oct. 1994;5(5):546-9.
Awdeh, Z.L., A.R. Williamson, and B.A. Askonas, One cell-one immunoglobulin. Origin of limited heterogeneity of myeloma proteins. Biochem J, 1970. 116(2): p. 241-8.
BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf <http://www.bdbiosciences.com/external_files/Doc_Recon_2.0/ab/others/Phytone_Soytone.pdf>), (last accessed Jan. 8, 2105), 4 pages.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biastoff, S.; et al.; Colorimetric Activity Measurement of a Recombinant Putrescine N-Methyltransferase from *Datura stramonium*; Planta Med. 2006, 72, 1136.
Burteau et al. (In Vitro Cell Dev Biol—Animal, Jul. / Aug. 2003. 39-291-296).
Chang, T. & Wu, L., Methylglyoxal, oxidative street, and hypertension, Can. J. Physiol.Pharmacol. 84: 1229-1238 (2006).
Chaplen, F.W.R., et al., Effect of endogenous methylgiyoxal on Chinese hamster ovary celis grown in culture Cytotechnology 1996, vol. 22, Issue 1-3, Abstract and references, 6 pages.
Chaplen, F.W.R., Incidence and potential implications of the toxic metabolite methylglyoxal in cell culture: A review, Cytotechnology 26: 173-183, 1998.
Chaplen, FWR; A dissertation entitled Analysis of Methylglyoxal Metabolism in Mammalian Cell Culture; Univ. of Wisconsin-Madison 1996, 218 pages.
Chelius, D. et al.; Identification and Characterization of Deamidation Sites in the Conserved Regions of Human Immunoglobulin Gamma Antibodies, Anal. Chem. 2005, 77,6004-6011.
Chumsae, C., et al., Comparison of methionine oxidation in thermal stability and chemically stressed samples of a fully human monoclonal antibody. Journal of Chromatography B, 2007. 850(1-2): p. 285-294.

(56) References Cited

OTHER PUBLICATIONS

Chumsae, C., Gaza-Bulseco, G., & Liu, H., Identification and localization of unpaired cysteine residues in monoclonal antibodies by fluorescence labeling and mass spectrometry. Anal Chem, 2009.81(15): p. 6449-57.
Chung et al. "Cetuximab-induced anaphylaxis and IgE specific for galactose-a-1,3-galactose" NEJM 358:11, 1109-1117 (2008).
Cordoba, A.J., et al., Non-enzymatic hinge region fragmentation of antibodies in solution. Journal of Chromatography B, 2005. 818(2): p. 115-121.
Crowell, C.K., et al., Amino acid and manganese supplementation modulates the glycosylation state of erythropoietin in a CHO culture system. Biotechnology and bioengineering, Feb. 15, 2007; 96(3):538-549.
Dai, S.; An Integrated Proteomic Analysis of Major Isoaspartyl-Containing Proteins in the Urine of Wild Type and Protein LIsoaspartate O-Methyltransferase-Deficient Mice; Anal. Chem. 2013, 85, 2423-2430.
Dionex Application Note 125 (Monitoring Protein Deamidation by Cation-Exchange Chromatography. 2009; pp. 1-7).
Dobo, A. & Kaltashov, I. A.; Detection of Multiple Protein Conformational Ensembles in Solution via Deconvolution of Charge-State Distributions in ESI MS; Anal. Chem. 2001,73, 4763-4773.
Ellison, Jay W. et al., "The Nucleotide Sequence of a Human Immunoglobulin Cγ1 Gene," Nucleic Acids Research, vol. 10, No. 13 (1982), 9 pages.
Emery, P. "Adalimumab therapy: Clinical findings and implications for integration into clinical guidelines for rheumatoid arthritis." *Drugs of Today*, 41(3): p. 155-163. (2005).
European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.
Fahrner et al., "Industrial purification of pharmaceutical antibodies: development, operation, and validation of chromatography processes" Biotechnology and Genetic Engineering Reviews, 18, 2001, pp. 301-327.
Fleisher B., Mechanism of glycosylation in the Golgi apparatus. J Histochem Cytochem, Aug. 1983; 31(8):1033-1040.
Gagnon, P., "Polishing methods for monoclonal IgG purification" Chapter 17, Taylor & Francis Group, LLC, pp. 491-505, 2007.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Goswami et al., "Developments and Challenges for mAb-Based Therapeutics," *Antibodies*, 2:452-500, 2013.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Harding et al., "Class switching in human immunoglobulin transgenic mice" (1995) *Ann. NY Acad. Sci.*, 764:536-547.
Harlow et al., Eds ("Antibodies: A Laboratory Manual" 1988. Cold Spring Harbor Laboratory Press, Chapter 7, pp. 245, 247,and 253).
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).

Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hossler et al., "Optimal and consistent protein glycosylation in mammalian cell culture", Glycobiology; (2009), 19(9):936-949.
Huang, L., et al., In Vivo Deamidation Characterization of Monoclonal Antibody by LC/MS/MS. Analytical Chemistry, 2005. 77(5): p. 1432-1439.
HyClone™ CDM4CHO Catalog listing (last accessed Nov. 17, 2014).
International Preliminary Report on Patentability for Application No. PCT/US2013/031352 dated Nov. 25, 2014, pp. 1-10.
International Preliminary Report on Patentability for Application No. PCT/US2013/031365, dated Mar. 3, 2015, 9 pages.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report for Application No. PCT/US2014/026606, Dated Dec. 8, 2014, 8 pages.
International Search Report for Application No. PCT/US2014/026636, Dated Jul. 29, 2014, 5 pages.
Jack, M.; Wright, D.; The Role of Advanced Glycation Endproducts and Glyoxalase I in Diabetic Peripheral Sensory Neuropathy; Transl. Res. 2012, 159, 355-365.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jefferis, R., Glycosylation of Recombinant Antibody Therapeutics. Biotechnology Progress, 2005.21(1): p. 11-16.
Johnson, K.A., et al., Cation exchange HPLC and mass spectrometry reveal C-terminal amidation of an IgG1 heavy chain. Analytical Biochemistry, 2007. 360(1): p. 75-83.
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118..
Kazuaki F et al "Enhancment of productivity of recombinant a-amidating enzyme by low temperature culture" Cytotechnology 31:85-94, 1999.
Kingkeohoi, S., Analysis of methylglyoxal metabolism in CHO celis grown in culture, Cytotechnology (2005) 48:1-13.
Kwon et al., "Production of lactic acid by *Lactobacillus rhamnosus* with vitamin-supplemented soybean hydrolysate", Enzyme Microb Technol. (2000), 26:209-215.
Leusch, "Failure to demonstrate TNFα-specific autoantibodies in human sera by ELISA and Western blot" (1991) *J. Immunol. Methods*, 139:145-47.
Li, Feng, et al., "Cell Culture Processes for Monoclonal Antibody Production," mAbs 2:5, 466479 (Sep.-Oct. 2010).
Liu et al. "Recovery and purificaiton process development for monoclonal antibody production" MABS, 2(5), pp. 480-499 (2010).

(56) References Cited

OTHER PUBLICATIONS

Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, H., et al., Heterogeneity of monoclonal antibodies. Journal of Pharmaceutical Sciences, 2008. 97(7): p. 2426-2447.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistrv, 269, 32299-32305.
Manning, M., et al., Stability of Protein Pharmaceuticals: An Update. Pharmaceutical Research, 2010.27(4): p. 544-575.
Matthews, R. G.; et al.; Cobalamin-Dependent and Cobalamin-Independent Methionine Synthases: Are There Two Solutions to the Same Chemical Problem?; Hely. Chim. Acta 2003, 86, 3939-3954.
Mizuochi, T., et al., Structural and numerical variations of the carbohydrate moiety of immunoglobulin G. J Immunol, 1982. 129(5): p. 2016-2020.
Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.
Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.
Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.
Ni, W.; Analysis of Isoaspartic Acid by Selective Proteolysis with Asp-N and Electron Transfer Dissociation Mass Spectrometry; Anal. Chem. 2010, 82,7485-7491.
Ouellette, D.; Studies in serum support rapid formation of disulfide bond between unpaired cysteine residues in the VH domain of an immunoglobulin G1 molecule; Anal. Biochem. 2010, 397, 37.
Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.
Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.
Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.
Parekh RB N-glycosylation and the production of recombinant glycoproteins vol. 7, Issue 5, p. 117-122, May 1989 Trends in Biotechnology.
Parekh, R.B., et al., Association of rheumatoid arthritis and primary osteoarthritis with changes in the glycosylation pattern of total serum IgG. Nature, 1985. 316(6027): p. 452-457.
PCT/US2013/069702 International Search Report & Written Opinion mailed Jan. 31, 2014, 13 pages.
Perkins, M.; et. Al. Determination of the Origin of Charge Heterogeneity in a Murine Monoclonal Antibody; M. Pharm. Res. 2000, 17, 1110-1117.
Quan, C., et al., A study in glycation of a therapeutic recombinant humanized monoclonal antibody: Where it is, how it got there, and how it affects charge-based behavior. Analytical Biochemistry, 2008. 373(2): p. 179-191.
Rabbani, N.; Thornalley, P. J.; Glyoxalase in diabetes, obesity and related disorders; Semin. Cell Dev. Biol. 2011, 22, 309-317.
Ren, D., et al., Reversed-phase liquid chromatography-mass spectrometry of site-specific chemical modifications in intact immunoglobulin molecules and their fragments. Journal of Chromatography A, 2008. 1179(2): p. 198-204.
Roy, B.M., et al., Toxic concentrations of exogenously supplied methylglyoxal in hybridoma cell culture, Cytotechnology (2004) 46:97-107.
Sargent (pp. 1-3, Internet Archive captured Aug. 28, 2013, http://cellculturedish.com/2012/01 /cho-cells-the-top-expressionsystem-of-best-selling-biologic-drugs/).
Saxena, R. K. et al.; Microbial production and applications of 1 ,2-propanediol; Indian J. Microbiol. 2010,50,2-11.
Shen, Amy Y. et al., "Recombinant DNA Technology and Cell Line Development," from "Cell Culture Technology for Pharmaceutical and Cell-Based Therapies," CRC Press, 1995, 15-40.
Shubert et al. "Comparison of ceramic hydroxy- and fluoroapatite versus Protein A/G—based resins in the isiolation of a recombinant human antibody from cell culture supernatant" J. Chromatography A, 114 (2007) 106-113.
Sigma Catalog "RPMI1640" (last accessed Jan. 22, 2015), 3 pages.
Sigma MSDS for RMPI1640 (last accessed Jan. 22, 2015), 6 pages.
TESS database "HYCLONE" Trademark #76244963. Filing date Apr. 23, 2001. Live mark. Last accessed Jan. 21, 2015.
TESS database "HYCLONE" Trademark #85769283. Filing date Sep. 30, 2012. Live mark. Last accessed Jan. 21, 2015.
The Kennedy Institute of Rheumatology, 1995 Annual Scientific Report, "Anti-TNF trials and studies of mechanisms of action".
United States Food and Drug Administration (FDA) Biological Licensing Application File No. 125057 (Adalimumab) (Dec. 31, 2002) (Last Accessed Mar. 4, 2015 at <http://www.fda.gov/Drugs/DevelopmentApprovalProcess/HowDrugsareDevelopedandApproved/ApprovalApplications/TherapeuticBiologicApplications/ucm080610.htm>), 1 page.
Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.
Vasilli, P. et al., the Pathophysiology of Tumor Necrosis Factors, Annu. Rev. Immunol. 10:411-452 (1992).
Vlasak, J. & Ionescu, R., Heterogeneity of Monoclonal Antibodies Revealed by Charge-Sensitive Methods. Current Pharmaceutical Biotechnology, 2008. 9(6): p. 468-481.
Walsh, et al.: "Post-translational modifications in the context of therapeutic proteins", Nature Biotechnology, vol. 24, No. 10, Oct. 2006, pp. 1241-1252.
Wang, Z.; et al. Desulfurization of Cysteine-Containing Peptides Resulting from Sample Preparation for Protein Characterization by MS; Rapid Commun. Mass Spectrom. 2010, 24, 267-275.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Williams, A. et al., Ion-Exchange Chromatography, Oct. 1998, Supplement 44, pp. 10-10-1-10-10-30.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yuk, I.H. et al., Controlling Glycation Of Recombinant Antibody in Fed Batch Cell Cultures, Nov. 2011 , Biotechnology and Bioengineering, vol. 108, No. 11 pp. 2600-2610.
Zang, T.; et al.; Chemical Methods for the Detection of Protein N-Homocysteinylation via Selective Reactions with Aldehydes; Anal. Chem. 2009, 81, 9065-9071.
Zhang, B., et al., Unveiling a Glycation Hot Spot in a Recombinant Humanized Monoclonal Antibody. Analytical Chemistry, 2008. 80(7): p. 2379-2390.

(56) References Cited

OTHER PUBLICATIONS

Zhang, T.; Identification and Characterization of Buried Unpaired Cysteines in a Recombinant Monoclonal IgG1 Antibody; Anal. Chem. 2012, 84, 7112-7123.

Zhang, W. and Czupryn, M.J., Free Sulfhydryl in Recombinant Monoclonal Antibodies. Biotechnology Progress, 2002. 18(3): p. 509-513.

Zhao, G.; Chemical Synthesis of S-Ribosyl-L-homocysteine and Activity Assay as a LuxS Substrate; Bioorg. Med. Chem. Lett. 2003,13,3897-3900.

Zhou, Z. et al.; An Antibody-Catalyzed Allylic Sulfoxide-Sulfenate Rearrangement; J. Org. Chem. 1999,64,8334-8341.

Zhou, Z. S. et al. An Antibody-Catalyzed Selenoxide Elimination; J. Am. Chem. Soc. 1997, 119, 3623-3624.

* cited by examiner

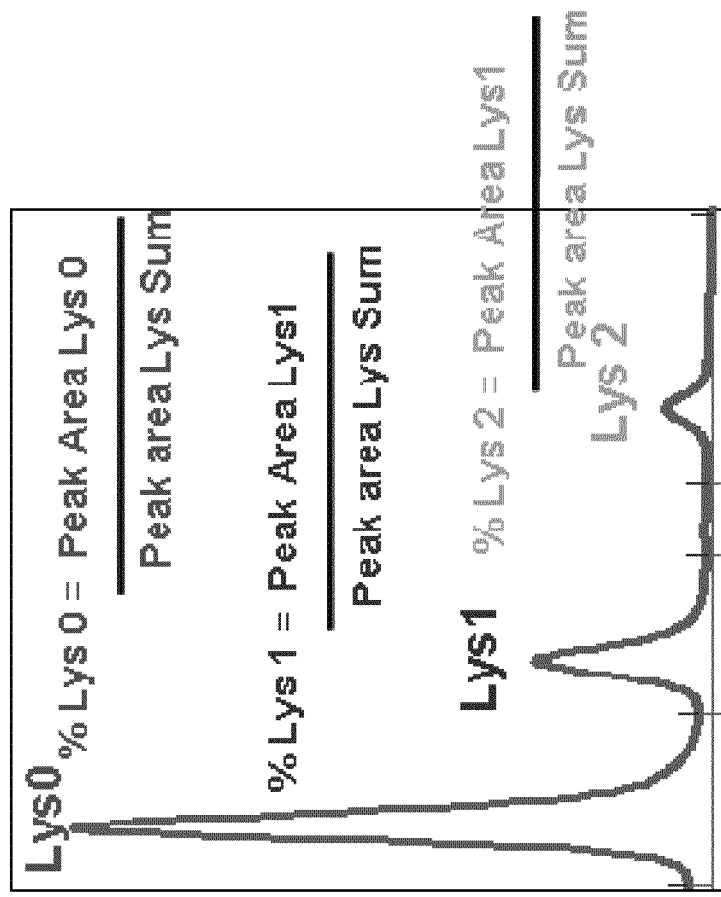
Figure 1) Representation of the lysine variants in a sample WCX-10 chromatogram and quantification scheme of each of the variants

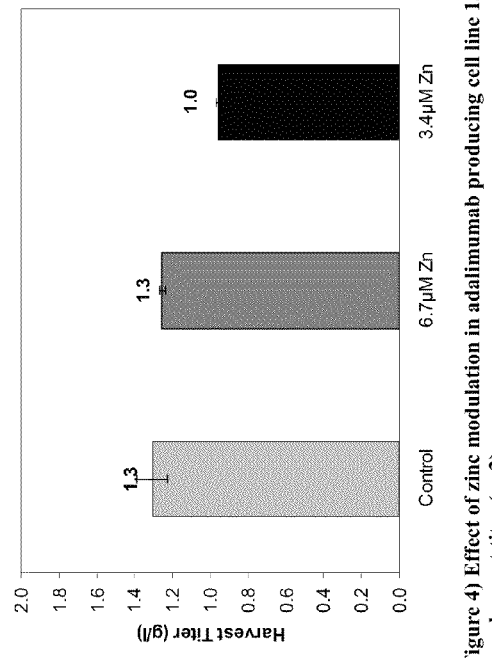

Figure 4) Effect of zinc modulation in adalimumab producing cell line 1, media 1 on harvest titer (n=2)

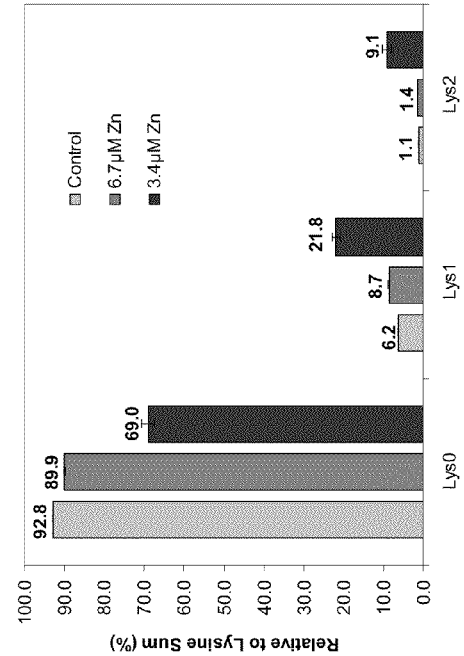

Figure 5) Effect of zinc modulation in adalimumab producing cell line 1, media 1 on day 10 WCX-10 profile relative lysine distribution (n=2)

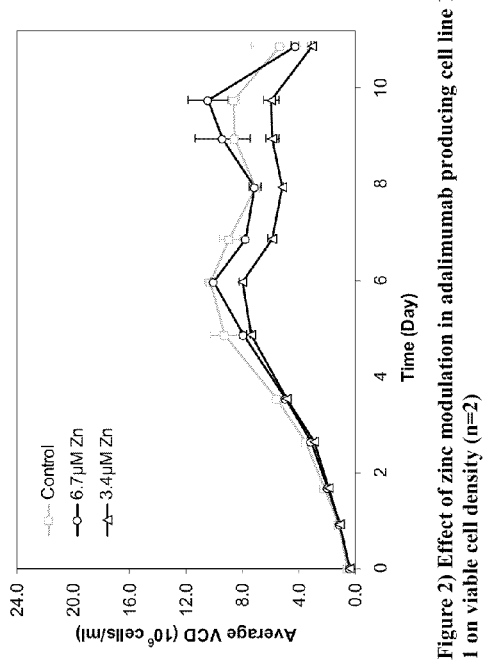

Figure 2) Effect of zinc modulation in adalimumab producing cell line 1, media 1 on viable cell density (n=2)

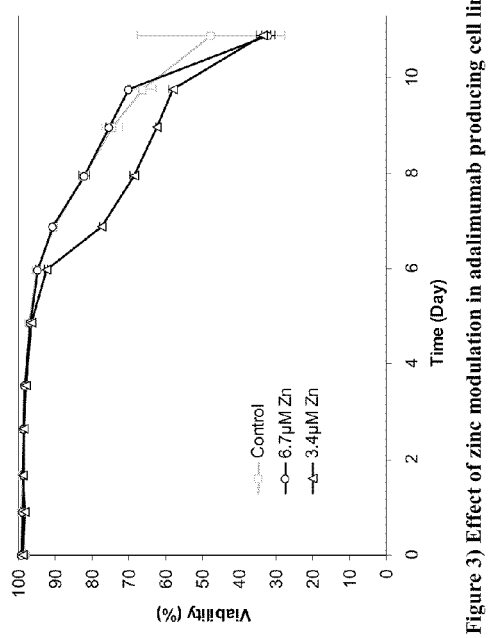

Figure 3) Effect of zinc modulation in adalimumab producing cell line 1, media 1 on viability (n=2)

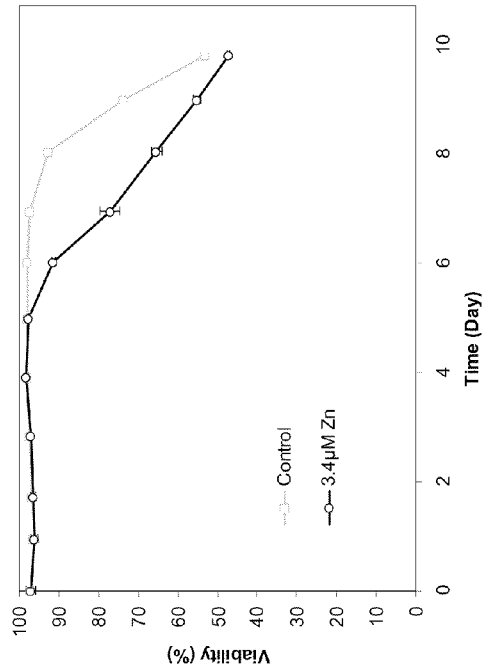
Figure 6) Effect of zinc modulation in adalimumab producing cell line 1, media 1 on viable cell density (n=2)
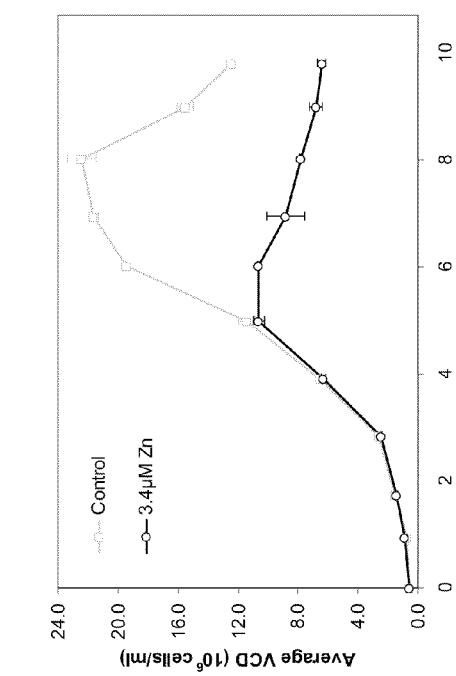
Figure 7) Effect of zinc modulation in adalimumab producing cell line 1, media 1 on viability (n=2)
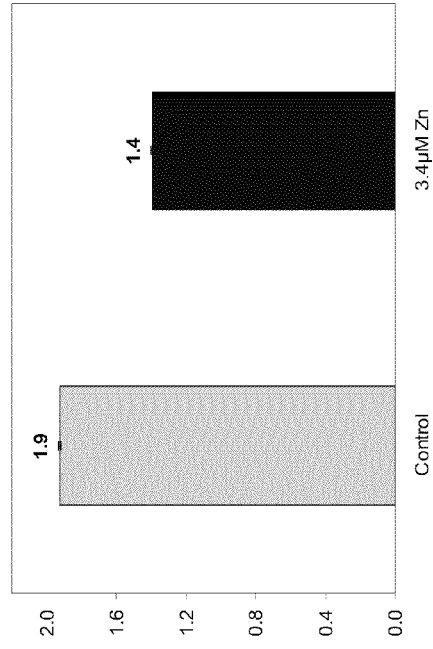
Figure 8) Effect of zinc modulation in adalimumab producing cell line 1, media 1 on harvest titer (n=2)

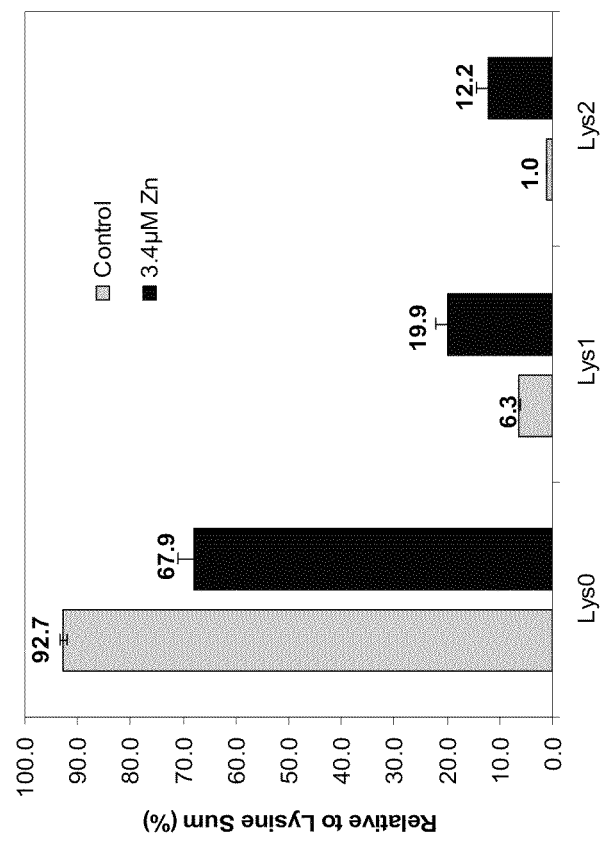
Figure 9) Effect of zinc modulation in adalimumab producing cell line 1, media 1 on day 10 WCX-10 profile relative lysine distribution (n=2)

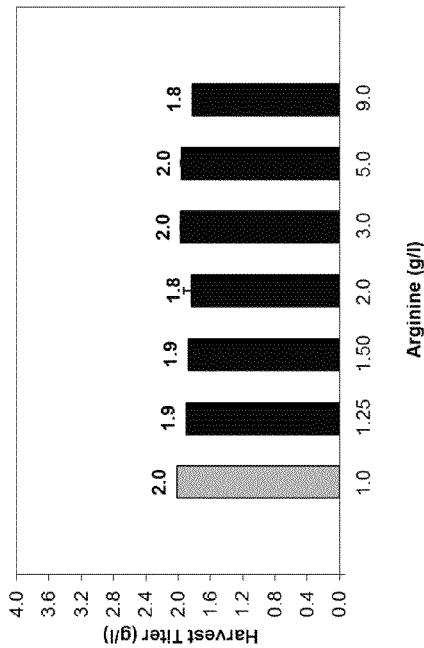

Figure 12) Effect of total arginine concentration in adalimumab producing cell line 2, media 1 on harvest titer (n=2)

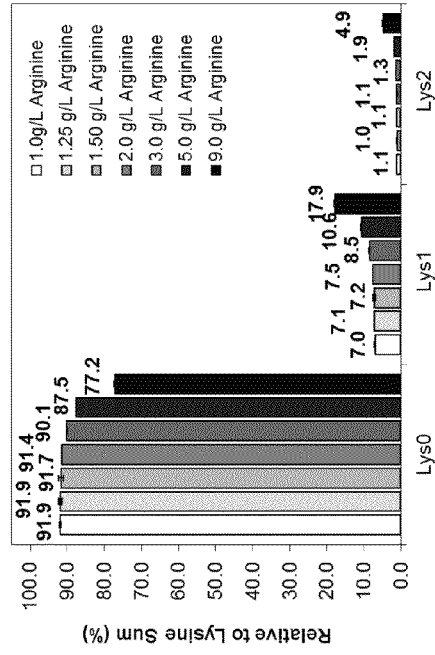

Figure 13) Effect of total arginine concentration in adalimumab producing cell line 2, media 1 on day 10 on WCX-10 profile relative lysine distribution (n=2)

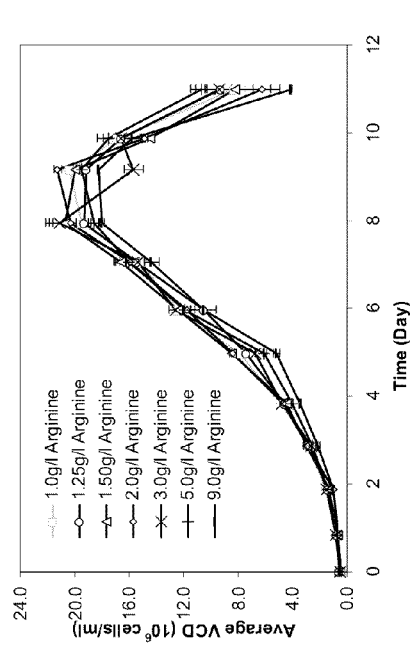

Figure 10) Effect of total arginine concentration in adalimumab producing cell line 2, media 1 on viable cell density (n=2)

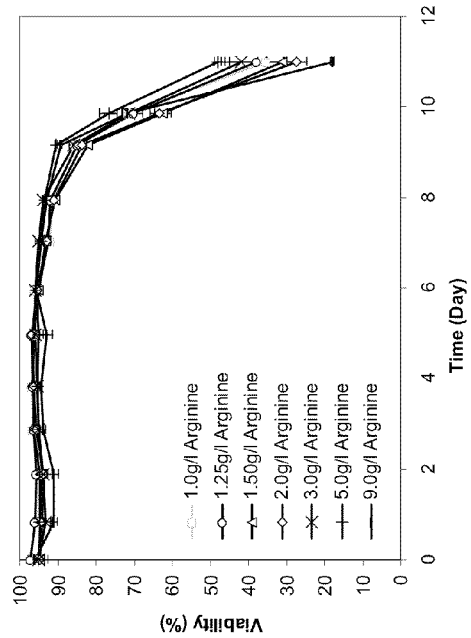

Figure 11) Effect of total arginine concentration in adalimumab producing cell line 2, media 1 on viability (n=2)

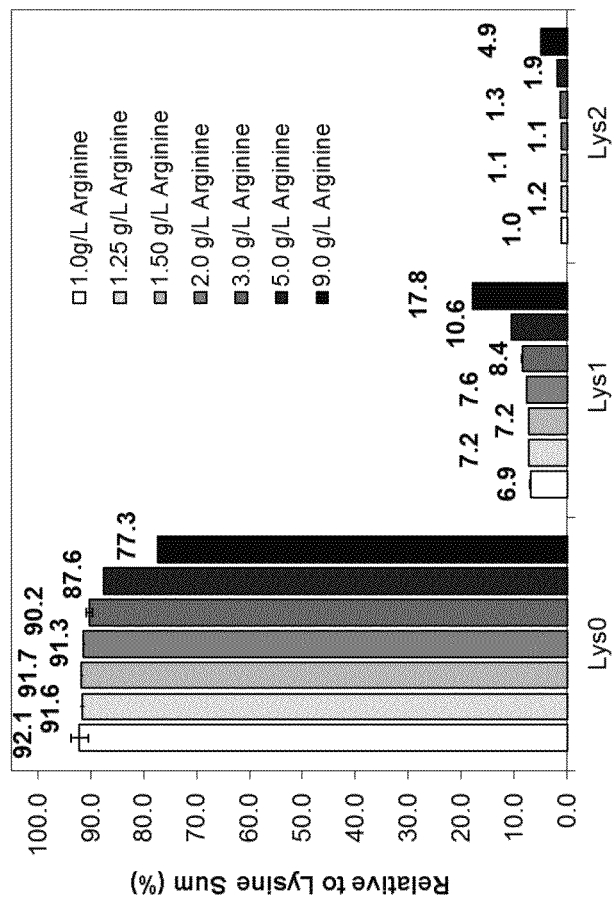
Figure 14) Effect of total arginine concentration in adalimumab producing cell line 2, media 1 on day 12 on WCX-10 profile relative lysine distribution (n=2)

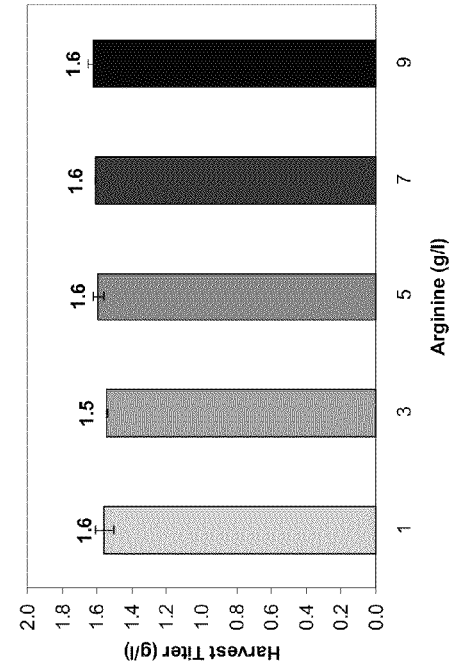
Figure 15) Effect of total arginine concentration in adalimumab producing cell line 3, media 1 on viable cell density (n=2)
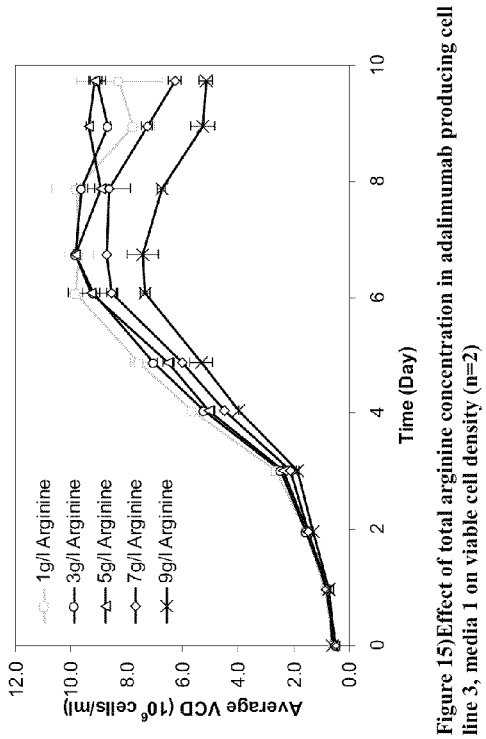
Figure 16) Effect of total arginine concentration in adalimumab producing cell line 3, media 1 on viability (n=2)
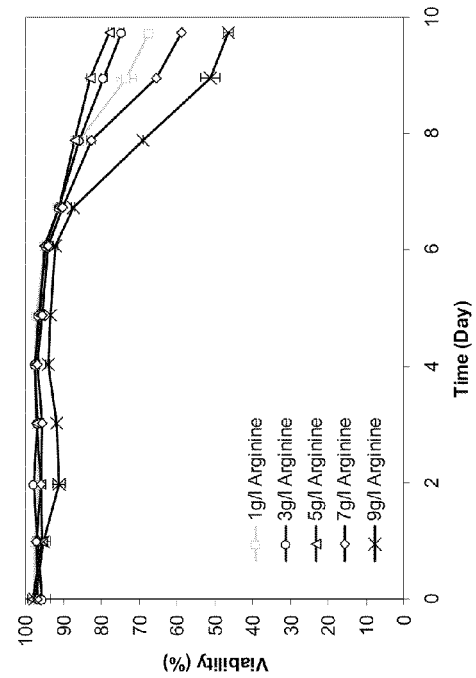
Figure 17) Effect of total arginine concentration in adalimumab producing cell line 3, media 1 on harvest titer (n=2)

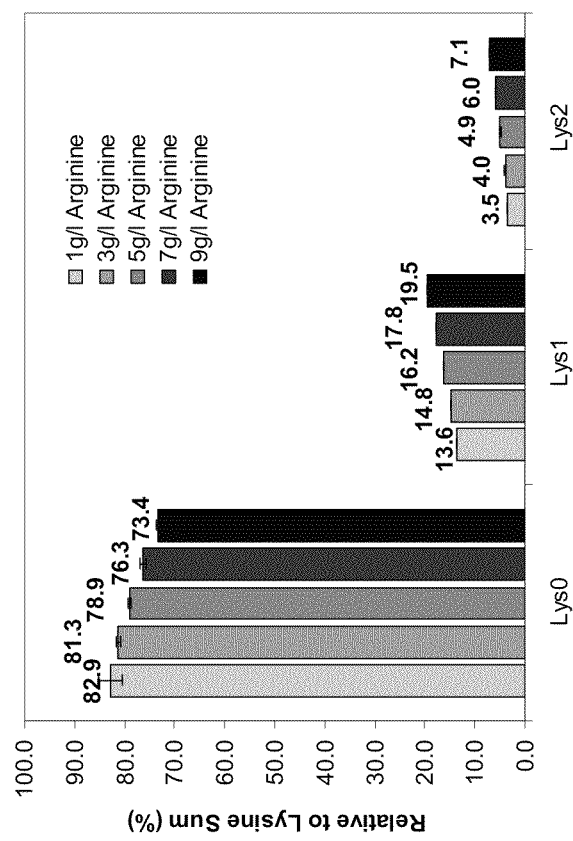
Figure 18) Effect of total arginine concentration in adalimumab producing cell line 3, media 1 on WCX-10 profile relative lysine distribution (n=2)

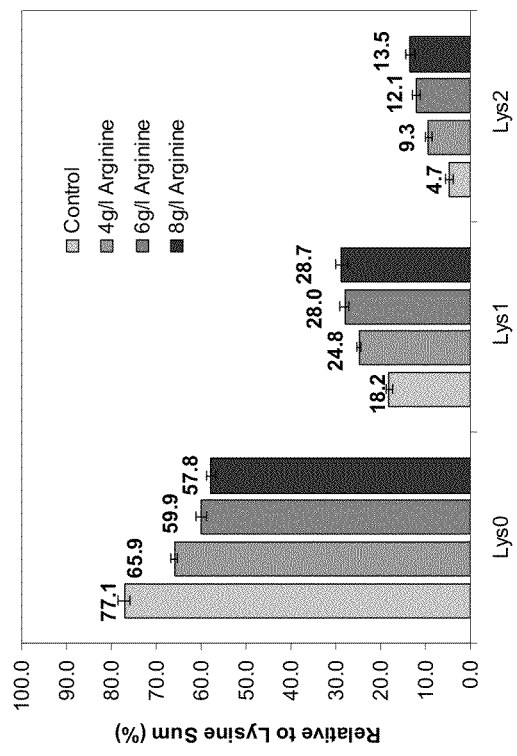
Figure 20) Effect of arginine addition to adalimumab producing cell line 1, media 2 on day 11 on WCX-10 profile relative lysine distribution (n=2)
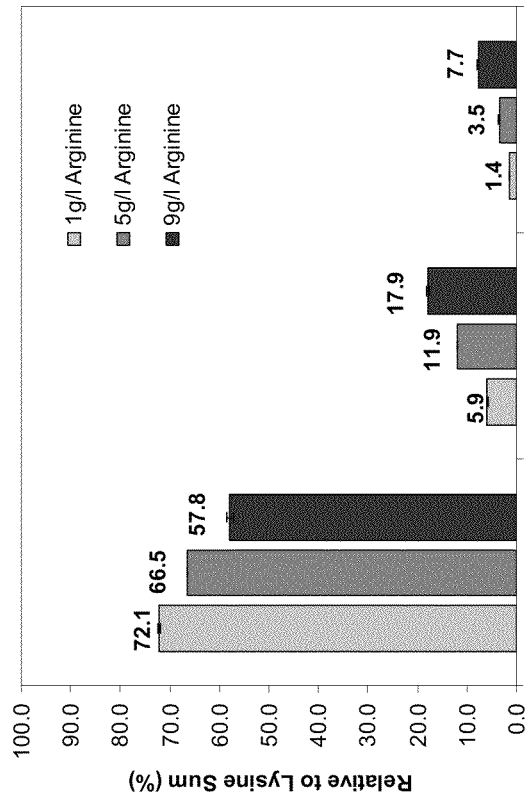
Figure 19) Effect of total arginine concentration in adalimumab producing cell line 1, media 1 on WCX-10 profile relative lysine distribution (n=2)

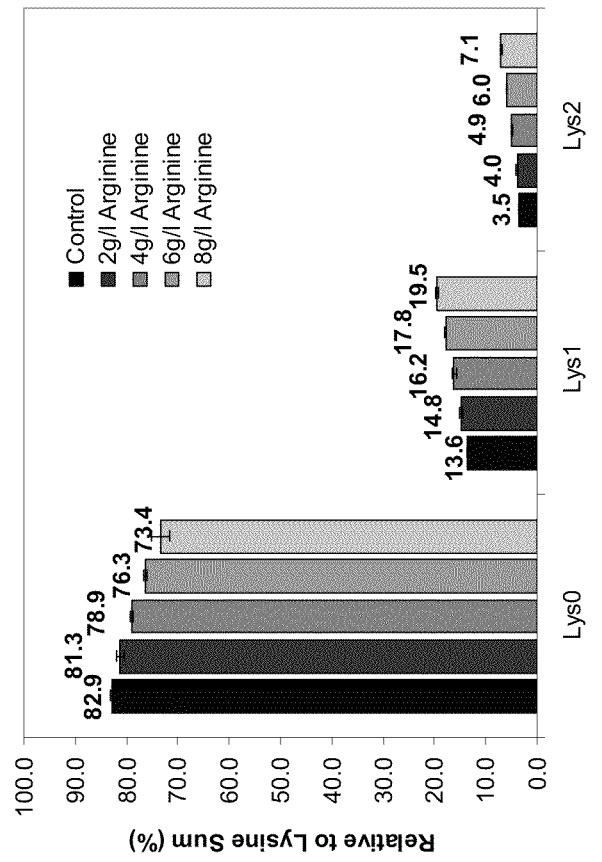
Figure 21) Effect of arginine addition to adalimumab producing cell line 2, media 3 on WCX-10 profile relative lysine distribution (n=2)

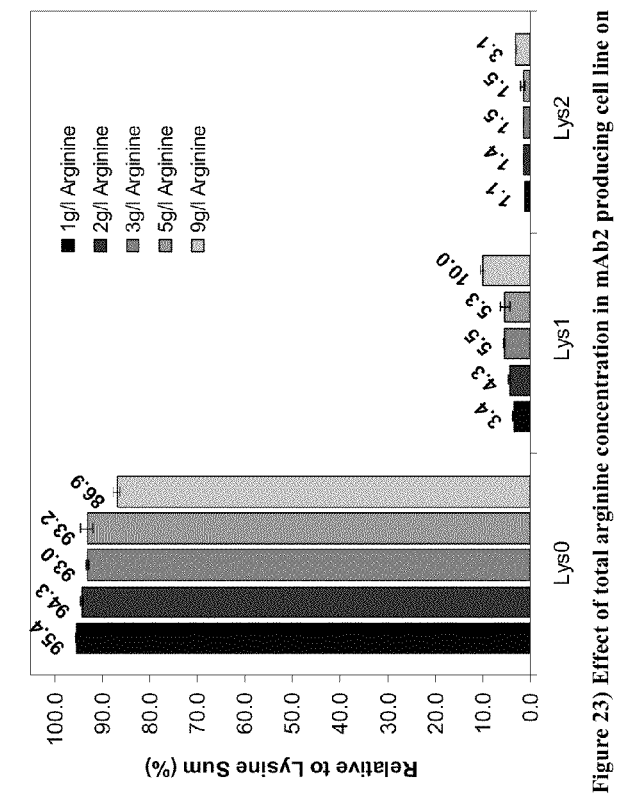
Figure 23) Effect of total arginine concentration in mAb2 producing cell line on WCX-10 profile relative lysine distribution (n=2)
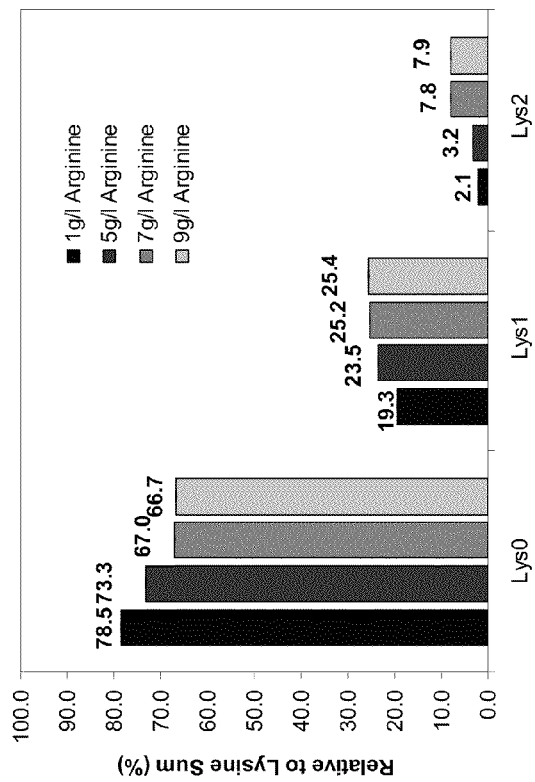
Figure 22) Effect of total arginine concentration in mAb1 producing cell line on WCX-10 profile relative lysine distribution (nn=1)

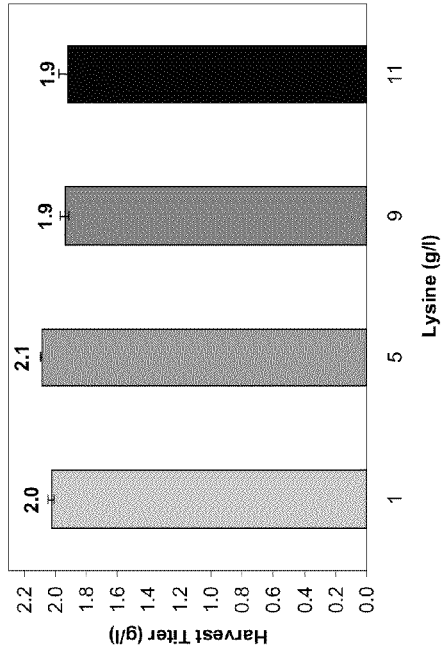

Figure 24) Effect total lysine concentration in adalimumab producing cell line 2, media 1 on viable cell density (n=2)

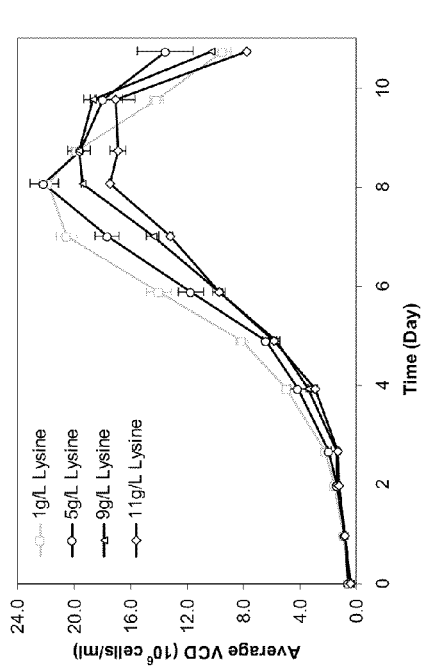

Figure 25) Effect of total lysine concentration in adalimumab producing cell line 2, media 1 on viability (n=2)

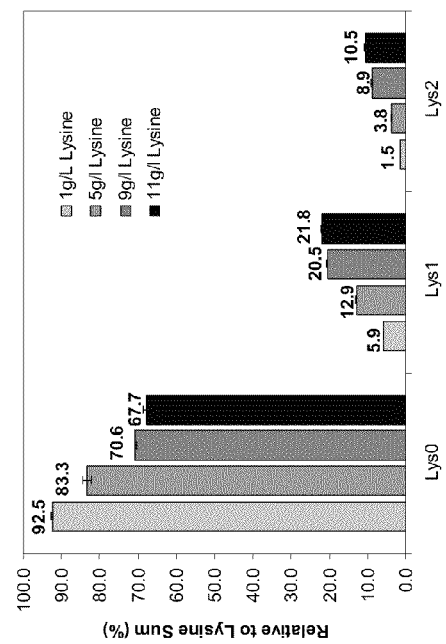

Figure 26) Effect of total lysine concentration in adalimumab producing cell line 2, media 1 on harvest titer (n=2)

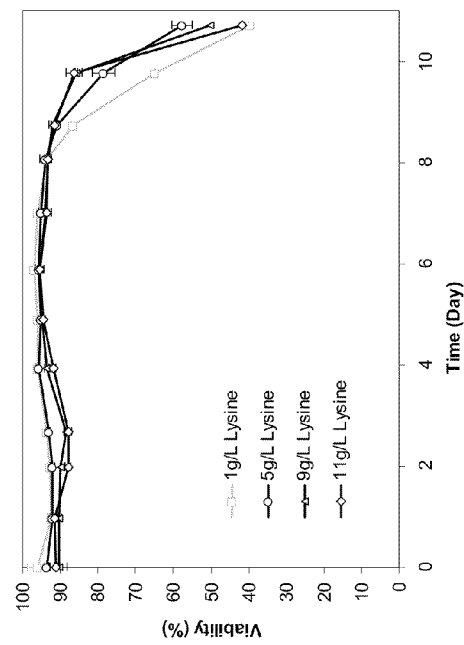

Figure 27) Effect of total lysine concentration in adalimumab producing cell line 2, media 1 on WCX-10 profile relative lysine distribution (n=2)

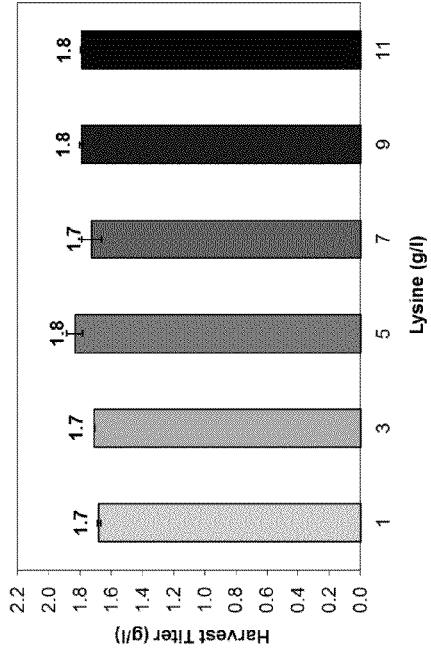
Figure 30) Effect of total lysine concentration in adalimumab producing cell line 3, media 1 on harvest titer (n=2)
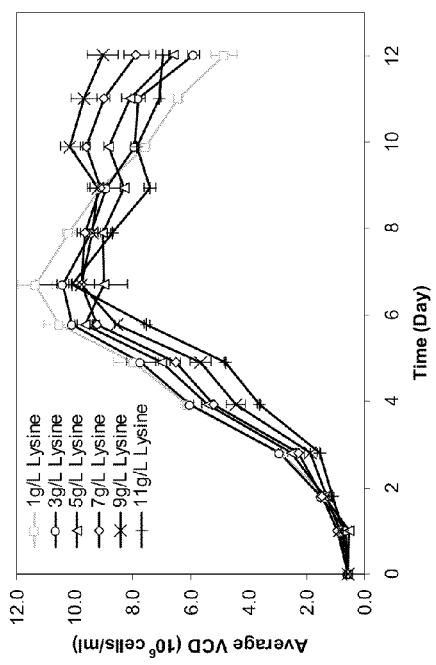
Figure 28) Effect of total lysine concentration in adalimumab producing cell line 3, media 1 on viable cell density (n=2)
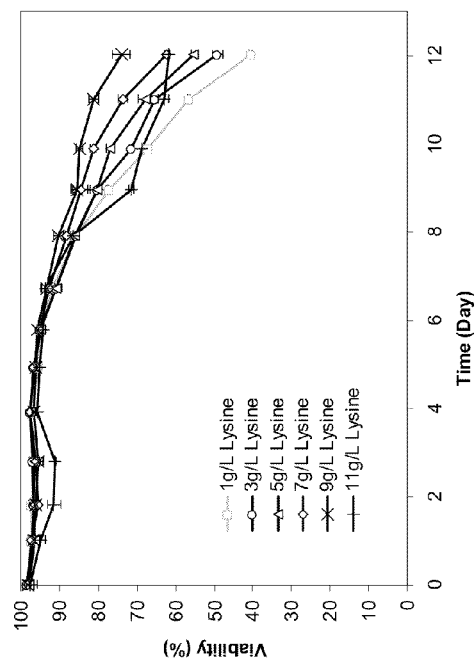
Figure 29) Effect of total lysine concentration in adalimumab producing cell line 3, media 1 on viability (n=2)

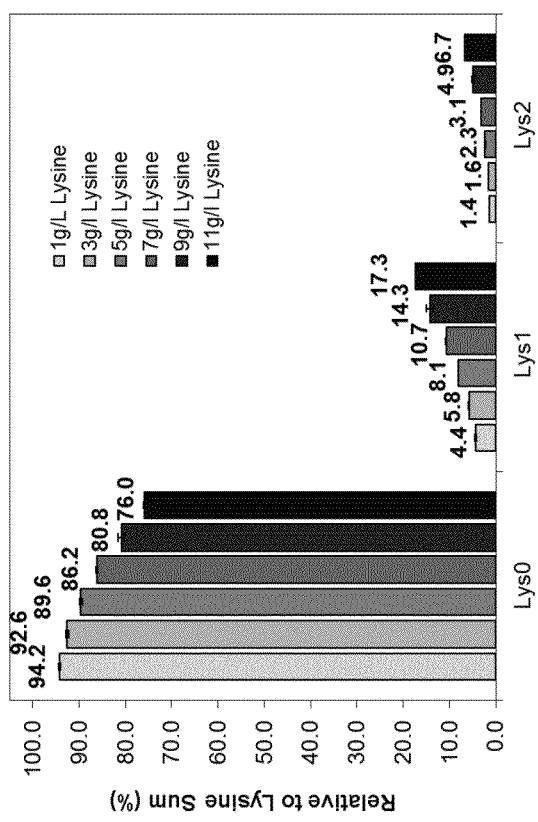
Figure 31) Effect of total lysine concentration in adalimumab producing cell line 3, media 1 on WCX-10 profile relative lysine distribution (n=2)

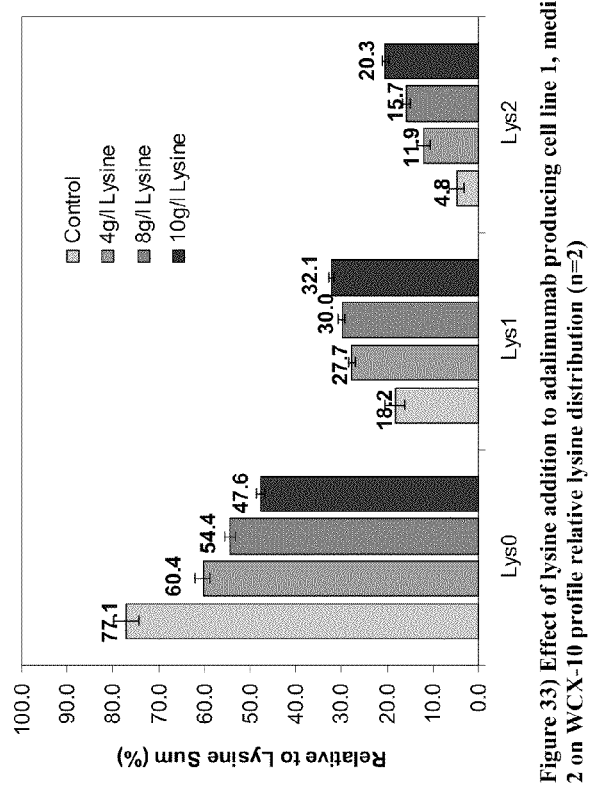
Figure 33) Effect of lysine addition to adalimumab producing cell line 1, media 2 on WCX-10 profile relative lysine distribution (n=2)
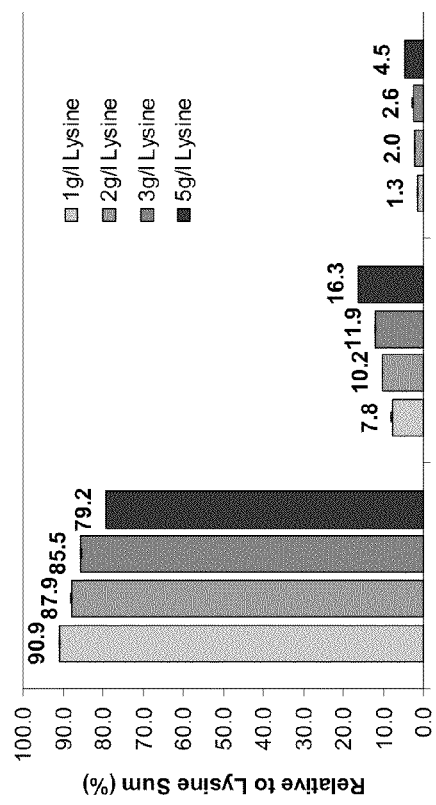
Figure 32) Effect of total lysine concentration in adalimumab producing cell line 1, media 1 on WCX-10 profile relative lysine distribution (n=2)

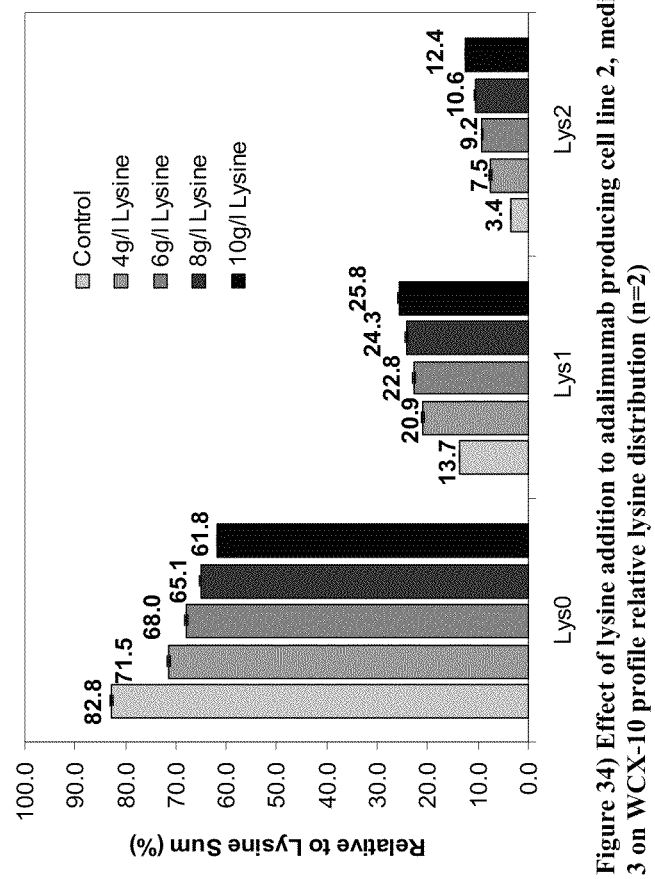
Figure 34) Effect of lysine addition to adalimumab producing cell line 2, media 3 on WCX-10 profile relative lysine distribution (n=2)

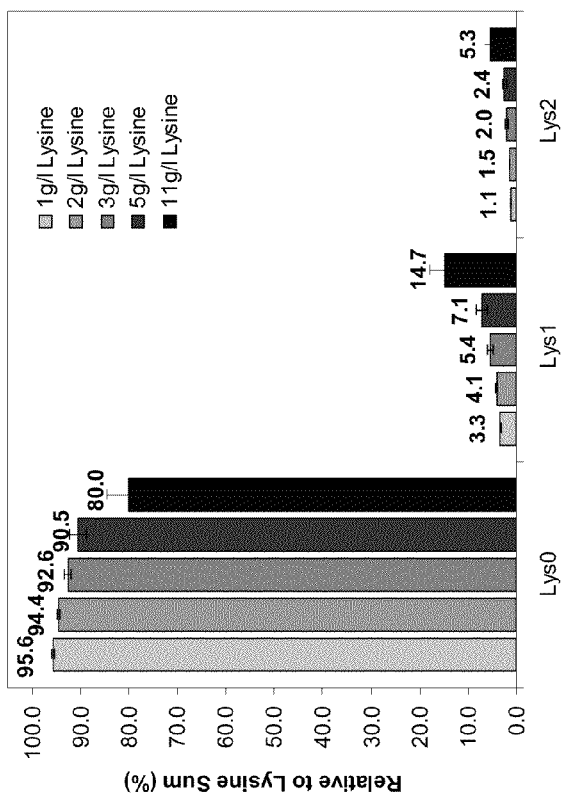
Figure 36) Effect of total lysine concentration in mAb2 producing cell line on WCX-10 profile relative lysine distribution (n=2)
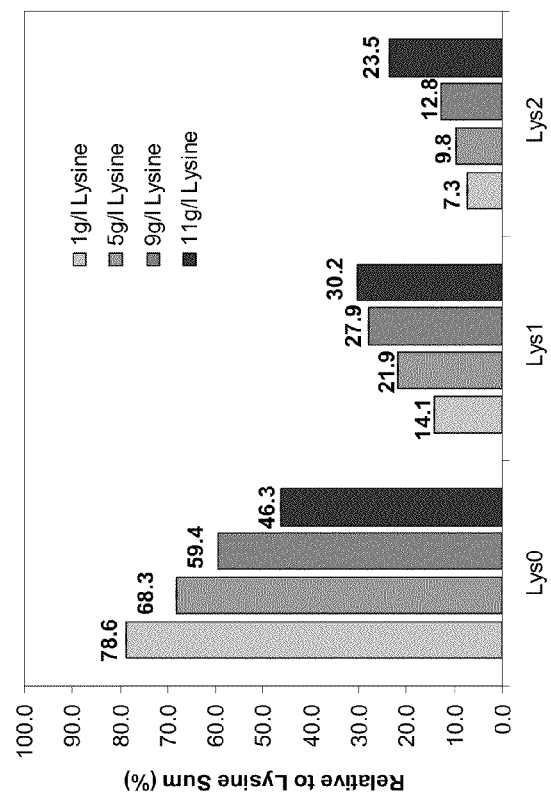
Figure 35) Effect of total lysine concentration in mAb1 producing cell line on WCX-10 profile relative lysine distribution (n=1)

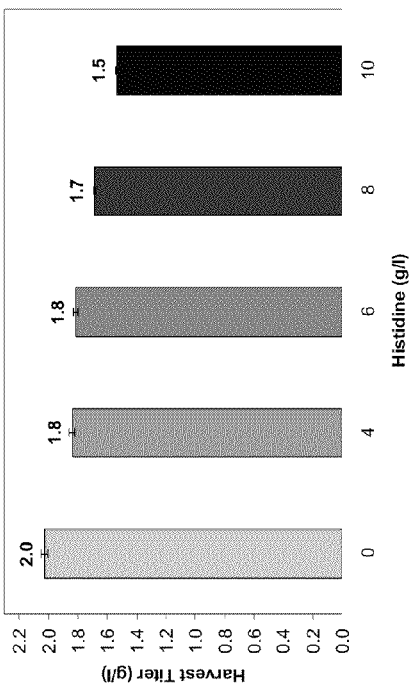

Figure 39) Effect of total histidine concentration in adalimumab producing cell line 2, media 1 on harvest titer (n=2)

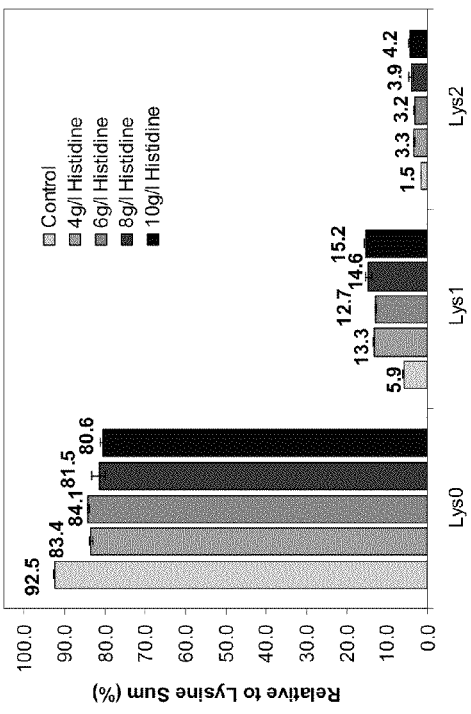

Figure 40) Effect of total histidine concentration in adalimumab producing cell line 2, media 1 on WCX-10 profile relative lysine distribution (n=2)

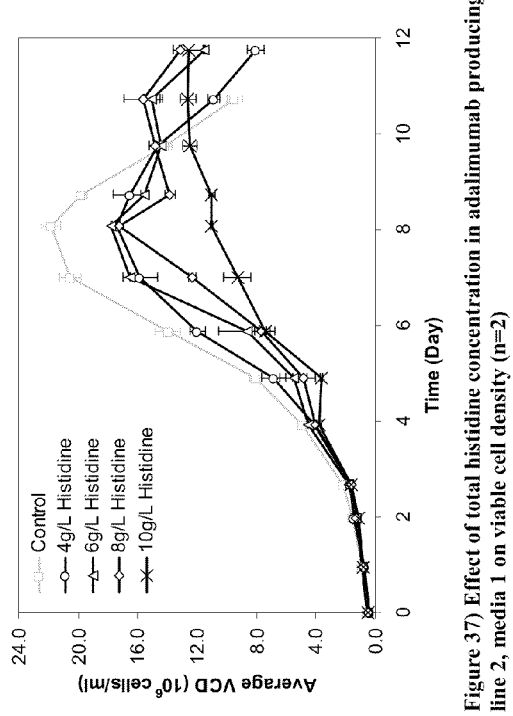

Figure 37) Effect of total histidine concentration in adalimumab producing cell line 2, media 1 on viable cell density (n=2)

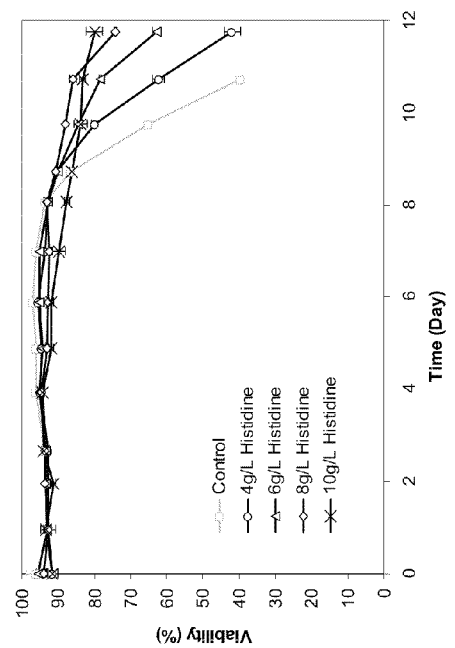

Figure 38) Effect of total histidine concentration in adalimumab producing cell line 2, media 1 on viability (n=2)

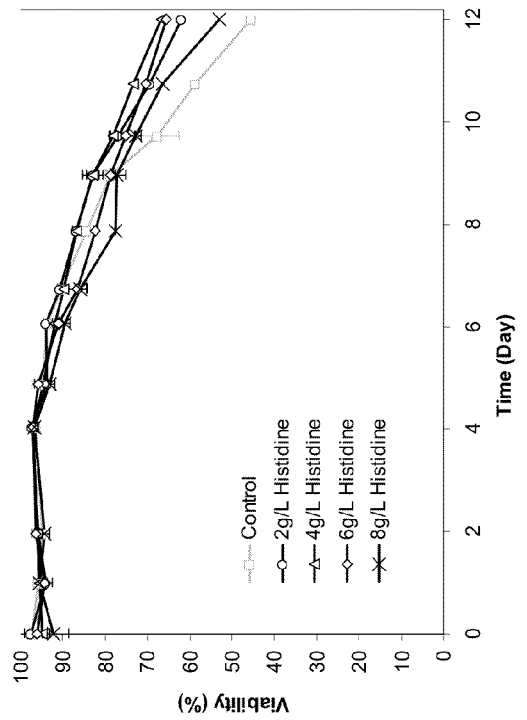
Figure 42) Effect of total histidine concentration in adalimumab producing cell line 3, media 1 on viability (n=2)
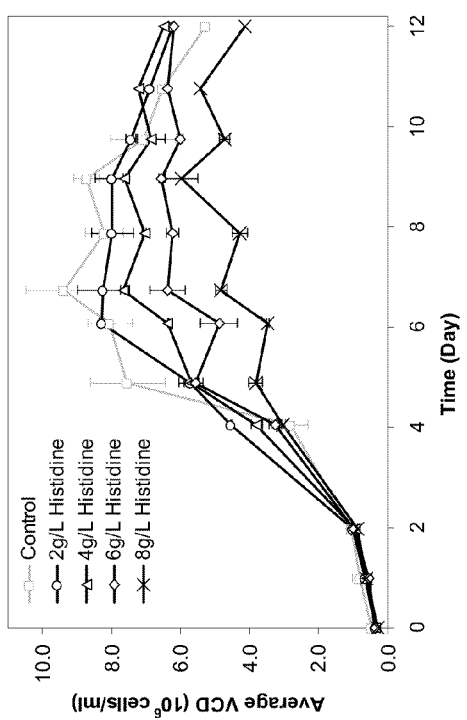
Figure 41) Effect of total histidine concentration in adalimumab producing cell line 3, media 1 on viable cell density (n=2)

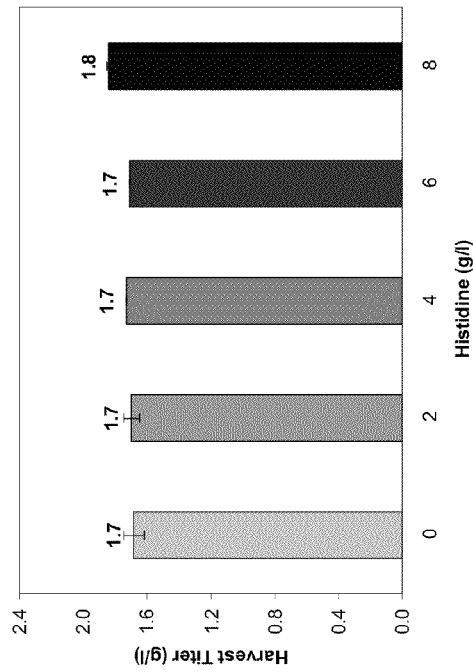
Figure 43) Effect of total histidine concentration in adalimumab producing cell line 3, media 1 on harvest titer (n=2)
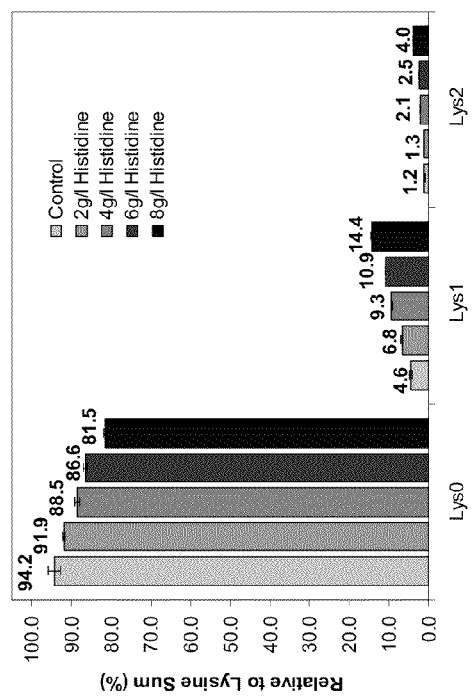
Figure 44) Effect of total histidine concentration in adalimumab producing cell line 3, media 1 on WCX-10 profile relative lysine distribution (n=2)

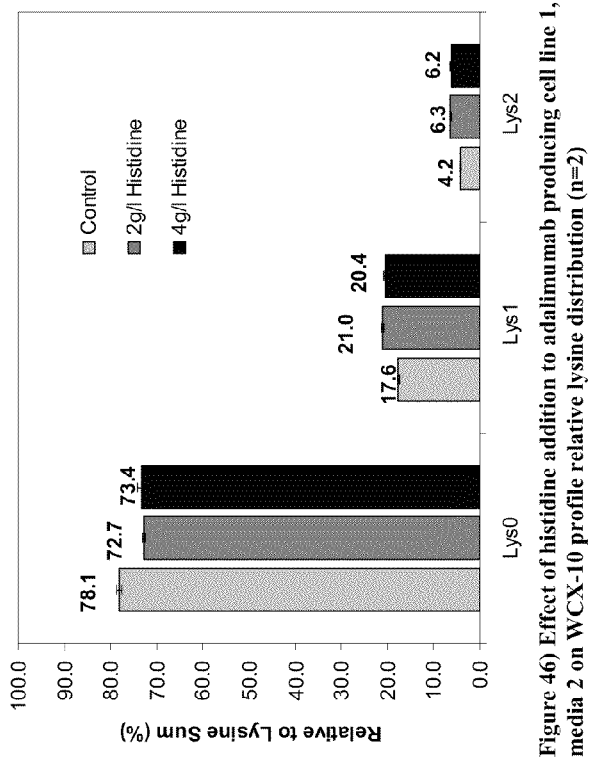
Figure 46) Effect of histidine addition to adalimumab producing cell line 1, media 2 on WCX-10 profile relative lysine distribution (n=2)
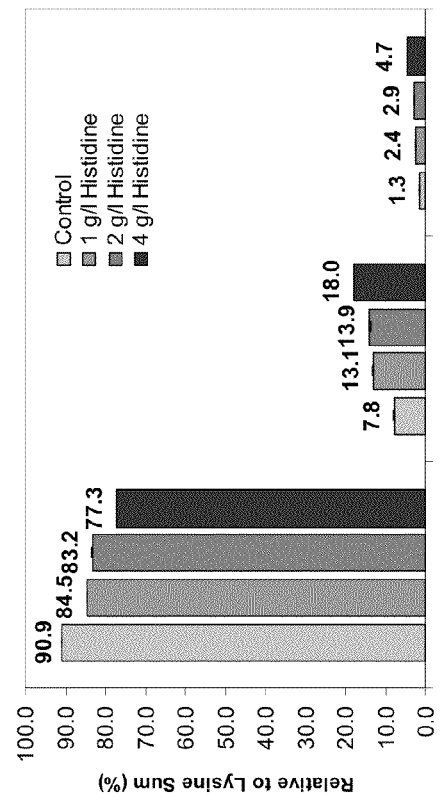
Figure 45) Effect total histidine concentration in adalimumab producing cell line 1, media 1 on WCX-10 profile relative lysine distribution (n=2)

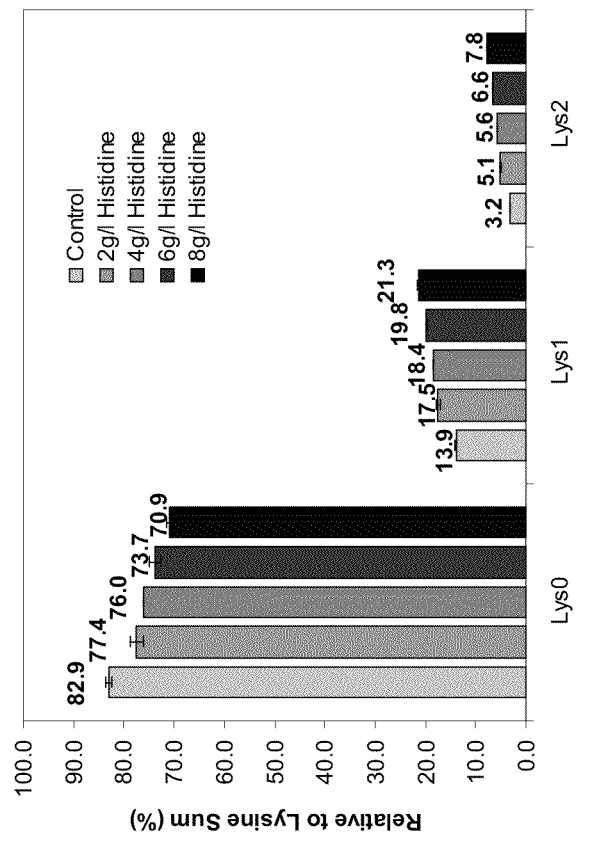
Figure 47) Effect of histidine addition to adalimumab producing cell line 2, media 3 on WCX-10 profile relative lysine distribution (n=2)

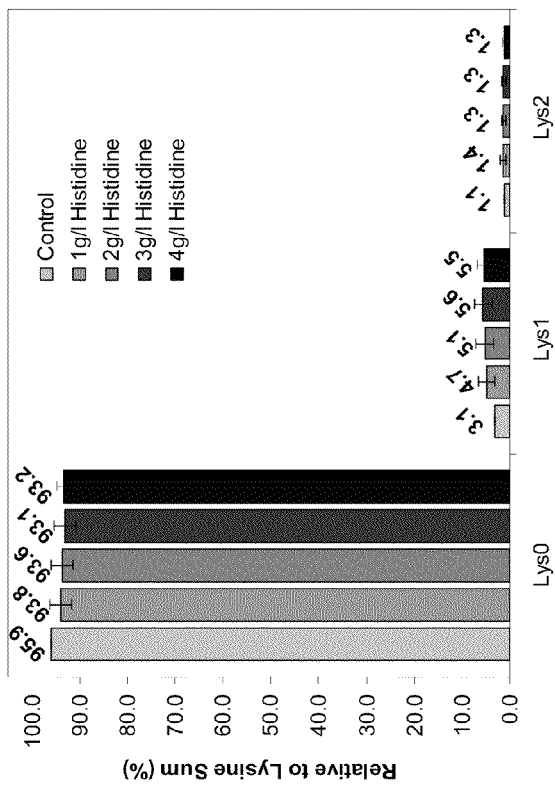
Figure 49) Effect of total histidine concentration in mAb2 producing cell line on WCX-10 profile relative lysine distribution (n=2)
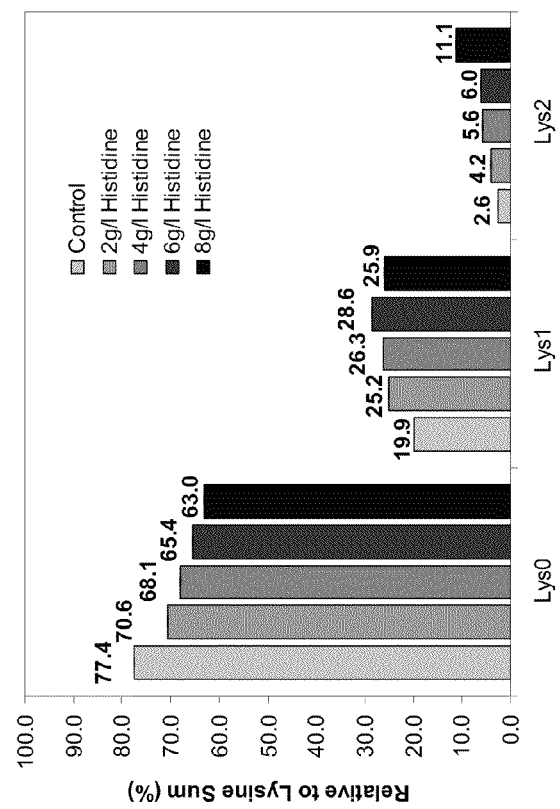
Figure 48) Effect of total histidine concentration in mAb1 producing cell line on WCX-10 profile relative lysine distribution (n=1)

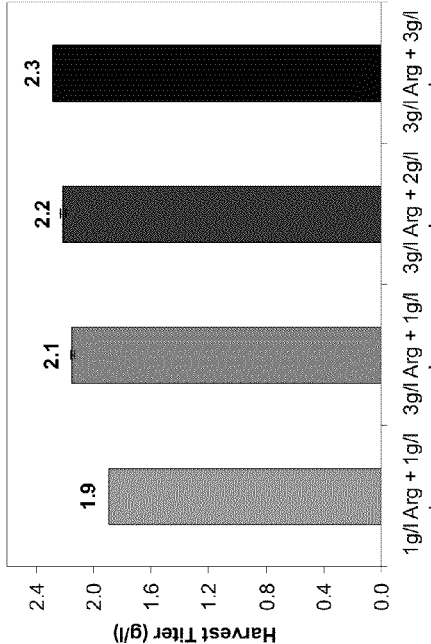

Figure 50) Effect of increase in multiple amino acids to adalimumab producing cell line 1, media 1 on viable cell density (n=2)

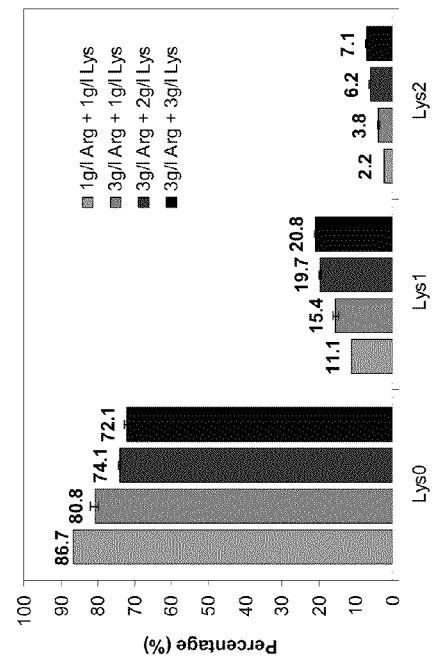

Figure 52) Effect of increase in multiple amino acids to adalimumab producing cell line 1, media 1 on harvest titer

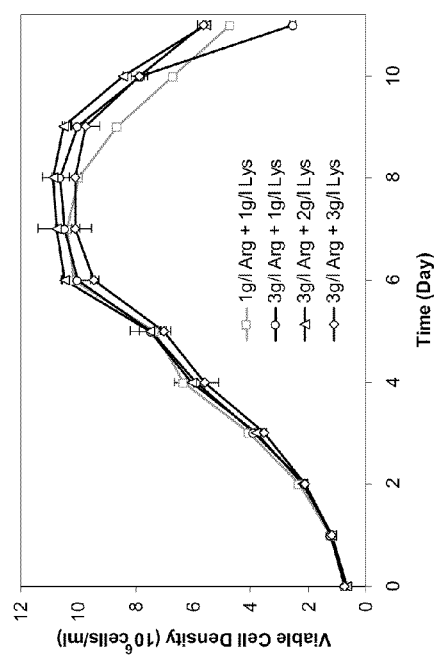

Figure 51) Effect of increase in multiple amino acids to adalimumab producing cell line 1, media 1 on viability

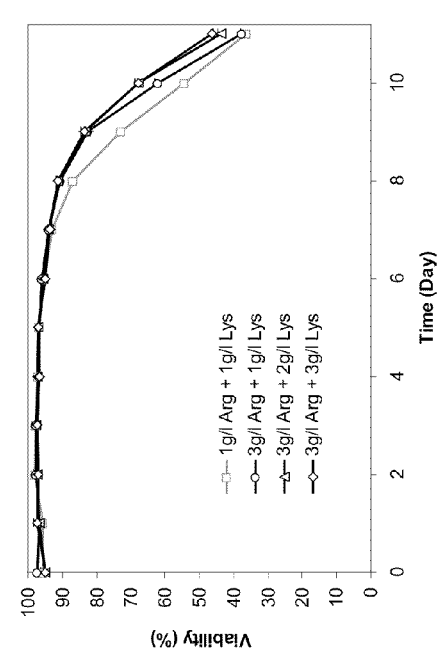

Figure 53) Effect of increase in multiple amino acids to adalimumab producing cell line 1, media 1 on WCX-10 profile relative lysine distribution

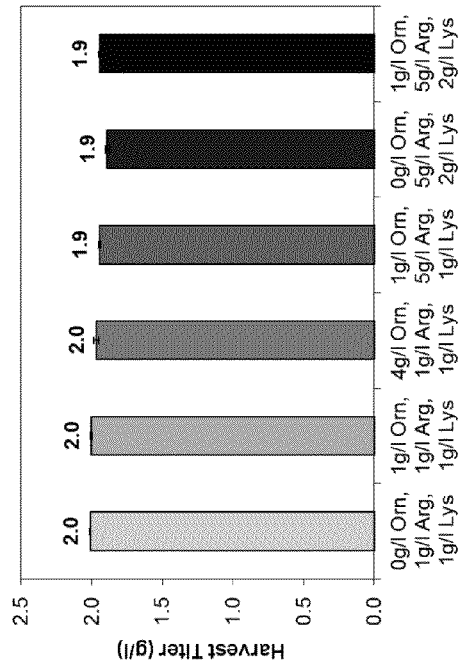

Figure 54) Effect of increase in multiple amino acids to adalimumab producing cell line 3, media 1 on viable cell density (n=2)

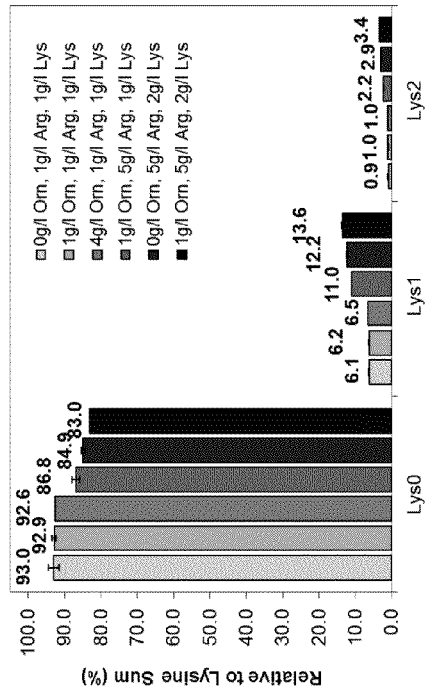

Figure 56) Effect of increase in multiple amino acids to adalimumab producing cell line 3, media 1 on harvest titer

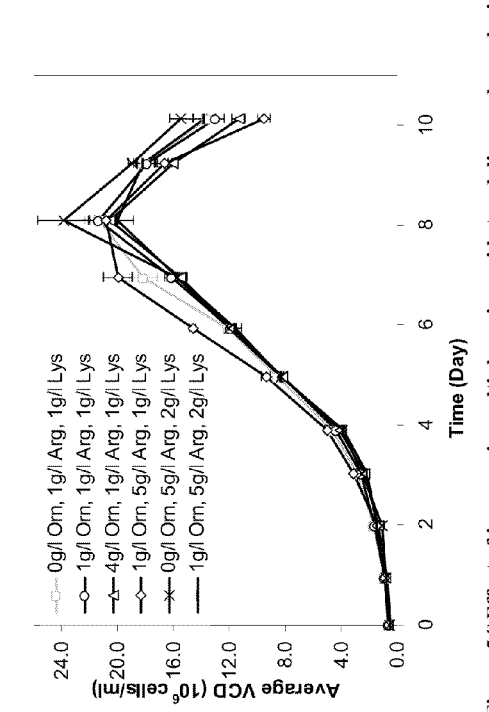

Figure 55) Effect of increase in multiple amino acids to adalimumab producing cell line 3, media 1 on viability

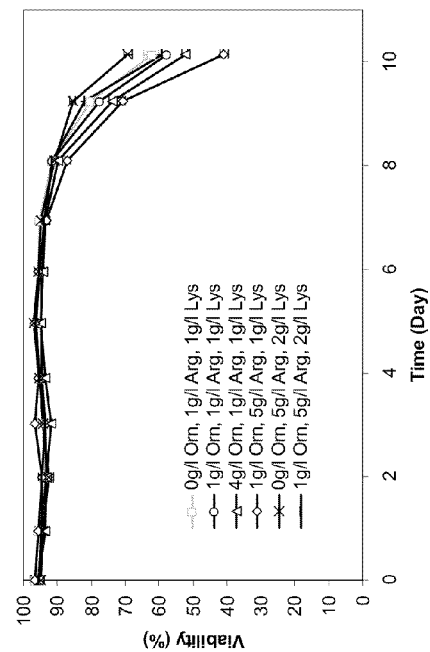

Figure 57) Effect of increase in multiple amino acids to adalimumab producing cell line 3, media 1 on WCX-10 profile relative lysine distribution

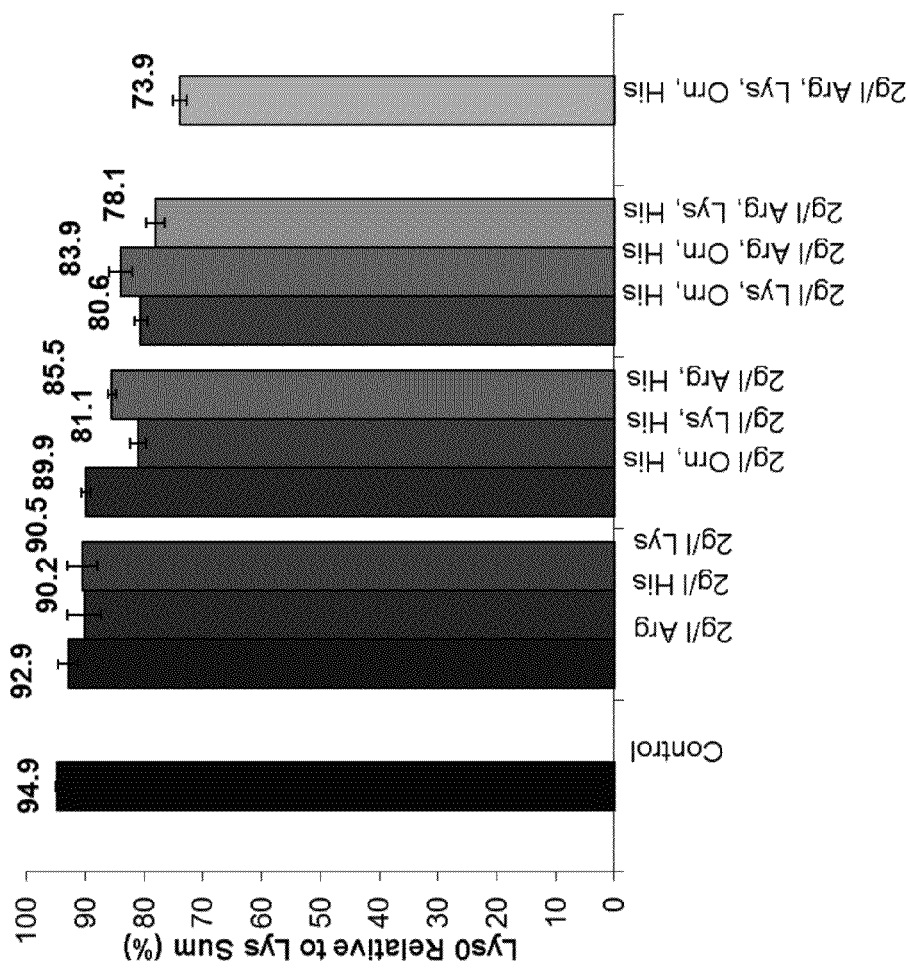
Figure 58) Effect of multiple amino acid additions to adalimumab producing cell line 2, media 1 containing 1g/l arginine and 1g/l lysine on WCX-10 profile relative lysine distribution (n=2)

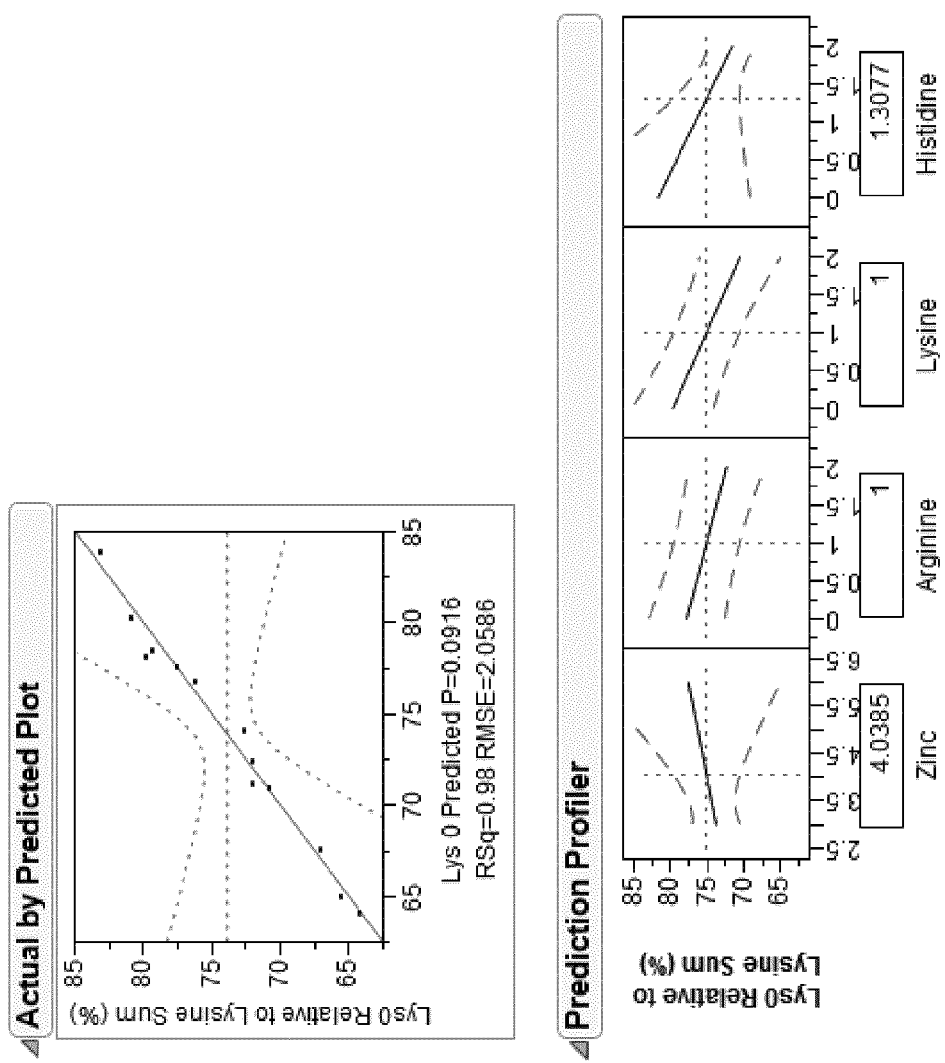
Figure 59) Effect of modulations of zinc and multiple amino acid concentrations in adalimumab producing cell line 1, media 1 on WCX-10 profile relative lysine distribution a) overall prediction plot, b) prediction plots for each additive

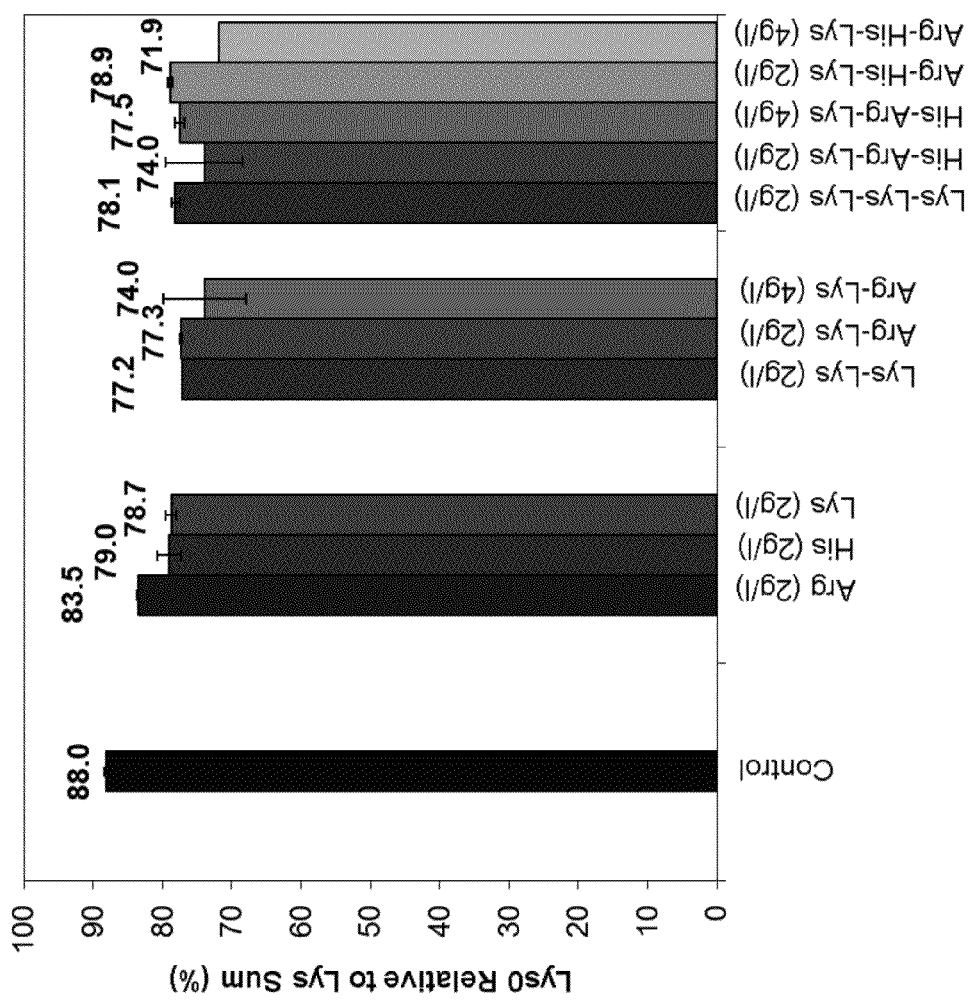
Figure 60) Effect of peptides of varying length addition to adalimumab producing cell line 2, media 1 containing 1g/l arginine and 1g/l lysine on WCX-10 profile relative lysine distribution (n=2)

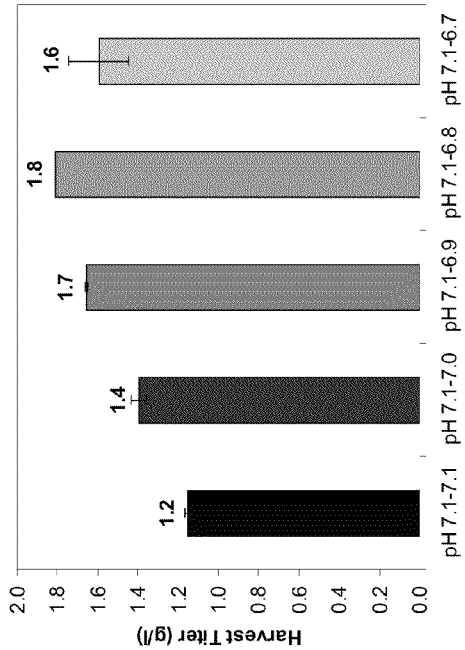

Figure 63) Effect of pH modulation to adalimumab producing cell line 1, media 1 on harvest titer

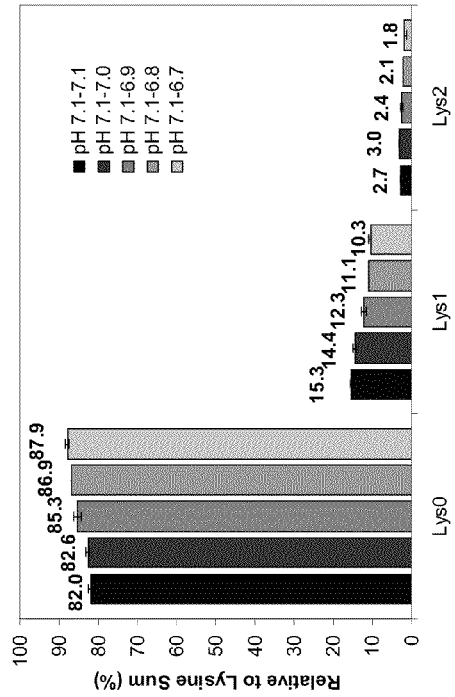

Figure 64) Effect of pH modulation to adalimumab producing cell line 1, media 1 on WCX-10 profile relative lysine distribution

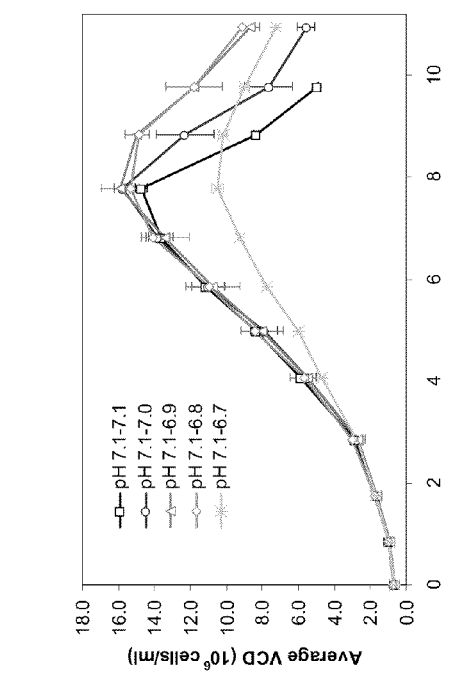

Figure 61) Effect of pH modulation to adalimumab producing cell line 1, media 1 on viable cell density

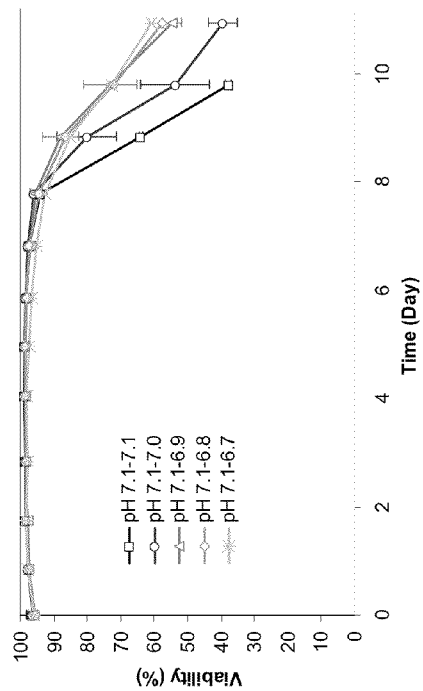

Figure 62) Effect of pH modulation to adalimumab producing cell line 1, media 1 on viability

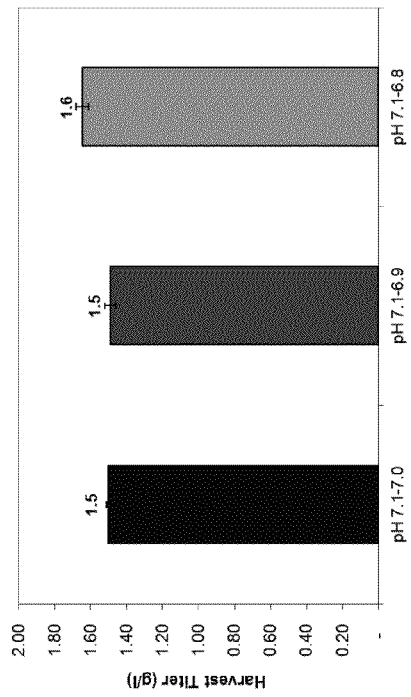

Figure 67) Effect of pH modulation to adalimumab producing cell line 1, media 2 on harvest titer

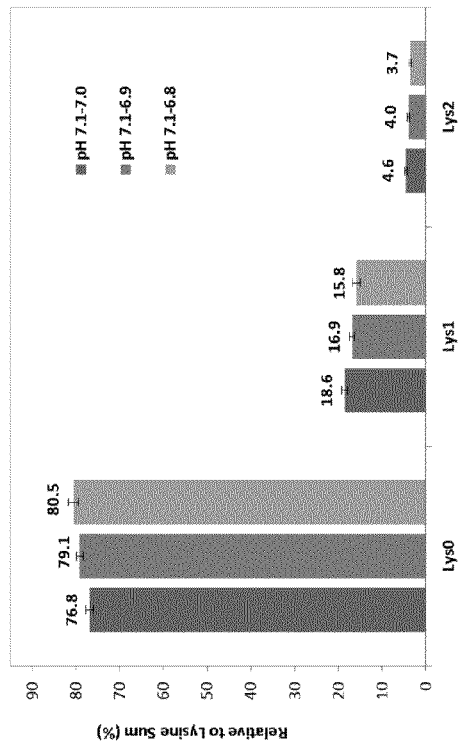

Figure 68) Effect of pH modulation to adalimumab producing cell line 1, media 2 on WCX-10 profile relative lysine distribution

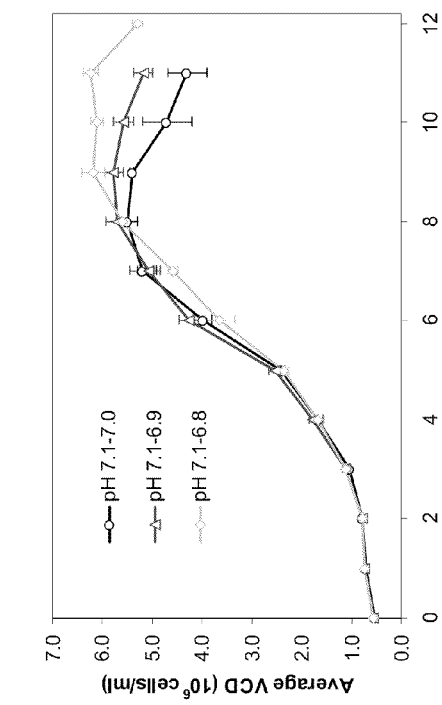

Figure 65) Effect of pH modulation to adalimumab producing cell line 1, media 2 on viable cell density

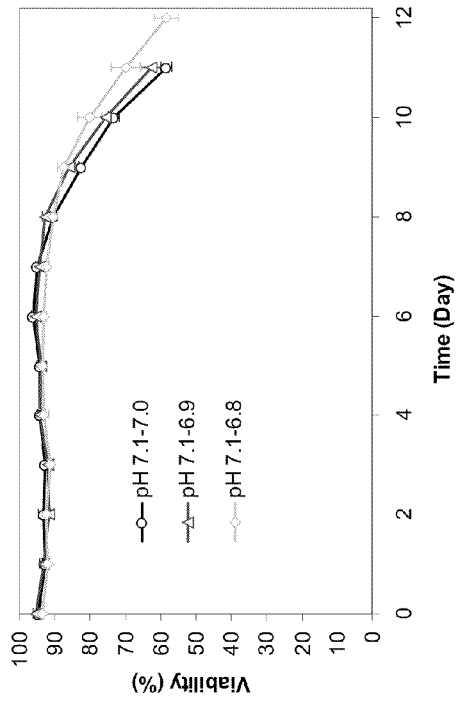

Figure 66) Effect of pH modulation to adalimumab producing cell line 1, media 2 on viability

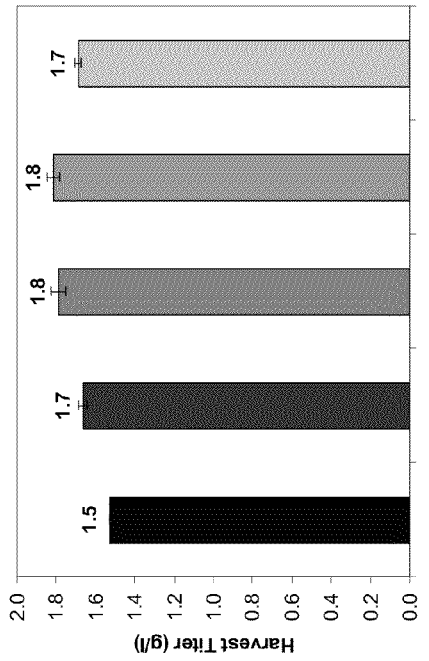

Figure 69) Effect of pH modulation to adalimumab producing cell line 3, media 1 on viable cell density

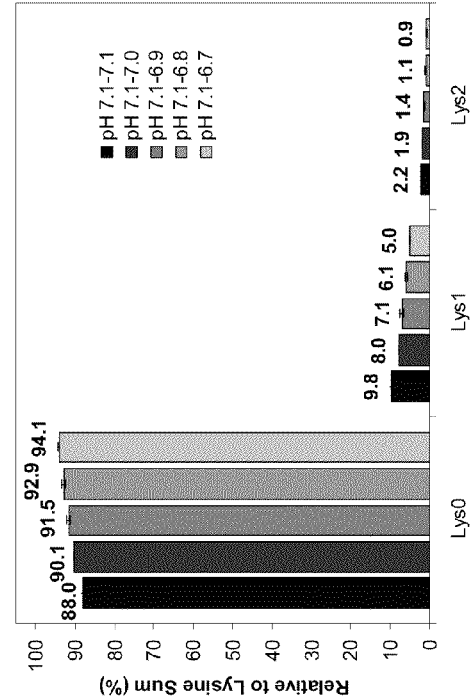

Figure 71) Effect of pH modulation to adalimumab producing cell line 3, media 1 on harvest titer

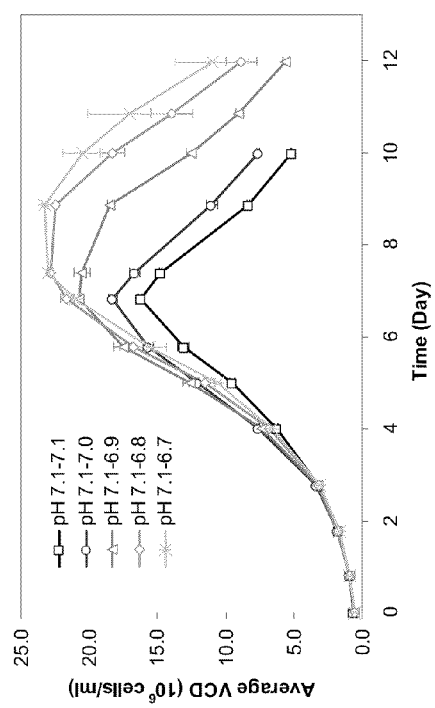

Figure 70) Effect of pH modulation to adalimumab producing cell line 3, media 1 on viability

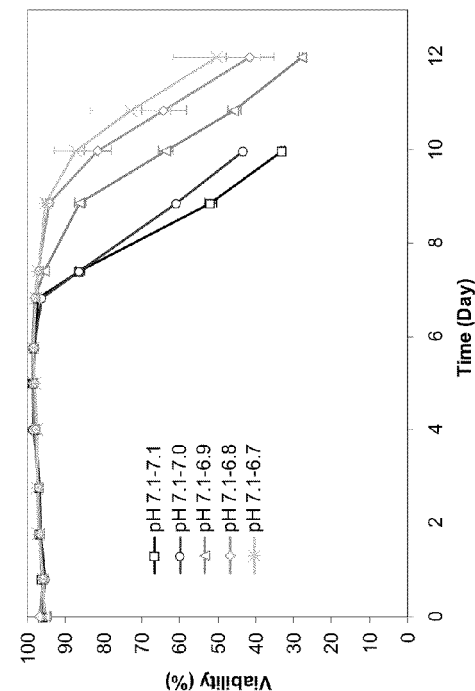

Figure 72) Effect of pH modulation to adalimumab producing cell line 3, media 1 on WCX-10 profile relative lysine distribution on day10

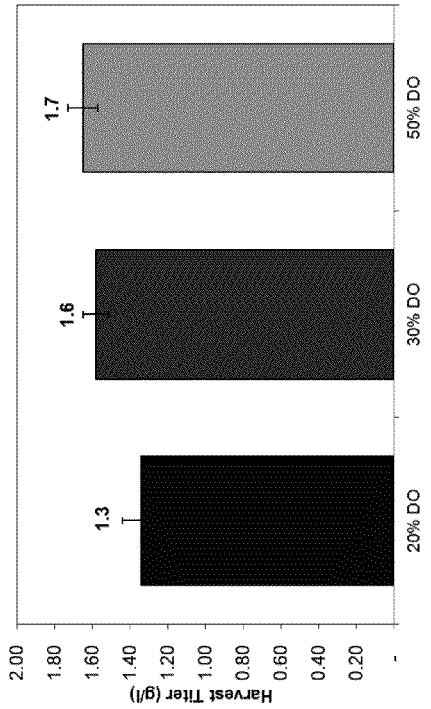

Figure 73) Effect of dissolved oxygen modulation to adalimumab producing cell line 1, media 2 at 35°C on viable cell density

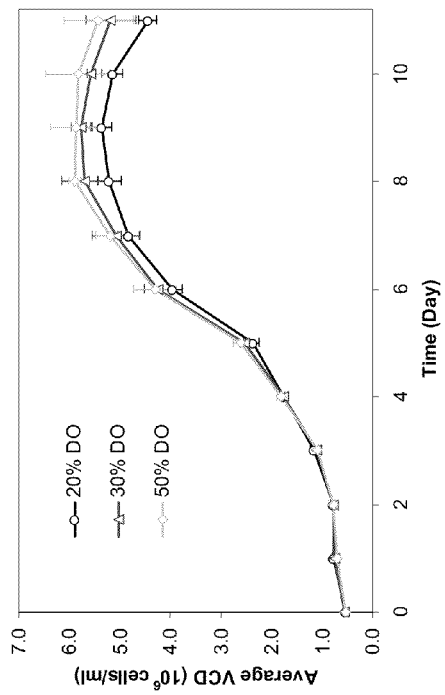

Figure 74) Effect of dissolved oxygen modulation to adalimumab producing cell line 1, media 2 at 35°C on viability

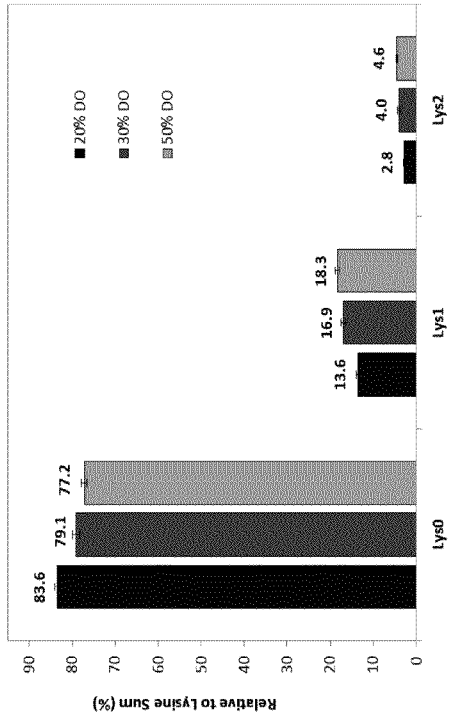

Figure 75) Effect of dissolved oxygen modulation to adalimumab producing cell line 1, media 2 at 35°C on harvest titer

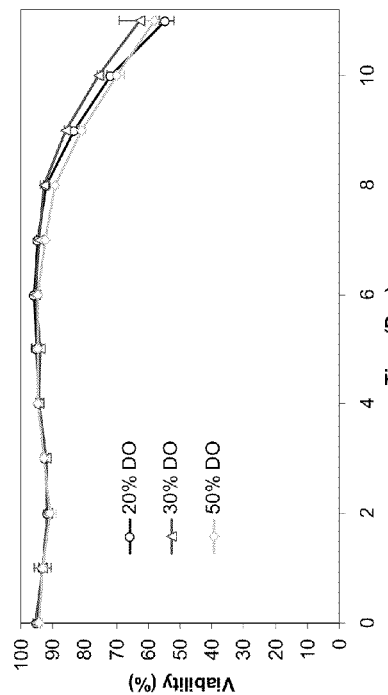

Figure 76) Effect of dissolved oxygen modulation to adalimumab producing cell line 1, media 2 at 35°C on WCX-10 profile relative lysine distribution

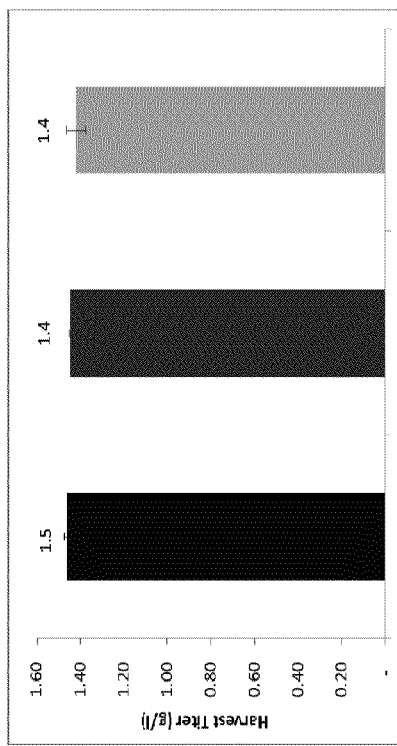

Figure 77) Effect of dissolved oxygen modulation to adalimumab producing cell line 1, media 2 at 33°C on viable cell density

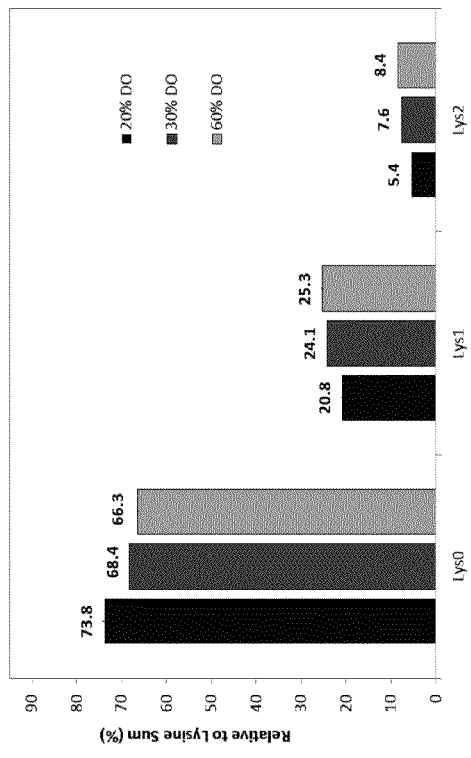

Figure 79) Effect of dissolved oxygen modulation to adalimumab producing cell line 1, media 2 at 33°C on harvest titer

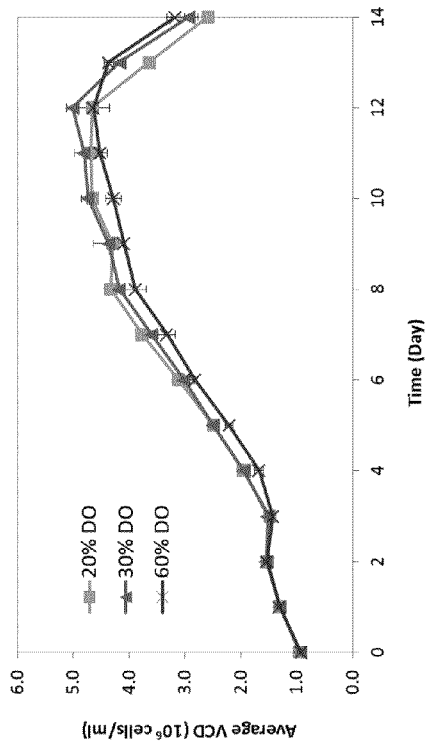

Figure 78) Effect of dissolved oxygen modulation to adalimumab producing cell line 1, media 2 at 33°C on viability

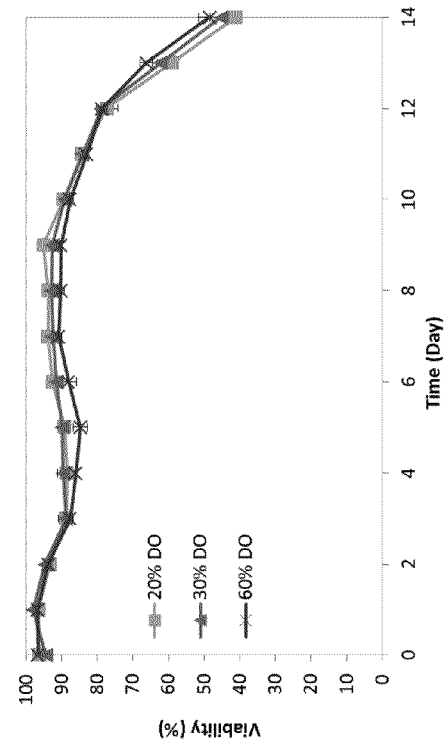

Figure 80) Effect of dissolved oxygen modulation to adalimumab producing cell line 1, media 2 at 33°C on WCX-10 profile relative lysine distribution

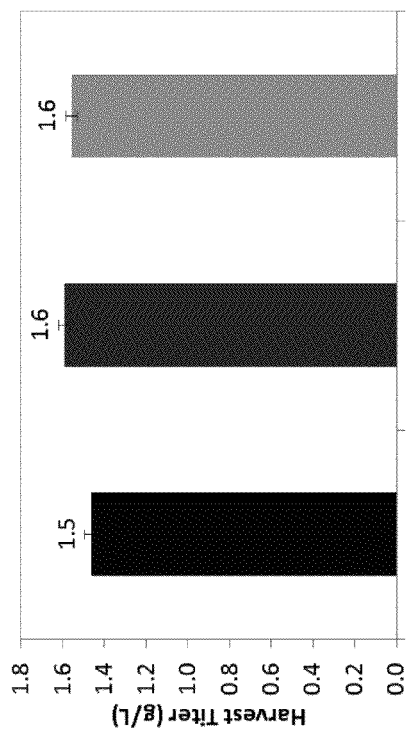

Figure 81) Effect of dissolved oxygen modulation to adalimumab producing cell line 1, media 1 on viable cell density.

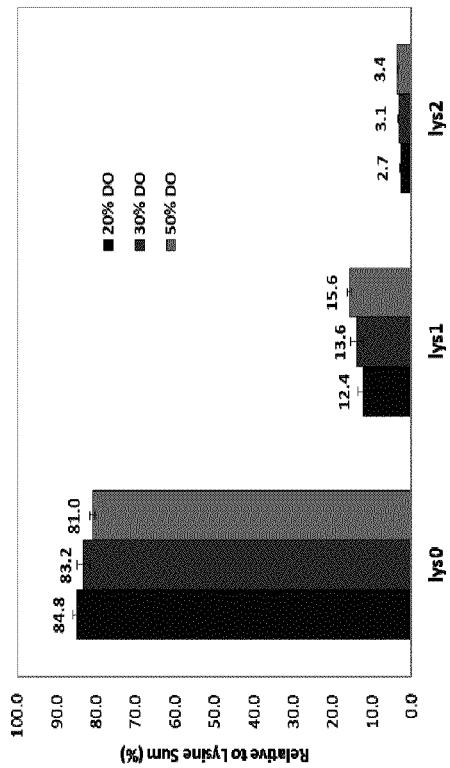

Figure 83) Effect of dissolved oxygen modulation to adalimumab producing cell line 1, media 1 on harvest titer.

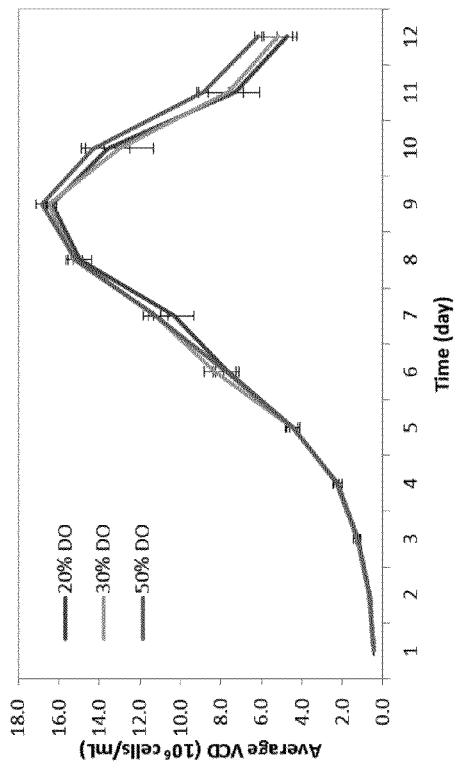

Figure 82) Effect of dissolved oxygen modulation to adalimumab producing cell line 1, media 1 on viability.

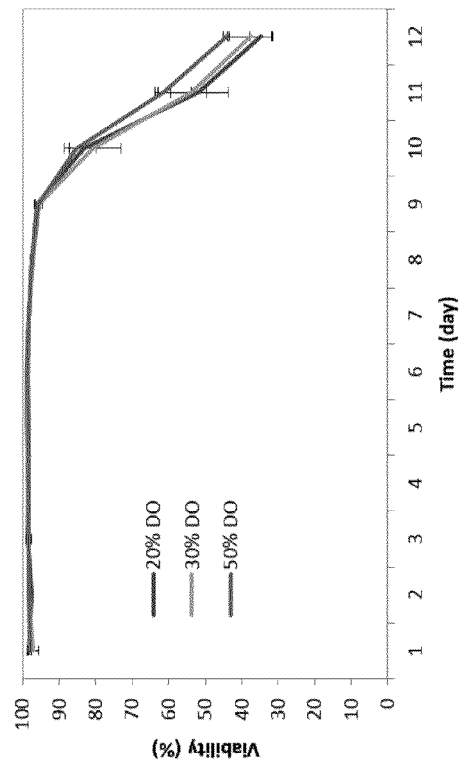

Figure 84) Effect of dissolved oxygen modulation to adalimumab producing cell line 1, media 1 on WCX-10 profile relative lysine distribution.

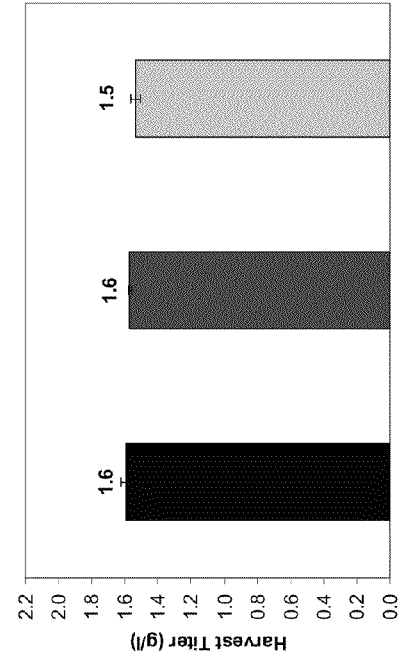

Figure 85) Effect of temperature modulation to adalimumab producing cell line 1, media 1 on viable cell density (n=2)

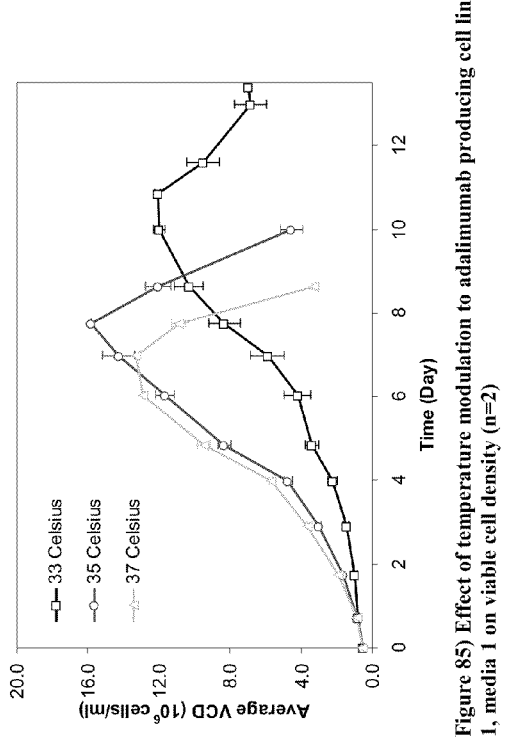

Figure 86) Effect of temperature modulation to adalimumab producing cell line 1, media 1 on viability (n=2)

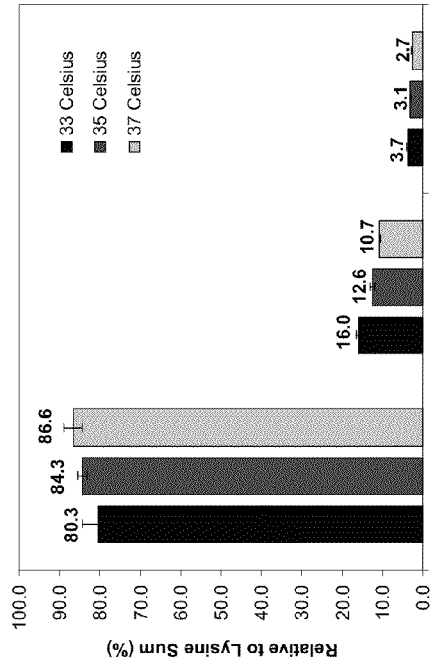

Figure 87) Effect of temperature modulation to adalimumab producing cell line 1, media 1 on harvest titer (n=2)

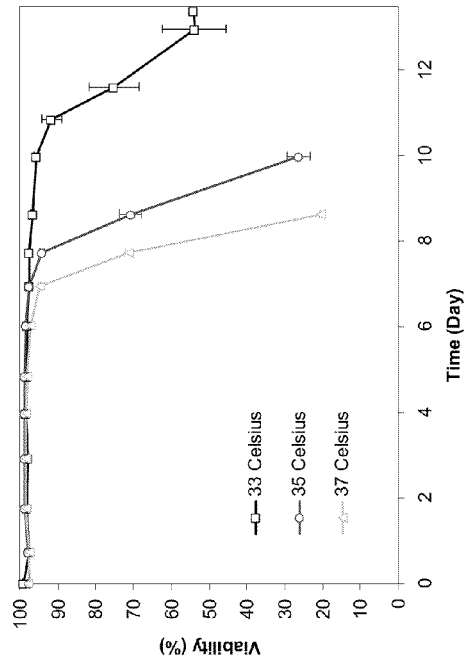

Figure 88) Effect of temperature modulation to adalimumab producing cell line 1, media 1 on WCX-10 profile relative lysine distribution (n=2)

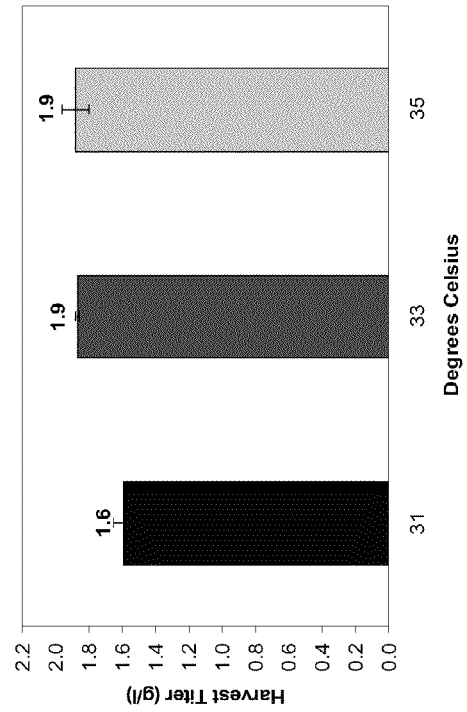

Figure 89) Effect of temperature modulation to adalimumab producing cell line 2, media 1 on viable cell density (n=2)

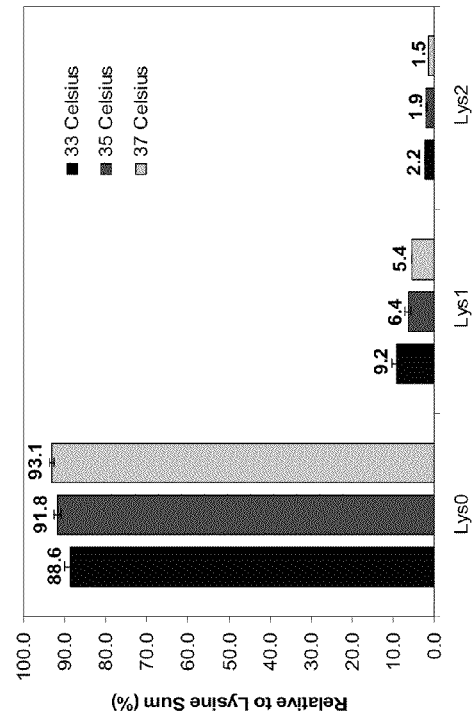

Figure 91) Effect of temperature modulation to adalimumab producing cell line 2, media 1 on harvest titer (n=2)

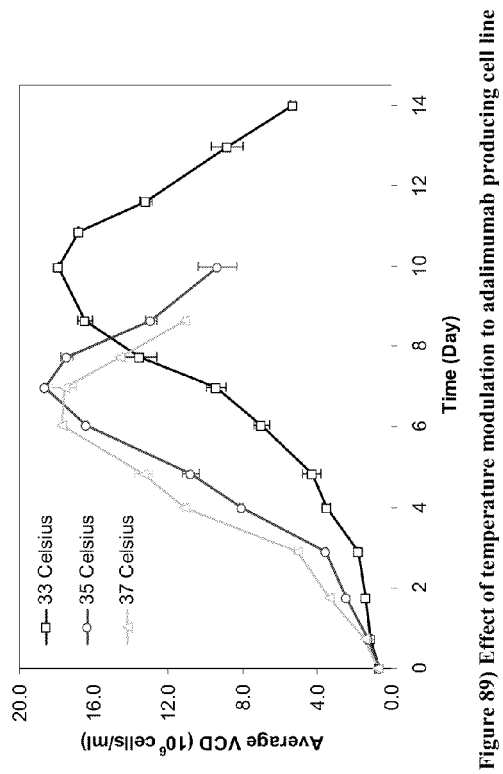

Figure 90) Effect of temperature modulation to adalimumab producing cell line 2, media 1 on viability (n=2)

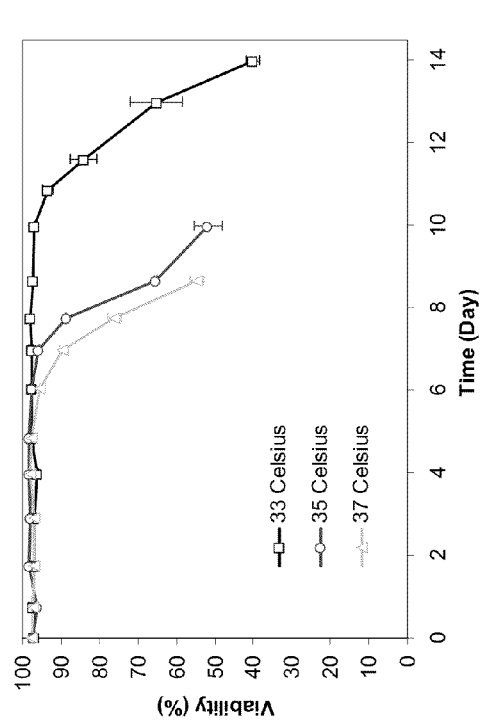

Figure 92) Effect of temperature modulation to adalimumab producing cell line 2, media 1 on WCX-10 profile relative lysine distribution (n=2)

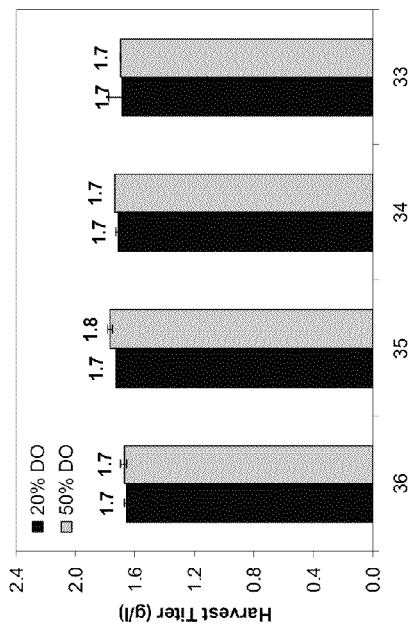

Figure 95) Effect of dissolve oxygen and temperature modulation to adalimumab producing cell line 3, media 1 on harvest titer

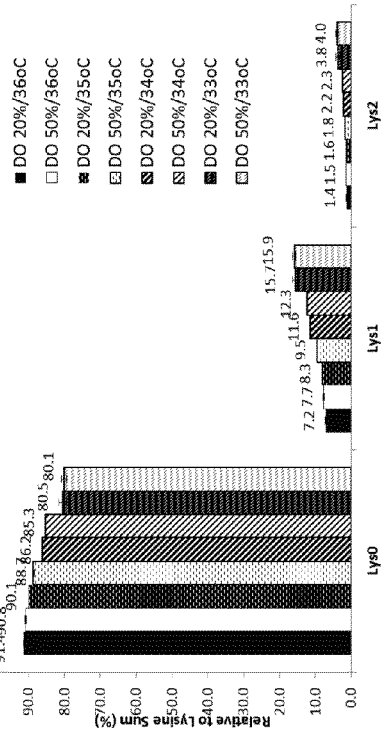

Figure 96) Effect of dissolved oxygen and temperature modulation to adalimumab producing cell line 3, media 1 on WCX-10 profile relative lysine distribution

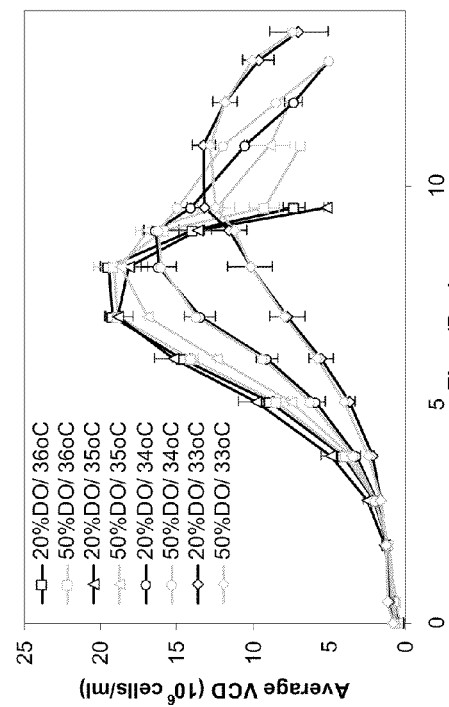

Figure 93) Effect of dissolved oxygen and temperature modulation to adalimumab producing cell line 3, media 1 on viable cell density

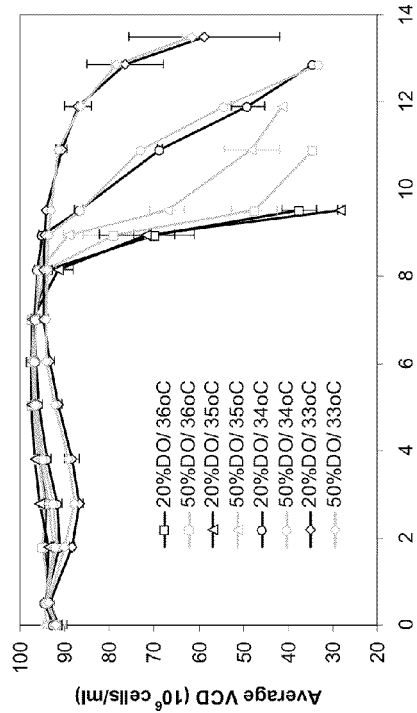

Figure 94) Effect of dissolved oxygen and temperature modulation to adalimumab producing cell line 3, media 1 on viability Figure 97 Effect of varying phosphate concentration in chemically defined media with cell line 1 on a) viable cell density profile b) viability profile c) harvest titer d) lysine variant distribution
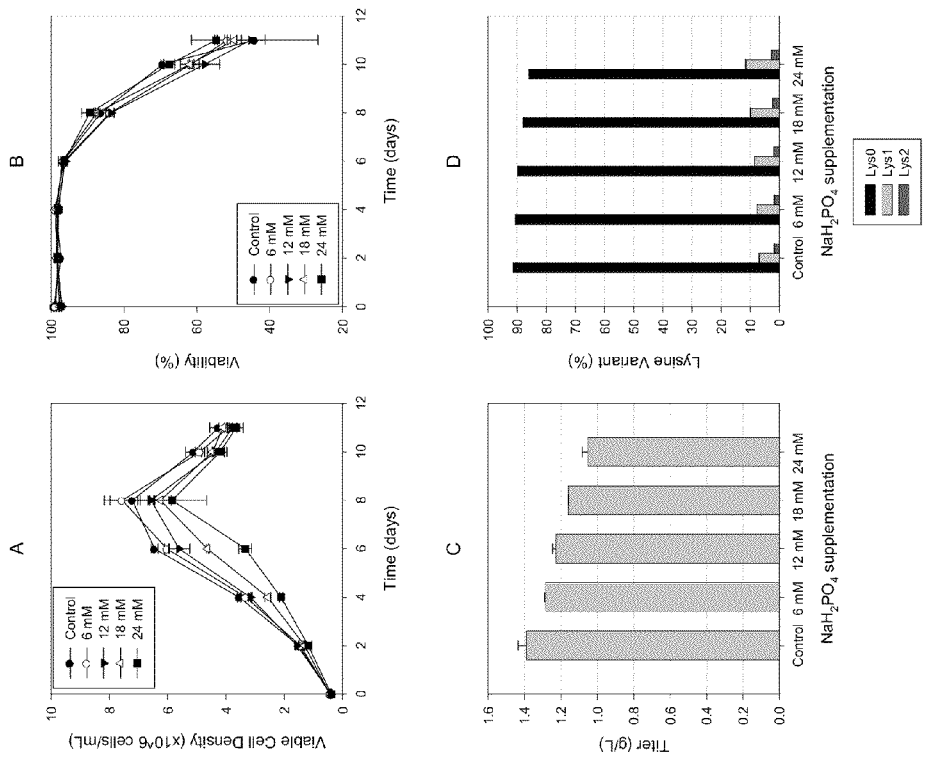

Figure 98 Effect of varying phosphate concentration in chemically defined media with cell line 2 on a) viable cell density profile b) viability profile c) harvest titer d) lysine variant distribution
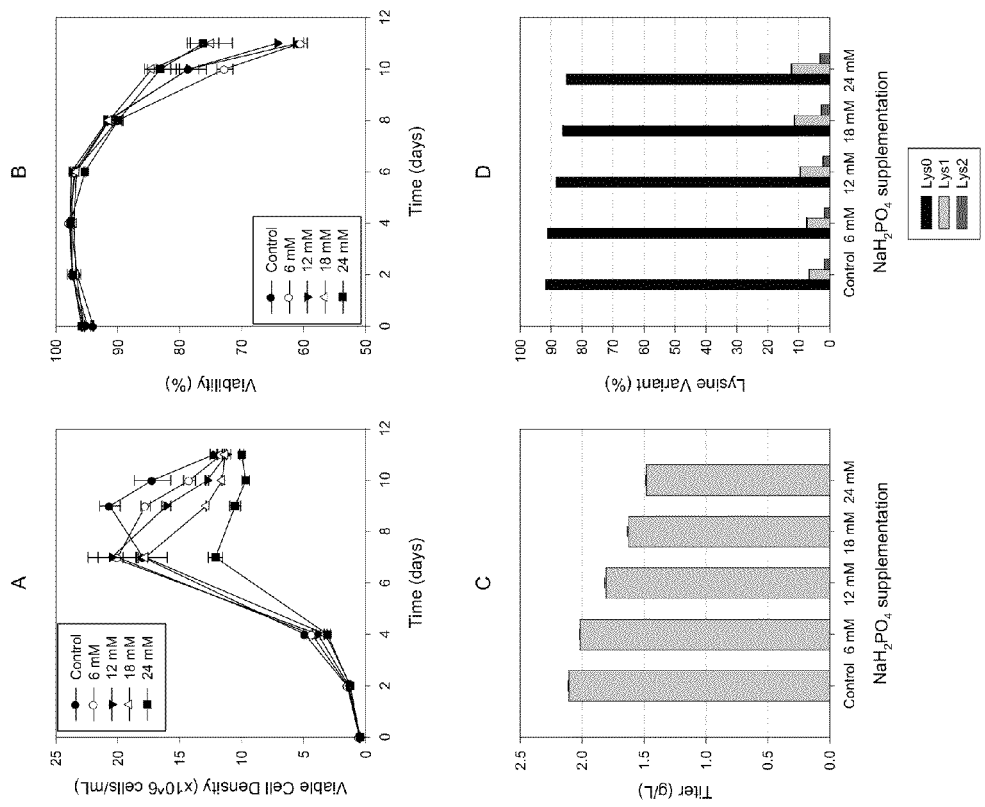

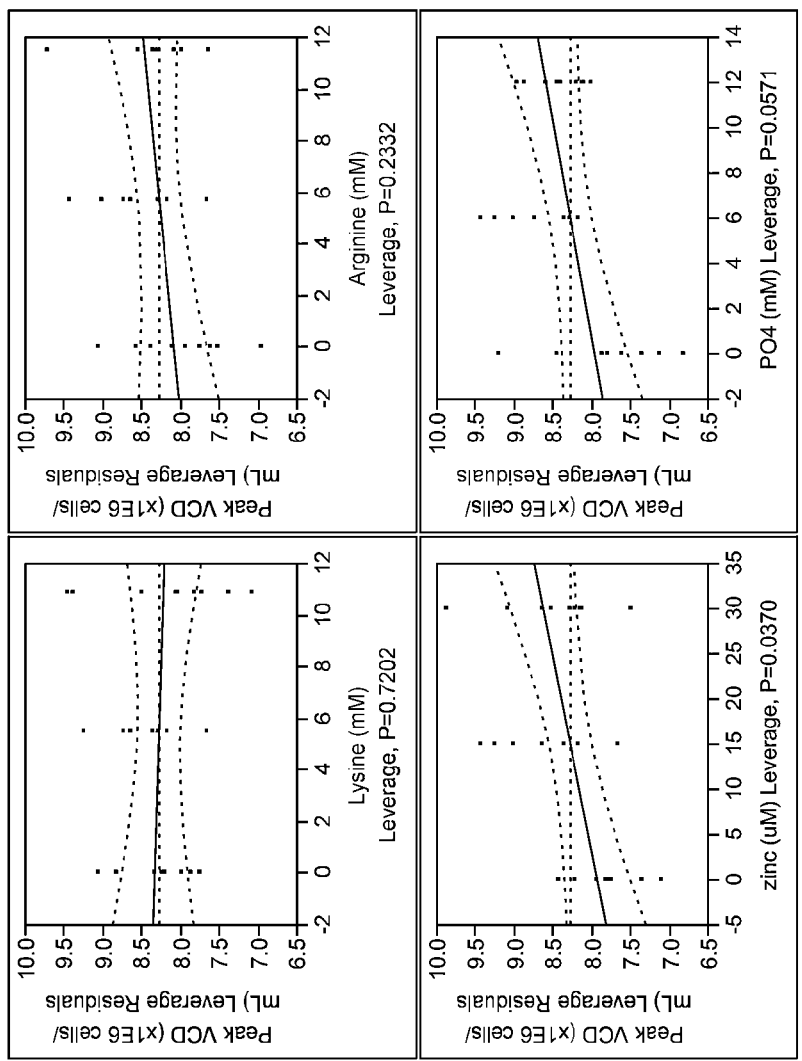
Figure 99A Effect of varying lysine, arginine, zinc and phosphate concentration in chemically defined media with cell line 1 on peak viable cell density

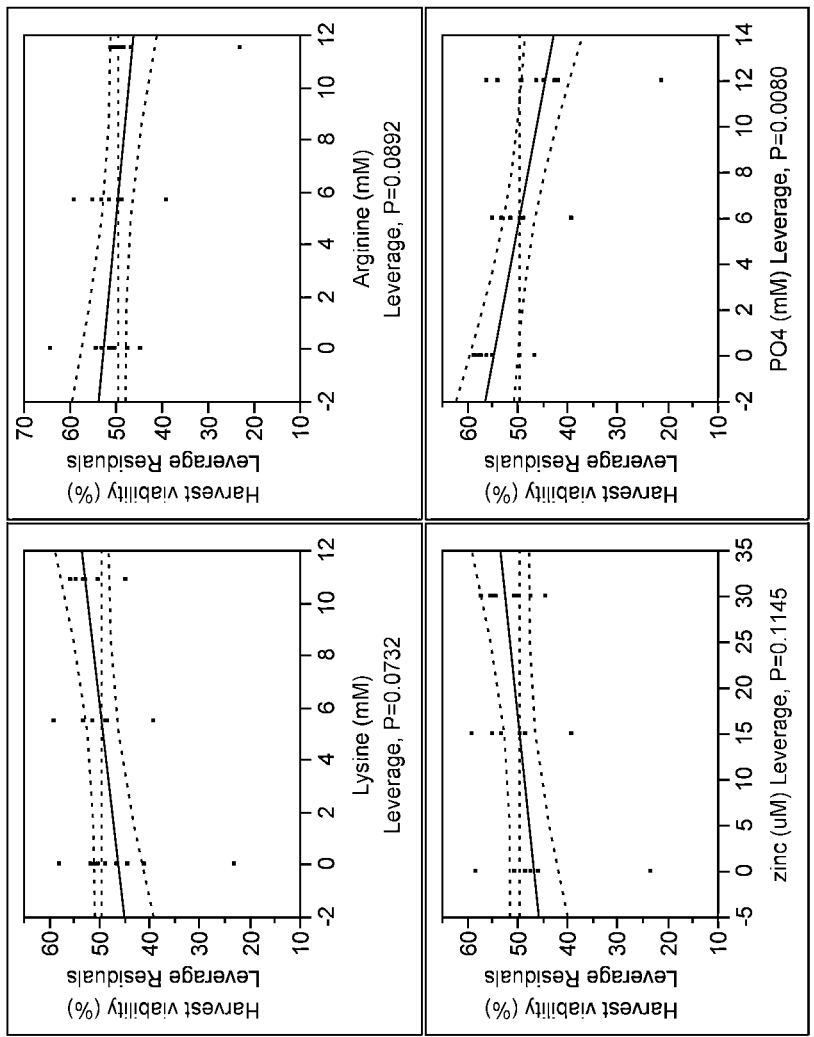
Figure 99B Effect of varying lysine, arginine, zinc and phosphate concentration in chemically defined media with cell line 1 on harvest viability

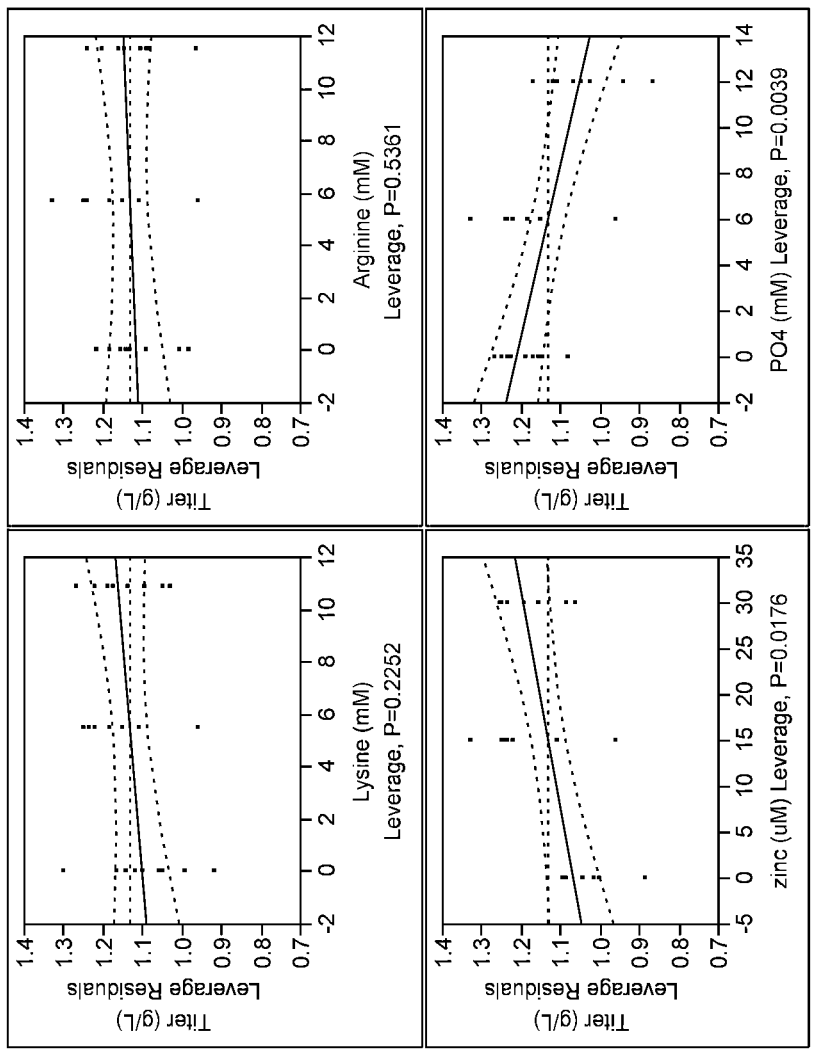
Figure 99C Effect of varying lysine, arginine, zinc and phosphate concentration in chemically defined media with cell line 1 on harvest titer

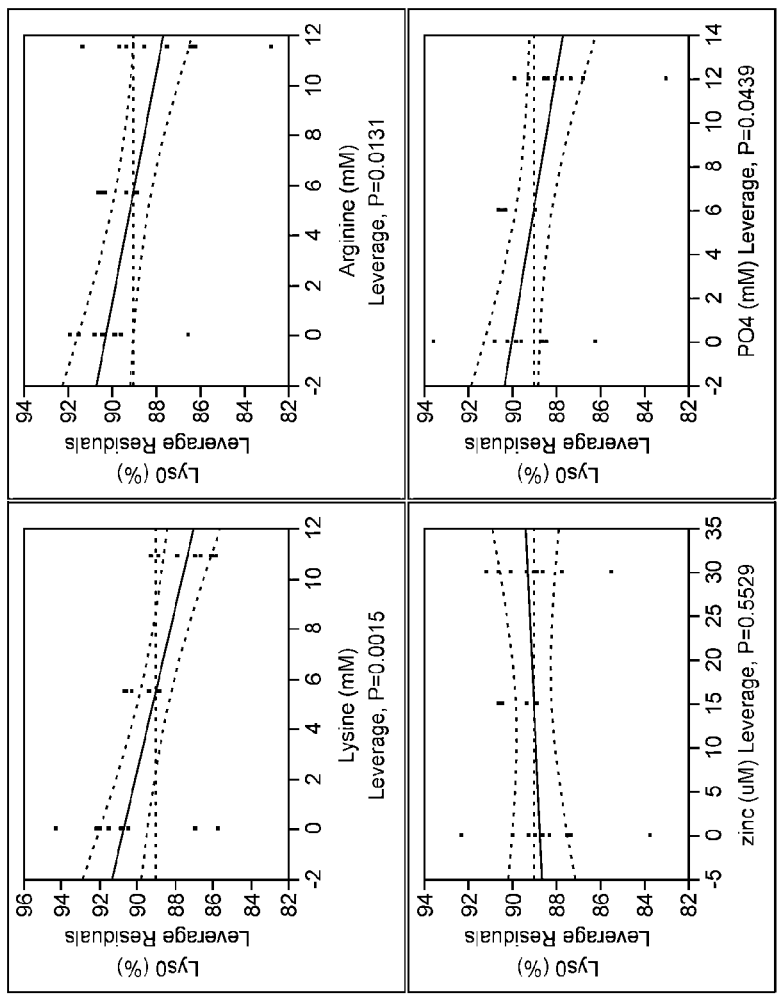
Figure 99D Effect of varying lysine, arginine, zinc and phosphate concentration in chemically defined media with cell line 1 on the relative fraction of Lys0

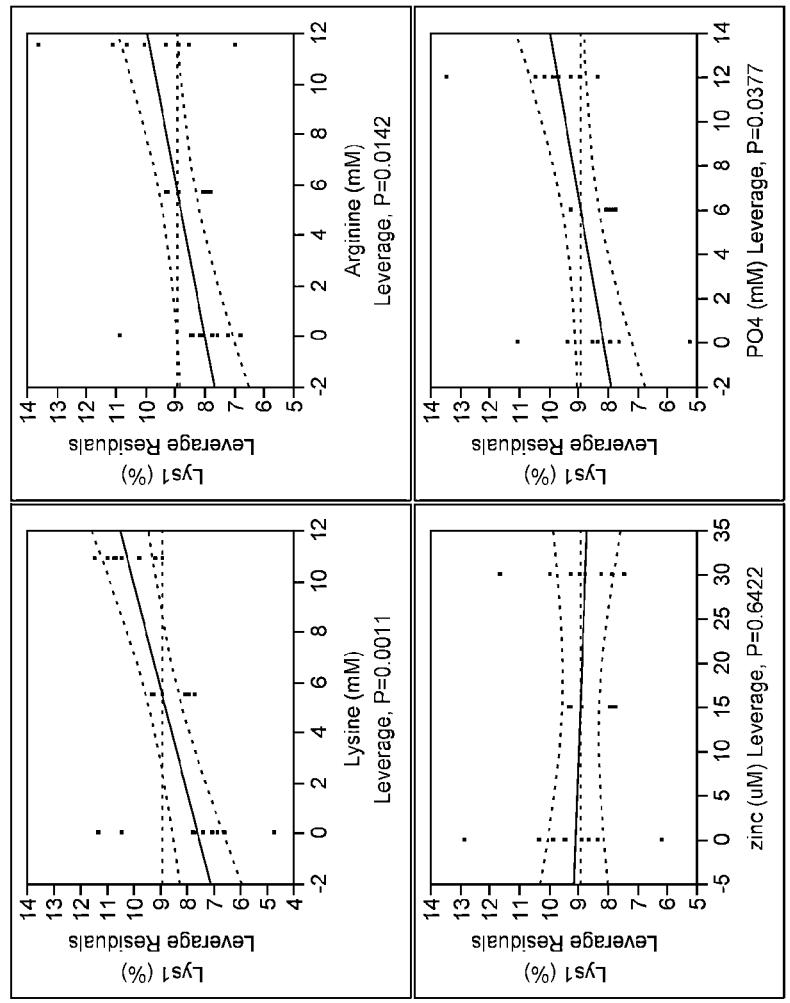
Figure 99E Effect of varying lysine, arginine, zinc and phosphate concentration in chemically defined media with cell line 1 on the relative fraction of Lys1

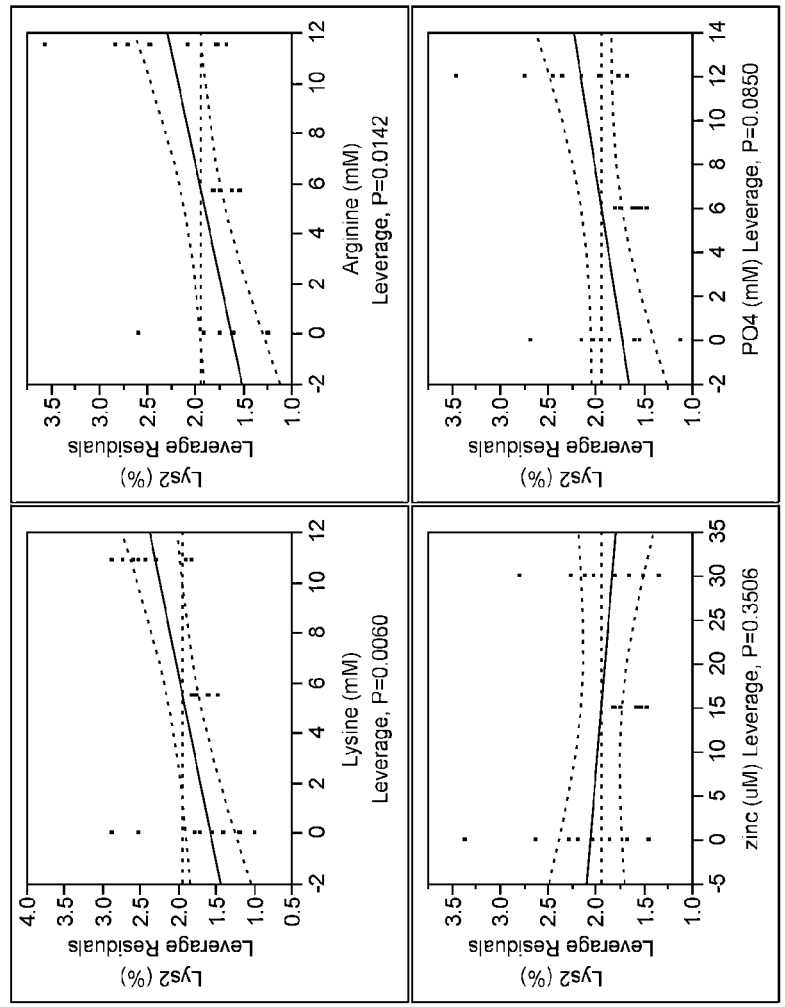
Figure 99F Effect of varying lysine, arginine, zinc and phosphate concentration in chemically defined media with cell line 1 on the relative fraction of Lys2

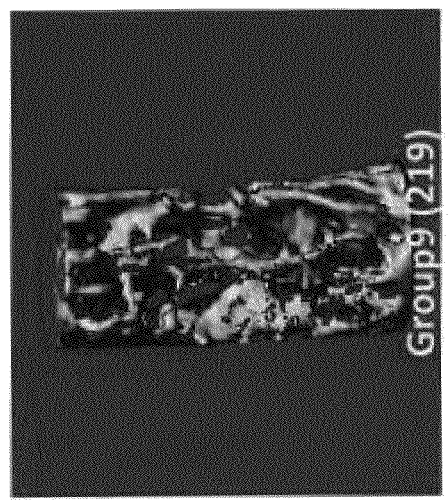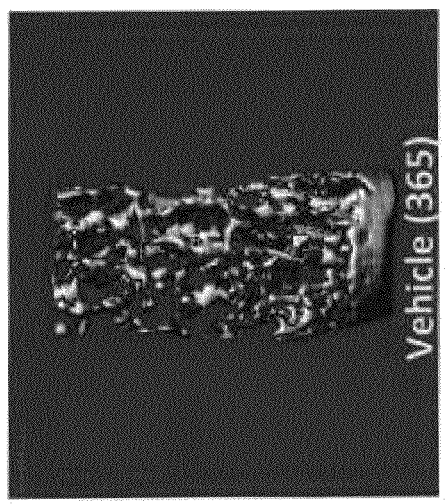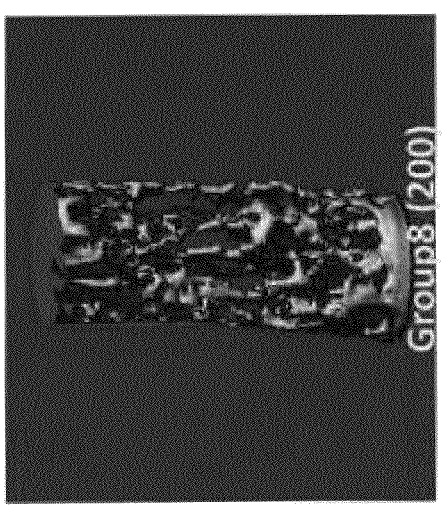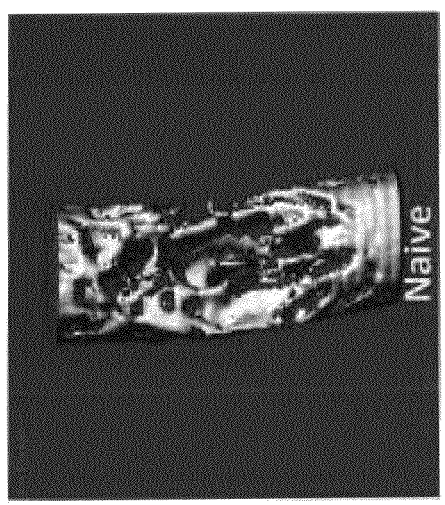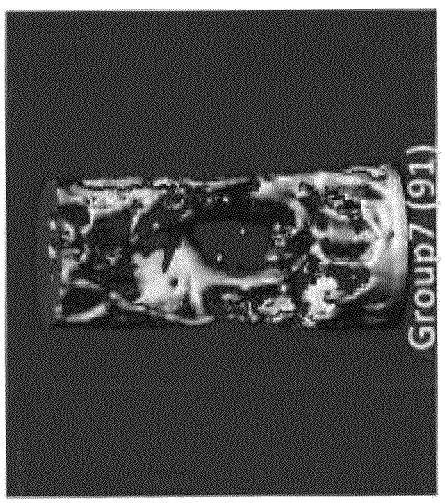
Figure 112 ial applications involves the use of cell cultures that are known to produce antibodies, and antigen-binding portions thereof, exhibiting varying levels of heterogeneity, which may lead to either decreased product efficacy and stability or just the opposite depending upon the nature of the heterogeneity. One source of antibody heterogeneity involves C-terminal lysine residues, such as those found on the heavy chains of antibody molecules. For example, C-terminal lysines can potentially be present on both the heavy chains of an antibody (Lys 2), on either one of the heavy chains (Lys 1), or neither of them (Lys 0). Since lysine can carry a positive charge, antibodies lacking the basic C-terminal lysine(s) differ in their charge state from ones that contain the lysine, so that the distribution of lysine variants (% Lys 0, % Lys 1, % Lys 2 of the total lysine sum) can be detected using ion-exchange chromatographic methods, for example, using a ProPac WCX-10 Weak Cation-Exchange column for high-resolution separation of protein isoforms (Dionex, Calif.), or other methods known in the art, and subsequently quantified.

C-terminal lysine heterogeneity is commonly observed in biopharmaceutical antibody and protein compositions. However, the development of compositions comprising antibodies, or antigen-binding portions thereof, with lower or higher levels of certain lysine variants is an important, need in the biopharmaceutical industry.

SEQUENCE LISTING

```
<160> NUMBER OF SEQ ID NOS: 12

<210> SEQ ID NO 1
<211> LENGTH: 107
<212> TYPE: PRT
<213> ORGANISM: Artificial Sequence
<220> FEATURE:
<223> OTHER INFORMATION: adalimumab light chain variable region

<400> SEQUENCE: 1

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Gly Ile Arg Asn Tyr
            20                  25                  30
```

```
Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: adalimumab heavy chain variable region

<400> SEQUENCE: 2

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
         35                  40                  45

Ser Ala Ile Thr Trp Asn Ser Gly His Ile Asp Tyr Ala Asp Ser Val
 50                  55                  60

Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
         115                 120

<210> SEQ ID NO 3
<211> LENGTH: 9
<212> TYPE: PRT
<213> ORGANISM: Artificial Sequence
<220> FEATURE:
<223> OTHER INFORMATION: adalimumab light chain variable region CDR3
<220> FEATURE:
<221> NAME/KEY: VARIANT
<222> LOCATION: 9
<223> OTHER INFORMATION: Xaa = Thr or Ala

<400> SEQUENCE: 3

Gln Arg Tyr Asn Arg Ala Pro Tyr Xaa
 1               5

<210> SEQ ID NO 4
<211> LENGTH: 12
<212> TYPE: PRT
<213> ORGANISM: Artificial Sequence
<220> FEATURE:
<223> OTHER INFORMATION: adalimumab heavy chain variable region CDR3
<220> FEATURE:
<221> NAME/KEY: VARIANT
<222> LOCATION: 12
<223> OTHER INFORMATION: Xaa = Tyr or Asn

<400> SEQUENCE: 4
```

```
Val Ser Tyr Leu Ser Thr Ala Ser Ser Leu Asp Xaa
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: adalimumab light chain variable region CDR2

<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: adalimumab heavy chain variable region CDR2

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: adalimumab light chain variable region CDR1

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: adalimumab heavy chain variable region CDR1

<400> SEQUENCE: 8

Asp Tyr Ala Met His
 1               5

<210> SEQ ID NO 9
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 9
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321
```

```
<210> SEQ ID NO 10
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 10
gaggtgcagc tggtggagtc tgggggaggc ttggtacagc ccggcaggtc cctgagactc    60
tcctgtgcgg cctctggatt cacctttgat gattatgcca tgcactgggt ccggcaagct   120
ccagggaagg gcctggaatg ggtctcagct atcacttgga atagtggtca catagactat   180
gcggactctg tggagggccg attcaccatc tccagagaca acgccaagaa ctccctgtat   240
ctgcaaatga acagtctgag agctgaggat acggccgtat attactgtgc gaaagtctcg   300
taccttagca ccgcgtcctc ccttgactat tggggccaag gtaccctggt caccgtctcg   360
agt                                                                  363

<210> SEQ ID NO 11
<211> LENGTH: 214
<212> TYPE: PRT
<213> ORGANISM: Artificial Sequence
<220> FEATURE:
<223> OTHER INFORMATION: adalimumab light chain

<400> SEQUENCE: 11

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
```

```
<211> LENGTH: 451
<212> TYPE: PRT
<213> ORGANISM: Artificial Sequence
<220> FEATURE:
<223> OTHER INFORMATION: adalimumab heavy chain

<400> SEQUENCE: 12

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

MODULATED LYSINE VARIANT SPECIES COMPOSITIONS AND METHODS FOR PRODUCING AND USING THE SAME

RELATED APPLICATIONS

This application claims priority to U.S. Provisional Patent Application Ser. No. 61/893,088, filed on Oct. 18, 2013, the contents of which are hereby incorporated herein by reference in their entirety.

BACKGROUND OF THE INVENTION

Large-scale production of antibodies for biopharmaceutical applications involves the use of cell cultures that are known to produce antibodies, and antigen-binding portions thereof, exhibiting varying levels of heterogeneity, which may lead to either decreased product efficacy and stability or just the opposite depending upon the nature of the heterogeneity. One source of antibody heterogeneity involves C-terminal lysine residues, such as those found on the heavy chains of antibody molecules. For example, C-terminal lysines can potentially be present on both the heavy chains of an antibody (Lys 2), on either one of the heavy chains (Lys 1), or neither of them (Lys 0). Since lysine can carry a positive charge, antibodies lacking the basic C-terminal lysine(s) differ in their charge state from ones that contain the lysine, so that the distribution of lysine variants (% Lys 0, % Lys 1, % Lys 2 of the total lysine sum) can be detected using ion-exchange chromatographic methods, for example, using a ProPac WCX-10 Weak Cation-Exchange column for high-resolution separation of protein isoforms (Dionex, Calif.), or other methods known in the art, and subsequently quantified.

C-terminal lysine heterogeneity is commonly observed in biopharmaceutical antibody and protein compositions. However, the development of compositions comprising antibodies, or antigen-binding portions thereof, with lower or higher levels of certain lysine variants is an important, need in the biopharmaceutical industry.

SUMMARY OF THE INVENTION

The present invention is based on the identification and optimization of processes for the production of antibodies or antigen-binding portions thereof (e.g., cell culture processes), which result in the production of compositions comprising antibodies, or antigen-binding portions thereof, that comprise modified distributions of C-terminal lysine variants. C-terminal lysines can be present on both the heavy chains of an antibody (Lys 2), on either one of them (Lys 1), or neither of them (Lys 0). Since antibodies lacking basic C-terminal lysines differ in the charge state from the ones that contain one or two lysines, the distribution of lysine variants (% Lys 0, % Lys 1, % Lys 2 of the total lysine sum in the composition) can be detected by ion-exchange chromatographic methods such as, for example, weak cation-exchange chromatography (WCX-10) and subsequently quantified (FIG. 1).

The present invention provides methods for producing compositions comprising modulated amounts (or percentages) of Lys 1, Lys 2, and/or Lys 0 variants as compared to the amount (or percentage) of Lys 1, Lys 2, and/or Lys 0 variants in a starting population of proteins (referred to herein as "modulated lysine variant species compositions"). In one embodiment, the methods of the invention are used to produce a protein composition comprising an increased amount of Lys 1 and/or Lys 2 variants and a decreased amount of Lys 0 variants, e.g., as compared to the amount (or percentage) of Lys 1, Lys 2, and/or Lys 0 variants in a starting population of proteins, e.g., a control composition. In another embodiment, the methods of the invention are used to produce a protein composition comprising a decreased amount of Lys 1 and/or Lys 2 variants and an increased amount of Lys 0 variants, e.g., as compared to the amount (or percentage) of Lys 1, Lys 2, and/or Lys 0 variants in a starting population of proteins, e.g., a control composition.

For example, a modulated lysine variant species composition of the invention may comprise more than about 20%, 25%, 30%, 35%, 40%, 45%, 50%, 55%, 60%, 65%, 70%, 75%, 80%, 85%, 90%, 95%, 96%, 97%, 98%, 99%, or 100% Lys 1 and/or Lys 2 antibodies, or antigen-binding portions thereof relative to the lysine sum (i.e., the sum of Lys 0, Lys 1 and Lys 2 in the composition). In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 and/or Lys 2 antibodies, or antigen-binding portions thereof relative to the lysine sum. Ranges within one or more of any of the preceding percentages are also included.

A modulated lysine variant species composition of the invention may also comprise less than about 80%, 75%, 70%, 65%, 60%, 55%, 50%, 45%, 40%, 30%, 25%, 20%, 15%, 10%, 5%, 4%, 3%, 2%, 1%, or zero antibodies, or antigen-binding portions thereof that are Lys 0, relative to the lysine sum. In one embodiment, a modulated lysine variant species composition of the invention may also comprise less than about 0% to about 10%, about 10% to about 20%, about 20% to about 30%, about 30% to about 40%, about 50% to about 60%, about 60% to about 70%, or about 70% to about 80%, antibodies or antigen-binding portions thereof that are Lys 0, relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have one C-terminal lysine (Lys 1) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 antibodies, or antigen-binding portions thereof relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have two C-terminal lysines (Lys 2) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 2 antibodies, or antigen-binding portions thereof relative to the lysine sum. Ranges within one or more of any of the preceding percentages are also included.

In one embodiment, the methods of the invention, alone or in combination, may reduce the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In one embodiment, the methods of the invention, alone or in combination, may increase the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition, As demonstrated herein, modulated lysine variant species compositions of the invention comprising adalimumab (e.g., modulated lysine variant species compositions that comprise only Lys 1 and Lys 2 variants, and not Lys 0 variants) have increased therapeutic efficacy and improved biological properties, such as, for example, increased tissue penetration (such as cartilage), reduced tissue destruction (such as cartilage), reduced synovial proliferation, reduced bone erosion, increased protection against the development of arthritic scores and/or histopathology scores, reduced cell infiltration, reduced proteoglycan loss, reduced chondrocyte death, and/or increased TNFα affinity, e.g., as compared to a control composition wherein the Lys distribution has not been modified by the methods described herein (see Example 5).

In one embodiment, a modulated lysine variant species composition of the invention comprises about 0.0% to about 10% acidic species (AR), about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding. In another embodiment, a modulated lysine variant species composition of the invention comprises, e.g., about 15% or less AR. In one aspect of this embodiment, a modulated lysine variant species composition comprises about 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In one embodiment, the acidic species comprise acidic region 1 (AR1) and acidic region 2 (AR2). In one aspect of this embodiment, a modulated lysine variant species composition comprises about 0.1% or less AR1 and about 3% or less AR2. In another aspect of this embodiment, the composition comprises about 0.0% AR1 and about 1.4% AR2. In another aspect of this embodiment, the composition comprises about 0% to about 3% AR, e.g., about 3%, 2.5%, 2%, 1.5%, 1.4%, 1.3%, 1.2%, 1%, 0.9%, 0.8%, 0.7%, 0.6%, 0.5%, 0.4%, 0.3%, 0.2%, 0.1%, or less AR1. In another aspect of this embodiment, the composition comprises about 0% to about 3% AR, e.g., about 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or less AR2.

In one embodiment, the distribution or amount of C-terminal lysine variants produced by cell culture is modulated by employing certain media components during production of a protein, for example, an antibody, of interest. In some embodiments, the modulated lysine variant species compositions of the invention are produced by supplementing the media of cells expressing the protein of interest with one or more amino acids during cell culture. In certain embodiments, one or more of the amino acids belong to a group of basic amino acids. In certain embodiments, the one or more amino acids is arginine, lysine, histidine, or combinations thereof, including combinations of arginine and/or lysine with ornithine. In certain embodiments, supplementing the media of cells expressing the protein of interest with one or more amino acids reduces the relative amount of a Lys 0 lysine variant, and increases the relative amount of a Lys 1 and/or Lys 2 lysine variant in the cell culture or a composition comprising the protein or antibody purified from the cell culture. In certain embodiments, these amino acids may be supplemented as dipeptides or tri-peptides of different combinations for lysine variant modulation In some embodiments, the modulated lysine variant species compositions of the invention are produced by supplementing the media of cells expressing the protein of interest with zinc during cell culture. In certain embodiments, supplementing the media of cells expressing the protein of interest with zinc to an overall concentration of less than about 10 µM reduces the relative amount of a Lys 0 lysine variant, and increases the relative amount of a Lys 1 and/or Lys 2 lysine variant in the cell culture or a composition comprising the protein or antibody purified from the cell culture. In certain embodiments, modulation of concentration of zinc in combination with that of the basic amino acids is used to modulate the lysine variant distribution.

In another embodiment, the modulated lysine variant species compositions of the invention are produced by adjusting the pH, and/or temperature of a cell culture expressing a protein or antibody of interest. In certain embodiments, increasing the pH of the cell culture expressing the protein or antibody of interest reduces the amount of a Lys 0 lysine variant, and increases the amount of a Lys 1 and/or Lys 2 lysine variant in the cell culture, or a composition comprising the protein or antibody purified from the cell culture, compared to a control cell culture at a lower pH. In certain embodiments, the final pH of the cell culture is adjusted to a pH of about 6.7 to about 7.1. In certain embodiments, the temperature of the cell culture is adjusted to a temperature of about 31° C. to about 37° C. In certain embodiments, decreasing the temperature of the cell culture expressing the protein or antibody of interest reduces the amount of a Lys 0 lysine variant, and increases the amount of a Lys 1 and/or Lys 2 lysine variant in the cell culture, or a composition comprising the protein or antibody purified from the cell culture, compared to a control cell culture at a higher temperature.

In certain embodiments, the methods of the invention modulate the distribution, reduce the amount, or increase the amount of lysine variants present in the resulting composition. In certain embodiments, the resulting composition has a reduced amount of Lys 0 lysine variant, and an increased amount of Lys 1 and Lys 2 lysine variants compare to a composition that was not prepared according to the methods of the present application. In one aspect, the sample comprises a cell harvest wherein the cell line is employed to produce specific proteins of the present invention. In a particular aspect, the sample is prepared from a cell line used to produce anti-TNF-α antibodies.

In certain embodiments, the methods of the invention for modulating the C-terminal lysine variants in a protein composition described herein is exerted by employing one or more of the foregoing methods during the production and purification of the desired protein, such as antibodies or antigen-binding portions thereof.

The purity/heterogeneity of the proteins of interest in the resultant sample product can be analyzed using methods well known to those skilled in the art, e.g., weak cation exchange chromatography (WCX), capillary isoelectric focusing (cIEF), size-exclusion chromatography, Poros™ A HPLC Assay, Host Cell Protein ELISA, Protein A ELISA, and western blot analysis.

In one embodiment, the antibody, or antigen-binding portion thereof, of the compositions disclosed herein is an anti-TNFα antibody, or antigen-binding portion thereof. For example, in one aspect of this embodiment, the anti-TNFα antibody, or antigen-binding portion thereof, dissociates from human TNFα with a $K_d$ of about $1 \times 10^{-8}$ M or less and a $K_{off}$ rate constant of $1 \times 10^{-3}$ $S^{-1}$ or less. In another aspect of this embodiment, the anti-TNFα antibody, or antigen-binding portion thereof, comprises a light chain variable region (LCVR) having a CDR1 domain comprising the amino acid sequence of SEQ ID NO: 7, a CDR2 domain comprising the amino acid sequence of SEQ ID NO: 5, and a CDR3 domain comprising the amino acid sequence of SEQ ID NO: 3; and a heavy chain variable region (HCVR) having a CDR1 domain comprising the amino acid sequence of SEQ ID NO: 8, a CDR2 domain comprising the amino acid sequence of SEQ ID NO: 6, and a CDR3 domain comprising the amino acid sequence of SEQ ID NO: 4. In still another aspect of this embodiment, the anti-TNFα antibody, or antigen-binding portion thereof, comprises a light chain variable region comprising the amino acid sequence set forth in SEQ ID NO: 1 and a heavy chain variable region comprising the amino acid sequence set forth in SEQ ID NO: 2. In yet another aspect of this embodiment, the anti-TNFα antibody, or antigen-binding portion thereof, is adalimumab, or an antigen binding-portion thereof.

In one embodiment, a modulated lysine variant species composition of the invention comprises adalimumab, and has a percentage of Lys 1/Lys 2 variants that is not the same as the percentage of Lys 1/Lys 2 variants present in adalimumab formulated as HUMIRA® as currently approved and described in the "Highlights of Prescribing Information" for HUMIRA® (adalimumab) Injection (Revised Jan. 2008), the contents of which are hereby incorporated herein by reference.

In another embodiment, a modulated lysine variant species composition of the invention comprises adalimumab, and has a percentage of Lys 1/Lys 2 variants that is higher than the percentage of Lys 1/Lys 2 variants present in adalimumab formulated as HUMIRA® as currently approved and described in the "Highlights of Prescribing Information" for HUMIRA® (adalimumab) Injection (Revised Jan. 2008).

As demonstrated herein, a modulated lysine variant species composition of the present invention exhibits increased efficacy in treating or preventing diseases in a subject compared to a corresponding non-modulated lysine variant species composition. In particular, modulated lysine variant species compositions comprising anti-TNFα antibodies, or antigen binding portions thereof, e.g., adalimumab, exhibit increased cartilage tissue penetration, reduced cartilage destruction, reduced synovial proliferation, and/or reduced bone erosion as compared to a non-modulated lysine variant species composition. In another aspect of this embodiment, modulated lysine variant species compositions comprising anti-TNFα antibodies, or antigen binding portions thereof, e.g., adalimumab, exhibit increased protection against the development of arthritic scores and/or increased protection against the development of histopathology scores as compared to a non-modulated lysine variant species composition, when administered to an animal model of arthritis.

In still another embodiment, a modulated lysine variant species composition comprising an anti-TNFα antibody, or antigen binding portion thereof, e.g., adalimumab, exhibits reduced cell infiltration, reduced proteoglycan loss, and/or reduced chondrocyte death as compared to a non-modulated lysine variant species composition.

In another embodiment, a modulated lysine variant species composition of the invention comprises anti-TNFα antibodies, or antigen-binding portions thereof, e.g., adalimumab, exhibit increased TNFα affinity as compared to a non-modulated lysine variant species composition.

Another aspect of the invention provides methods for treating a subject having a disorder in which TNFα activity is detrimental, e.g., rheumatoid arthritis, juvenile idiopathic arthritic, psoriatic arthritis, ankylosing spondylitis, Crohn's Disease, plaque psoriasis, active axial spondyloarthritis (active axSpA) and non-radiographic axial spondyloarthritis (nr-axSpA), comprising administering a therapeutically effective amount of the composition of a modulated lysine variant species composition to the subject, thereby treating the TNFα-associated disease or disorder.

Other features and advantages of the invention will be apparent from the following detailed description and claims.

BRIEF DESCRIPTION OF THE DRAWINGS

FIG. 1 is a representation of the lysine variants in a sample WCX-10 chromatogram and quantification scheme of each of the variants.

FIG. 2 depicts the effect of zinc modulation in adalimumab producing cell line 1, media 1 on viable cell density (n=2).

FIG. 3 depicts the effect of zinc modulation in adalimumab producing cell line 1, media 1 on viability (n=2).

FIG. 4 depicts the effect of zinc modulation in adalimumab producing cell line 1, media 1 on harvest titer (n=2)

FIG. 5 depicts the effect of zinc modulation in adalimumab producing cell line 1, media 1 on day 10 WCX-10 profile relative lysine distribution (n=2).

FIG. 6 depicts the effect of zinc modulation in adalimumab producing cell line 1, media 1 on viable cell density (n=2).

FIG. 7 depicts the effect of zinc modulation in adalimumab producing cell line 1, media 1 on viability (n=2).

FIG. 8 depicts the effect of zinc modulation in adalimumab producing cell line 1, media 1 on harvest titer (n=2).

FIG. 9 depicts the effect of zinc modulation in adalimumab producing cell line 1, media 1 on day 10 WCX-10 profile relative lysine distribution (n=2).

FIG. 10 depicts the effect of varying total arginine concentration in adalimumab producing cell line 2, media 1 on viable cell density (n=2).

FIG. 11 depicts the effect of varying total arginine concentration in adalimumab producing cell line 2, media 1 on viability (n=2).

FIG. 12 depicts the effect of varying total arginine concentration in adalimumab producing cell line 2, media 1 on harvest titer (n=2).

FIG. 13 depicts the effect of varying total arginine concentration in adalimumab producing cell line 2, media 1 on day 10 on WCX-10 profile relative lysine distribution (n=2).

FIG. 14 depicts the effect of varying total arginine concentration in adalimumab producing cell line 2, media 1 on day 12 on WCX-10 profile relative lysine distribution (n=2).

FIG. 15 depicts the effect of varying total arginine concentration in adalimumab producing cell line 3, media 1 on viable cell density (n=2).

FIG. 16 depicts the effect of varying total arginine concentration in adalimumab producing cell line 3, media 1 on viability (n=2).

FIG. 17 depicts the effect of varying total arginine concentration in adalimumab producing cell line 3, media 1 on harvest titer (n=2).

FIG. 18 depicts the effect of varying total arginine concentration in adalimumab producing cell line 3, media 1 on WCX-10 profile relative lysine distribution (n=2).

FIG. 19 depicts the effect of varying total arginine concentration in adalimumab producing cell line 1, media 1 on WCX-10 profile relative lysine distribution (n=2).

FIG. 20 depicts the effect of arginine addition to adalimumab producing cell line 1, media 2 on day 11 on WCX-10 profile relative lysine distribution (n=2).

FIG. 21 depicts the effect of arginine addition to adalimumab producing cell line 2, media 3 on WCX-10 profile relative lysine distribution (n=2).

FIG. 22 depicts the effect of varying total arginine concentration in mAb1 producing cell line on WCX-10 profile relative lysine distribution (n=1).

FIG. 23 depicts the effect of varying total arginine concentration in mAb2 producing cell line on WCX-10 profile relative lysine distribution (n=2).

FIG. 24 depicts the effect of varying total lysine concentration in adalimumab producing cell line 2, media 1 on viable cell density (n=2).

FIG. 25 depicts the effect of varying total lysine concentration in adalimumab producing cell line 2, media 1 on viability (n=2).

FIG. 26 depicts the effect of varying total lysine concentration in adalimumab producing cell line 2, media 1 on harvest titer (n=2).

FIG. 27 depicts the effect of varying total lysine concentration in adalimumab producing cell line 2, media 1 on WCX-10 profile relative lysine distribution (n=2).

FIG. 28 depicts the effect of varying total lysine concentration in adalimumab producing cell line 3, media 1 on viable cell density (n=2).

FIG. 29 depicts the effect of varying total lysine concentration in adalimumab producing cell line 3, media 1 on viability (n=2).

FIG. 30 depicts the effect of varying total lysine concentration in adalimumab producing cell line 3, media 1 on harvest titer (n=2).

FIG. 31 depicts the effect of varying total lysine concentration in adalimumab producing cell line 3, media 1 on WCX-10 profile relative lysine distribution (n=2).

FIG. 32 depicts the effect of varying total lysine concentration in adalimumab producing cell line 1, media 1 on WCX-10 profile relative lysine distribution (n=2).

FIG. 33 depicts the effect of lysine addition to adalimumab producing cell line 1, media 2 on WCX-10 profile relative lysine distribution (n=2).

FIG. 34 depicts the effect of lysine addition to adalimumab producing cell line 2, media 3 on WCX-10 profile relative lysine distribution (n=2).

FIG. 35 depicts the effect of varying total lysine concentration in mAb1 producing cell line on WCX-10 profile relative lysine distribution (n=1).

FIG. 36 depicts the effect of varying total lysine concentration in mAb2 producing cell line on WCX-10 profile relative lysine distribution (n=2).

FIG. 37 depicts the effect of varying total histidine concentration in adalimumab producing cell line 2, media 1 on viable cell density (n=2).

FIG. 38 depicts the effect of varying total histidine concentration in adalimumab producing cell line 2, media 1 on viability (n=2).

FIG. 39 depicts the effect of varying total histidine concentration in adalimumab producing cell line 2, media 1 on harvest titer (n=2).

FIG. 40 depicts the effect of varying total histidine concentration in adalimumab producing cell line 2, media 1 on WCX-10 profile relative lysine distribution (n=2).

FIG. 41 depicts the effect of varying total histidine concentration in adalimumab producing cell line 3, media 1 on viable cell density (n=2).

FIG. 42 depicts the effect of total histidine concentration in adalimumab producing cell line 3, media 1 on viability (n=2).

FIG. 43 depicts the effect of varying total histidine concentration in adalimumab producing cell line 3, media 1 on harvest titer (n=2).

FIG. 44 depicts the effect of varying total histidine concentration in adalimumab producing cell line 3, media 1 on WCX-10 profile relative lysine distribution (n=2).

FIG. 45 depicts the effect of varying total histidine concentration in adalimumab producing cell line 1, media 1 on WCX-10 profile relative lysine distribution (n=2).

FIG. 46 depicts the effect of histidine addition to adalimumab producing cell line 1, media 2 on WCX-10 profile relative lysine distribution (n=2).

FIG. 47 depicts the effect of histidine addition to adalimumab producing cell line 2, media 3 on WCX-10 profile relative lysine distribution (n=2).

FIG. 48 depicts the effect of varying total histidine concentration in mAb1 producing cell line on WCX-10 profile relative lysine distribution (n=1).

FIG. 49 depicts the effect of varying total histidine concentration in mAb2 producing cell line on WCX-10 profile relative lysine distribution (n=2).

FIG. 50 depicts the effect of concentration modulation of multiple amino acids to adalimumab producing cell line 1, media 1 on viable cell density (n=2).

FIG. 51 depicts the effect of concentration modulation of multiple amino acids to adalimumab producing cell line 1, media 1 on viability.

FIG. 52 depicts the effect of concentration modulation of multiple amino acids to adalimumab producing cell line 1, media 1 on harvest titer.

FIG. 53 depicts the effect of concentration modulation of multiple amino acids to adalimumab producing cell line 1, media 1 on WCX-10 profile relative lysine distribution.

FIG. 54 depicts the effect of concentration modulation of multiple amino acids to adalimumab producing cell line 3, media 1 on viable cell density (n=2).

FIG. 55 depicts the effect of concentration modulation of multiple amino acids to adalimumab producing cell line 3, media 1 on viability.

FIG. 56 depicts the effect of concentration modulation of multiple amino acids to adalimumab producing cell line 3, media 1 on harvest titer.

FIG. 57 depicts the effect of concentration modulation of multiple amino acids to adalimumab producing cell line 3, media 1 on WCX-10 profile relative lysine distribution.

FIG. 58 depicts the effect of concentration modulation of multiple amino acids to adalimumab producing cell line 2, media 1 on WCX-10 profile relative lysine distribution (n=2).

FIG. 59 depicts the effect of concentration modulation of zinc and multiple amino acids to adalimumab producing cell line 1, media 1 on WCX-10 profile relative lysine distribution a) overall prediction plot, b) prediction plots for each additive.

FIG. 60 depicts the effect of peptides of varying length added to adalimumab producing cell line 2, media 1 on WCX-10 profile relative lysine distribution (n=2).

FIG. 61 depicts the effect of pH modulation on adalimumab producing cell line 1, media 1 on viable cell density.

FIG. 62 depicts the effect of pH modulation on adalimumab producing cell line 1, media 1 on viability.

FIG. 63 depicts the effect of pH modulation on adalimumab producing cell line 1, media 1 on harvest titer.

FIG. 64 depicts the effect of pH modulation on adalimumab producing cell line 1, media 1 on WCX-10 profile relative lysine distribution.

FIG. 65 depicts the effect of pH modulation on adalimumab producing cell line 1, media 2 on viable cell density.

FIG. 66 depicts the effect of pH modulation on adalimumab producing cell line 1, media 2 on viability.

FIG. 67 depicts the effect of pH modulation on adalimumab producing cell line 1, media 2 on harvest titer.

FIG. 68 depicts the effect of pH modulation on adalimumab producing cell line 1, media 2 on WCX-10 profile relative lysine distribution.

FIG. 69 depicts the effect of pH modulation on adalimumab producing cell line 3, media 1 on viable cell density.

FIG. 70 depicts the effect of pH modulation on adalimumab producing cell line 3, media 1 on viability.

FIG. 71 depicts the effect of pH modulation on adalimumab producing cell line 3, media 1 on harvest titer.

FIG. 72 depicts the effect of pH modulation on adalimumab producing cell line 3, media 1 on WCX-10 profile relative lysine distribution.

FIG. 73 depicts the effect of dissolved oxygen modulation on adalimumab producing cell line 1, media 2 at 35° C. on viable cell density.

FIG. 74 depicts the effect of dissolved oxygen modulation on adalimumab producing cell line 1, media 2 at 35° C. on viability.

FIG. 75 depicts the effect of dissolved oxygen modulation on adalimumab producing cell line 1, media 2 at 35° C. on harvest titer.

FIG. 76 depicts the effect of dissolved oxygen modulation on adalimumab producing cell line 1, media 2 at 35° C. on WCX-10 profile relative lysine distribution.

FIG. 77 depicts the effect of dissolved oxygen modulation on adalimumab producing cell line 1, media 2 at 33° C. on viable cell density.

FIG. 78 depicts the effect of dissolved oxygen modulation on adalimumab producing cell line 1, media 2 at 33° C. on viability.

FIG. 79 depicts the effect of dissolved oxygen modulation on adalimumab producing cell line 1, media 2 at 33° C. on harvest titer.

FIG. 80 depicts the effect of dissolved oxygen modulation on adalimumab producing cell line 1, media 2 at 33° C. on WCX-10 profile relative lysine distribution.

FIG. 81 depicts effect of dissolved oxygen modulation on adalimumab producing cell line 1, media 1 on viable cell density.

FIG. 82 depicts effect of dissolved oxygen modulation on adalimumab producing cell line 1, media 1 on viability.

FIG. 83 depicts effect of dissolved oxygen modulation on adalimumab producing cell line 1, media 1 on harvest titer.

FIG. 84 depicts effect of dissolved oxygen modulation on adalimumab producing cell line 1, media 1 on WCX-10 profile relative lysine distribution.

FIG. 85 depicts the effect of temperature modulation on adalimumab producing cell line 1, media 1 on viable cell density (n=2).

FIG. 86 depicts the effect of temperature modulation on adalimumab producing cell line 1, media 1 on viability (n=2).

FIG. 87 depicts the effect of temperature modulation on adalimumab producing cell line 1, media 1 on harvest titer (n=2).

FIG. 88 depicts the effect of temperature modulation on adalimumab producing cell line 1, media 1 on WCX-10 profile relative lysine distribution (n=2).

FIG. 89 depicts the effect of temperature modulation on adalimumab producing cell line 1, media 1 on viable cell density (n=2).

FIG. 90 depicts the effect of temperature modulation on adalimumab producing cell line 1, media 1 on viability (n=2).

FIG. 91 depicts the effect of temperature modulation on adalimumab producing cell line 1, media 1 on harvest titer (n=2).

FIG. 92 depicts the effect of temperature modulation on adalimumab producing cell line 1, media 1 on WCX-10 profile relative lysine distribution (n=2).

FIG. 93 depicts the effect of dissolved oxygen and temperature modulation on adalimumab producing cell line 3, media 1 on viable cell density.

FIG. 94 depicts the effect of dissolved oxygen and temperature modulation on adalimumab producing cell line 3, media 1 on viability.

FIG. 95 depicts the effect of dissolved oxygen and temperature modulation on adalimumab producing cell line 3, media 1 on harvest titer.

FIG. 96 depicts the effect of dissolved oxygen and temperature modulation on adalimumab producing cell line 3, media 1 on WCX-10 profile relative lysine distribution.

FIGS. 97A-D depict the effect of varying phosphate concentration in chemically defined media with cell line 1 on (A) viable cell density profile; (B) viability profile; (C) harvest titer; and (D) lysine variant distribution (n=2).

FIGS. 98A-D depict the effect of varying phosphate concentration in chemically defined media with cell line 2 on (A) viable cell density profile; (B) viability profile; (C) harvest titer; and (D) lysine variant distribution (n=2).

FIGS. 99A-F depict the effects of varying lysine, arginine, zinc and phosphate concentration in chemically defined media with cell line 1 on (A) peak viable cell density; (B) harvest viability; (C) harvest titer; (D) the relative fraction of Lys 0; (E) the relative fraction of Lys 1; and (F) the relative fraction of Lys 2.

FIG. 112 depicts micro CT images of the spine from each of six groups of mice administered the following compositions: naïve, vehicle (control), low AR composition (group 5), low host cell protein (HCP) composition (group 7), AR1 composition (containing only AR1 acidic variants) (group 8), and modulated lysine variant species composition (Lys-1/2) (containing only Lys 1 and Lys 2 variants) (group 9).

DETAILED DESCRIPTION OF THE INVENTION

Figure 100:
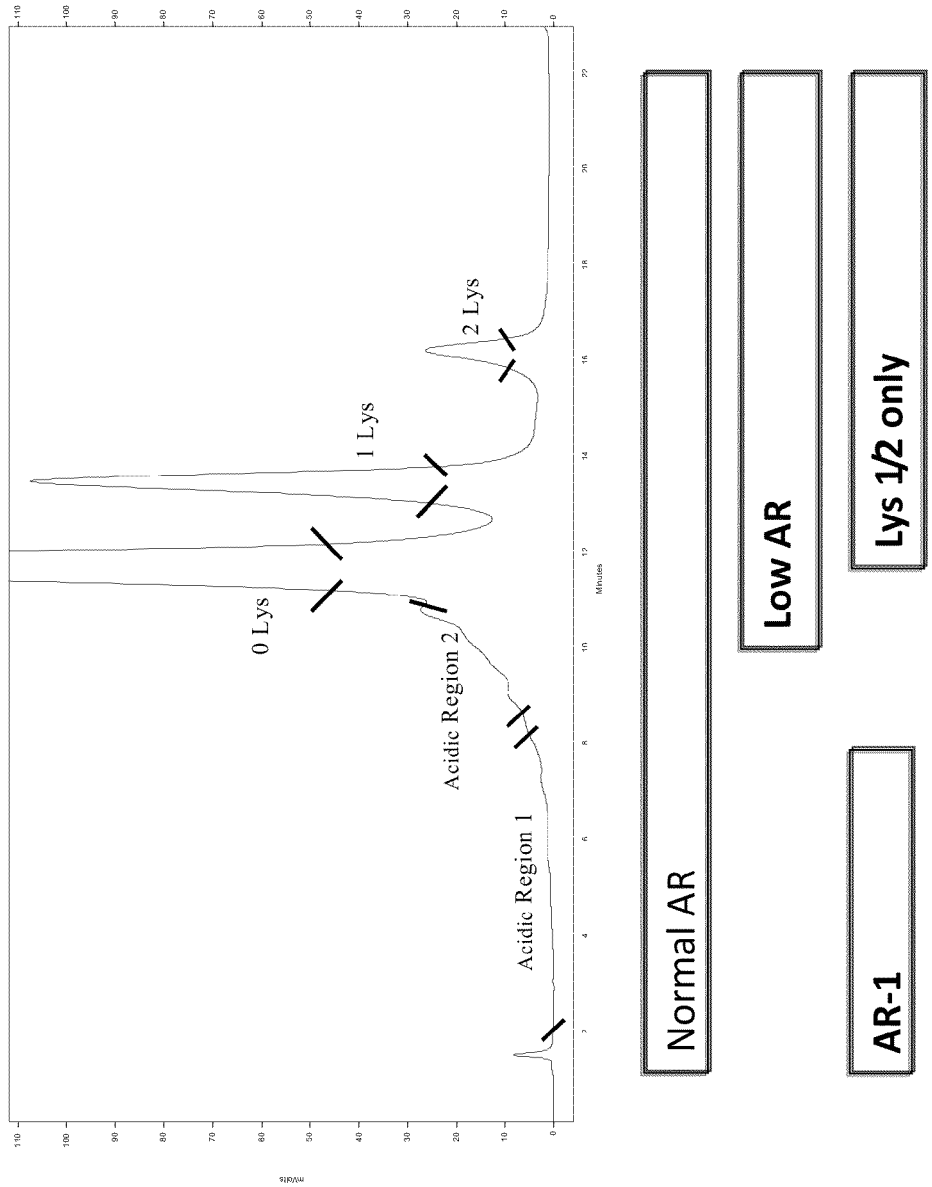
FIG. 100 depicts a chromatogram wherein acidic and basic species are identified in adalimumab and various fractions are delineated.

The present invention is based on the identification and optimization of processes for the production of antibodies or antigen-binding portions thereof (e.g., cell culture processes), to produce compositions comprising antibodies, or antigen-binding portions thereof, that contain modified distributions of C-terminal lysine variants in a population of proteins, e.g., antibodies or antigen binding portions thereof. C-terminal lysines can be present on both the heavy chains of the antibody (Lys 2), on either one of the heavy chains of the antibody (Lys 1), or neither of the heavy chains of the antibody (Lys 0). Antibodies lacking basic C-terminal lysines differ in the charge state from those that contain one or two lysines. Therefore, as shown in FIG. 1, the distribution of lysine variants (% Lys 0, % Lys 1, % Lys 2) of the total lysine sum in the composition can be detected by ion-exchange chromatographic methods such as weak cation-exchange chromatography (WCX-10) and subsequently quantified.

The present invention provides methods for producing compositions comprising modulated amounts (or percentages) of Lys 1, Lys 2, and/or Lys 0 variants as compared to the amount (or percentage) of Lys 1, Lys 2, and/or Lys 0 variants in a starting population of proteins (referred to herein as "modulated lysine variant species compositions"). In one embodiment, the methods of the invention are used to produce a protein composition comprising an increased amount of Lys 1 and/or Lys 2 variants and a decreased amount of Lys 0 variants, e.g., as compared to the amount (or percentage) of Lys 1, Lys 2, and/or Lys 0 variants in a starting population of proteins, e.g., a control composition. In another embodiment, the methods of the invention are used to produce a protein composition comprising a decreased amount of Lys 1 and/or Lys 2 variants and an increased amount of Lys 0 variants, e.g., as compared to the amount (or percentage) of Lys 1, Lys 2, and/or Lys 0 variants in a starting population of proteins, e.g., a control composition.

As demonstrated herein, modulated lysine variant species compositions of the invention comprising adalimumab that have increased Lys 1/Lys2 percentages and decreased Lys 0 percentages, e.g., compositions that comprise only Lys 1 and Lys 2 variants, and not Lys 0 variants, have improved therapeutic efficacy and improved biological properties, for example, increased cartilage tissue penetration, reduced cartilage destruction, reduced synovial proliferation, reduced bone erosion, increased protection against the development of arthritic scores and/or histopathology scores, reduced cell infiltration, reduced proteoglycan loss, reduced chondrocyte death, and/or increased TNFα affinity, as compared to a non-modulated lysine variant species composition (see Example 5).

In one embodiment, the present invention provides methods for culturing host cells under conditions that modulate the distribution or amount of C-terminal lysine variants that are expressed by the cells or are present in purified protein compositions, e.g., compositions comprising an antibody or antigen-binding portion thereof. In some aspects of this embodiment, the methods described herein comprise culturing cells in the presence of one or more amino acids. In other aspects of this embodiment, the methods described herein comprise culturing cells in the presence of zinc, alone or in combination with one or more amino acids. In still other aspects of this embodiment, the methods described herein comprise culturing cells under conditions of increased or decreased temperatures compared to a control temperature. In other aspects of this embodiment, the methods described herein comprise culturing cells under conditions of increased or decreased pH compared to a control pH. In still other aspects of this embodiment, the methods described herein comprise culturing cells under conditions of increased or decreased dissolved oxygen (DO) concentration as compared to a control level of DO. In yet a further embodiment, the methods described herein employ culturing cells under conditions of increased or decreased phosphate concentration compared to a control level of phosphate concentration. Combinations of one or more of these methods are also included within the methods of the invention.

I. Definitions

In order that the present invention may be more readily understood, certain terms are first defined.

Ion exchange chromatography (e.g., WCX-10) analysis of adalimumab has shown that it has three main basic charge variants (i.e., Lys 0, Lys 1, and Lys 2). These variants, or charged isomers, are the result of incomplete post-translational cleavage of the C-terminal lysine residues on the heavy chains of the antibody. In addition to the lysine variants, ion exchange chromatography, e.g., the WCX-10 analysis, measures the presence of acidic species (AR), e.g., AR1 and AR2.

As used herein, the term "lysine variant species" refers to an antibody, or antigen-binding portion thereof, comprising heavy chains with either zero, one or two C-terminal lysines. For example, the "Lys 0" variant comprises an antibody, or antigen-binding portion thereof, with heavy chains that do not comprise a C-terminal lysine. The "Lys 1" variant comprises an antibody, or antigen-binding portion thereof, with one heavy chain that comprises a C-terminal lysine. The "Lys 2" variant comprises an antibody, or antigen-binding portion thereof, with both heavy chains comprising a C-terminal lysine. Lysine variants can be detected by ion chromatography, including weak cation exchange chromatography, for example, WCX-10, of the expression product of a host cell expressing the antibody, or antigen-binding portion thereof. For example, but not by way of limitation, FIG. 1 depicts WCX analysis of adalimumab wherein the three lysine variants, as well as two acidic species, are resolved from each other.

A composition of the invention may comprise more than one lysine variant species of an antibody, or antigen-binding portion thereof. For example, in one embodiment, the composition may comprise a Lys 2 variant of an antibody, or antigen-binding portion thereof. The composition may comprise a Lys 1 variant of an antibody, or antigen-binding portion thereof. The composition may comprise a Lys 0 variant of an antibody, or antigen-binding portion thereof. In another embodiment, the composition may comprise both Lys 1 and Lys 2, or Lys 1 and Lys 0, or Lys 2 and Lys 0 variants of an antibody, or antigen-binding portion thereof. In another embodiment, the composition may comprise all three lysine variant species, i.e., Lys 0, Lys 1 and Lys 2, of an antibody, or antigen-binding portion thereof.

As used herein, the term "modulated lysine variant species composition," refers to a composition comprising an antibody, or antigen-binding portion thereof, that comprises a modulated, e.g., increased or decreased, percentage of Lys 1, Lys 2, and/or Lys 0 variants in the composition after production using one or more of the cell culture methods described herein, as compared to a corresponding non-modulated lysine variant species composition (e.g., a control composition). In one embodiment, a modulated lysine variant species composition comprises an increased percentage of Lys 1 and/or Lys 2 variants and a decreased percentage of Lys 0 variants after production using one or more of the cell culture methods described herein, as compared to a corresponding non-modulated lysine variant species composition (e.g., a control composition).

For example, a modulated lysine variant species composition of the invention may comprise more than about 20%, 25%, 30%, 35%, 40%, 45%, 50%, 55%, 60%, 65%, 70%, 75%, 80%, 85%, 90%, 95%, 96%, 97%, 98%, 99%, or 100% Lys 1 and/or Lys 2 antibodies, or antigen-binding portions thereof relative to the lysine sum (i.e., the sum of Lys 0, Lys 1 and Lys 2 in the composition). In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 and/or Lys 2 antibodies, or antigen-binding portions thereof relative to the lysine sum. Ranges within one or more of any of the preceding percentages are also included.

A modulated lysine variant species composition of the invention may also comprise less than about 80%, 75%, 70%, 65%, 60%, 55%, 50%, 45%, 40%, 30%, 25%, 20%, 15%, 10%, 5%, 4%, 3%, 2%, 1%, or zero antibodies, or antigen-binding portions thereof that are Lys 0, relative to the lysine sum. In one embodiment, a modulated lysine variant species composition of the invention may also comprise less than about 0% to about 10%, about 10% to about 20%, about 20% to about 30%, about 30% to about 40%, about 50% to about 60%, about 60% to about 70%, or about 70% to about 80%, antibodies or antigen-binding portions thereof that are Lys 0, relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have one C-terminal lysine (Lys 1) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 antibodies, or antigen-binding portions thereof relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have two C-terminal lysines (Lys 2) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 2 antibodies, or antigen-binding portions thereof relative to the lysine sum. Ranges within one or more of any of the preceding percentages are also included.

In one embodiment, the methods of the invention, alone or in combination, may reduce the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In one embodiment, the methods of the invention, alone or in combination, may increase the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition.

As used herein, the term "non-modulated lysine variant species composition," refers to a composition in which the levels of lysine variant species have not been modulated. In one embodiment, a non-modulated lysine variant species composition is a composition comprising an antibody, or antigen-binding portion thereof, that was not produced using one or more methods disclosed herein for producing a modulated lysine variant species composition (e.g., a control composition). For example, the control composition can be a starting composition of antibodies whose lysine variant species need to be modulated, e.g., in order to increase therapeutic efficacy and/or stability. For example, the starting composition of antibodies may be an adalimumab composition, e.g., a commercial adalimumab (HUMIRA®) formulation, as described in the "Highlights of Prescribing Information" for HUMIRA® (adalimumab) Injection (Revised Jan. 2008), the contents of which are hereby incorporated herein by reference.

As used herein, the phrases "antibody resistant to C-terminal processing" or "antibody resistant to C-terminal processing by a carboxypeptidase" refer to an antibody, or antigen-binding portion thereof, that is resistant to processing of the C-terminus of its heavy chains by a carboxypeptidase enzyme, e.g., carboxypeptidase B or carboxypeptidase U. An "antibody resistant to C-terminal processing" exhibits decreased removal of a C-terminal lysine of its heavy chains by a carboxypeptidase enzyme, e.g., carboxypeptidase B or carboxypeptidase U. The antibody, or antigen-binding portion thereof, may be modified as described in (U.S. Patent Application Ser. No. 61/892,710, filed Oct. 18, 2013), the contents of which are expressly incorporated herein by reference, to exhibit decreased removal of a C-terminal lysine as compared to an antibody, or antigen-binding portion thereof, that has not been modified. In one embodiment, the antibody, or antigen-binding portion thereof, retains both C-terminal lysines ("Lys 2") and, thus, exhibits no removal (i.e., exhibits no C-terminal processing) of the C-terminal lysines of the heavy chains by a carboxypeptidase. C-terminal processing by a carboxypeptidase may be measured using assays that are well-known in the art including, but not limited to, the peptidase assays described in (U.S. Patent Application Ser. No. 61/892,710, filed Oct. 18, 2013).

As used herein, the term "carboxypeptidase" refers to a protease enzyme that hydrolyzes a peptide bond at the carboxy-terminal ("C-terminal") region of a protein or antibody. Carboxypeptidases are well-known in the art and are involved in post-translational modification of proteins. Specifically, "Carboxypeptidase B" (EC 3.4.17.2) refers to a carboxypeptidase that preferentially cleaves positively charged, or basic, amino acids, such as arginine and lysine from the c-terminus of proteins and antibodies. "Carboxypeptidase U" or "unstable carboxypeptidase" (EC 3.4.17.20) refers to a carboxypeptidase that is activated by thrombin or plasmin during clotting.

The term "modify," "modifying" or "modified," as used herein, is intended to refer to changing one or more amino acids in an antibody, or antigen-binding portion thereof. The change can be produced by adding, substituting or deleting an amino acid at one or more positions. The change can be produced using standard techniques known in the art and described in more detail herein, such as PCR mutagenesis and site-directed mutagenesis.

As used herein, the phrase "increased cartilage tissue penetration" refers to the property of an antibody, or antigen-binding portion thereof, of the invention showing increased penetration of cartilage tissue. This property can be measured or determined by, for example, using an in vitro or an in vivo cartilage model. One non-limiting example of an art-recognized mouse model of arthritis is the human TNF transgenic 197 mouse model of arthritis TNF-Tg197) (see Keffer, J. et al., *EMBO J* (1991) 10:4025-4031, the contents of which are expressly incorporated herein by reference, for further description of the TNF-Tg197 model of arthritis). Cartilage penetration can be measured using assays that are well-known in the art including, but not limited to, the assays described in the Examples section below.

As used herein, the terms "acidic species" and "AR," refer to the variants of a protein, e.g., an antibody or antigen-binding portion thereof, which are characterized by an acidic charge. Acidic species are the component molecular entities that comprise AR. For example, in monoclonal antibody (mAb) preparations, such acidic species can be detected by various methods, such as, for example, WCX-10 HPLC (a weak cation exchange chromatography), or IEF (isoelectric focusing).

Acidic species of an antibody include charge variants, structure variants, and/or fragmentation variants. Exemplary charge variants include, but are not limited to, deamidation variants, afucosylation variants, methylglyoxal (MGO) variants, glycation variants, and citric acid variants. Exemplary structure variants include, but are not limited to, glycosylation variants and acetonation variants. Exemplary fragmentation variants include any truncated protein species from the target molecule due to dissociation of peptide chain, enzymatic and/or chemical modifications, including, but not limited to, Fc and Fab fragments, fragments missing a Fab, fragments missing a heavy chain variable domain, C-terminal truncation variants, variants with excision of N-terminal Asp in the light chain, and variants having N-terminal truncation of the light chain. Other acidic species variants include variants containing unpaired disulfides, host cell proteins, and host nucleic acids, chromatographic materials, and media components.

In certain embodiments, a protein composition may comprise more than one type of acidic species variant. For example, but not by way of limitation, the total acidic species can be divided based on chromatographic residence time. For example, the total acidic species associated with the expression of adalimumab may be divided into a first acidic species region (AR1) and a second acidic species region (AR2). AR1 may comprise, for example, charge variants such as deamidation variants, MGO modified species, glycation variants, and citric acid variants, structural variants such as glycosylation variants and acetonation variants, and/or fragmentation variants. Other acidic variants such as host cells and unknown species may also be present. AR2 may comprise, for example, charge variants such as glycation variants and deamidation variants.

In one embodiment, a modulated lysine variant species composition of the invention comprises about 0.0% to about 10% acidic species (AR), about 0.0% to about 5% AR, about 0.0% to about 4% AR, about 0.0% to about 3% AR, about 0.0% to about 2% AR, about 3% to about 5% AR, about 5% to about 8% AR, or about 8% to about 10% AR, or about 10% to about 15% AR, and ranges within one or more of the preceding. In another embodiment, a modulated lysine variant species composition of the invention comprises, e.g., about 15% or less AR. In one aspect of this embodiment, a modulated lysine variant species composition comprises about 14% or less AR, 13% or less AR, 12% or less AR, 11% or less AR, 10% or less AR, 9% or less AR, 8% or less AR, 7% or less AR, 6% or less AR, 5% or less AR, 4.5% or less AR, 4% or less AR, 3.5% or less AR, 3% or less AR, 2.5% or less AR, 2% or less AR, 1.9% or less AR, 1.8% or less AR, 1.7% or less AR, 1.6% or less AR, 1.5% or less AR, 1.4% or less AR, 1.3% or less AR, 1.2% or less AR, 1.1% or less AR, 1% or less AR, 0.9% or less AR, 0.8% or less AR, 0.7% or less AR, 0.6% or less AR, 0.5% or less AR, 0.4% or less AR, 0.3% or less AR, 0.2% or less AR, 0.1% or less AR, or 0.0% AR, and ranges within one or more of the preceding.

In another embodiment, a modulated lysine variant species composition comprises about 0.1% or less AR1 and about 3% or less AR2. In another aspect of this embodiment, the composition comprises about 0.0% AR1 and about 1.4% AR2. In another aspect of this embodiment, the composition comprises about 0% to about 3% AR, e.g., about 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or less AR1. In another aspect of this embodiment, the composition comprises about 0% to about 3% AR, e.g., about 3%, 2.5%, 2%, 1.5%, 1.4%, 1.3%, 1.2%, 1.1%, 1%, 0.9%, 0.8%, 0.7%, 0.6%, 0.5%, 0.4%, 0.3%, 0.2%, 0.1%, or less AR2.

The term "antibody", as used herein, broadly refers to any immunoglobulin (Ig) molecule comprised of four polypeptide chains, two heavy (H) chains and two light (L) chains, or any functional fragment, mutant, variant, or derivative thereof, which retains the essential epitope binding features of an Ig molecule. Such mutant, variant, or derivative antibody formats are known in the art and non-limiting embodiments of which are discussed herein.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG$_1$, IgG$_2$, IgG$_3$, IgG$_4$, IgA1 and IgA2) or subclass. The present invention is particularly useful for IgG$_1$ antibodies.

As used herein, the term "adalimumab," also known by its trade name HUMIRA® (AbbVie) refers to a human IgG$_1$ antibody that binds human tumor necrosis factor α (TNFα). In general, the heavy chain constant domain 2 (CH2) of the adalimumab IgG-Fc region is glycosylated through covalent attachment of oligosaccharide at asparagine 297 (Asn-297). The light chain variable region of adalimumab is provided herein as SEQ ID NO:1, and the heavy chain variable region of adalimumab is provided herein as SEQ ID NO:2. Adalimumab comprises a light chain variable region comprising a CDR1 of SEQ ID NO:7, a CDR2 of SEQ ID NO:5, and a CDR3 of SEQ ID NO:3. Adalimumab comprises a heavy chain variable region comprising a CDR1 of SEQ ID NO:8, a CDR2 of SEQ ID NO:6 and CDR3 of SEQ ID NO:4. The nucleic acid sequence of the light chain variable region is set forth in SEQ ID NO:9. The nucleic acid sequence of the heavy chain variable region is set forth in SEQ ID NO:10. The full length amino acid sequence of the light chain is set forth as SEQ ID NO:11 and the full length amino acid sequence of the heavy chain is set forth as SEQ ID NO:12. Adalimumab is described in U.S. Pat. Nos. 6,090,382; 6,258,562; 6,509,015; 7,223,394; 7,541,031; 7,588,761; 7,863,426; 7,919,264; 8,197,813; 8,206,714; 8,216,583; 8,420,081; 8,092,998; 8,093,045; 8,187,836; 8,372,400; 8,034,906; 8,436,149; 8,231,876; 8,414,894; 8,372,401, the entire contents of each which are expressly incorporated herein by reference in their entireties. Adalimumab is also described in "Highlights of Prescribing Information" for HUMIRA® (adalimumab) Injection (Revised Jan. 2008) the contents of which are hereby incorporated herein by reference.

The term "antigen-binding portion" of an antibody (or simply "antibody portion"), as used herein, refers to one or more fragments of an antibody that retain the ability to specifically bind to an antigen (e.g., TNFα) and still contain at least one heavy chain. It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include a Fv fragment consisting of the VL and VH domains of a single arm of an antibody or a halfbody (as described in, for example, PCT Publication No. WO12/088302, the entire contents of which are incorporated herein by reference). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more of the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Human IgG heavy chain and light chain constant domain amino acid sequences are known in the art.

An antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds human TNFα). An isolated antibody that specifically binds human TNFα may, however, have cross-reactivity to other antigens, such as the TNFα molecules from other species. Alternatively, an isolated antibody, or antigen-binding portion thereof, may not cross-react with the TNFα molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. In another embodiment, the human monoclonal antibodies are produced by phage display technologies as described, for example, in the Examples section below.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., U.S. Pat. No. 6,713,610; Taylor, L. D., et al. (1992) Nucl. Acids Res. 20:6287-6295; Kellermann S-A., and Green L. L. (2002) Current Opinion in Biotechnology 13:593-597; Little M. et al (2000) Immunology Today 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "human antibody derivatives" refers to any modified form of the human antibody, e.g., a conjugate of the antibody and another agent or antibody.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Such antibodies were generated by obtaining murine anti-TNFα monoclonal antibodies using traditional hybridoma technology followed by humanization using in vitro genetic engineering.

The term "antibody mimetic" or "antibody mimic" is intended to refer to molecules capable of mimicking an antibody's ability to bind an antigen, but which are not limited to native antibody structures. Examples of such antibody mimetics include, but are not limited to, Adnectins (i.e., fibronectin based binding molecules), Affibodies, DARPins, Anticalins, Avimers, and Versabodies all of which employ binding structures that, while they mimic traditional antibody binding, are generated from and function via distinct mechanisms. The embodiments of the instant invention, as they are directed to antibodies, or antigen binding portions thereof, also apply to the antibody mimetics described above.

As used herein, "isotype" refers to an antibody class (e.g., IgM or IgG1) that is encoded by the heavy chain constant region genes.

The terms "Kabat numbering", "Kabat definitions and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad. Sci. 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 96%, at least 97%, at least 98%, at least 99%, or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although some embodiments use Kabat or Chothia defined CDRs.

As used herein, the term "canonical" residue refers to a residue in a CDR or framework that defines a particular canonical CDR structure as defined by Chothia et al. (J. Mol. Biol. 196:901-907 (1987); Chothia et al., J. Mol. Biol. 227: 799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In one embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages of germ line antibody genes stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 96%, at least 97%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. In one embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. Such mutations, however, will not be extensive. Usually, at least 80%, at least 85%, at least 90%, or at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. In one embodiment, the multivalent binding protein is engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e. capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of TNFα. In one embodiment, a neutralizing binding protein is a neutralizing antibody whose binding to TNFα and/or a mutant TNFα protein results in inhibition of a biological activity of TNFα and/or the mutant TNFα. The neutralizing binding protein can bind TNFα and/or a mutant TNFα protein and reduces a biologically activity of TNFα and/or a mutant TNFα protein by at least about 20%, 30%, 40%, 50%, 60%, 70%, 80%, 85%, 90%, 95% or more. Inhibition of a biological activity of TNFα and/or a mutant TNFα protein by a neutralizing binding protein can be assessed by measuring one or more indicators of TNFα and/or mutant TNFα biological activity well known in the art.

The term "activity" includes activities such as the binding specificity/affinity of an antibody for an antigen, for example, an anti-TNFα antibody that binds to a TNFα antigen and/or the neutralizing potency of an antibody, for example, an anti-TNFα antibody whose binding to TNFα inhibits the biological activity of TNFα.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The terms "specific binding" or "specifically binding", as used herein, in reference to the interaction of an antibody with another moiety, e.g., TNFα, mean an interaction that is dependent upon the presence of a particular structure (e.g., an antigenic determinant or epitope) on the moiety, e.g., TNFα. For example, an antibody recognizes and binds to a specific protein structure rather than to proteins, generally. If an antibody is specific for epitope "A", the presence of a molecule containing epitope A (or free, unlabeled A), in a reaction containing labeled "A" and the antibody, will reduce the amount of labeled A bound to the antibody.

As used herein, an antibody that "binds" or "specifically binds" to an antigen, e.g., TNFα, is intended to refer to an antibody, or antigen-binding portion thereof, that specifically binds to the antigen. The term "$K_{on}$" (also "Kon", "kon"), as used herein, is intended to refer to the on rate constant for association of a binding protein of the invention (e.g., an antibody of the invention) to an antigen to form an association complex, e.g., antibody/antigen complex, as is known in the art. The "$K_{on}$" also is known by the terms "association rate constant", or "ka", as used interchangeably herein. This value indicates the binding rate of an antibody to its target antigen or the rate of complex formation between an antibody and antigen as is shown by the equation below:

Antibody ("Ab")+Antigen ("Ag")→Ab-Ag.

The term "$K_{off}$" (also "Koff", "koff"), as used herein, is intended to refer to the off rate constant for dissociation, or "dissociation rate constant", of a binding protein of the invention (e.g., an antibody of the invention) from an association complex (e.g., an antibody/antigen complex) as is known in the art. This value indicates the dissociation rate of an antibody from its target antigen or separation of Ab-Ag complex over time into free antibody and antigen as shown by the equation below:

Ab+Ag←Ab-Ag.

The term "$K_D$" (also "$K_d$"), as used herein, is intended to refer to the "equilibrium dissociation constant", and refers to the value obtained in a titration measurement at equilibrium, or by dividing the dissociation rate constant (Koff) by the association rate constant (Kon). The association rate constant (Kon), the dissociation rate constant (Koff), and the equilibrium dissociation constant (K are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "antibody conjugate" refers to a binding protein, such as an antibody, linked, e.g., chemically linked, to a second chemical moiety, such as a therapeutic or cytotoxic agent. The term "agent" is used herein to denote a chemical compound, a mixture of chemical compounds, a biological macromolecule, or an extract made from biological materials. The therapeutic or cytotoxic agents can include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The term "polynucleotide" as referred to herein, means a polymeric form of two or more nucleotides, either ribonucleotides or deoxynucleotides or a modified form of either type of nucleotide. The term includes single and double stranded forms of DNA but typically is double-stranded DNA.

The term "isolated polynucleotide" as used herein shall mean a polynucleotide (e.g., of genomic, cDNA, or synthetic origin, or some combination thereof) that, by virtue of its origin, is not associated with all or a portion of a polynucleotide with which the "isolated polynucleotide" is found in nature; is operably linked to a polynucleotide to which it is not linked in nature; or does not occur in nature as part of a larger sequence.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Host cells include prokaryotic and eukaryotic cells selected from any of the Kingdoms of life. Eukaryotic cells include protist, fungal, plant and animal cells. Host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The terms "regulate" and "modulate" as used interchangeably, and refer to a change or an alteration in the activity of a molecule of interest (e.g., the biological activity of TNFα). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). In one embodiment, an "effective amount" refers to the amount of an antibody, or antigen-binding portion thereof, of the invention, e.g., an anti-TNFα antibody, or antigen-binding portion thereof, that is sufficient to treat a disorder in which TNFα activity is detrimental.

As used herein, the term "a disorder in which TNFα activity is detrimental" is intended to include diseases and other disorders in which the presence of TNFα in a subject suffering from the disorder has been shown to be or is suspected of being either responsible for the pathophysiology of the disorder or a factor that contributes to a worsening of the disorder. Accordingly, a disorder in which TNFα activity is detrimental is a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, or synovial fluid of the subject), which can be detected, for example, using an anti-TNFα antibody as described above. There are numerous examples of disorders in which TNFα activity is detrimental. In one embodiment, the disorder in which TNFα activity is detrimental is an autoimmune disorder. In one embodiment, the autoimmune disorder is selected from the group consisting of rheumatoid arthritis, juvenile idiopathic arthritis, rheumatoid spondylitis, ankylosing spondylitis, psoriasis, osteoarthritis, gouty arthritis, an allergy, multiple sclerosis, psoriatic arthritis, autoimmune diabetes, autoimmune uveitis, nephrotic syndrome, juvenile rheumatoid arthritis, Crohn's disease, active axial spondyloarthritis (active axSpA) and non-radiographic axial spondyloarthritis (nr-axSpA), and ulcerative colitis. Disorders in which TNFα activity is detrimental are set forth in U.S. Pat. No. 6,090,382 and also in the "Highlights of Prescribing Information" for HUMIRA® (adalimumab) Injection (Revised Jan. 2008), the contents of which are hereby incorporated herein by reference. The use of TNFα antibodies and antibody portions obtained using methods of the invention for the treatment of specific disorders is discussed in further detail below.

The phrase "clarified harvest" refers to a liquid material containing a protein of interest, for example, an antibody of interest such as a monoclonal or polyclonal antibody of interest, that has been extracted from cell culture, for example, a fermentation bioreactor, after undergoing centrifugation to remove large solid particles and subsequent filtration to remove finer solid particles and impurities from the material.

As used herein, the term "cell culture" refers to methods for generating and maintaining a population of host cells capable of producing a recombinant protein of interest, as well as the methods and techniques for optimizing the production and collection of the protein of interest. For example, once an expression vector has been incorporated into an appropriate host, the host can be maintained under conditions suitable for expression of the relevant nucleotide coding sequences, and the collection and purification of the desired recombinant protein.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization) can be removed by a variety of means, including but not limited to, centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit.

II. Modulated Lysine Variant Species Compositions of the Invention

In one embodiment, the present invention provides modulated lysine variant species compositions comprising antibodies, or antigen-binding portions thereof, such as adalimumab, comprising modulated percentages of Lys 1, Lys 2, and/or Lys 0 variants relative to the percentage of Lys 1, Lys 2, and Lys 0 proteins in a population of proteins. In one embodiment, the methods of the invention are used to produce a protein composition comprising an increased amount of Lys 1 and/or Lys 2 variants and a decreased amount of Lys 0 variants in a population of proteins, e.g., as compared to a non-modulated lysine variant species composition, e.g., a control composition. In another embodiment, the methods of the invention are used to produce a protein composition comprising a decreased amount of Lys 1 and/or Lys 2 variants, and an increased amount of Lys 0 variants in a population of proteins, e.g., as compared to a non-modulated lysine variant species composition, e.g., a control composition.

For example, a modulated lysine variant species composition of the invention may comprise more than about 20%, 25%, 30%, 35%, 40%, 45%, 50%, 55%, 60%, 65%, 70%, 75%, 80%, 85%, 90%, 95%, 96%, 97%, 98%, 99%, or 100% Lys 1 and/or Lys 2 antibodies, or antigen-binding portions thereof relative to the lysine sum (i.e., the sum of Lys 0, Lys 1 and Lys 2 in the composition). In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 and/or Lys 2 antibodies, or antigen-binding portions thereof relative to the lysine sum. Ranges within one or more of any of the preceding percentages are also included.

A modulated lysine variant species composition of the invention may also comprise less than about 80%, 75%, 70%, 65%, 60%, 55%, 50%, 45%, 40%, 30%, 25%, 20%, 15%, 10%, 5%, 4%, 3%, 2%, 1%, or zero antibodies, or antigen-binding portions thereof that are Lys 0, relative to the lysine sum. In one embodiment, a modulated lysine variant species composition of the invention may also comprise less than about 0% to about 10%, about 10% to about 20%, about 20% to about 30%, about 30% to about 40%, about 50% to about 60%, about 60% to about 70%, or about 70% to about 80%, antibodies or antigen-binding portions thereof that are Lys 0, relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have one C-terminal lysine (Lys 1) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 1 antibodies, or antigen-binding portions thereof relative to the lysine sum. Ranges within one or more of any of the preceding percentages are also included.

A modulated lysine variant species composition also includes a composition comprising an antibody, or antigen-binding portion thereof, that comprises more than about 20%, 25%, 30%, 35%, 40%, 45%, 50%, 55%, 60%, 65%, 70%, 75%, 80%, 85%, 90%, 95%, 96%, 97%, 98%, 99%, or 100% antibodies, or antigen-binding portions thereof that have two C-terminal lysines (Lys 2) relative to the lysine sum. Ranges within one or more of any of the preceding percentages are also included. In one embodiment, a modulated lysine variant species composition of the invention may comprise more than about 20% to about 30%, about 30% to about 40%, about 40% to about 50%, about 60% to about 70%, or about 70% to about 80%, about 80% to about 90%, or about 90% to about 100% Lys 2 antibodies, or antigen-binding portions thereof relative to the lysine sum. Ranges within one or more of any of the preceding percentages are also included.

In one embodiment, the methods of the invention, alone or in combination, may reduce the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In one embodiment, the methods of the invention, alone or in combination, may increase the amount or percentage of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition.

As demonstrated herein, certain modulated lysine variant species compositions have improved therapeutic efficacy and improved biological properties, for example, increased cartilage tissue penetration, reduced cartilage destruction, reduced synovial proliferation, reduced bone erosion, increased protection against the development of arthritic scores and/or histopathology scores, reduced cell infiltration, reduced proteoglycan loss, reduced chondrocyte death, and/or increased TNFα affinity, as compared to non-modulated lysine variant species composition (Example 5).

In one embodiment, the protein in the modulated lysine variant species compositions of the invention is an antibody or antigen binding portion thereof. For example, the antibody, or antigen binding portion thereof may be an anti-TNFα antibody, or antigen binding portion thereof, such as adalimumab, or an antigen binding portion thereof. In one aspect of this embodiment, antibody, or antigen binding portion thereof, can comprise a light chain variable region comprising the sequence set forth as SEQ ID NO:1, and a heavy chain variable region comprising the sequence set forth as SEQ ID NO:2. In another aspect of this embodiment, the antibody can comprise a light chain variable region comprising a CDR1 having the sequence set forth as SEQ ID NO:7, a CDR2 having the sequence set forth as SEQ ID NO:5, and a CDR3 having the sequence set forth as SEQ ID NO:3. In another aspect of this embodiment, the antibody can comprise a heavy chain variable region comprising a CDR1 having the sequence set forth as SEQ ID NO:8, a CDR2 having the sequence set forth as SEQ ID NO:6 and a CDR3 having the sequence set forth as SEQ ID NO:4.

The antibody, or antigen binding portion thereof, used in the modulated lysine variant species compositions of the invention, may be a human, humanized, or chimeric antibody.

The antibodies, or antigen-binding portions thereof, used in the modulated lysine variant species compositions of the invention, can be generated by a variety of techniques, including immunization of an animal with the antigen of interest followed by conventional monoclonal antibody methodologies e.g., the standard somatic cell hybridization technique of Kohler and Milstein (1975) Nature 256: 495. Somatic cell hybridization procedures can be used. In principle, other techniques for producing monoclonal antibody can be employed as well, including viral or oncogenic transformation of B lymphocytes.

One animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody used in the modulated lysine variant species compositions of the invention can be a human, a chimeric, or a humanized antibody. Chimeric or humanized antibodies used in the modulated lysine variant species compositions of the invention can be prepared based on the sequence of a non-human monoclonal antibody prepared as described above. DNA encoding the heavy and light chain immunoglobulins can be obtained from the non-human hybridoma of interest and engineered to contain non-murine (e.g., human)

immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies, or antigen-binding portions thereof, used in the modulated lysine variant species compositions of the invention are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen). The antibodies, or antigen-binding portions thereof, used in the modulated lysine variant species compositions of the invention can also be produced using the methods described in U.S. Pat. No. 6,090,382, the entire contents of which is expressly incorporated herein by reference.

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies, or antigen-binding portions thereof, used in the modulated lysine variant species compositions of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

The antibodies, or antigen-binding portions thereof, used in the modulated lysine variant species compositions of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the antibodies, or antigen-binding portions thereof, used in the modulated lysine variant species compositions of the invention include anti-TNFα antibodies and antigen-binding portions thereof, anti-TNFα-related antibodies and antigen-binding portions thereof, and human antibodies and antigen-binding portions thereof with equivalent properties to anti-TNFα, such as high affinity binding to hTNFα with low dissociation kinetics and high neutralizing capacity. In one aspect, the modulated lysine variant species compositions of the invention, include an isolated human antibody, or an antigen-binding portion thereof, that dissociates from hTNFα with a Kd of about $1\times10^{-8}$ M or less and a Koff rate constant of $1\times10^{-3}$ $s^{-1}$ or less, both determined by surface plasmon resonance. In specific non-limiting embodiments, an anti-TNFα antibody, or antigen-binding portions thereof, purified according to the invention competitively inhibits binding of adalimumab to TNFα under physiological conditions. In one embodiment, the modulated lysine variant species compositions of the invention comprise adalimumab or an antigen binding portion thereof.

Antibodies or antigen-binding portions thereof used in the modulated lysine variant species compositions of the invention can be altered wherein the constant region of the antibody is modified to reduce at least one constant region-mediated biological effector function relative to an unmodified antibody. To modify an antibody used in the modulated lysine variant species compositions of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147: 2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

III. Protein Production

To express an antibody, or antigen-binding portion thereof, used in the modulated lysine variant species compositions of the invention, such as an antibody or antigen-binding fragment thereof, DNAs encoding the protein, such as DNAs encoding partial or full-length light and heavy chains, are inserted into one or more expression vector such that the genes are operatively linked to transcriptional and translational control sequences. (See, e.g., U.S. Pat. No. 6,090,382, the entire teaching of which is incorporated herein by reference.) In this context, the term "operatively linked" is intended to mean that a gene encoding the protein of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the protein of interest will comprise multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but not limited to, antibody constant region sequences. For example, one approach to converting the antibody or antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector of the invention can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the protein coding genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antigen-binding portion thereof, used in the modulated lysine variant species compositions of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant proteins of the invention include Chinese Hamster Ovary (CHO cells) (including dhfr- CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767, 704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, dissolved oxygen (DO) concentration, phosphate concentration, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antigen, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Some proteins can be secreted directly from the cell into the surrounding growth media; others are made intracellularly. For the latter proteins, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the protein is secreted, supernatants from such expression systems are generally first concentrated using a commercially available protein concentration filter, e.g., an Amicon™ or Millipore Pellicon™ ultrafiltration unit. Where the protein is secreted into the medium, the recombinant host cells can also be separated from the cell culture medium, e.g., by tangential flow filtration. Protein can be further recovered from the culture medium using the protein purification methods of the invention.

Numerous populations of proteins expressed by host cells, including, but not limited to, host cells expressing antibodies, such as adalimumab, may comprise a number of lysine variants, for example, combinations of two or more of Lys 0, Lys 1 and Lys 2, and are therefore amenable to the methods described herein for modification of C-terminal lysine variant heterogeneity. For example, ion chromatography analysis, such as weak cation-exchange chromatography (WCX) analysis, of adalimumab has shown the presence of the three lysine variants corresponding to Lys 0, Lys 1 and Lys 2. Therefore, WCX provides an exemplary system for identifying modification of Lys 0, Lys 1, and Lys 2 in a composition comprising an antibody, or antigen binding portion thereof, and therefore allowing for identification of particular cell culture conditions that allow for control over lysine variant heterogeneity.

The production of C-terminal lysine variants can be dependent upon changes in process parameters. (Lawrence, D. (2008), C-terminal Lysine Variants in Fully Human Monoclonal Antibodies: Investigation of Test Methods and Possible Causes. Biotechnology and Bioengineering. 100: 1132-1143). Native glycoproteins and/or recombinant glycoproteins (e.g., natural antibodies and/or therapeutic antibodies) that are translated at the endoplasmic reticulum (ER) must fold properly and often assemble into multimeric complexes. There are several proteins that help these proteins to fold properly. Some of these proteins only need the cleavage of the ER N-terminal sequence of the protein to become a mature protein. However, other glycoproteins can require further processing ("posttranslational modifications") to become a mature and fully-functional. Some of these posttranslational modifications include glycosylation, formation of disulfide bonds, N-terminal pyroglutamate, methionine oxidation, asparagine deamination, phosphorylation, acetylation, and enzymatic removal of C-terminal lysine or arginine residues. (Ahrer et al., (2006), Chromatographic and Electrophoretic Characterization of Protein Variants. Journal of Chromatography. 841:110-122; Li et al. (2005), Current Therapeutic Antibody Production and Process Optimization. Bioprocessing Journal; Harris, J. (1995), Processing of C-terminal Lysine and Arginine Residues of Proteins Isolated from Mammalian Cell Culture. Journal of Chromatography. 705: 129-134; and Parkins, M., Theiler, R., et al. (2000), Determination of the Origin of Charge Heterogeneity in a Murine Monoclonal Antibody. Pharmaceutical Research. 17: 1110-1117).

Without being bound by theory, studies have demonstrated that the enzymatic removal of the C-terminal Lys residues is a primary contributor to the heterogeneity of recombinant monoclonal antibodies, including, but not limited to, the adalimumab glycoprotein. (Harris et al. (2004), Commercial Manufacturing Scale Formulation and Analytical Characterization of Therapeutic Recombinant Antibodies. Drug Development Research. 61: 137-154). Additional studies have determined that the charge heterogeneity can be generated by: 1) removal of the lysine or arginine C-terminal residue in the IgG heavy chains; 2) conversion of N-terminal glutamate to pyroglutamate; 3) dehydration of aspartate residues; and 4) alternate cleavage of a signal peptide that results in the presence of basic residues. The adalimumab heavy chain terminal sequence is proline-glycine-lysine. However, as noted above, the lysine residues are partially removed during the manufacturing process, alternatively, they appear to be cleaved subsequent to administration to a mammalian subject. Thus, adalimumab can comprise a mixture of antibodies bearing zero, one, or two C-terminal lysine residues. The specific sequence can be detected by cation exchange chromatography. It has been observed that this charge heterogeneity, caused by the incomplete posttranslational cleavage, may not affect the potency of the protein to bind TNF-$\alpha$. (Santora et al., (2001), Characterization of Noncovalent Complexes of Recombinant Human Monoclonal Antibody and Antigen Using Cation Exchange, Size Exclusion Chromatography, and BIAcore. Analytical Biochemistry 299: 119-129). However, even though the removal of C-terminal lysine residues may not couple with the biological function of the antibody, it is a factor to consider in maintaining batch-to-batch consistency and efficacy. (Parkins et al. (2000), Determination of the Origin of Charge Heterogeneity in a Murine Monoclonal Antibody. Pharmaceutical Research. 17: 1110-1117).

Experiments have shown that the charge heterogeneity of an antibody, associated with the incomplete removal of C-terminal lysine residues, is due to carboxypeptidase activity/expression differences due to process parameter variability or changes. Since the penultimate residue, glycine, is not removed, this suggests that the carboxypeptidase is specific for basic residues, such as lysine and arginine. (Lawrence, D. (2008), C-terminal Lysine Variants in Fully Human Monoclonal Antibodies: Investigation of Test Methods and Possible Causes. Biotechnology and Bioengineering. 100: 1132-1143; and Harris, J. (1995), Processing of C-terminal Lysine and Arginine Residues of Proteins Isolated from Mammalian Cell Culture. Journal of Chromatography. 705: 129-134).

Antibodies resistant to C-terminal processing by a carboxypeptidase, which are resistant to removal of a C-terminal lysine of a heavy chains and exhibit decreased removal of a C-terminal lysine by a carboxypeptidase enzyme, e.g., carboxypeptidase B or carboxypeptidase U, can be produced using the methods described in (U.S. Patent Application Ser. No. 61/892,710, filed Oct. 18, 2013), the contents of which are expressly incorporated herein by reference. In one embodiment, the antibody, or antigen-binding portion thereof, retains both C-terminal lysines ("Lys 2") and, thus, exhibits no removal (i.e., exhibits no C-terminal processing) of the C-terminal lysines of the heavy chains by a carboxypeptidase. C-terminal processing by a carboxypeptidase may be measured using assays that are well-known in the art including, but not limited to, the peptidase assays described in (U.S. Patent Application Ser. No. 61/892,710, filed Oct. 18, 2013).

The experiments outlined in the Examples below demonstrate strategies for modifying the lysine distribution in compositions comprising an antibody or antigen binding portion thereof. In particular, the methods described herein can be used to increase the Lys 1 and/or Lys 2 variants in a composition, and decrease the Lys 0 variants in the composition, not to mention decrease the AR contribution, to thereby produce a high Lys 1 and/or Lys 2 composition.

The experiments disclosed herein demonstrate that, in certain embodiments, variation in raw materials used in cell culture, and particularly in the context of media preparation, can vary C-terminal Lys variant distribution. For example, as outlined herein, control over the amount of zinc present in cell culture media can allow for the modulation of C-terminal lysine variant heterogeneity. zinc has been previously reported in literature to be a cofactor of the enzyme carboxypeptidase (Valee B et.al (1960), The role of zinc in carboxypeptidase, Journal of Biological Chemistry, 235, 1, 64-69). However, it was not appreciated until the filing of the instant application that adjusting the levels of zinc in culture media could allows for modulation of the lysine variants.

Adjusting Zinc Concentration to Control Lysine Variation

In certain embodiments of the instant invention, control of C-terminal lysine variants in a composition comprising an antibody, or antigen binding portion thereof, can be attained by adjustment of the zinc concentration in a media employed in the cell culture run. In one non-limiting embodiment, such adjustment will be to decrease the amount of zinc in the media, while in other non-limiting embodiments, the necessary adjustment to achieve the desired control over lysine variant heterogeneity will involve an increase in the amount of zinc in the media. Such increases or decreases in the amount of zinc can be of a magnitude of about 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, cell culture media containing no zinc is supplemented with zinc to achieve a final zinc concentration in the cell culture media of less than 60 μM. In certain embodiments, the cell culture will contain a total concentration of zinc of between about 0.025 and about 10 μM, between about 0.05 and 10 μM, between about 0.1 and 10 μM, between about 0.2 and 10 μM, between about 0.25 and 10 μM, between about 0.5 and 10 μM, between about 1 and 10 μM, between about 1.5 and 9.5 μM, between about 2 and 9 μM, between about 2.5 and 8.5 μM, between about 3 and 8 μM, between about 3.5 and 7.5 μM, between about 4 and 7 μM, between about 4.5 and 6.5 μM, between about 5 and 6 μM. In certain embodiments, the cell culture media containing no zinc is supplemented with zinc to achieve a final zinc concentration in the cell culture media of about 3.4 μM or about 6.7 μM.

In certain embodiments, the cell culture media contains zinc in an amount effective to reduce the amount of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In certain embodiments, the cell culture media contains zinc in an amount effective to increase the amount of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition, In certain embodiments, the cell culture media contains zinc in an amount effective to reduce the amount of a Lys 0 lysine variant, and to increase the amount of a Lys 1 and/or Lys 2 lysine variant expressed by the cell culture.

For example, and not by way of limitation, as detailed in Example 1, below, certain embodiments include reducing the zinc concentration of the cell culture medium employed from a control concentration of about 10 μM to about 3.4 μM, and the % Lys 0 of an adalimumab sample purified from the supplemented culture is reduced to 67.9% from a control amount of 92.7%. Additionally, the amounts of Lys 1 and Lys 2 in the adalimumab sample are increased to 19.9% (Lys 1) and 12.2% (Lys 2) from an adalimumab sample purified from the control culture (10 μM zinc) having 6.3% Lys 1 and 1.0% Lys 2. Furthermore, as detailed in Example 1, below, certain embodiments include reducing the zinc concentration of the cell culture medium employed from a control concentration of about 10 μM to about 3.4 μM or about 6.7 μM, and the % Lys 0 of an adalimumab sample purified from the supplemented culture is reduced to 69.0% (3.4 μM) or 89.9% (6.7 μM) from a control amount of 92.8%. Additionally, the amounts of Lys 1 and Lys 2 in the adalimumab sample are increased to 21.8% (Lys 1-3.4 μM), 8.7% (Lys 1-6.7 μM), 9.1% (Lys 2-3.4 μM), and 1.4% (Lys 2-6.7 μM) from an adalimumab sample purified from the control culture (10 μM zinc) having 6.2% Lys 1 and 1.1% Lys 2.

In certain embodiments, the cell culture contains zinc as well as arginine, lysine, and histidine, each at a concentration sufficient to reduce the amount of a Lys 0 lysine variant, and to increase the amount of a Lys 1 and/or Lys 2 lysine variant expressed by the cell culture. For example, but not by way of limitation, the concentration range for arginine and lysine can be between about 1 to about 3 g/L, while the concentration range for histidine is between about 0 to about 1 g/L and the concentration range for zinc is about 30 μM to about 60 μM.

Adjusting Amino Acid Concentration to Control C-Terminal Lysine Variation

In certain embodiments of the instant invention, control of C-terminal lysine variants in a composition comprising an antibody, or antigen binding portion thereof, can be attained by adjustment of the amino acid composition of the cell culture media. In certain embodiments, the amount of one or more amino acids in the media is increased, while in other embodiments the amount of one or more amino acids in the media is decreased. Such increases or decreases in the amount of the one or more amino acids can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, the cell culture media is supplemented with one or more amino acids wherein each of the one or more amino acids is supplemented in an amount of between about 0.025 and 20 g/L, or between about 0.05 and 15 g/L, or between about 0.1 and 14 g/L, or between about 0.2 and 13 g/L, or between about 0.25 and 12 g/L, or between about 0.5 and 11 g/L, or between about 1 and 10 g/L, or between about 1.5 and 9.5 g/L, or between about 2 and 9 g/L, or between about 2.5 and 8.5 g/L, or between about 3 and 8 g/L, or between about 3.5 and 7.5 g/L, or between about 4 and 7 g/L, or between about 4.5 and 6.5 g/L, or between about 5 and 6 g/L. In certain embodiments, the cell culture media is supplemented with one or more amino acids wherein each of the one or more amino acids is supplemented in an amount of about 0.5 g/L, or about 1 g/L, or about 2 g/L, or about 4 g/L, or about 8 g/L.

In certain embodiments, the cell culture media is supplemented with one or more amino acids wherein each of the one or more amino acids is supplemented in an amount effective to reduce the amount of one or more lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In certain embodiments, the cell culture media is supplemented with one or more amino acids wherein each of the one or more amino acids is supplemented in an amount effective to increase the amount of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition.

In certain embodiments, the cell culture media is supplemented with one or more amino acids wherein each of the one or more amino acids is supplemented in an amount effective to reduce the amount of a Lys 0 lysine variant, and to increase the amount of a Lys 1 and/or Lys 2 lysine variant expressed by the cell culture.

In certain embodiments, the one or more amino acids used to supplement the cell culture media is arginine, lysine, histidine, or combinations of arginine or lysine with ornithine. In certain embodiments, the amino acids are provided as single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids.

For example, and not by way of limitation, as detailed in Example 2, below, when the production medium employed in the example was supplemented with 3 g/L arginine and 3 g/L lysine, the % Lys 0 of an adalimumab sample purified from the supplemented culture was reduced to 72.1% from a control amount of 86.7%. Additionally, the amounts of Lys 1 and Lys 2 in the adalimumab sample was increased to 20.8% (Lys 1) and 7.1% (Lys 2) from an adalimumab sample purified from a control culture having 11.1% Lys 1 and 2.2% Lys 2.

Similarly, although the percentage of Lys 0 relative to lysine sum in the control sample was 82.9% on day 10, in the sample with the highest concentration of arginine in this experiment (9 g/L), the percentage of relative Lys 0 was reduced to 73.4%. This relative modulation of Lys 0, Lys 1 and Lys 2 was directly related to the concentration of arginine in the media. Thus, in certain embodiments, the relative level of Lys 0 to lysine sum can be modulated, i.e., increased or decreased, by adjusting the concentration of arginine in the culture media.

In certain embodiments, a lysine supplementation of cell culture is employed to modulate the ratio of Lys 0 to lysine sum. As detailed Example 2, below, in the sample with the highest concentration of lysine (11 g/L), the percentage of relative levels of Lys 0 was reduced to 67.7%, which contrasts with the percentage of Lys 0 relative to lysine sum (sum of the peak areas corresponding to Lys 0, Lys 1 and Lys 2) in the control sample of 92.5%. A dose dependent decrease in relative Lys 0, and a dose dependent increase in relative Lys 1 and Lys 2 regions was observed in test conditions with increased lysine concentration. Thus, in certain embodiments, the relative level of Lys 0 to lysine sum can be modulated, i.e., increased or decreased, by adjusting the concentration of lysine in the culture media.

In certain embodiments, a histidine supplementation of cell culture is employed to modulate the ratio of Lys 0 to lysine sum. As detailed Example 2, below, in the sample with the highest concentration of histidine (10 g/L), the percentage of relative Lys 0 was reduced to 80.6% from a control sample percentage of 92.5%. The decrease in Lys 0 corresponded with the increase in relative levels of both Lys 1 and Lys 2. In an alternative example, the percentage of Lys 0 relative to lysine sum in the control sample was 94.2%. In the sample with the highest concentration of histidine in this experiment (8 g/L), the percentage of relative Lys 0 was reduced to 81.5%. The decrease in Lys 0 corresponded with the increase in relative levels of both Lys 1 and Lys 2. A dose dependent decrease in relative Lys 0, and a dose dependent increase in relative Lys 1 and Lys 2 regions was observed in test conditions with increased histidine concentration. Thus, in certain embodiments, the relative level of Lys 0 to lysine sum can be modulated, i.e., increased or decreased, by adjusting the concentration of histidine in the culture media.

In certain embodiments, an ornithine/arginine or ornithine/lysine supplementation of cell culture is employed to modulate the ratio of Lys 0 to lysine sum. As detailed Example 2, below, the combination of ornithine with arginine or lysine reduced the relative level of Lys 0 to 81.9% in comparison with the condition with just arginine and lysine increase with a relative level Lys 0 of 84.7%. Thus, the increase of ornithine may exhibit synergistic effects in modulating lysine variant distribution when added in combination with arginine and lysine. Thus, in certain embodiments, the relative level of Lys 0 to lysine sum can be modulated, i.e., increased or decreased, by adjusting the concentration of a combination of ornithine and either arginine and/or lysine in the culture media.

In certain embodiments, an arginine/lysine/histidine/ornithine combination supplementation of cell culture is employed to modulate the ratio of Lys 0 to lysine sum. As detailed in Example 2, below, in comparison to the lower concentrations, or conditions where amino acids were supplemented individually, a further reduction in Lys 0 relative to lysine sum was observed in conditions where combinations of amino acids were increased in the media. A progressive decrease was observed in relative Lys 0 when more amino acids were increased in combination. The percentage of relative Lys 0 was reduced from 94.9% in the control sample to 73.9% in the sample with all four amino acid concentrations increased. Thus, in certain embodiments, the relative level of Lys 0 to lysine sum can be modulated, i.e., increased or decreased, by adjusting the concentration of a combination of all four amino acids (arginine, lysine, histidine, and ornithine) in the culture media.

In certain embodiments, the three amino acid monomers arginine, lysine, and histidine, the dipeptides lys-lys and arg-lys, or the tripeptides lys-lys-lys, his-arg-lys, and arg-his-lys are used as supplements to cell culture in order to modulate the ratio of Lys 0 to lysine sum. As detailed in Example 2, below, in comparison to the control, a reduction in Lys 0 relative to lysine sum was also observed in conditions where dipeptides and tripeptides were supplemented to the media. Specifically, a decrease was observed in relative Lys 0 when polypeptides were supplemented. The percentage of relative Lys 0 was reduced from 88.0% in the control sample to 71.9% in a sample supplemented with tripeptide arg-his-lys (4 g/L), and to 74.0% in a sample supplemented with his-arg-lys (2 g/L).

In certain embodiments, the medium supplements described herein are such that they can be included in the medium at the start of culture, or can be added in a fed-batch or in a continuous manner. The medium supplements could be supplemented to chemically defined or hydrolysate based basal media. The methods described in this invention may be used in combination with different cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. The methods described here may also be combined with the appropriate choice of process parameters as described herein.

Adjusting Phosphate Concentration to Control Lysine Variation

In certain embodiments of the instant invention, control of C-terminal lysine variants in a composition comprising an antibody, or antigen binding portion thereof, can be attained by adjustment of the phosphate concentration of the media employed in the cell culture run. In one non-limiting embodiment, such adjustment will be to increase the amount of phosphate in the media, while in other non-limiting embodiments, the necessary adjustment to achieve the desired control over lysine variant heterogeneity will involve an decrease in the amount of phosphate in the media. Such increases or decreases in the amount of phosphate can be of a magnitude of about 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, the cell culture media is supplemented with phosphate in an amount of between about 6 and 24 mM, or between about 0.05 and 22 mM, or between about 0.1 and 20 mM, or between about 0.2 and 18 mM, or between about 0.25 and 16 mM, or between about 0.5 and 14 mM, or between about 1 and 12 mM, or between about 1.5 and 10 mM, or between about 2 and 8 mM, or between about 2.5 and 6 mM, or between about 3 and 4 mM, In certain embodiments, the cell culture media contains phosphate in an amount effective to reduce the amount of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In certain embodiments, the cell culture media contains phosphate in an amount effective to increase the amount of one or more C-terminal lysine variants (Lys 0, Lys 1, or Lys 2) in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition.

In certain embodiments, the cell culture media contains phosphate in an amount effective to reduce the amount of a Lys 0 lysine variant, and to increase the amount of a Lys 1 and/or Lys 2 lysine variant expressed by the cell culture.

In certain embodiments, a phosphate supplementation of cell culture is employed to modulate the ratio of Lys 0 to lysine sum. As detailed Example 4, below, in the sample with the highest concentration of phosphate supplementation (24 mM), the percentage of relative levels of Lys 0 was reduced to 85.7%, which contrasts with the percentage of Lys 0 relative to lysine sum (sum of the peak areas corresponding to Lys 0, Lys 1 and Lys 2) in the control sample of 91.3%. A dose dependent decrease in relative Lys 0, and a dose dependent increase in relative Lys 1 and Lys 2 regions was observed in test conditions with increased phosphate concentration. Thus, in certain embodiments, the relative level of Lys 0 to lysine sum can be modulated, i.e., increased or decreased, by adjusting the concentration of phosphate in the culture media.

In certain embodiments, the cell culture contains phosphate as well as arginine, lysine, and zinc, each at a concentration sufficient to reduce the amount of a Lys 0 lysine variant, and to increase the amount of a Lys 1 and/or Lys 2 lysine variant expressed by the cell culture. For example, but not by way of limitation, the concentration range for arginine can be between 6.0 mM to about 19.9 mM, and the concentration range for lysine can be between about 4.0 to about 15.5 mM, while the concentration range for zinc is between about 10 to about 40 µM and the concentration range for phosphate is about 5.8 to 17.8 mM.

Adjusting Process Parameters to Control Lysine Variation

The variation in the process parameters, such as the temperature, dissolved oxygen (DO) concentration, and/or pH, at which cells are cultured, can vary product quality significantly. In certain embodiments of the instant invention, control of C-terminal lysine variant heterogeneity can be attained by adjustment of the temperature, DO concentration, phosphate concentration, and/or pH of the cell culture run. In certain embodiments, such adjustment will be to increase the temperature, DO concentration, phosphate concentration, and/or pH at which a cell culture is cultured, while in other embodiments the necessary adjustment to achieve the desired control over lysine variant heterogeneity will involve a modulation of the temperature, DO concentration, phosphate concentration, and/or pH at which a cell culture is cultured. Such increases or decreases in cell culture temperature, DO concentration, phosphate concentration, and/or pH can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original temperature DO concentration, and/or pH.

In certain embodiments, the cell culture is cultured at a temperature of between about 25 and 50° C., or between about 30° C. and 40° C., or between about 31° C. and 39° C., or between about 31.5° C. and 38.5° C., or between about 32° C. and 38° C., or between about 32.5° C. and 37.5° C., or between about 33° C. and 37° C., or between about 33.5° C. and 36.5° C., or between about 34° C. and 36° C., or between about 34.5° C. and 35.5° C. In certain embodiments, the cell culture is cultured at a temperature of about 30° C., 31° C., 32° C., 33° C., 34° C., 35° C., 36° C., or 37° C.

For example, and not by way of limitation, as detailed in Example 3, below, when the temperature of a cell culture run was decreased from 37° C. to 31° C., the % Lys 0 of an adalimumab sample purified from the culture was reduced from 84.9% to 72.8%. Additionally, the amounts of Lys 1 and Lys 2 in the adalimumab sample was increased from 13.4% (Lys 1) and 1.7% (Lys 2), to 22.2% (Lys 1) and 5.0% (Lys 2). Thus, in certain embodiments, the relative level of Lys 0 to lysine sum can be modulated, i.e., increased or decreased, by adjusting the temperature of the cell culture run.

In certain embodiments, but not by way of limitation, DO concentrations maintained above 15%, e.g., between about 30% and about 50% or at about 80%, can be used to achieve the desired change in lysine sum distribution.

For example, and not by way of limitation, as detailed in Example 3, below, when the DO concentration in a cell culture run was assessed at 20% and 50%, at a temperature of 35° C., the relative fraction of Lys 0 decreased from 84.8% at 20% DO to 81.0% at 50% DO, with a corresponding 3.2% increase in relative levels of Lys 1 and 0.7% increase in Lys 2. Thus, in certain embodiments, the relative level of Lys 0 to lysine sum can be modulated, i.e., increased or decreased, by adjusting the DO concentration of the cell culture run.

In certain embodiments, pH is either increased or decreased in order to increase or decrease the amount of Lys 0 relative to the lysine sum. For example, but not by way of limitation, a reduction in pH to 6.7 from a control pH of 7.1 can be employed to increase the amount of Lys 0 relative to the lysine sum.

For example, and not by way of limitation, as detailed in Example 3, below, when the pH of a cell culture run was decreased from 7.1 to 6.7, the % Lys 0 of an adalimumab sample purified from the culture was increased from 82.0% to 88.7%. In certain embodiments the pH is increased from 6.7 to 6.8, 6.9, 7.0, or 7.1 in order to achieve a decrease in the amount of Lys 0 relative to the lysine sum.

In certain embodiments, the temperature, DO concentration, and/or pH of the cell culture is decreased or increased in an amount effective to reduce the amount of one or more lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are reduced by about 1% to about 25%, about 5% to about 20%, about 5% to about 15%, or about 5% to about 10%, and ranges within one or more of the preceding, as compared to a non-modulated lysine variant species composition.

In certain embodiments, the temperature, DO concentration, and/or pH of the cell culture is decreased or increased in an amount effective to increase the amount of one or more lysine variants in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, as compared to a non-modulated lysine variant species composition. In one aspect of this embodiment, the percentage of Lys 0, Lys 1, or Lys 2 variants are increased by about 1% to about 25%, about 5% to about 20%, about 5% to about 15%, or about 5% to about 10%, and ranges within one or more of the preceding, as compared to a non-modulated lysine variant species composition.

In certain embodiments, the temperature, DO concentration, and/or pH of the cell culture is decreased or increased in an amount effective to reduce the amount of a Lys 0 lysine variant, and to increase the amount of a Lys 1 and/or Lys 2 lysine variant expressed by the cell culture.

Additional Exemplary Strategies

In addition to the above-described embodiments, the present invention is also directed to embodiments wherein the medium supplements described herein are added in a batch-wise fashion, a continuous feeding fashion, or a combination of both during cell culture. In addition, certain embodiments will involve the adding such media supplements one at a time and/or addition at multiple time points during the cell culture process. In certain embodiments, the cell culture process will involve preloading the culture media with excess of one or more medium supplements. In certain embodiments, the addition of one or more supplements will be based on measurements taken on-line, in-line, and/or at line. In certain embodiments, the addition of one or more supplements will occur with other substrates, metal scavengers, and/or combination with other culture conditions such as temperature, DO concentration, phosphate concentration, pH, etc. In certain embodiments, one or more media supplements will be added as multimers, e.g., arg-arg, his-his, arg-his-orn, etc., and/or as chemical variants of amino acids or analogs of amino acids, salt forms of amino acids, controlled release of amino acids by immobilizing in gels, etc, and/or in fully or partially dissolved form.

In certain embodiments, the culture process will occur in bags, flasks, disposables, hollow fiber, perfusion, and/or air lift process equipment. In certain embodiments, one or more media supplements will be added to seed bioreactor before transfer to achieve a final concentration in the fermentor. In certain embodiments, achieving a known concentration of one or more of the media supplements can occur either through an in-situ combination resulting the generation of the supplement or a degradation/reaction resulting the generation of the supplement, i.e., adding a substrate and enzyme/catalyst to produce the components necessary. In certain embodiments the addition of one or more media supplement will based on measured amount of lysine distribution.

IV. Protein Purification

Protein Purification Generally

In certain embodiments, the methods for producing the modulated lysine variant species compositions of the present invention can be used in combination with techniques for protein purification to provide for the production of a purified protein preparation, for example, a preparation comprising an antibody or an antigen binding fragment thereof, from a mixture comprising a protein and at least one process-related impurity or product-related substance (e.g., acidic species).

For example, but not by way of limitation, once a clarified solution or mixture comprising the protein of interest, for example, an antibody or antigen binding fragment thereof, has been obtained, separation of the protein of interest from the process-related impurities and/or product-related substances (e.g., acidic species) can be effected using a combination of different purification techniques, including, but not limited to, affinity separation steps, ion exchange separation steps, mixed mode separation steps, and hydrophobic interaction separation steps, singly or in combination. The separation steps separate mixtures of proteins on the basis of their charge, degree of hydrophobicity, or size depending upon the particular form of separation, including chromatographic separation. In one aspect of the invention, separation is performed using chromatography, including cationic, anionic, and hydrophobic interaction. Several different chromatography resins are commercially available for each of these techniques, allowing accurate tailoring of the purification scheme to the particular protein involved. The essence of each of the separation methods is that proteins can be caused either to traverse at different rates through a column's resin, achieving a physical separation that increases as they pass further through the column, or to adhere selectively to a column's separation resin, and then differentially eluted using different eluents. In some cases, the antibody is separated from impurities when the impurities specifically adhere to the column's resin and the antibody does not, i.e., the antibody is contained in the eluent, while in other cases the antibody of interest will adhere to the column's resin, while impurities and/or product-related substances are extruded from the column during a wash cycle.

As noted above, accurate tailoring of a purification scheme relies on consideration of the protein to be purified. In certain embodiments, the separation steps employed in connection with the cell culture methods of the instant invention facilitate the separation of an antibody from one or more process-related impurity (acidic or basic species) and/or product-related substance. Antibodies that can be successfully purified using the methods described herein include, but are not limited to, human IgA1, IgA2, IgD, IgE, IgG1, IgG2, IgG3, IgG4, and IgM antibodies. In certain embodiments, Protein A affinity chromatography can be useful. However, IgG3 antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

Methods for purification of proteins, e.g., antibodies, are described in detail in (U.S. Patent Application Ser. No. 61/893,068), filed on Oct. 18, 2013, the contents of which are expressly incorporated herein by reference.

Primary Recovery and Virus Inactivation

In certain embodiments, it will be advantageous to subject a sample produced by the techniques of the instant invention to at least a first phase of clarification and primary recovery. In addition, the primary recovery process can also be a point at which to reduce or inactivate viruses that can be present in the sample mixture. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire contents of which are incorporated herein by reference.

The primary recovery may also include one or more centrifugation steps to further clarify the sample mixture and thereby aid in purifying the protein of interest. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery may also include the use of one or more depth filtration steps to further clarify the sample matrix and thereby aid in purifying the antibodies produced using the cell culture techniques of the present invention. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments, the depth filtration step can be a delipid depth filtration step. Although certain embodiments employ depth filtration steps only during the primary recovery phase, other embodiments employ depth filters, including delipid depth filters, during one or more additional phases of purification. Non-limiting examples of depth filters that can be used in the context of the instant invention include the Cuno™ model 30/60ZA depth filters (3M Corp.), and 0.45/0.2 μm Sartopore™ bi-layer filter cartridges.

Affinity Chromatography

In certain embodiments, it will be advantageous to subject a modulated Lysine sample produced by the methods of the instant invention to affinity chromatography to further purify the protein of interest away from process-related impurities and/or product-related substances. In certain embodiments the chromatographic material is capable of selectively or specifically binding to the protein of interest. Non-limiting examples of such chromatographic material include: Protein A, Protein G, chromatographic material comprising, for example, an antigen bound by an antibody of interest, and chromatographic material comprising an Fc binding protein. In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin is MabSelect™ from GE Healthcare. A non-limiting example of a suitable column packed with Mab-Select™ is an about 1.0 cm diameter×about 21.6 cm long column (~17 ml bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™.

Ion Exchange Chromatography

In certain embodiments, it will be advantageous to subject a modulated Lysine sample produced by the methods of the instant invention to ion exchange chromatography in order to purify the protein of interest away from process-related impurities and/or product-related substances. Ion exchange separation includes any method by which two substances are separated based on the difference in their respective ionic charges, and can employ either cationic exchange material or anionic exchange material. For example, the use of a cationic exchange material versus an anionic exchange material is based on the localized charges of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial protein mixture can be contacted with the ion exchange material by using any of a variety of techniques, e.g., using a batch purification technique or a chromatographic technique.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange resins such as DE23™, DE32™ DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Fe all available from Pharmacia AB. Further, both DEAE and CM derivitized ethylene glycol-methacrylate copolymer such as TOYOPEARL™ DEAE-6505 or M and TOYOPEARL™ CM-650S or M are available from Toso Haas Co., Philadelphia, Pa.

Ultrafiltration/Diafiltration

In certain embodiments, it will be advantageous to subject a modulated Lysine sample produced by the methods of the instant invention to ultrafiltration and/or diafiltration in order to purify the protein of interest away from process-related impurities and/or product-related substances. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). One filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 µm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained protein. In certain embodiments of the present invention, a diafiltration step is employed to exchange the various buffers used in connection with the instant invention, optionally prior to further chromatography or other purification steps, as well as to remove impurities from the protein preparations.

Hydrophobic Interaction Chromatography

In certain embodiments, it will be advantageous to subject a modulated Lysine sample produced by the methods of the instant invention to hydrophobic interaction chromatography in order to purify the protein of interest away from process-related impurities and/or product-related substances. For example, a first eluate obtained from an ion exchange column can be subjected to a hydrophobic interaction material such that a second eluate having a reduced level of impurity is obtained. Hydrophobic interaction chromatography (HIC) steps, such as those disclosed herein, are generally performed to remove protein aggregates, such as antibody aggregates, and process-related impurities.

In performing an HIC-based separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

Whereas ion exchange chromatography relies on the charges of the protein to isolate them, hydrophobic interaction chromatography uses the hydrophobic properties of the protein. Hydrophobic groups on the protein interact with hydrophobic groups on the column. The more hydrophobic a protein is the stronger it will interact with the column. Thus the HIC step removes host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the protein of interest to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}$; $Ca^{++}$; $Mg^{++}$; $Li^+$; $Cs^+$; $Na^+$; $K^+$; $Rb^+$; $NH4^+$, while anions may be ranked in terms of increasing chaotropic effect as $PO^{---}$; $SO_4^{--}$; $CH_3CO_3^-$; $Cl^-$; $Br^-$; $NO_3^-$; $ClO_4^-$; $I^-$; $SCN^-$.

In general, Na, K or $NH_4$ sulfates effectively promote ligand-protein interaction in HIC. Salts may be formulated that influence the strength of the interaction as given by the following relationship: $(NH_4)_2SO_4$>$Na_2SO_4$>NaCl> $NH_4Cl$>NaBr>NaSCN. In general, salt concentrations of between about 0.75 and about 2 M ammonium sulfate or between about 1 and 4 M NaCl are useful.

HIC columns normally comprise a base matrix (e.g., cross-linked agarose or synthetic copolymer material) to which hydrophobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Mehyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, Pa.).

Multimodal Chromatography

In certain embodiments, it will be advantageous to subject a modulated Lysine sample produced by the methods of the instant invention to multimodal chromatography in order to purify the protein of interest away from process-related impurities and/or product-related substances. Multimodal chromatography is chromatography that utilizes a multimodal media resin. Such a resin comprises a multimodal chromatography ligand. In certain embodiments, such a ligand refers to a ligand that is capable of providing at least two different, but co-operative, sites which interact with the substance to be bound. One of these sites gives an attractive type of charge-charge interaction between the ligand and the substance of interest. The other site typically gives electron acceptor-donor interaction and/or hydrophobic and/or hydrophilic interactions. Electron donor-acceptor interactions include interactions such as hydrogen-bonding, π-π, cation-π, charge transfer, dipole-dipole, induced dipole etc. Multimodal chromatography ligands are also known as "mixed mode" chromatography ligands.

In certain embodiments, the multimodal chromatography resin is comprised of multimodal ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

V. Methods of Treatment Using the Modulated Lysine Variant Species Compositions of the Invention The modulated lysine variant species compositions of the invention may be used to treat any disorder in a subject for which the therapeutic protein comprised in the composition is appropriate for treating.

A "disorder" is any condition that would benefit from treatment with the protein. This includes chronic and acute disorders or diseases including those pathological conditions which predispose the subject to the disorder in question. In the case of an anti-TNFα antibody, or antigen binding portion thereof, such as adalimumab, a therapeutically effective amount of the modulated lysine variant species composition may be administered to treat a disorder in which TNFα activity is detrimental.

A disorder in which TNFα activity is detrimental includes a disorder in which inhibition of TNFα activity is expected to alleviate the symptoms and/or progression of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody.

TNFα has been implicated in the pathophysiology of a wide variety of a TNFα-related disorders including sepsis, infections, autoimmune diseases, transplant rejection and graft-versus-host disease (see e.g., Moeller, A., et al. (1990) *Cytokine* 2:162-169; U.S. Pat. No. 5,231,024 to Moeller et al.; European Patent Publication No. 260 610 B1 by Moeller, A., et al. Vasilli, P. (1992) *Annu. Rev. Immunol.* 10:411-452; Tracey, K. J. and Cerami, A. (1994) *Annu. Rev. Med.* 45:491-503). Accordingly, the modulated lysine variant species compositions or a low process-related impurity compositions of the invention may be used to treat an autoimmune disease, such as rheumatoid arthritis, juvenile idiopathic arthritis, or psoriatic arthritis, an intestinal disorder, such as Crohn's disease or ulcerative colitis, a spondyloarthropathy, such as ankylosing spondylitis, or a skin disorder, such as psoriasis.

Disorders in which TNFα activity is detrimental are well known in the art and described in detail in U.S. Pat. Nos. 8,231,876 and 6,090,382, the entire contents of each of which are expressly incorporated herein by reference. In one embodiment, "a disorder in which TNFα activity is detrimental" includes sepsis (including septic shock, endotoxic shock, gram negative sepsis and toxic shock syndrome), autoimmune diseases (including rheumatoid arthritis, rheumatoid spondylitis, osteoarthritis and gouty arthritis, allergy, multiple sclerosis, autoimmune diabetes, autoimmune uveitis, nephrotic syndrome, multisystem autoimmune diseases, lupus (including systemic lupus, lupus nephritis and lupus cerebritis), Crohn's disease and autoimmune hearing loss), active axial spondyloarthritis (active axSpA) and non-radiographic axial spondyloarthritis (nr-axSpA), infectious diseases (including malaria, meningitis, acquired immune deficiency syndrome (AIDS), influenza and cachexia secondary to infection), allograft rejection and graft versus host disease, malignancy, pulmonary disorders (including adult respiratory distress syndrome (ARDS), shock lung, chronic pulmonary inflammatory disease, pulmonary sarcoidosis, pulmonary fibrosis, silicosis, idiopathic interstitial lung disease and chronic obstructive airway disorders (COPD), such as asthma), intestinal disorders (including inflammatory bowel disorders, idiopathic inflammatory bowel disease, Crohn's disease and Crohn's disease-related disorders (including fistulas in the bladder, vagina, and skin; bowel obstructions; abscesses; nutritional deficiencies; complications from corticosteroid use; inflammation of the joints; erythem nodosum; pyoderma gangrenosum; lesions of the eye, Crohn's related arthralgias, fistulizing Crohn's indeterminant colitis and pouchitis), cardiac disorders (including ischemia of the heart, heart insufficiency, restenosis, congestive heart failure, coronary artery disease, angina pectoris, myocardial infarction, cardiovascular tissue damage caused by cardiac arrest, cardiovascular tissue damage caused by cardiac bypass, cardiogenic shock, and hypertension, atherosclerosis, cardiomyopathy, coronary artery spasm, coronary artery disease, valvular disease, arrhythmias, and cardiomyopathies), spondyloarthropathies (including ankylosing spondylitis, psoriatic arthritis/spondylitis, enteropathic arthritis, reactive arthritis or Reiter's syndrome, and undifferentiated spondyloarthropathies), metabolic disorders (including obesity and diabetes, including type 1 diabetes mellitus, type 2 diabetes mellitus, diabetic neuropathy, peripheral neuropathy, diabetic retinopathy, diabetic ulcerations, retinopathy ulcerations and diabetic macrovasculopathy), anemia, pain (including acute and chronic pains, such as neuropathic pain and post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis), hepatic disorders (including hepatitis, alcoholic hepatitis, viral hepatitis, alcoholic cirrhosis, a1 antitypsin deficiency, autoimmune cirrhosis, cryptogenic cirrhosis, fulminant hepatitis, hepatitis B and C, and steatohepatitis, cystic fibrosis, primary biliary cirrhosis, sclerosing cholangitis and biliary obstruction), skin and nail disorders (including psoriasis (including chronic plaque psoriasis, guttate psoriasis, inverse psoriasis, pustular psoriasis and other psoriasis disorders), pemphigus vulgaris, scleroderma, atopic dermatitis (eczema), sarcoidosis, erythema nodosum, hidradenitis suppurative, lichen planus, Sweet's syndrome, scleroderma and vitiligo), vasculitides (including Behcet's disease), and other disorders, such as juvenile rheumatoid arthritis (JRA), endometriosis, prostatitis, choroidal neovascularization, sciatica, Sjogren's syndrome, uveitis, wet macular degeneration, osteoporosis and osteoarthritis.

As used herein, the term "subject" is intended to include living organisms, e.g., prokaryotes and eukaryotes. Examples of subjects include mammals, e.g., humans, dogs, cows, horses, pigs, sheep, goats, cats, mice, rabbits, rats, and transgenic non-human animals. In specific embodiments of the invention, the subject is a human.

As used herein, the term "treatment" or "treat" refers to both therapeutic treatment and prophylactic or preventative measures. Those in need of treatment include those already with the disorder, as well as those in which the disorder is to be prevented.

In one embodiment, the invention provides a method of administering a modulated lysine variant species composition comprising an anti-TNFα antibody, or antigen binding portion thereof, to a subject such that TNFα activity is inhibited or a disorder in which TNFα activity is detrimental is treated. In one embodiment, the TNFα is human TNFα and the subject is a human subject. In one embodiment, the anti-TNFα antibody is adalimumab.

The modulated lysine variant species compositions can be administered by a variety of methods known in the art. Exemplary routes/modes of administration include subcutaneous injection, intravenous injection or infusion. In certain aspects, a modulated lysine variant species compositions may be orally administered. As will be appreciated by the skilled artisan, the route and/or mode of administration will vary depending upon the desired results.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a modulated lysine variant species composition of the invention is 0.01-20 mg/kg, or 1-10 mg/kg, or 0.3-1 mg/kg. With respect to modulated lysine variant species compositions comprising an anti-TNFα antibody, or antigen-binding portion thereof, such as adalimumab, an exemplary dose is 40 mg every other week. In some embodiments, in particular for treatment of ulcerative colitis or Crohn's disease, an exemplary dose includes an initial dose (Day 1) of 160 mg (e.g., four 40 mg injections in one day or two 40 mg injections per day for two consecutive days), a second dose two weeks later of 80 mg, and a maintenance dose of 40 mg every other week beginning two weeks later. Alternatively, for psoriasis for example, a dosage can include an 80 mg initial dose followed by 40 mg every other week starting one week after the initial dose.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

VI. Pharmaceutical Formulations Containing the Modulated Lysine Variant Species Compositions of the Invention The present invention further provides preparations and formulations comprising the modulated lysine variant species compositions of the invention. It should be understood that any of the antibodies and antibody fragments described herein, including antibodies and antibody fragments having any one or more of the structural and functional features described in detail throughout the application, may be formulated or prepared as described below. When various formulations are described in this section as including an antibody, it is understood that such an antibody may be an antibody or an antibody fragment having any one or more of the characteristics of the antibodies and antibody fragments described herein. In one embodiment, the antibody is an anti-TNFα antibody, or antigen-binding portion thereof.

In certain embodiments, the modulated lysine variant species compositions of the invention may be formulated with a pharmaceutically acceptable carrier as pharmaceutical (therapeutic) compositions, and may be administered by a variety of methods known in the art. As will be appreciated by the skilled artisan, the route and/or mode of administration will vary depending upon the desired results. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also routinely contain compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the antibodies of the present invention, and with each other, in a manner such that there is no interaction which would substantially impair the desired pharmaceutical efficacy.

The modulated lysine variant species compositions of the invention are present in a form known in the art and acceptable for therapeutic uses. In one embodiment, a formulation of the modulated lysine variant species compositions of the invention is a liquid formulation. In another embodiment, a formulation of the modulated lysine variant species compositions of the invention is a lyophilized formulation. In a further embodiment, a formulation of the modulated lysine variant species compositions of the invention is a reconstituted liquid formulation. In one embodiment, a formulation of the modulated lysine variant species compositions of the invention is a stable liquid formulation. In one embodiment, a liquid formulation of the modulated lysine variant species compositions of the invention is an aqueous formulation. In another embodiment, the liquid formulation is non-aqueous. In a specific embodiment, a liquid formulation of the modulated lysine variant species compositions of the invention is an aqueous formulation wherein the aqueous carrier is distilled water.

The formulations of the modulated lysine variant species compositions of the invention comprise an antibody in a concentration resulting in a w/v appropriate for a desired dose. The antibody may be present in the formulation at a concentration of about 1 mg/ml to about 500 mg/ml, e.g., at a concentration of at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 200 mg/ml, at least 250 mg/ml, or at least 300 mg/ml.

In a specific embodiment, a formulation of the modulated lysine variant species compositions of the invention comprises at least about 100 mg/ml, at least about 125 mg/ml, at least 130 mg/ml, or at least about 150 mg/ml of an antibody of the invention.

In one embodiment, the concentration of antibody, which is included in the formulation of the invention, is between about 1 mg/ml and about 25 mg/ml, between about 1 mg/ml and about 200 mg/ml, between about 25 mg/ml and about 200 mg/ml, between about 50 mg/ml and about 200 mg/ml, between about 75 mg/ml and about 200 mg/ml, between about 100 mg/ml and about 200 mg/ml, between about 125 mg/ml and about 200 mg/ml, between about 150 mg/ml and about 200 mg/ml, between about 25 mg/ml and about 150 mg/ml, between about 50 mg/ml and about 150 mg/ml, between about 75 mg/ml and about 150 mg/ml, between about 100 mg/ml and about 150 mg/ml, between about 125 mg/ml and about 150 mg/ml, between about 25 mg/ml and about 125 mg/ml, between about 50 mg/ml and about 125 mg/ml, between about 75 mg/ml and about 125 mg/ml, between about 100 mg/ml and about 125 mg/ml, between about 25 mg/ml and about 100 mg/ml, between about 50 mg/ml and about 100 mg/ml, between about 75 mg/ml and about 100 mg/ml, between about 25 mg/ml and about 75 mg/ml, between about 50 mg/ml and about 75 mg/ml, or between about 25 mg/ml and about 50 mg/ml.

In a specific embodiment, a formulation of the modulated lysine variant species compositions of the invention comprises between about 90 mg/ml and about 110 mg/ml or between about 100 mg/ml and about 210 mg/ml of an antibody.

The formulations of the modulated lysine variant species compositions of the invention comprising an antibody may further comprise one or more active compounds as necessary for the particular indication being treated, including those with complementary activities that do not adversely affect each other. Such additional active compound/s is/are suitably present in combination in amounts that are effective for the purpose intended.

The formulations of the modulated lysine variant species compositions of the invention may be prepared for storage by mixing the antibody having the desired degree of purity with optional physiologically acceptable carriers, excipients or stabilizers, including, but not limited to buffering agents, saccharides, salts, surfactants, solubilizers, polyols, diluents, binders, stabilizers, salts, lipophilic solvents, amino acids, chelators, preservatives, or the like (Goodman and Gilman's The Pharmacological Basis of Therapeutics, $12^{th}$ edition, L. Brunton, et al. *Remington's Pharmaceutical Sciences,* 16th edition, Osol, A. Ed. (1999)), in the form of lyophilized formulations or aqueous solutions at a desired final concentration. Acceptable carriers, excipients, or stabilizers are nontoxic to recipients at the dosages and concentrations employed, and include buffers such as histidine, phosphate, citrate, glycine, acetate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrolidone; amino acids such as glycine, glutamine, asparagine, histidine, arginine, or lysine; monosaccharides, disaccharides, and other carbohydrates including trehalose, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, polysorbate 80, PLURONICS™ or polyethylene glycol (PEG).

The buffering agent may be histidine, citrate, phosphate, glycine, or acetate. The saccharide excipient may be trehalose, sucrose, mannitol, maltose or raffinose. The surfactant may be polysorbate 20, polysorbate 40, polysorbate 80, or Pluronic F68. The salt may be NaCl, KCl, $MgCl_2$, or $CaCl_2$ The formulations of the modulated lysine variant species compositions of the invention may include a buffering or pH adjusting agent to provide improved pH control. A formulation of the invention may have a pH of between about 3.0 and about 9.0, between about 4.0 and about 8.0, between about 5.0 and about 8.0, between about 5.0 and about 7.0, between about 5.0 and about 6.5, between about 5.5 and about 8.0, between about 5.5 and about 7.0, or between about 5.5 and about 6.5. In a further embodiment, a formulation of the invention has a pH of about 3.0, about 3.5, about 4.0, about 4.5, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.5, about 8.0, about 8.5, or about 9.0. In a specific embodiment, a formulation of the invention has a pH of about 6.0. One of skill in the art understands that the pH of a formulation generally should not be equal to the isoelectric point of the particular antibody to be used in the formulation.

Typically, the buffering agent is a salt prepared from an organic or inorganic acid or base. Representative buffering agents include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. In addition, amino acid components can also function in a buffering capacity. Representative amino acid components which may be utilized in the formulations of the invention as buffering agents include, but are not limited to, glycine and histidine. In certain embodiments, the buffering agent is chosen from histidine, citrate, phosphate, glycine, and acetate. In a specific embodiment, the buffering agent is histidine. In another specific embodiment, the buffering agent is citrate. In yet another specific embodiment, the buffering agent is glycine. The purity of the buffering agent should be at least 98%, or at least 99%, or at least 99.5%. As used herein, the term "purity" in the context of histidine and glycine refers to chemical purity of histidine or glycine as understood in the art, e.g., as described in The Merck Index, 13$^{th}$ ed., O'Neil et al. ed. (Merck & Co., 2001).

Buffering agents are typically used at concentrations between about 1 mM and about 200 mM or any range or value therein, depending on the desired ionic strength and the buffering capacity required. The usual concentrations of conventional buffering agents employed in parenteral formulations can be found in: Pharmaceutical Dosage Form: Parenteral Medications, Volume 1, 2$^{nd}$ Edition, Chapter 5, p. 194, De Luca and Boylan, "Formulation of Small Volume Parenterals", Table 5: Commonly used additives in Parenteral Products. In one embodiment, the buffering agent is at a concentration of about 1 mM, or of about 5 mM, or of about 10 mM, or of about 15 mM, or of about 20 mM, or of about 25 mM, or of about 30 mM, or of about 35 mM, or of about 40 mM, or of about 45 mM, or of about 50 mM, or of about 60 mM, or of about 70 mM, or of about 80 mM, or of about 90 mM, or of about 100 mM. In one embodiment, the buffering agent is at a concentration of 1 mM, or of 5 mM, or of 10 mM, or of 15 mM, or of 20 mM, or of 25 mM, or of 30 mM, or of 35 mM, or of 40 mM, or of 45 mM, or of 50 mM, or of 60 mM, or of 70 mM, or of 80 mM, or of 90 mM, or of 100 mM. In a specific embodiment, the buffering agent is at a concentration of between about 5 mM and about 50 mM. In another specific embodiment, the buffering agent is at a concentration of between 5 mM and 20 mM.

In certain embodiments, the formulation of the modulated lysine variant species compositions of the invention comprises histidine as a buffering agent. In one embodiment the histidine is present in the formulation of the invention at a concentration of at least about 1 mM, at least about 5 mM, at least about 10 mM, at least about 20 mM, at least about 30 mM, at least about 40 mM, at least about 50 mM, at least about 75 mM, at least about 100 mM, at least about 150 mM, or at least about 200 mM histidine. In another embodiment, a formulation of the invention comprises between about 1 mM and about 200 mM, between about 1 mM and about 150 mM, between about 1 mM and about 100 mM, between about 1 mM and about 75 mM, between about 10 mM and about 200 mM, between about 10 mM and about 150 mM, between about 10 mM and about 100 mM, between about 10 mM and about 75 mM, between about 10 mM and about 50 mM, between about 10 mM and about 40 mM, between about 10 mM and about 30 mM, between about 20 mM and about 75 mM, between about 20 mM and about 50 mM, between about 20 mM and about 40 mM, or between about 20 mM and about 30 mM histidine. In a further embodiment, the formulation comprises about 1 mM, about 5 mM, about 10 mM, about 20 mM, about 25 mM, about 30 mM, about 35 mM, about 40 mM, about 45 mM, about 50 mM, about 60 mM, about 70 mM, about 80 mM, about 90 mM, about 100 mM, about 150 mM, or about 200 mM histidine. In a specific embodiment, a formulation may comprise about 10 mM, about 25 mM, or no histidine.

The formulations of the modulated lysine variant species compositions of the invention may comprise a carbohydrate excipient. Carbohydrate excipients can act, e.g., as viscosity enhancing agents, stabilizers, bulking agents, solubilizing agents, and/or the like. Carbohydrate excipients are generally present at between about 1% to about 99% by weight or volume, e.g., between about 0.1% to about 20%, between about 0.1% to about 15%, between about 0.1% to about 5%, between about 1% to about 20%, between about 5% to about 15%, between about 8% to about 10%, between about 10% and about 15%, between about 15% and about 20%, between 0.1% to 20%, between 5% to 15%, between 8% to 10%, between 10% and 15%, between 15% and 20%, between about 0.1% to about 5%, between about 5% to about 10%, or between about 15% to about 20%. In still other specific embodiments, the carbohydrate excipient is present at 1%, or at 1.5%, or at 2%, or at 2.5%, or at 3%, or at 4%, or at 5%, or at 10%, or at 15%, or at 20%.

Carbohydrate excipients suitable for use in the formulations of the invention include, but are not limited to, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and the like. In one embodiment, the carbohydrate excipients for use in the present invention are chosen from, sucrose, trehalose, lactose, mannitol, and raffinose. In a specific embodiment, the carbohydrate excipient is trehalose. In another specific embodiment, the carbohydrate excipient is mannitol. In yet another specific embodiment, the carbohydrate excipient is sucrose. In still another specific embodiment, the carbohydrate excipient is raffinose. The purity of the carbohydrate excipient should be at least 98%, or at least 99%, or at least 99.5%.

In a specific embodiment, the formulations of the modulated lysine variant species compositions of the invention may comprise trehalose. In one embodiment, a formulation of the invention comprises at least about 1%, at least about 2%, at least about 4%, at least about 8%, at least about 20%, at least about 30%, or at least about 40% trehalose. In another embodiment, a formulation of the invention comprises between about 1% and about 40%, between about 1% and about 30%, between about 1% and about 20%, between about 2% and about 40%, between about 2% and about 30%, between about 2% and about 20%, between about 4% and about 40%, between about 4% and about 30%, or between about 4% and about 20% trehalose. In a further embodiment, a formulation of the invention comprises about 1%, about 2%, about 4%, about 6%, about 8%, about 15%, about 20%, about 30%, or about 40% trehalose. In a specific embodiment, a formulation of the invention comprises about 4%, about 6% or about 15% trehalose.

In certain embodiments, a formulation of the modulated lysine variant species compositions of the invention comprises an excipient. In a specific embodiment, a formulation of the invention comprises at least one excipient chosen from: sugar, salt, surfactant, amino acid, polyol, chelating agent, emulsifier and preservative. In one embodiment, a formulation of the invention comprises a salt, e.g., a salt selected from: NaCl, KCl, $CaCl_2$, and $MgCl_2$. In a specific embodiment, the formulation comprises NaCl.

A formulation of the modulated lysine variant species compositions of the invention may comprise at least about 10 mM, at least about 25 mM, at least about 50 mM, at least about 75 mM, at least about 80 mM, at least about 100 mM, at least about 125 mM, at least about 150 mM, at least about 175 mM, at least about 200 mM, or at least about 300 mM sodium chloride (NaCl). In a further embodiment, the formulation may comprise between about 10 mM and about 300 mM, between about 10 mM and about 200 mM, between about 10 mM and about 175 mM, between about 10 mM and about 150 mM, between about 25 mM and about 300 mM, between about 25 mM and about 200 mM, between about 25 mM and about 175 mM, between about 25 mM and about 150 mM, between about 50 mM and about 300 mM, between about 50 mM and about 200 mM, between about 50 mM and about 175 mM, between about 50 mM and about 150 mM, between about 75 mM and about 300 mM, between about 75 mM and about 200 mM, between about 75 mM and about 175 mM, between about 75 mM and about 150 mM, between about 100 mM and about 300 mM, between about 100 mM and about 200 mM, between about 100 mM and about 175 mM, or between about 100 mM and about 150 mM sodium chloride. In a further embodiment, the formulation may comprise about 10 mM, about 25 mM, about 50 mM, about 75 mM, about 80 mM, about 100 mM, about 125 mM, about 150 mM, about 175 mM, about 200 mM, or about 300 mM sodium chloride.

A formulation of the modulated lysine variant species compositions of the invention may also comprise an amino acid, e.g., lysine, arginine, glycine, histidine or an amino acid salt. The formulation may comprise at least about 1 mM, at least about 10 mM, at least about 25 mM, at least about 50 mM, at least about 100 mM, at least about 150 mM, at least about 200 mM, at least about 250 mM, at least about 300 mM, at least about 350 mM, or at least about 400 mM of an amino acid. In another embodiment, the formulation may comprise between about 1 mM and about 100 mM, between about 10 mM and about 150 mM, between about 25 mM and about 250 mM, between about 25 mM and about 300 mM, between about 25 mM and about 350 mM, between about 25 mM and about 400 mM, between about 50 mM and about 250 mM, between about 50 mM and about 300 mM, between about 50 mM and about 350 mM, between about 50 mM and about 400 mM, between about 100 mM and about 250 mM, between about 100 mM and about 300 mM, between about 100 mM and about 400 mM, between about 150 mM and about 250 mM, between about 150 mM and about 300 mM, or between about 150 mM and about 400 mM of an amino acid. In a further embodiment, a formulation of the invention comprises about 1 mM, 1.6 mM, 25 mM, about 50 mM, about 100 mM, about 150 mM, about 200 mM, about 250 mM, about 300 mM, about 350 mM, or about 400 mM of an amino acid.

The formulations of the modulated lysine variant species compositions of the invention may further comprise a surfactant. The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. Pharmaceutically acceptable surfactants like polysorbates (e.g., polysorbates 20 or 80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc.), can optionally be added to the formulations of the invention to reduce aggregation. In one embodiment, a formulation of the invention comprises Polysorbate 20, Polysorbate 40, Polysorbate 60, or Polysorbate 80. Surfactants are particularly useful if a pump or plastic container is used to administer the formulation. The presence of a pharmaceutically acceptable surfactant mitigates the propensity for the protein to aggregate. The formulations may comprise a polysorbate which is at a concentration ranging from between about 0.001% to about 1%, or about 0.001% to about 0.1%, or about 0.01% to about 0.1%. In other specific embodiments, the formulations of the invention comprise a polysorbate which is at a concentration of 0.001%, or 0.002%, or 0.003%, or 0.004%, or 0.005%, or 0.006%, or 0.007%, or 0.008%, or 0.009%, or 0.01%, or 0.015%, or 0.02%.

The formulations of the modulated lysine variant species compositions of the invention may optionally further comprise other common excipients and/or additives including, but not limited to, diluents, binders, stabilizers, lipophilic solvents, preservatives, adjuvants, or the like. Pharmaceutically acceptable excipients and/or additives may be used in the formulations of the invention. Commonly used excipients/additives, such as pharmaceutically acceptable chelators (for example, but not limited to, EDTA, DTPA or EGTA) can optionally be added to the formulations of the invention to reduce aggregation. These additives are particularly useful if a pump or plastic container is used to administer the formulation.

Preservatives, such as phenol, m-cresol, p-cresol, o-cresol, chlorocresol, benzyl alcohol, phenylmercuric nitrite, phenoxyethanol, formaldehyde, chlorobutanol, magnesium chloride (for example, but not limited to, hexahydrate), alkylparaben (methyl, ethyl, propyl, butyl and the like), benzalkonium chloride, benzethonium chloride, sodium dehydroacetate and thimerosal, or mixtures thereof can optionally be added to the formulations of the invention at any suitable concentration such as between about 0.001% to about 5%, or any range or value therein. The concentration of preservative used in the formulations of the invention is a concentration sufficient to yield a microbial effect. Such concentrations are dependent on the preservative selected and are readily determined by the skilled artisan.

Other contemplated excipients/additives, which may be utilized in the formulations of the invention include, for example, flavoring agents, antimicrobial agents, sweeteners, antioxidants, antistatic agents, lipids such as phospholipids or fatty acids, steroids such as cholesterol, protein excipients such as serum albumin (human serum albumin (HSA), recombinant human albumin (rHA), gelatin, casein, salt-forming counterions such as sodium and the like. These and additional known pharmaceutical excipients and/or additives suitable for use in the formulations of the invention are known in the art, e.g., as listed in "Remington: The Science & Practice of Pharmacy", 21$^{st}$ ed., Lippincott Williams & Wilkins, (2005), and in the "Physician's Desk Reference", 60$^{th}$ ed., Medical Economics, Montvale, N.J. (2005). Pharmaceutically acceptable carriers can be routinely selected that are suitable for the mode of administration, solubility and/or stability of an antibody, as well known those in the art or as described herein.

In one embodiment, the modulated lysine variant species compositions of the invention are formulated with the same or similar excipients and buffers as are present in the commercial adalimumab (HUMIRA®) formulation, as described in the "Highlights of Prescribing Information" for HUMIRA® (adalimumab) Injection (Revised Jan. 2008), the contents of which are hereby incorporated herein by reference. For example, each prefilled syringe of HUMIRA®, which is administered subcutaneously, delivers 0.8 ml (40 mg) of drug product to the subject. Each 0.8 ml of HUMIRA® contains 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80, and water for Injection, USP. Sodium hydroxide is added as necessary to adjust pH.

It will be understood by one skilled in the art that the formulations of the modulated lysine variant species compositions of the invention may be isotonic with human blood, wherein the formulations of the invention have essentially the same osmotic pressure as human blood. Such isotonic formulations will generally have an osmotic pressure from about 250 mOSm to about 350 mOSm. Isotonicity can be measured by, for example, using a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonity of the formulation. Tonicity modifiers suitable for this invention include, but are not limited to, saccharides, salts and amino acids.

In certain embodiments, the formulations of the modulated lysine variant species compositions of the invention have an osmotic pressure from about 100 mOSm to about 1200 mOSm, or from about 200 mOSm to about 1000 mOSm, or from about 200 mOSm to about 800 mOSm, or from about 200 mOSm to about 600 mOSm, or from about 250 mOSm to about 500 mOSm, or from about 250 mOSm to about 400 mOSm, or from about 250 mOSm to about 350 mOSm.

The concentration of any one component or any combination of various components, of the formulations of the modulated lysine variant species compositions of the invention is adjusted to achieve the desired tonicity of the final formulation. For example, the ratio of the carbohydrate excipient to antibody may be adjusted according to methods known in the art (e.g., U.S. Pat. No. 6,685,940). In certain embodiments, the molar ratio of the carbohydrate excipient to antibody may be from about 100 moles to about 1000 moles of carbohydrate excipient to about 1 mole of antibody, or from about 200 moles to about 6000 moles of carbohydrate excipient to about 1 mole of antibody, or from about 100 moles to about 510 moles of carbohydrate excipient to about 1 mole of antibody, or from about 100 moles to about 600 moles of carbohydrate excipient to about 1 mole of antibody.

The desired isotonicity of the final formulation may also be achieved by adjusting the salt concentration of the formulations. Pharmaceutically acceptable salts and those suitable for this invention as tonicity modifiers include, but are not limited to, sodium chloride, sodium succinate, sodium sulfate, potassium chloride, magnesium chloride, magnesium sulfate, and calcium chloride. In specific embodiments, formulations of the invention comprise NaCl, $MgCl_2$, and/or $CaCl_2$. In one embodiment, concentration of NaCl is between about 75 mM and about 150 mM. In another embodiment, concentration of $MgCl_2$ is between about 1 mM and about 100 mM. Pharmaceutically acceptable amino acids including those suitable for this invention as tonicity modifiers include, but are not limited to, proline, alanine, L-arginine, asparagine, L-aspartic acid, glycine, serine, lysine, and histidine.

In one embodiment the formulations of the modulated lysine variant species compositions of the invention are pyrogen-free formulations which are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with antibodies, even trace amounts of harmful and dangerous endotoxin must be removed. In certain specific embodiments, the endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg.

When used for in vivo administration, the formulations of the modulated lysine variant species compositions of the invention should be sterile. The formulations of the invention may be sterilized by various sterilization methods, including sterile filtration, radiation, etc. In one embodiment, the antibody formulation is filter-sterilized with a presterilized 0.22-micron filter. Sterile compositions for injection can be formulated according to conventional pharmaceutical practice as described in "Remington: The Science & Practice of Pharmacy", 21$^{st}$ ed., Lippincott Williams & Wilkins, (2005). Formulations comprising antibodies, such as those disclosed herein, ordinarily will be stored in lyophilized form or in solution. It is contemplated that sterile compositions comprising antibodies are placed into a container having a sterile access port, for example, an intravenous solution bag or vial having an adapter that allows retrieval of the formulation, such as a stopper pierceable by a hypodermic injection needle. In one embodiment, a composition of the invention is provided as a pre-filled syringe.

In one embodiment, a formulation of the modulated lysine variant species compositions of the invention is a lyophilized formulation. The term "lyophilized" or "freeze-dried"

includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers.

A "lyoprotectant" is a molecule which, when combined with a protein of interest (such as an antibody of the invention), significantly prevents or reduces chemical and/or physical instability of the protein upon lyophilization and subsequent storage. Lyoprotectants include, but are not limited to, sugars and their corresponding sugar alcohols; an amino acid such as monosodium glutamate or histidine; a methylamine such as betaine; a lyotropic salt such as magnesium sulfate; a polyol such as trihydric or higher molecular weight sugar alcohols, e.g., glycerin, dextran, erythritol, glycerol, arabitol, xylitol, sorbitol, and mannitol; propylene glycol; polyethylene glycol; PLURONICS™; and combinations thereof. Additional examples of lyoprotectants include, but are not limited to, glycerin and gelatin, and the sugars mellibiose, melezitose, raffinose, mannotriose and stachyose. Examples of reducing sugars include, but are not limited to, glucose, maltose, lactose, maltulose, iso-maltulose and lactulose. Examples of non-reducing sugars include, but are not limited to, non-reducing glycosides of polyhydroxy compounds selected from sugar alcohols and other straight chain polyalcohols. Examples of sugar alcohols include, but are not limited to, monoglycosides, compounds obtained by reduction of disaccharides such as lactose, maltose, lactulose and maltulose. The glycosidic side group can be either glucosidic or galactosidic. Additional examples of sugar alcohols include, but are not limited to, glucitol, maltitol, lactitol and iso-maltulose. In specific embodiments, trehalose or sucrose is used as a lyoprotectant.

The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

In one embodiment, the molar ratio of a lyoprotectant (e.g., trehalose) and antibody molecules of a formulation of the invention is at least about 10, at least about 50, at least about 100, at least about 200, or at least about 300. In another embodiment, the molar ratio of a lyoprotectant (e.g., trehalose) and antibody molecules of a formulation of the invention is about 1, is about 2, is about 5, is about 10, about 50, about 100, about 200, or about 300.

A "reconstituted" formulation is one which has been prepared by dissolving a lyophilized antibody formulation in a diluent such that the antibody is dispersed in the reconstituted formulation. The reconstituted formulation is suitable for administration (e.g., parenteral administration) to a patient to be treated with the antibody and, in certain embodiments of the invention, may be one which is suitable for intravenous administration.

The "diluent" of interest herein is one which is pharmaceutically acceptable (safe and non-toxic for administration to a human) and is useful for the preparation of a liquid formulation, such as a formulation reconstituted after lyophilization. In some embodiments, diluents include, but are not limited to, sterile water, bacteriostatic water for injection (BWFI), a pH buffered solution (e.g., phosphate-buffered saline), sterile saline solution, Ringer's solution or dextrose solution. In an alternative embodiment, diluents can include aqueous solutions of salts and/or buffers.

In certain embodiments, a formulation of the modulated lysine variant species compositions of the invention is a lyophilized formulation comprising an antibody of the invention, wherein at least about 90%, at least about 95%, at least about 97%, at least about 98%, or at least about 99% of said antibody may be recovered from a vial upon shaking said vial for 4 hours at a speed of 400 shakes per minute wherein the vial is filled to half of its volume with the formulation. In another embodiment, a formulation of the invention is a lyophilized formulation comprising an antibody of the invention, wherein at least about 90%, at least about 95%, at least about 97%, at least about 98%, or at least about 99% of the antibody may be recovered from a vial upon subjecting the formulation to three freeze/thaw cycles wherein the vial is filled to half of its volume with said formulation. In a further embodiment, a formulation of the invention is a lyophilized formulation comprising an antibody of the invention, wherein at least about 90%, at least about 95%, at least about 97%, at least about 98%, or at least about 99% of the antibody may be recovered by reconstituting a lyophilized cake generated from said formulation.

In one embodiment, a reconstituted liquid formulation may comprise an antibody at the same concentration as the pre-lyophilized liquid formulation.

In another embodiment, a reconstituted liquid formulation may comprise an antibody at a higher concentration than the pre-lyophilized liquid formulation, e.g., .about 2 fold, about 3 fold, about 4 fold, about 5 fold, about 6 fold, about 7 fold, about 8 fold, about 9 fold, or about 10 fold higher concentration of an antibody than the pre-lyophilized liquid formulation.

In yet another embodiment, a reconstituted liquid formulation may comprise an antibody of the invention at a lower concentration than the pre-lyophilized liquid formulation, e.g., about 2 fold, about 3 fold, about 4 fold, about 5 fold, about 6 fold, about 7 fold, about 8 fold, about 9 fold or about 10 fold lower concentration of an antibody than the pre-lyophilized liquid formulation.

In one embodiment, the pharmaceutical formulations of the modulated lysine variant species compositions of the invention are stable formulations, e.g., stable at room temperature.

The terms "stability" and "stable" as used herein in the context of a formulation comprising an antibody of the invention refer to the resistance of the antibody in the formulation to aggregation, degradation or fragmentation under given manufacture, preparation, transportation and storage conditions. The "stable" formulations of the invention retain biological activity under given manufacture, preparation, transportation and storage conditions. The stability of the antibody can be assessed by degrees of aggregation, degradation or fragmentation, as measured by HPSEC, static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference formulation. For example, a reference formulation may be a reference standard frozen at −70° C. consisting of 10 mg/ml of an antibody of the invention in PBS.

Therapeutic formulations of the modulated lysine variant species compositions of the invention may be formulated for a particular dosage. Dosage regimens may be adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the antibody and the particular therapeutic effect to be achieved, and (b) the limitations inherent in the art of compounding such an antibody for the treatment of sensitivity in individuals.

Therapeutic compositions of the modulated lysine variant species compositions of the invention can be formulated for particular routes of administration, such as oral, nasal, pulmonary, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. By way of example, in certain embodiments, the antibodies (including antibody fragments) are formulated for intravenous administration. In certain other embodiments, the antibodies (including antibody fragments) are formulated for local delivery to the cardiovascular system, for example, via catheter, stent, wire, intramyocardial delivery, intrapericardial delivery, or intraendocardial delivery.

Formulations of the modulated lysine variant species compositions of the invention which are suitable for topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required (U.S. Pat. Nos. 7,378,110; 7,258,873; 7,135,180; 7,923,029; and US Publication No. 20040042972).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Actual dosage levels of the active ingredients in the pharmaceutical compositions of the modulated lysine variant species compositions of the invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In certain embodiments, antibodies of the invention can be formulated to ensure proper distribution in vivo. For example, the blood-brain barrier (BBB) excludes many highly hydrophilic compounds. To ensure that the therapeutic compounds of the invention can cross the BBB (if desired), they can be formulated, for example, in liposomes. For methods of manufacturing liposomes, see, e.g., U.S. Pat. Nos. 4,522,811; 5,374,548; 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations of the invention, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment of the invention, the therapeutic compounds of the invention are formulated in liposomes; in another embodiment, the liposomes include a targeting moiety. In another embodiment, the therapeutic compounds in the liposomes are delivered by bolus injection to a site proximal to the desired area. When administered in this manner, the composition must be fluid to the extent that easy syringability exists. It must be stable under the conditions of manufacture and storage and may be preserved against the contaminating action of microorganisms such as bacteria and fungi. Additionally or alternatively, the antibodies of the invention may be delivered locally to the brain to mitigate the risk that the blood brain barrier slows effective delivery.

In certain embodiments, the modulated lysine variant species compositions of the invention may be administered with medical devices known in the art. For example, in certain embodiments an antibody or antibody fragment is administered locally via a catheter, stent, wire, or the like. For example, in one embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The efficient dosages and the dosage regimens for the modulated lysine variant species compositions of the invention depend on the disease or condition to be treated and can be determined by the persons skilled in the art. One of ordinary skill in the art would be able to determine such amounts based on such factors as the subject's size, the severity of the subject's symptoms, and the particular composition or route of administration selected.

VII. Alternative Formulations Containing the Modulated Lysine Variant Species Compositions of the Invention Alternative Aqueous Formulations The invention also provides a modulated lysine variant species composition formulated as an aqueous formulation comprising a protein and water, as described in U.S. Pat. No. 8,420,081 and WO2012/065072, the contents of which are hereby incorporated by reference. In these aqueous formulations, the protein is stable without the need for additional agents. This aqueous formulation has a number of advantages over conventional formulations in the art, including stability of the protein in water without the requirement for additional excipients, increased concentrations of protein without the need for additional excipients to maintain solubility of the protein, and low osmolality. These also have advantageous storage properties, as the proteins in the formulation remain stable during storage, e.g., stored as a liquid form for more than 3 months at 7° C. or freeze/thaw conditions, even at high protein concentrations and repeated freeze/thaw processing steps. In one embodiment, formulations described herein include high concentrations of proteins such that the aqueous formulation does not show significant opalescence, aggregation, or precipitation.

In one embodiment, an aqueous modulated lysine variant species composition comprising a protein, e.g., an antibody, e.g., an anti-TNFα antibody or antigen biding portion thereof, and water is provided, wherein the formulation has certain characteristics, such as, but not limited to, low conductivity, e.g., a conductivity of less than about 2.5 mS/cm, a protein concentration of at least about 10 μg/ml, an osmolality of no more than about 30 mOsmol/kg, and/or the protein has a molecular weight (Mw) greater than about 47 kDa. In one embodiment, the formulation has improved stability, such as, but not limited to, stability in a liquid form for an extended time (e.g., at least about 3 months or at least about 12 months) or stability through at least one freeze/thaw cycle (if not more freeze/thaw cycles). In one embodiment, the formulation is stable for at least about 3 months in a form selected from the group consisting of frozen, lyophilized, or spray-dried.

In one embodiment, the formulation has a low conductivity, including, for example, a conductivity of less than about 2.5 mS/cm, a conductivity of less than about 2 mS/cm, a conductivity of less than about 1.5 mS/cm, a conductivity of less than about 1 mS/cm, or a conductivity of less than about 0.5 mS/cm.

In another embodiment, modulated lysine variant species compositions included in the formulation have a given concentration, including, for example, a concentration of at least about 1 mg/ml, at least about 10 mg/ml, at least about 50 mg/ml, at least about 100 mg/ml, at least about 150 mg/ml, at least about 200 mg/ml, or greater than about 200 mg/ml. In another embodiment, the formulation of the invention has an osmolality of no more than about 15 mOsmol/kg.

The aqueous formulations described herein do not rely on standard excipients, e.g., a tonicity modifier, a stabilizing agent, a surfactant, an anti-oxidant, a cryoprotectant, a bulking agent, a lyoprotectant, a basic component, and an acidic component. In other embodiments of the invention, the formulation contains water, one or more proteins, and no ionic excipients (e.g., salts, free amino acids).

In certain embodiments, the aqueous formulation as described herein comprise a modulated lysine variant species composition comprising a protein concentration of at least 50 mg/ml and water, wherein the formulation has an osmolality of no more than 30 mOsmol/kg. Lower limits of osmolality of the aqueous formulation are also encompassed by the invention. In one embodiment the osmolality of the aqueous formulation is no more than 15 mOsmol/kg. The aqueous formulation of the invention may have an osmolality of less than 30 mOsmol/kg, and also have a high protein concentration, e.g., the concentration of the protein is at least 100 mg/ml, and may be as much as 200 mg/ml or greater. Ranges intermediate to the above recited concentrations and osmolality units are also intended to be part of this invention. In addition, ranges of values using a combination of any of the above recited values as upper and/or lower limits are intended to be included.

The concentration of the aqueous formulation as described herein is not limited by the protein size and the formulation may include any size range of proteins. Included within the scope of the invention is an aqueous formulation comprising at least 40 mg/ml and as much as 200 mg/ml or more of a protein, for example, 40 mg/ml, 65 mg/ml, 130 mg/ml, or 195 mg/ml, which may range in size from 5 kDa to 150 kDa or more. In one embodiment, the protein in the formulation of the invention is at least about 15 kD in size, at least about 20 kD in size; at least about 47 kD in size; at least about 60 kD in size; at least about 80 kD in size; at least about 100 kD in size; at least about 120 kD in size; at least about 140 kD in size; at least about 160 kD in size; or greater than about 160 kD in size. Ranges intermediate to the above recited sizes are also intended to be part of this invention. In addition, ranges of values using a combination of any of the above recited values as upper and/or lower limits are intended to be included.

The aqueous formulation as described herein may be characterized by the hydrodynamic diameter ($D_h$) of the proteins in solution. The hydrodynamic diameter of the protein in solution may be measured using dynamic light scattering (DLS), which is an established analytical method for determining the $D_h$ of proteins. Typical values for monoclonal antibodies, e.g., IgG, are about 10 nm. Low-ionic formulations may be characterized in that the $D_h$ of the proteins are notably lower than protein formulations comprising ionic excipients. It has been discovered that the $D_h$ values of antibodies in aqueous formulations made using the disfiltration/ultrafiltration (DF/UF) process, as described in U.S. Pat. No. 8,420,081, using pure water as an exchange medium, are notably lower than the $D_h$ of antibodies in conventional formulations independent of protein concentration. In one embodiment, antibodies in the aqueous formulation as described herein have a $D_h$ of less than 4 nm, or less than 3 nm.

In one embodiment, the $D_h$ of the protein in the aqueous formulation is smaller relative to the $D_h$ of the same protein in a buffered solution, irrespective of protein concentration. Thus, in certain embodiments, protein in an aqueous formulation made in accordance with the methods described herein, will have a $D_h$ which is at least 25% less than the $D_h$ of the protein in a buffered solution at the same given concentration. Examples of buffered solutions include, but are not limited to phosphate buffered saline (PBS). In certain embodiments, proteins in the aqueous formulation of the invention have a $D_h$ that is at least 50% less than the $D_h$ of the protein in PBS in at the given concentration; at least 60% less than the $D_h$ of the protein in PBS at the given concentration; at least 70% less than the $D_h$ of the protein in PBS at the given concentration; or more than 70% less than the $D_h$ of the protein in PBS at the given concentration. Ranges intermediate to the above recited percentages are also intended to be part of this invention, e.g., 55%, 56%, 57%, 64%, 68%, and so forth. In addition, ranges of values using a combination of any of the above recited values as upper and/or lower limits are intended to be included, e.g., 50% to 80%.

In one aspect, the aqueous formulation includes the protein at a dosage of about 0.01 mg/kg-10 mg/kg. In another aspect, the dosages of the protein include approximately 1 mg/kg administered every other week, or approximately 0.3 mg/kg administered weekly. A skilled practitioner can ascertain the proper dosage and regime for administering to a subject.

Alternative Solid Unit Formulations

The invention also provides a modulated lysine variant species composition of the invention formulated as a stable solid composition of a protein (preferably a therapeutic protein) and a stabilizer, referred to herein as solid units, as described in U.S. Provisional Patent Application 61/893,123, the contents of which are hereby incorporated by reference herein.

Specifically, it has been discovered that despite having a high proportion of sugar relative to the protein, the solid units of the invention maintain structural rigidity and resist changes in shape and/or volume when stored under ambient conditions, room temperature and humidity, for extended periods of time. The solid units of the invention remain free-flowing and are able to maintain long-term physical and chemical stability of the protein without significant degradation and/or aggregate formation. The solid units of the invention have many advantages over the art, including that they can be formulated for oral delivery and are easily reconstituted in a diluent, such as water. Because the solid units are readily dissolved, they may be used in dual chamber delivery devices and may be prepared directly in a device for patient use.

As used herein, the term "solid unit," refers to a composition which is suitable for pharmaceutical administration and comprises a protein, an antibody or peptide, and a stabilizer, e.g., a sugar. The solid unit has a structural rigidity and resistance to changes in shape and/or volume. In a preferred embodiment, the solid unit is obtained by lyophilizing a pharmaceutical formulation of a therapeutic protein. The solid unit may be any shape, e.g., geometric shape, including, but not limited to, a sphere, a cube, a pyramid, a hemisphere, a cylinder, a teardrop, and so forth, including irregularly shaped units. In one embodiment, the solid unit has a volume ranging from about 1 ml to about 20 ml. In one embodiment, the solid unit is not obtained using spray drying techniques, e.g., the solid unit is not a powder or granule.

As used herein, the phrase "a plurality of solid units" refers to a collection or population of solid units, wherein the collection comprises two or more solid units having a substantially uniform shape, e.g., sphere, and/or volume distribution. In one embodiment, the plurality of solid units is free-flowing.

VIII. Kits and Articles of Manufacture Comprising the Modulated Lysine Variant Species Compositions of the Invention Also within the scope of the present invention are kits comprising the modulated lysine variant species compositions of the invention and instructions for use. The term "kit" as used herein refers to a packaged product comprising components with which to administer the antibody, or antigen-binding portion thereof, of the invention for treatment of a disease or disorder. The kit can comprise a box or container that holds the components of the kit. The box or container is affixed with a label or a Food and Drug Administration approved protocol. In one embodiment, the box or container holds components of the invention which are contained within plastic, polyethylene, polypropylene, ethylene, or propylene vessels. The vessels can be capped-tubes or bottles. The kit can also include instructions for administering an antibody of the invention.

The kit can further contain one more additional reagents, such as an immunosuppressive reagent, a cytotoxic agent or a radiotoxic agent or one or more additional antibodies of the invention (e.g., an antibody having a complementary activity which binds to an epitope in the TNFα antigen distinct from a first anti-TNFα antibody). Kits typically include a label indicating the intended use of the contents of the kit. The term label includes any writing, or recorded material supplied on or with the kit, or which otherwise accompanies the kit.

The invention also provides a pharmaceutical pack or kit comprising one or more containers filled with a liquid formulation or lyophilized formulation of an antibody or antibody fragment thereof of the invention. In one embodiment, a container filled with a liquid formulation of the invention is a pre-filled syringe. In a specific embodiment, the formulations of the invention are formulated in single dose vials as a sterile liquid. For example, the formulations may be supplied in 3 cc USP Type I borosilicate amber vials (West Pharmaceutical Services—Part No. 6800-0675) with a target volume of 1.2 ml. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a container filled with a liquid formulation of the invention is a pre-filled syringe. Any pre-filled syringe known to one of skill in the art may be used in combination with a liquid formulation of the invention. Pre-filled syringes that may be used are described in, for example, but not limited to, PCT Publications WO05032627, WO08094984, WO9945985, WO03077976, U.S. Pat. Nos. 6,792,743, 5,607,400, 5,893,842, 7,081,107, 7,041,087, 5,989,227, 6,807,797, 6,142,976, 5,899,889, 7,699,811, 7,540,382, 7,998,120, 7,645,267, and US Patent Publication No. US20050075611. Pre-filled syringes may be made of various materials. In one embodiment a pre-filled syringe is a glass syringe. In another embodiment a pre-filled syringe is a plastic syringe. One of skill in the art understands that the nature and/or quality of the materials used for manufacturing the syringe may influence the stability of a protein formulation stored in the syringe. For example, it is understood that silicon based lubricants deposited on the inside surface of the syringe chamber may affect particle formation in the protein formulation. In one embodiment, a pre-filled syringe comprises a silicone based lubricant. In one embodiment, a pre-filled syringe comprises baked on silicone. In another embodiment, a pre-filled syringe is free from silicone based lubricants. One of skill in the art also understands that small amounts of contaminating elements leaching into the formulation from the syringe barrel, syringe tip cap, plunger or stopper may also influence stability of the formulation. For example, it is understood that tungsten introduced during the manufacturing process may adversely affect formulation stability. In one embodiment, a pre-filled syringe may comprise tungsten at a level above 500 ppb. In another embodiment, a pre-filled syringe is a low tungsten syringe. In another embodiment, a pre-filled syringe may comprise tungsten at a level between about 500 ppb and about 10 ppb, between about 400 ppb and about 10 ppb, between about 300 ppb and about 10 ppb, between about 200 ppb and about 10 ppb, between about 100 ppb and about 10 ppb, between about 50 ppb and about 10 ppb, between about 25 ppb and about 10 ppb.

In certain embodiments, kits comprising antibodies of the invention are also provided that are useful for various purposes, e.g., research and diagnostic including for purification or immunoprecipitation of protein of interest from cells, detection of the protein of interest in vitro or in vivo. For isolation and purification of a protein of interest, the kit may contain an antibody coupled to beads (e.g., sepharose beads). Kits may be provided which contain the antibodies for detection and quantitation of a protein of interest in vitro, e.g., in an ELISA or a Western blot. As with the article of manufacture, the kit comprises a container and a label or package insert on or associated with the container. The container holds a composition comprising at least one antibody of the invention. Additional containers may be included that contain, e.g., diluents and buffers, control antibodies. The label or package insert may provide a description of the composition as well as instructions for the intended in vitro or diagnostic use.

The present invention also encompasses a finished packaged and labeled pharmaceutical product. This article of manufacture includes the appropriate unit dosage form in an appropriate vessel or container such as a glass vial, pre-filled syringe or other container that is hermetically sealed. In one embodiment, the unit dosage form is provided as a sterile particulate free solution comprising an antibody that is suitable for parenteral administration. In another embodiment, the unit dosage form is provided as a sterile lyophilized powder comprising an antibody that is suitable for reconstitution.

In one embodiment, the unit dosage form is suitable for intravenous, intramuscular, intranasal, oral, topical or subcutaneous delivery. Thus, the invention encompasses sterile solutions suitable for each delivery route. The invention further encompasses sterile lyophilized powders that are suitable for reconstitution.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question, as well as how and how frequently to administer the pharmaceutical. In other words, the article of manufacture includes instruction means indicating or suggesting a dosing regimen including, but not limited to, actual doses, monitoring procedures, and other monitoring information.

Specifically, the invention provides an article of manufacture comprising packaging material, such as a box, bottle, tube, vial, container, pre-filled syringe, sprayer, insufflator, intravenous (i.v.) bag, envelope and the like; and at least one unit dosage form of a pharmaceutical agent contained within said packaging material, wherein said pharmaceutical agent comprises a liquid formulation containing an antibody. The packaging material includes instruction means which indicate how that said antibody can be used to prevent, treat and/or manage one or more symptoms associated with a disease or disorder.

The present invention is further illustrated by the following examples which should not be construed as limiting in any way.

IX. Examples

Example 1

Methods for Modulating the Lysine Variant Distribution in Cell Culture by the Modulation of Zinc Concentration in Culture Medium This Example provides methods to modulate the lysine variant distribution of monoclonal antibodies by modulating the levels of zinc in the medium.

Materials and Methods

Cell Lines and Adaptation Cultures

Two adalimumab producing cell lines were employed in the studies discussed herein (cell line 1 and cell line 2). Upon thaw, cells were typically cultured in a combination of 250 ml and 500 ml Corning vented non-baffled shake flasks on a shaker platform at 110 RPM for cell line 1 and 180 rpm for cell line 2 in a 35° C., 5% $CO_2$ incubator. Subsequent to the initial cell growth in the standard IVGN CD basal growth media, cells were adapted for two passages in separate flasks in basal media containing different concentrations of zinc. Only the cultures that demonstrated good cell growth in the adaptation phase were carried forward to the production stage.

Cell Culture Media

The initial growth media was prepared from proprietary basal CD media GIA1 (Invitrogen, media 1). For the adaptation and production culture stages (in different concentrations of zinc), media was prepared starting from either proprietary basal CD media GIA1 (media 1) or CD media without zinc (Basal 2). The control cultures were carried through the adaptation and production stage in Basal 1 media. The test conditions were carried through both the adaptation and production stages in Basal 2 media supplemented with different concentrations of zinc. The trace element compounds supplemented to media are listed in Table 1. The detailed descriptions of the culture media for the different conditions for both cell lines are listed in Table 2. All media was filtered through Corning 1 L filter systems (0.22 μm PES) and stored at 4° C. until usage.

TABLE 1

List of trace element compounds supplemented to culture media

| Compound | Catalog No./Source |
|---|---|
| Zinc Chloride | Fluka, 96468 |
| Zinc Sulfate Heptahydrate | Sigma, Z0251 |

TABLE 2

Detailed description of culture media for different experimental conditions

| Cell line | Condition | Estimated final concentration of zinc (μM) |
|---|---|---|
| 1 | 1 | 10 |
|   | 2 | 3.4 |
| 2 | 1 | 10 |
|   | 2 | 6.7 |
|   | 3 | 3.4 |

Production Cultures

Production cultures were initiated in duplicates in 500 ml Corning vented non-baffled shake flasks (200 ml working volume). The shake flasks were kept in incubators maintained at 35° C. and 5% $CO_2$ on shaker platforms that were either set at 110 rpm for cell line 1 or 180 rpm for cell line 2. In all experiments, the cells were transferred from the adaptation stage to the production stage at a split ratio of 1:5.

The harvest procedure of the shake flasks and reactors involved centrifugation of the culture sample at 3,000 RPM for 30 minutes and storage of supernatant in PETG bottles at −80° C. before submission for Protein A purification and WCX-10 analysis.

WCX-10 Assay

For quantification of charge variants of antibodies, action exchange chromatography was performed on a Dionex Pro-Pac WCX-10, Analytical column 4 mm×250 mm (Dionex, Calif.). A Shimadzu LC10A HPLC system was used as the HPLC. The mobile phases used were 10 mM sodium phosphate dibasic pH 7.5 (Mobile phase A) and 10 mM sodium phosphate dibasic, 500 mM sodium phosphate pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. Quantitation was based on the relative area percent of detected peaks (FIG. 1).

Results and Discussion

Effect of Varying Zinc Concentration in Chemically Defined Media with Cell Line 1

In this Example, the effect of varying total zinc concentration (control (10 μM), 6.7 μM, 3.4 μM) in cell culture media on culture performance and product quality was evaluated using cell line 1. The ratios of the concentration of the two zinc salts (zinc chloride and zinc sulfate) were kept constant between the test conditions. As described in the materials and methods, above, each of the production stage cultures were initiated from respective adaptation cultures with corresponding levels of total zinc.

A difference in cell growth and viability profiles was observed between the test conditions and the control (FIG. 2, FIG. 3). While the peak viable cell density (VCD) in the control condition was about $11 \times 10^6$ cells/ml, the peak VCD for the 3.4 μM zinc condition was about $8 \times 10^6$ cells/ml. Corresponding to difference in peak VCD, the harvest titer was also slightly reduced in the 3.4 μM zinc condition (1.0 g/L) compared to the control (1.3 g/L) (FIG. 4). The cultures were harvested on day 10 at viability of 50% or lower for each condition and the harvest was taken through Protein A purification before WCX-10 analysis. From the WCX-10 analysis, the lysine variant distribution was characterized and the relative proportion of Lys 0, Lys 1, and Lys 2 variants were quantified as a fraction of the total lysine sum. A zinc dose dependent decrease in the relative fraction of relative Lys 0 was observed from 92.8% in the control condition to 69.0% in the 3.4 μM zinc condition. A corresponding relative increase in both Lys 1/Lys 2 variants was also observed (FIG. 5).

Thus, lowering the zinc concentration provides an effective method to increase the relative proportion of the product antibody with a C-terminal lysine on one or both the heavy chains (Lys 1/Lys 2).

Effect of Varying Zinc Concentration in Chemically Defined Media with Cell Line 2

In this Example, the effect of varying total zinc concentration (control (10 μM), 3.4 μM) in basal cell culture media on cell culture performance and product quality was evaluated using cell line 2. The ratios of the concentration of the two zinc salts (zinc chloride, zinc sulfate) were kept constant between the test conditions. As described in the materials and methods, above, each of the production stage cultures were initiated from respective adaptation cultures with corresponding levels of total zinc.

A significant difference in cell growth and viability profile was observed between the two test conditions (FIG. 6, FIG. 7). While the peak viable cell density (VCD) in the control condition was about $22 \times 10^6$ cells/ml, the peak VCD for the 3.4 μM zinc condition was about $11 \times 10^6$ cells/ml. Corresponding to difference in peak VCD, the harvest titer was also significantly reduced in the 3.4 μM zinc condition compared to the control (FIG. 8). The cultures were harvested on day 10 at the target viability of 50% for each condition and the harvest was taken through Protein A purification before WCX-10 analysis. From the WCX-10 analysis, the lysine variant distribution was characterized and the relative proportion of Lys 0, Lys 1, and Lys 2 variants were quantified as a fraction of the total lysine sum. There was a decrease in the relative fraction of Lys 0 in the control condition (92.7%) versus the relative Lys 0 in the 3.4 μM zinc condition (67.9%). The relative fractions of Lys 1/Lys 2 variants were also correspondingly higher (FIG. 9).

Thus, an increase in the relative proportion of the product antibody with C-terminal lysine on one or both the heavy chains (Lys 1/Lys 2) corresponding to reduction in levels of zinc in basal media, was also observed in this Example.

Example 2

Methods for Modulating the Lysine Variant Distribution in Cell Culture by the Addition of Amino Acids This Example provides methods to modulate the lysine variant distribution of monoclonal antibodies by supplementing amino acids (arginine, lysine, and histidine added individually and ornithine in combination with arginine, lysine and/or histidine) to the cell culture medium.

Materials and Methods

Cell Source and Adaptation Cultures

Three adalimumab producing cell lines (cell line 1, cell line 2, and cell line 3), one mAb1 producing cell line and one mAb2 producing cell line were employed in the experiments described in this Example.

For adalimumab producing cell lines, cells were cultured in their respective growth media (chemically defined media (media 1) or a hydrolysate based media (media 2 or media 3)) in a combination of vented non-baffled shake flasks (Corning) on a shaker platform at 110 RPM (cell line 1), 180 RPM (cell line 2), 140 RPM (cell line 3) and 10 L or 20 L wave bags (GE). For experiments with cells in the hydrolysate based media (media 3), cells were thawed in media 1 and then adapted to media 3 over a few passages. Cultures were propagated in a 35° C., 5% $CO_2$ incubator for cell line 1 and 2 and in a 36° C., 5% $CO_2$ incubator for cell line 3 in order to obtain the required number of cells to be able to initiate production stage cultures.

For the mAb1 producing cell line, cells were cultured in chemically defined growth media (media 1) in a combination of vented non-baffled shake flasks (Corning) on a shaker platform at 130 RPM and 20 L wave bags (GE). Cultures were propagated in a 36° C., 5% $CO_2$ incubator to obtain the required number of cells to be able to initiate production stage cultures.

For the mAb2 producing cell line, cells were cultured in chemically defined growth media (media 1) in a combination of vented non-baffled shake flasks (Corning) on a shaker platform at 140 RPM and 20 L wave bags (GE). Cultures were propagated in a 35° C., 5% $CO_2$ incubator to obtain the required number of cells to be able to initiate production stage cultures.

Cell Culture Media

Growth and production media were prepared from either a chemically defined media formulation (media 1) or hydrolysate-based medium formulations (media 2 and media 3). For preparation of the media 1, the media (IVGN GIA-1, proprietary formulation) was supplemented with L-glutamine, sodium bicarbonate, sodium chloride, and methotrexate solution. Production media consisted of all the components in the growth medium, excluding methotrexate. For cell line 1, mAb1, and mAb2, both growth and production medium were also supplemented with insulin.

For the hydrolysate-based formulation (media 2), the growth media was composed of PFCHO (proprietary CD formulation from SAFC), dextrose, L-glutamine, L-asparagine, HEPES, Poloxamer 188, ferric citrate, recombinant human insulin, Yeastolate (BD), Phytone Peptone (BD), mono- and di-basic sodium phosphate, sodium bicarbonate, sodium phosphate and methotrexate. Production media consisted of all the components listed in the growth medium, excluding methotrexate.

For the hydrolysate-based formulation (media 3), the growth media was composed of OptiCHO (Invitrogen), L-glutamine, Yeastolate (BD), Phytone Peptone (BD) and methotrexate. Production media consisted of all the components listed in the growth medium, excluding methotrexate.

Amino acids used for the experiments were reconstituted in Milli-Q water to make a 100 g/L stock solution, which was subsequently supplemented to both growth and production basal media. After addition of amino acids, media was brought to a pH similar to non-supplemented (control) media using 5N hydrochloric acid/5N NaOH, and it was brought to an osmolality similar to unsupplemented (control) media by adjusting the concentration of sodium chloride. All media was filtered through Corning 1 L filter systems (0.22 μm PES) and stored at 4° C. until used.

The amino acids supplemented to media are listed in Table 3.

TABLE 3

List of Amino Acids Supplemented to Culture Media and the Relevant Concentration Ranges Tested

| Amino Acid | Catalog No./Source |
|---|---|
| Arginine | Sigma, A8094 |
| Lysine | Calbiochem, 4400 |
| Histidine | Sigma, H5659 |
| Ornithine | Sigma, 06503 |

Production Cultures

Production cultures were initiated either in 500 ml shake flasks (Corning) or in 3 L Bioreactors (Applikon). For shake flask experiments, duplicate 500 ml Corning vented non-baffled shake flasks (200 ml working volume) were used for each condition. The shake flasks were kept in incubators either maintained at 35° C. or 36° C. and 5% $CO_2$ on shaker platforms that were either set at 110 rpm for adalimumab producing cell line 1, 180 rpm for adalimumab producing cell line 2, 140 rpm for adalimumab producing cell line 3, 130 rpm for mAb1 producing cell line, or 140 rpm for mAb2 producing cell line. For the bioreactor experiments, 3 L bioreactors (1.5 L working volume) were run at 37° C.-33° C. (temperature shift), 30% dissolved oxygen (DO), 200 rpm, pH profile from 7.1 to 6.9 in three days and pH 6.9 thereafter. In all experiments, the cells were transferred from the seed train to the production stage at a split ratio of about 1:5.

Cultures were run in either batch or fed-batch mode. In the batch mode, cells were cultured in the respective production medium. A 1.25% (v/v) of 40% glucose stock solution was fed when the media glucose concentration reduced to less than 3 g/L. In the fed-batch mode, cultures were run with either the IVGN feed as per the following feed schedule— (4% (v/v)—day 3, 6%—day 5, 8%—day 7, 10%—day 9, 10%—day 11) or 10× Ex-Cell PFCHO feed (SAFC, 67411)—3% (v/v) on day 3. In fed-batch cultures with IVGN feed, cultures were also fed with 1.25% (v/v) of 40% glucose stock solution when the glucose concentration fell below 1.5 g/L on IVGN feed days and when the concentration fell below 2.5 g/L on other days. In fed-batch cultures with 10×PFCHO feed, 1.25% (v/v) of 40% glucose stock solution was fed when the media glucose concentration was below 3 g/L.

Retention samples for titer analysis of 2×1.5 ml, were collected daily for the bioreactor experiments beginning on Day 8, and frozen at −80° C. The samples taken from each were later subjected to titer analysis.

The harvest procedure of the shake flasks and reactors involved centrifugation of the culture sample at 3,000 RPM for 30 min and storage of supernatant in PETG bottles at −80° C. before submission for Protein A purification and WCX-10 analysis.

WCX-10 Assay

The acidic species and other charge variants present in cell culture harvest samples were quantified. Cation exchange chromatography was performed on a Dionex ProPac WCX-10, Analytical column (Dionex, Calif.). A Shimadzu LC10A HPLC system was used as the HPLC.

For the adalimumab and mAb1 samples, the mobile phases used were 10 mM sodium phosphate dibasic pH 7.5 (Mobile phase A) and 10 mM sodium phosphate dibasic, 500 mM sodium phosphate pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

For mAb2 samples, the mobile phases used were 20 mM (4-Morpholino)ethanesulfonic Acid Monohydrate (MES) pH 6.5 (Mobile phase A) and 20 mM MES, 500 mM sodium phosphate pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak (Lys 0) corresponding to the drug product are together represented as the acidic peaks. The peaks that eluted at a relative residence time later than the main peak in the basic region correspond to Lys 1 and Lys 2, respectively.

Results and Discussion

Effect of Supplementation of Arginine to Culture Media

Two experiments where two different adalimumab producing cell lines (cell line 1 and cell line 2) were cultured in a chemically defined media (media 1) are described below.

Cell line 2 was cultured in media 1 with different total concentrations of arginine (1 (control), 1.25, 1.5, 2, 3, 5, 9 g/L). The cultures were performed in shake flasks in batch format with only glucose feed as described in the materials and methods. The cells grew to maximum viable cell densities (VCD) in the range of $18-22 \times 10^6$ cells/ml for the different conditions tested. The growth and viability profiles were comparable between the different conditions, although a slight decrease in viable cell density profile was observed in samples with the 9 g/L arginine condition (FIG. 10, FIG. 11).

The harvest titers were comparable between the conditions (FIG. 12). On Day 10 and Day 12 of culture, duplicate shake flasks for each of the conditions were harvested and then subsequently analyzed using WCX-10 after Protein A purification and the percentages of total peak(s) area corresponding to Lys 0, Lys 1 and Lys 2 were quantified (FIG. 13, FIG. 14). The percentage of Lys 0 relative to lysine sum (sum of areas corresponding to peaks Lys 0, Lys 1 and Lys 2) in the control sample was as 91.9% on day 10. In the sample with the highest tested concentration of arginine in this experiment (9 g/L), the relative percentage of Lys 0 was reduced to 77.2%. A dose dependent decrease in relative Lys 0 was observed in conditions with arginine concentrations beyond 2 g/L (FIG. 13). The decrease in relative Lys 0 corresponded with the increase in relative levels of both Lys 1 and Lys 2. A dose dependent decrease in relative levels of Lys 0, and a corresponding dose dependent increase in Lys 1 and Lys 2 were observed in conditions with increased arginine. A similar trend in reduction of relative levels of Lys 0 with arginine increase was also observed in the day 12 harvest samples (FIG. 14).

Cell line 3 was cultured in media 1 with different concentrations of arginine (1 (control), 3, 5, 7, 9 g/L). The cultures were performed in shake flasks in batch format with only glucose feed as described in the materials and methods above. The cells grew to maximum viable cell densities (VCD) in the range of $7\text{-}10 \times 10^6$ cells/ml for the different conditions tested. The growth and viability profiles were comparable between the different test conditions, although a slight decrease in viable cell density and viability profiles was observed in samples with the 9 g/L arginine condition (FIG. 15, FIG. 16). The product titer was also comparable between the conditions (FIG. 17). On Day 10 of culture, duplicate shake flasks for each of the conditions were harvested and then subsequently analyzed using WCX-10 post Protein A purification and the percentages of total peak(s) area corresponding to the Lys 0, Lys 1 and Lys 2 species were quantified (FIG. 18). The percentage of Lys 0 relative to lysine sum in the control sample was 82.9% on day 10. In the sample with the highest concentration of arginine in this experiment (9 g/L), the percentage of relative Lys 0 was reduced to 73.4%. The decrease in Lys 0 corresponded with the increase in relative levels of both Lys 1 and Lys 2. This relative modulation of Lys 0, Lys 1 and Lys 2 was directly related to the concentration of arginine in the media.

Thus, although the lysine variant distributions were substantially different between the control conditions in the studies presented above, significant modulation in the relative levels of the lysine variants (decrease in Lys 0 and increase in Lys 1/Lys 2) with increased arginine concentration was observed in both cases.

Additional experiments were performed with multiple cell lines in chemically defined or hydrolysate based media to demonstrate the wide range of applicability of this method. The experimental setup for each of these experiments was similar to that described above. The summaries of results of the different experiments performed for adalimumab are set forth in FIG. 19, FIG. 20 and FIG. 21. A reduction in relative Lys 0, and increase in relative Lys 1 and Lys 2 species with increased arginine concentration was observed in each case.

In addition to adalimumab, the utility of this method for lysine variant modulation was also demonstrated for processes involving two other mAbs. The experimental setup for each of these experiments was similar to that described in the materials and methods above. The reduction of acidic species with arginine increase for experiments corresponding to each mAb is summarized in FIG. 22 and FIG. 23. A reduction in relative Lys 0, and increase in relative Lys 1 and Lys 2 species with increase in arginine concentration was observed in both cases.

Effect of Supplementation of Lysine to Culture Media

The following is a description of two experiments where two different adalimumab producing cell lines (cell line 1 and cell line 2) were cultured in a chemically defined media (media 1).

Cell line 2 was cultured in media 1 with different concentrations of lysine (1 (control), 5, 7, 9, 11 g/L). The cultures were performed in shake flasks in batch format with only glucose feed as described in the materials and methods above. The cells grew to maximum viable cell densities (VCD) in the range of $17\text{-}23 \times 10^6$ cells/ml for the different conditions tested. A slight dose dependent decrease in viable cell density profile was observed in all test conditions, with no significant effect on viability profiles (FIG. 24 and FIG. 25). On Days 10 and 11 of culture samples were collected for titer analysis. The harvest titers for all conditions were comparable (FIG. 26). On Day 11 of culture, duplicate shake flasks for each of the conditions were harvested and then subsequently analyzed using WCX-10 post Protein A purification and the percentages of total peak(s) area corresponding to the Lys 0, Lys 1 and Lys 2 peaks were quantified (FIG. 27). The percentage of Lys 0 relative to lysine sum (sum of the peak areas corresponding to Lys 0, Lys 1 and Lys 2) in the control sample was 92.5%. In the sample with the highest concentration of lysine in this experiment (11 g/L), the percentage of relative levels of Lys 0 was reduced to 67.7%. The decrease in Lys 0 corresponded with the increase in relative levels of both Lys 1 and Lys 2. A dose dependent decrease in relative Lys 0, and a dose dependent increase in relative Lys 1 and Lys 2 regions was observed in test conditions with increased lysine concentration.

Cell line 3 was cultured in media 1 with different concentrations of lysine (1 (control), 3, 5, 7, 9, 11 g/L). The cultures were performed in shake flasks in batch format with only glucose feed as described in the materials and methods above. The cells grew to maximum viable cell densities (VCD) in the range of $9.5\text{-}11.5 \times 10^6$ cells/ml for the different conditions tested. The growth and viability profiles were comparable between the different conditions, although a slight decrease in viable cell density and viability profiles was observed in samples with lysine concentration greater than 1 g/L, (FIG. 28, FIG. 29). On Days 10, 11 and 12 of culture samples were collected for titer analysis. The harvest titers for all conditions were comparable (FIG. 30). On Day 12 of culture, duplicate shake flasks for each of the conditions were harvested and then subsequently analyzed using WCX-10 post Protein A purification and the percentages of total peak(s) area corresponding to the Lys 0, Lys 1 and Lys 2 peaks were quantified (FIG. 31). The percentage of Lys 0 relative to lysine sum in the control sample was 94.2%. In the sample with the highest concentration of lysine in this experiment (11 g/L), the percentage of relative level of Lys 0 was reduced to 76.0%. The decrease in Lys 0 corresponded with the increase in relative levels of both Lys 1 and Lys 2. A dose dependent decrease in relative levels of Lys 0, and a corresponding increase in relative levels of Lys 1 and Lys 2 was observed in test conditions with increased lysine concentration.

Additional experiments were performed with multiple cell lines in chemically defined or hydrolysate based media to demonstrate the wide range of applicability of this method. The experimental setup for each of these experiments was similar to that described in the materials and methods above. The summaries of results of the different experiments performed for adalimumab are set forth in FIG. 32, FIG. 33 and FIG. 34. A reduction in relative levels of Lys 0, and a corresponding increase in relative levels of Lys 1 and Lys 2 with increased lysine was also observed in each case.

In addition to adalimumab, the utility of this method for acidic species reduction was also demonstrated for processes involving two other mABs. The experimental setup for each of these experiments was similar to that described in the materials and methods above. The modulation of lysine variants with arginine addition for experiments corresponding to each mAb is summarized in FIG. 35 and FIG. 36. A reduction in relative levels of Lys 0, and increase in relative levels of Lys 1 and Lys 2 species with increased lysine was observed in each case.

Effect of Supplementation of Histidine to Culture Media

The following describes two experiments where two different adalimumab producing cell lines (cell line 1 and cell line 2), were cultured in a chemically defined media (media 1).

Cell line 2 was cultured in media 1 with different concentrations of histidine (0 (control), 4, 6, 8, 10 g/L). The cultures were performed in shake flasks in batch format with only glucose feed as described in the materials and methods above. The cells grew to maximum viable cell densities (VCD) in the range of $12-22 \times 10^6$ cells/ml for the different conditions tested. A dose dependent decrease in viable cell density profile was observed in all conditions, with the 10 g/L histidine condition having significant reduction in growth (FIG. 37). A corresponding significant impact on the viability profile was also observed (FIG. 38). There was a small dose dependent decrease in titers for all conditions with histidine supplementation (FIG. 39). On Day 11 for control sample and Day 12 for the remaining conditions, duplicate shake flasks were harvested and then subsequently analyzed using WCX-10 post Protein A purification and the percentages of total peak(s) area corresponding to the lysine species were quantified (FIG. 40). The percentage of Lys 0 relative to lysine sum in the control sample was 92.5%. In the sample with the highest concentration of histidine in this experiment (10 g/L), the percentage of relative Lys 0 was reduced to 80.6%. The decrease in Lys 0 corresponded with the increase in relative levels of both Lys 1 and Lys 2.

Cell line 3 was cultured in media 1 with different concentrations of histidine (0 (control), 2, 4, 6, 8 g/L). The cultures were performed in shake flasks in batch format with only glucose feed as described in the materials and methods above. The cells grew to maximum viable cell densities (VCD) in the range of $6-10 \times 10^6$ cells/ml for the different conditions tested. A dose dependent decrease in viable cell density profile was observed in all samples supplemented with histidine (FIG. 41). In comparison to the impact on VCD profile, the viability profiles were more comparable between the conditions (FIG. 42). The harvest titers for all conditions were comparable (FIG. 43). On Day 12 of culture, duplicate shake flasks for each of the conditions were harvested and then subsequently analyzed using WCX-10 post Protein A purification and the percentages of total peak(s) area corresponding to Lys 0, Lys 1 and Lys 2 species were quantified (FIG. 44). The percentage of Lys 0 relative to lysine sum in the control sample was 94.2%. In the sample with the highest concentration of histidine in this experiment (8 g/L), the percentage of relative Lys 0 was reduced to 81.5%. The decrease in Lys 0 corresponded with the increase in relative levels of both Lys 1 and Lys 2. A dose dependent decrease in relative Lys 0, and a dose dependent increase in relative Lys 1 and Lys 2 regions was observed in test conditions with increased histidine concentration.

Additional experiments were performed with multiple cell lines in chemically defined or hydrolysate based media to demonstrate the wide range of applicability of this method. The experimental setup for each of these experiments was similar to that described above. The results of the different experiments performed for adalimumab are summarized in FIG. 45, FIG. 46 and FIG. 47. A reduction in relative Lys 0, and increase in relative Lys 1 and Lys 2 species with increased histidine was observed in each case.

In addition to adalimumab, the utility of this method for modulation of lysine variants was evaluated for processes involving two other mAbs. The experimental setup for each of these experiments was similar to that described in the materials and methods. The results for experiments corresponding to each mAb are summarized in FIG. 48 and FIG. 49. For mAb1, a dose dependent reduction in relative levels of Lys 0 was evident with increased histidine. However, for mAb2, the relative change was minimal within the histidine concentration range tested.

Effect of Amino Acid Modulation on Culture Media in 3 L Bioreactors

In this study, 3 L bioreactors were set up to confirm the effect of amino acid addition on lysine variant distribution in more controlled conditions (pH and dissolved oxygen (DO)) at a larger scale. Eight Bioreactors (1.5 L working volume) were set up with cell line 2 in IVGN production media. The process included a temperature shift from 37° C. to 33° C. when the cell density criterion of $6 \times 10^6$ cells/ml was met. The pH was controlled via $CO_2$ gas flow/0.5 N Sodium Hydroxide base at a starting pH of 7.1 that was subsequently allowed to ramp down to 6.9 over the initial three days of the process. The DO was controlled at 30% and the agitation rate was maintained at 200 rpm. The cultures were fed with Ex-Cell PFCHO (SAFC, 67411) (3% (v/v)) on Day 3 of culture and with 18.8 g of 40% (w/v) glucose solution on days when glucose in the reactor was measured to be below 3 g/L. The test conditions included the amino acid concentration in media to be as follows: control (1 g/L arginine and 1 g/L lysine), 3 g/L arginine, 3 g/L arginine/2 g/L lysine and 3 g/L arginine/3 g/L lysine. Reactors were run in duplicates for each condition.

The culture performance was comparable between the different conditions with similar growth and viability profiles (FIG. 50, 51). The cultures were harvested on Day 11 with the harvest viability between 40-50% in all the different conditions. Culture harvests were processed through Protein A purification and WCX-10 analysis for quantification of the lysine variants. The lysine variant distribution in the control samples were 86.7% (Lys 0), 11.1% (Lys 1) and 2.2% (Lys 2). The Lys 0 was reduced to 72.1% in the condition with the highest concentration of amino acids (3 g/L arginine/3 g/L lysine sample) (FIG. 53). The decrease in Lys 0 corresponded with the increase in relative levels of both Lys 1 and Lys 2. Thus, increase of amino acids arginine and lysine can modulate lysine distribution even in 3 L bioreactors under controlled conditions of DO and pH.

Effect of Ornithine Modulation on Culture Media

In this Example, the effect of increased ornithine concentration was tested both individually as well as in combination with other amino acids arginine and lysine. The study was performed with adalimumab producing cell line 2 in media 1. The experiment was carried out in 500 ml shake flasks (200 ml working volume) and was run on shaker platforms set at 180 rpm in incubators set to be controlled at 35.0° C. and 5% $CO_2$. The conditions tested included a control (only 1 g/L arginine and 1 g/L lysine), and test conditions including condition 2 (1 g/L ornithine, 1 g/L arginine, 1 g/L lysine), test condition 3 (4 g/L ornithine, 1 g/L arginine and 1 g/L lysine), test conditions 4 (1 g/L ornithine, 5 g/L arginine, 1 g/L lysine), test condition 5 (0 g/L ornithine, 5 g/L arginine, 2 g/L lysine), and test condition 6 (1 g/L ornithine, 5 g/L arginine, 2 g/L lysine). The cell culture performed comparably between the control and the test conditions with similar growth and viability profiles (FIG. 54, FIG. 55). Samples were collected for all conditions on day 10 for titer, which were comparable (FIG. 56). The cultures were harvested at day 10, processed through Protein A purification and WCX-10 analysis, and the relative fractions of lysine variants were estimated. There was no significant change in the lysine variant distribution in the conditions where only the ornithine concentration was increased (at 1 g/L or 4 g/L) compared to the control. However, the combination of ornithine increase with arginine or lysine increase reduced the relative level of Lys 0 in comparison with the condition with just arginine and lysine increase with a relative level of Lys 0 (FIG. 57). Thus, the increase of ornithine may exhibit synergistic effects in modulating lysine variant distribution when added in combination with arginine and lysine.

Effect of Increase in Concentration of a Combination of Arginine, Lysine, Histidine, and Ornithine to Culture Media In this experiment, the combined use of the four amino acids arginine, lysine, histidine and ornithine for modulation of the lysine variants is demonstrated. The experiment described here was performed using adalimumab producing cell line 2 in chemically defined media (media 1). The concentration range for arginine and lysine in this experiment was 1-3 g/L while the concentration range for histidine and ornithine in this experiment was between 0-2 g/L. In comparison to the lower concentrations, or conditions where amino acids were supplemented individually, a further reduction in Lys 0 relative to lysine sum was observed in conditions where combinations of amino acids were increased in the media (FIG. 58). A progressive decrease was observed in relative Lys 0 when more amino acids were increased in combination. The percentage of relative Lys 0 was reduced from 94.9% in the control sample to 73.9% in the sample with all four amino acid concentrations increased.

Effect of Increase in Concentration of a Combination of Arginine, Lysine, Histidine, and Zinc to Culture Media In this experiment, the combined use of zinc and the three amino acids arginine, lysine, and histidine for lysine species modulation is demonstrated. The experiment described here was performed using adalimumab producing cell line 1 in chemically defined media (media 1). The concentration range for arginine and lysine in this experiment was between 1-3 g/L. The concentration range for histidine was between 0-1 g/L. The concentration range for zinc in this experiment was 30 µM-60 µM. Using the data from the experiment, a model predicting the effects of addition of these supplements to media for relative Lys 0 reduction ($R^2$: 0.98, P=0.09) is described in FIG. 59. The model predicted a contribution from each of the amino acids towards relative Lys 0 reduction. The model also predicted an increase in relative Lys 0 with an increase in zinc, which further supports the claim that reduction of zinc in culture causes a reduction in relative Lys 0. It may be also possible to utilize this model to predict the choice of concentrations of these different components to the media, in order to achieve a target reduction in relative Lys 0.

Effect of Supplementation of Single Peptides, Dipeptides and Tripeptides to Culture Media In this experiment, the use of the three amino acid monomers arginine, lysine, and histidine, use of the dipeptides lys-lys and arg-lys, and use of the tripeptides lys-lys-lys, his-arg-lys, and arg-his-lys for lysine species modulation is demonstrated. The experiment described here was performed using adalimumab producing cell line 1 in chemically defined media (media 1). The concentration range for each peptide set tested in this experiment was between 0-4 g/L. In comparison to the control, a reduction in Lys 0 relative to lysine sum was also observed in conditions where dipeptides and tripeptides were supplemented to the media (FIG. 60). A decrease was observed in relative Lys 0 when polypeptides were supplemented. The percentage of relative Lys 0 was reduced from 88.0% in the control sample to 71.9% in a sample supplemented with tripeptide arg-his-lys (4 g/L), and to 74.0% in a sample supplemented with his-arg-lys (2 g/L).

The experiments outlined above demonstrate the different methods that can be used either alone or in suitable combinations to modulate the lysine variant distribution profile of a protein of interest. Specifically, increasing the concentration in culture media of the amino acids lysine, arginine, histidine, or combinations thereof along with ornithine and limiting the concentration of zinc in media, resulted in the relative modulation of the lysine variants with a decrease in the relative levels of Lys 0 and a corresponding increase in both Lys 1 and Lys 2.

Example 3

Methods for Modulating the Lysine Variant Distribution in Cell Culture by Adjusting Process Parameters Materials and Methods Cell Source and Adaptation Cultures Three adalimumab producing CHO cell lines (call line 1, cell line 2, and cell line 3) were employed in the studies in this Example.

For adalimumab producing cell lines, cells were cultured in their respective growth media (chemically defined media (media 1) or a hydrolysate based media (media 2 or media 3)) in a combination of vented non-baffled shake flasks (Corning) on a shaker platform at 110 RPM (cell line 1), 180 RPM (cell line 2), 140 RPM (cell line 3) and 10 L or 20 L wave bags (GE). For experiments with cells in the hydrolysate based media (media 3), cells were thawed in media 1 and then adapted to media 3 over a few passages. Cultures were propagated in a 35° C., 5% $CO_2$ incubator for cell line 1 and 2 and in a 36° C., 5% $CO_2$ incubator for cell line 3 in order to obtain the required number of cells to be able to initiate production stage cultures.

In some cases, the culture might be transferred into a seed reactor with pH 7.1, 35° C. and 30% dissolved oxygen (DO). In some cases, the culture was adapted to either media 1 or media 2 by propagated in a 10 L or 20 L wavebag for 7-13 days with one or two passages before initiating production stage cultures.

Cell Culture Media

Media 1, the chemical defined growth or production media, was prepared from basal IVGN CD media GIA1. For preparation of the IVGN CD media formulation, the proprietary media was supplemented with L-glutamine, sodium bicarbonate, sodium chloride, and methotrexate solution. Production media consisted of all the components in the growth medium, excluding methotrexate. For cultures with adalimumab producing cell line 1, the medium was also supplemented with insulin. In some cases, 10 mM or 5 mM of Galactose (Sigma, G5388) and 0.2 µM or 10 µM of Manganese (Sigma, M1787) were supplemented into production medium for cultures with adalimumab producing cell line 3 and adalimumab producing cell line 1, respectively. Osmolality was adjusted by the addition of sodium chloride. All media was filtered through filter systems (0.22 μm PES) and stored at 4° C. until usage.

For the hydrolysate-based formulation (media 2), the growth media was composed of PFCHO (proprietary CD formulation from SAFC), dextrose, L-glutamine, L-asparagine, HEPES, Poloxamer 188, ferric citrate, recombinant human insulin, yeastolate (BD), phytone peptone (BD), mono- and di-basic sodium phosphate, sodium bicarbonate, sodium chloride and methotrexate. Production media consisted of all the components listed in the growth medium, excluding methotrexate.

Production Cultures

Production cultures were initiated in 3 L Bioreactors (Applikon). The bioreactors (1.5-2.0 L working volume) were run at the following conditions (except for the different experimental conditions): 35° C., 30% DO (dissolved oxygen), 200 rpm, pH profile from 7.1 to 6.9 in three days and pH 6.9 thereafter. In all experiments, the cells were transferred from the wavebag to the production stage at a split ratio of 1:5.6. When the media glucose concentration reduced to less than 3 g/L, approximately 1.25% (v/v) of 40% glucose stock solution was fed.

The harvest procedure of reactors involved centrifugation of the culture sample at 3,000 RPM for 30 min and storage of supernatant in PETG bottles at −80° C. before submission for Protein A purification and WCX-10 analysis.

WCX-10 Assay

The acidic species and other charge variants present in cell culture harvest samples were quantified. Cation exchange chromatography was performed on a Dionex ProPac WCX-10, Analytical column (Dionex, Calif.).

For adalimumab samples, the mobile phases used were 10 mM sodium phosphate dibasic pH 7.5 (Mobile phase A) and 10 mM sodium phosphate dibasic, 500 mM sodium chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Results and Discussion

Effect of Process pH in Media 1 with Cell Line 1

Five different pH conditions were assessed in this study: 7.1, 7.0, 6.9, 6.8 and 6.7. The cultures were started at pH set point of 7.1; then were ramped down to the target pH set points within 4 days. All cultures reached similar maximum viable cell densities on day 8, except for the culture at pH 6.7 condition, for which the maximum cell density was much lower than the other cultures (FIG. 61). In addition, the viability of the culture at pH 7.1 and pH 7.0 dropped much earlier than the other cultures (FIG. 62). The viability of cultures at pH 7.1 and pH 7.0 were 38% and 54% on day 10, respectively; while the viability of the cultures at lower pH (including pH 6.9, 6.8 and 6.7) was above 70% on the same day. Samples were taken on the day of the cultures and measured for titer. The titer of each tested condition increased corresponding to the decrease in pH, from 1.2 g/L in the pH 7.1 condition to 1.8 g/L in the pH 6.8 condition; however, product titer was not continued to increase at pH 6.7 (1.6 g/L) (FIG. 63). The cultures were harvested at ≤50% viability. The harvest was purified via Protein A chromatography, then analyzed using WCX-10. From the WCX-10 analysis, the lysine variant distribution was characterized and the relative proportion of Lys 0, Lys 1 and Lys 2 variants were quantified as a fraction of the total lysine sum. The relative fraction of Lys 0 increased with decrease in pH from 82.0% in the pH 7.1 condition to 87.9% in the pH 6.7 condition, with corresponding 5.0% decrease in relative levels of Lys 1 and 0.9% decrease in Lys 2 (FIG. 64).

Effect of Process pH in Media 2 with Cell Line 1

Three different pH conditions were assessed in this study: 7.0, 6.9, and 6.8. The cultures were started at pH of 7.1; then were ramped down to the target pH set points within 3 days of culture. The viable cell density and viability were comparable across the different pH set points until day 8. After day 8, the viable cell density and viability were slightly higher corresponding to lower pH set points (FIG. 65, FIG. 66). The cultures were harvested at ~50% viability. The product titer was slightly higher at pH 6.8 comparing to pH 6.9 and 7.0 (FIG. 67). The resulting peak areas from WCX-10 analysis were quantified (FIG. 68). The relative fraction of Lys 0 increased with decrease in pH from 76.8% in the pH 7.0 condition to 80.5 in the pH 6.8 condition, with corresponding 2.8% decrease in relative levels of Lys 1 and 0.9% decrease in Lys 2.

Effect of Process pH in Media 1 with Cell Line 3

Five different pH conditions were assessed in this study: 7.1 7.0, 6.9, 6.8, and 6.7. The cultures were started at pH set point of 7.1; then were ramped down to the target pH set points within 4 days of culture. The pH set points showed significant effect on the cell growth and viability with this cell line and media. Cell density was lower at higher pH and viability also dropped earlier at higher pH (FIG. 69, FIG. 70). The cells were harvested at an approximate viability of 50%. The titer was slightly increased as the pH was reduced, reached the highest titer at pH 6.8 condition (FIG. 71). The resulting peak areas from WCX-10 analysis were quantified (FIG. 72). The relative fraction of Lys 0 increased with decrease in pH from 88.0% in the pH 7.1 condition to 94.1% in the pH 6.7 condition, with a corresponding 4.8% decrease in relative levels of Lys 1 and 1.3% decrease in Lys 2.

Effect of Process Dissolved Oxygen (DO) in Media 2 with Cell Line 1

Three different dissolved oxygen (DO) concentrations were assessed in this study: 20%, 30% and 50% at a culture temperature of 35° C. The cell density and viability were very comparable at different DO conditions (FIGS. 73 and 74). The cultures were harvested at the target viability of 50% for each condition. The harvest titer was higher at 50% DO concentration compared to 20% DO concentration (FIG. 75). The harvest was also purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 76). The relative fraction of Lys 0 decreased with an increase in DO concentration from 83.6% in the 20% DO concentration to 77.2% in the 50% DO concentration, with a corresponding 4.7% increase in relative levels of Lys 1 and 1.8% increase in Lys 2.

In the next study, three different DO concentrations were assessed: 20%, 30% and 60% at a culture temperature of 33° C. The cell density, viability and product titer were very comparable at different DO conditions (FIGS. 77, 78 and 79). The cultures were harvested at the target viability of 50% for each condition. The harvest was also purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 80). The relative fraction of Lys 0 decreased with an increase in DO concentration from 73.8% in the 20% DO concentration to 66.3% in the 60% DO concentration, with a corresponding 4.5% increase in relative levels of Lys 1 and 3.0% increase in Lys 2.

Effect of Process Dissolved Oxygen (DO) in Media 1 with Cell Line 1

In this study, three different dissolved oxygen (DO) concentrations were assessed: 20%, 30% and 50%. The cultures were set at a temperature of 35° C. The cell density and viability were very comparable at different DO conditions (FIGS. 81, 82). The cultures were harvested at the target viability of 40% for each condition. The harvest titer was higher at 30% and 50% DO comparing to 20% DO (FIG. 83). The harvest was also purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 84). The relative fraction of Lys 0 decreased with an increase in DO concentration from 84.8% in the 20% DO concentration to 81.0% in the 50% DO concentration, with a corresponding 3.2% increase in relative levels of Lys 1 and 0.7% increase in Lys 2.

Effect of Process Temperature in Media 1 with Cell Line 1

Three different temperature conditions were assessed: 33° C., 35° C. and 37° C. The cultures were harvested at the target viability of 50% for each condition. At a lower temperature, the culture duration was longer with higher viability through the culture (FIG. 85, FIG. 86). Samples were collected for titer analysis on harvest days. The titer for all conditions was comparable (FIG. 87). The harvest was purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 88). The relative fraction of Lys 0 increased with increase in temperature from 80.3% in the 33° C. concentration to 86.6% in the 37° C. concentration, with corresponding 5.3% decrease in relative levels of Lys 1 and 1.0% decrease in Lys 2. Thus, lowering the process temperature provides an effective method to increase the relative proportion of the product antibody with C-terminal lysine on one or both the heavy chains.

Effect of Process Temperature in Media 1 with Cell Line 2

Three different temperature conditions were assessed: 33° C., 35° C., and 37° C. The cultures were harvested at the target viability of 50% for each condition. The viability cell density (VCD) and viability profiles were similar for the 37° C. and 35° C. conditions, but the 33° C. condition took longer to drop to 50% (FIG. 89, FIG. 90). The product titers were lower at 31° C. compared to the titers at 33° C. and 35° C. (FIG. 91). The harvest was purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 92). The relative fraction of Lys 0 increased with increase in temperature from 88.6% in the 33° C. condition to 93.1% in the 37° C. condition, with corresponding 3.8% decrease in relative levels of Lys 1 and 0.7% decrease in Lys 2. Thus, the results here are consistent with that observed for cell line 1.

Effect of Process Dissolved Oxygen and Temperature in Media 1 with Cell Line 3

The study was performed at four different temperature levels (33° C., 34° C., 35° C. and 36° C.) with two different DO concentrations (20% DO and 50% DO). In general, the cell growth at different dissolved oxygen concentrations was similar except at 35° C., in which the cell density was lower at 50% DO concentration (FIG. 93). In addition, the cultures reached higher maximum cell density at higher temperatures (at 36° C. and 35° C.), while viability dropped earlier and faster (FIG. 94). The cultures were harvested at approximately 50% viability. The product titers were comparable at all conditions (FIG. 95). The harvest was purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum (FIG. 96).

The relative distribution of lysine variants was influenced by the choice of % DO concentration and temperature. The effect of lowering temperature was more significant than increasing % DO concentration in this case. At 20% DO, the relative fraction of Lys 0 increased with increase in temperature from 80.5% in the 33° C. condition to 91.4% in the 36° C. condition, with corresponding 8.5% decrease in relative levels of Lys 1 and 2.4% decrease in Lys 2. At 50% DO, the relative fraction of Lys 0 increased with increase in temperature from 80.1% in the 33° C. condition to 90.8% in the 36° C. condition, with corresponding 8.2% decrease in relative levels of Lys 1 and 2.5% decrease in Lys 2. On the other hand, at different temperatures, the relative fraction of Lys 0 decreased with an increase in DO concentration, with the maximum difference observed at 35° C. from 90.1% in the 20% DO concentration to 88.7% in the 50% DO concentration, with a corresponding 1.2% increase in relative levels of Lys 1 and 0.2% increase in Lys 2. Therefore the results here are consistent with that observed with other cell lines.

The experiments described above demonstrate the different methods that can be used either alone or in suitable combination to control the lysine variant distribution profile of a protein of interest, e.g., the antibody adalimumab. These experiments also indicate that altering cell culture process parameters on-line can be used to modulate the lysine variant distribution. Increasing dissolved oxygen concentration, increasing pH set points or reducing temperature set points results in a relative shift in lysine variant distribution from Lys 0 to Lys 1 Lys 2.

Example 4

Effect of Phosphate Salt Concentration on the Lysine Variant Distribution of Product Antibody In this Example, the effect of varying the concentration of phosphate salt individually and in combination with other amino acids (lysine or arginine) and trace elements (zinc ion) in chemically defined media on the Lys variant distribution of the antibody adalimumab was studied. Subsections 4.1 and 4.2, below, show that increasing the concentration of phosphate in media leads to a relative shift in lysine variant distribution from Lys 0 to Lys 1/Lys 2 in two adalimumab producing CHO cell lines (cell line 1 and cell line 2). Subsection 4.3 demonstrates that increasing the concentration of phosphate salt in combination with the addition of lysine or arginine provides modulation of lysine variants in an additive manner in cell line 3.

Materials and Methods
Cell Lines and Adaptation Cultures
Two adalimumab producing CHO cell lines were employed in the studies covered here (cell line 1 and cell line 2).
Cell Culture Media
The initial growth media used in the seed train phase was prepared from proprietary growth CD media GIA1 (Invitrogen). In the experiments testing phosphate salt individually, the production media was prepared staring from proprietary basal CD media GIA1 (Basal) and supplemented with various level of $NaH_2PO_4 \cdot H_2O$. A description of the culture conditions for both cell lines is listed in Table 4, below. In the combination experiment, the production media were prepared staring from proprietary basal CD media GIA1 (Basal) and supplemented with various level of $NaH_2PO_4 \cdot H_2O$, L-lysine.HCl, L-arginine and zinc salt (containing $ZnSO_4$ and $ZnCl_2$) based on central composite design with two center points. A description of the culture conditions for cell line 1 is listed in Table 5. The L-lysine, L-arginine, phosphate salt and zinc ion concentration in the CD media GIA1 were approximately 6.0 mM, 4.0 mM, 5.8 mM and 10 μM, respectively.

TABLE 4

Cell culture media and cell line conditions used for Examples 4.1 and 4.2

| Experiment | Cell line | Condition | Basal media | $NaH_2PO_4 \cdot H_2O$ Supplementation |
|---|---|---|---|---|
| Example 4.1 | Cell line 1 batch | Control | CD media GIA1 | None |
| | | 6 mM | | 6 mM |
| | | 12 mM | | 12 mM |
| | | 18 mM | | 18 mM |
| | | 24 mM | | 24 mM |
| Example 4.2 | Cell line 2 batch | Control | CD media GIA1 | None |
| | | 6 mM | | 6 mM |
| | | 12 mM | | 12 mM |
| | | 18 mM | | 18 mM |
| | | 24 mM | | 24 mM |

Cell Culture Conditions

Upon thaw, cells were typically cultured in a combination of 250 ml and 500 ml Corning vented non-baffled shake flasks on a shaker platform at 110 RPM for cell line 1 and 180 rpm for cell line 2 in a 35° C., 5% $CO_2$ incubator. Growth media was used to carry both cell lines in seed train stages.

In the experiments that tested phosphate individually (Example 4.1 and Example 4.2, below), production cultures were initiated in duplicates according to Table 4. In Example 4.2, which tested phosphate in combination with lysine, arginine and zinc ion, a production culture was started according to Table 5 based on centre composite design, which is an experimental design that is useful in response surface methodology, for building a second order (quadratic) model for the response variable without needing to use a complete three-level factorial experiment. All the cultures were kept in 500 ml Corning vented non-baffled shake flasks (200 ml working volume) with temperature and $CO_2$ maintained at 35° C. and 5%. The shaker platforms were set at 110 rpm for cell line 1 and 180 rpm for cell line 2. In all experiment conditions, the cells were transferred from the seed train stage to the production stage at a split ratio of 1:5. 40% glucose solution was feed as necessary to maintain the culture at adequate levels. The cultures were harvested on day 11 (generally maintaining harvest viability at approximately 50%).

The harvest procedure of the shake flasks involved centrifugation of the culture sample at 3,000 RPM for 30 min and storage of supernatant in PETG bottles at −80° C. before submission for Protein A purification and WCX-10 analysis.

WCX-10 Assay

For quantification of charge variants of antibodies, action exchange chromatography was performed on a Dionex Pro-

TABLE 5

Cell culture media conditions used for Example 4.3 conducted on cell line 1.

| Experiment | Condition | Basal Media | Lysine•HCl (mM) | Arginine (mM) | $NaH_2PO_4 \cdot H_2O$ (mM) | Zn * (μM) |
|---|---|---|---|---|---|---|
| Example 4.3 | 1 | CD media GIA1 | 5.5 | 5.7 | 6.0 | 30 |
| | 2 | | 10.9 | 0.0 | 0.0 | 0 |
| | 3 | | 5.5 | 11.5 | 6.0 | 15 |
| | 4 | | 5.5 | 5.7 | 6.0 | 15 |
| | 5 | | 5.5 | 0.0 | 6.0 | 15 |
| | 6 | | 5.5 | 5.7 | 12.0 | 15 |
| | 7 | | 5.5 | 5.7 | 6.0 | 15 |
| | 8 | | 10.9 | 11.5 | 12.0 | 0 |
| | 9 | | 0.0 | 0.0 | 0.0 | 0 |
| | 10 | | 10.9 | 5.7 | 6.0 | 15 |
| | 11 | | 0.0 | 0.0 | 0.0 | 30 |
| | 12 | | 10.9 | 0.0 | 12.0 | 30 |
| | 13 | | 10.9 | 11.5 | 12.0 | 30 |
| | 14 | | 0.0 | 11.5 | 12.0 | 0 |
| | 15 | | 5.5 | 5.7 | 0.0 | 15 |
| | 16 | | 10.9 | 11.5 | 0.0 | 30 |
| | 17 | | 0.0 | 11.5 | 0.0 | 30 |
| | 18 | | 10.9 | 11.5 | 0.0 | 0 |
| | 19 | | 0.0 | 5.7 | 6.0 | 15 |
| | 20 | | 5.5 | 5.7 | 6.0 | 0 |
| | 21 | | 10.9 | 0.0 | 0.0 | 30 |
| | 22 | | 0.0 | 11.5 | 0.0 | 0 |
| | 23 | | 10.9 | 0.0 | 12.0 | 0 |
| | 23 | | 0.0 | 0.0 | 12.0 | 0 |
| | 25 | | 0.0 | 0.0 | 12.0 | 30 |
| | 26 | | 0.0 | 11.5 | 12.0 | 30 |

* Zn was supplemented using combination of $ZnCl_2$ and $ZnSO_4$ with fixed molar ratio of 0.56:1.

Pac WCX-10, Analytical column 4 mm×250 mm (Dionex, Calif.). A Shimadzu LC10A HPLC system was used as the HPLC. The mobile phases used were 10 mM sodium phosphate dibasic pH 7.5 (Mobile phase A) and 10 mM sodium phosphate dibasic, 500 mM sodium phosphate pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation was based on the relative area percent of detected peaks.

Example 4.1

Effect of Phosphate Supplementation in Chemically Defined Media with Cell Line 1

In this Example, the effect of varying phosphate concentration in production cell culture media on cell culture performance and product quality was evaluated using cell line 1. Slightly increased peak viable cell density (VCD) was observed at 6 mM phosphate supplementation level compared with control (FIG. 97A). Nevertheless, slightly to moderate growth inhibition was observed as the phosphate supplementation amount was increased from 12 mM to 24 mM (FIG. 97A). All the cultures were harvested on day 11, and slightly higher viabilities were observed in phosphate supplemented conditions compared with control (FIG. 97B). Corresponding to the growth inhibition, the harvest titer was also reduced in the phosphate supplemented conditions (1.1 to 1.3 g/L) compared with control (1.4 g/L) (FIG. 97C). All the harvested cultures were purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum. Dose dependent modification of lysine variant distribution was shown with the increase of the phosphate concentration. As the phosphate concentration in the production media increased from 5.8 mM (control condition) to 29.8 mM (24 mM phosphate supplementation condition), the relative fraction of Lys 0 was reduced from 91.3 to 85.7%, Lys 1 was increased from 7.0 to 11.5% and Lys 2 was increased from 1.7 to 2.8% (FIG. 97D).

Thus, the higher phosphate concentrations provide an effective method to increase the relative proportion of the product antibody with C-terminal lysine on both the heavy chains (Lys 1/Lys 2).

Example 4.2

Effect of Varying Phosphate Concentration in Chemically Defined Media with Cell Line 2

In this Example, the effect of varying phosphate concentration in production cell culture media on cell culture performance and product quality was evaluated using cell line 2. Compared with cell line 1, the reduction of peak viable cell density (VCD) and the increase of harvest viability effects associated with high concentration level phosphate supplementation (18 mM and 24 mM) were also observed on cell line 2 (FIGS. 98A and 98B). The harvest titer reduction resulting from phosphate supplementation also remained significant. The harvest titers were in the range of 1.5-2.0 g/L with 6 mM to 24 mM phosphate supplementation, compared with 2.1 g/L titer for the control condition (FIG. 98C). All the cultures were harvested on day 11 and purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum. Dose dependent modification of lysine variant distribution was also shown with the increase of the phosphate concentration in cell line 2. As the phosphate concentration in the production media increased from 5.8 mM (control condition) to 29.8 mM (24 mM phosphate supplementation condition), the relative fraction of Lys 0 was reduced from 91.7 to 84.8%, Lys 1 was increased from 6.6 to 12.3% and Lys 2 was increased from 1.7 to 2.9% (FIG. 98D).

Therefore, the increase in the relative proportion of the product antibody with C-terminal lysine on one or both the heavy chains (Lys 1/Lys 2) corresponding to an increase in levels of phosphate in basal media, was also observed in this Example.

Example 4.3

Effect of Varying Phosphate, Lysine, Arginine and Zinc Concentrations in Chemically Defined Media with Cell Line 1

In this Example, the effect of varying phosphate was evaluated in combination with altering lysine, arginine and zinc concentrations in production cell culture media on cell culture performance and product quality. The study was conducted using cell line 1 based on centre composite design. Data were analyzed using JMP software (a computer program for statistics developed by the JMP business unit of SAS Institute). The effects of varying lysine, arginine, zinc and phosphate concentration on peak viable cell density (VCD), harvest viability, harvest titer were evaluated and ARE shown in FIGS. 99A-99C. Within the studied range, no significant peak VCD, harvest viability and harvest tier impact was observed as the concentration of lysine or arginine was varied. However, increasing the zinc concentration corresponded to the significantly increased peak VCD and harvest titer; while increasing the phosphate concentration resulted in significantly reduced harvest viability and titer.

All the cultures were harvested on day 11 and purified via Protein A chromatography before WCX-10 analysis. From the WCX-10 analysis, the lysine variant distribution was characterized and the relative proportion of Lys 0, Lys 1 and Lys 2 variants were quantified as a fraction of the total lysine sum. The effects of varying lysine, arginine, zinc and phosphate concentration on lysine variant distribution are shown in FIGS. 99D-99F. Supplementation of lysine, arginine, and phosphate all lead to significantly decreased Lys 0 and increased Lys 1 and Lys 2. The effect of varying zinc concentration on lysine variant was minimal within the evaluated range. No interaction effects between the additives had statistical significance indicating that the modulation of lysine variants was additive and not synergistic.

Thus, manipulating phosphate concentration in the production media provides not only one additional way to modulate the lysine variant distribution but also provides additive modulation of lysine variants in combination with the addition of amino acids.

The Examples above (Examples 4.1, 4.2, and 4.3) demonstrate that altering the concentration of phosphate in chemically defined media can lead to modulation of the lysine variant distribution. In Examples 4.1 and 4.2, it is demonstrated that increasing the concentration of phosphate in media leads to a relative shift in lysine variant distribution from Lys 0 to Lys 1/Lys 2. In Example 4.3 it is demonstrated that the effect of phosphate salt in combination with lysine or arginine provides additive modulation of lysine variants.

Example 5

Increased Biological Activity of Modified Lysine Compositions

This Example describes the increased efficacy of an exemplary modulated lysine variant species composition comprising adalimumab in vivo. The modulated lysine variant species composition used in this Example was produced by collecting fractions from a preparative scale HPLC column of WCX-10, using purified adalimumab. Specifically, the Lys 1 and Lys2 peaks from the WCX column were collected and then subsequently combined and further concentrated to prepare the modulated lysine variant species composition, referred to in this Example as Lys-1/2.

Animal Model for Arthritis

In order to study the efficacy of this modulated lysine variant species composition, experiments were carried out in vivo using human TNF-Tg197 mice. The TNF-Tg197 mouse model is a well recognized mouse model of arthritis used to test anti-human TNFα treatment modalities. The TNF-Tg197 mouse model is described in Keffer, J. et al., (1991) *EMBO J* 10:4025-4031, the contents of which are incorporated herein by reference. The transgenic mice carrying human TNF gene were developed to study the effects of excess TNFα production in vivo.

Tg197 mice develop swelling in the ankle joints of both hind paws and impaired movement, which is very similar to human rheumatoid arthritis. Clinical signs of disease in Tg197 mice start at 4 weeks of age and include slower weight gain, joint distortion and swelling, joint deformation and ankylosis and impaired movement. Histopathological analysis reveals hyperplasia of synovial membrane, leukocyte infiltration at around 3 weeks of age, and then pannus formation, articular cartilage destruction and massive production of fibrous tissue at advanced stage of disease at 9-11 weeks of age. This model has been used in the development of anti-TNFα biologics, including adalimumab.

Methods

Groups of mice (6 males and 6 females), were administered one of the following adalimumab formulations: low AR composition (group 5; which contains 3.1% acidic species (AR), wherein the composition comprises 0.1% acidic region 1 (AR1) acidic variants and 3.0% acidic region 2 (AR2) acidic variants); low host cell protein (HCP) composition (group 7); AR1 composition (containing only AR1 acidic variants) (group 8); and a Lys 1 and Lys 2 composition (referred to in this Example as the modulated lysine variant species composition or Lys-1/2, and which contains only Lys 1 and Lys 2 variants) (group 9). These compositions (fractions) are shown in the chromatograph in FIG. 100. Another group of mice was administered a control composition, also referred to as the "control AR composition," or "normal" composition, which contains adalimumab with unmodified AR levels and unmodified Lys variants. A placebo group, comprising 6 mice, was also included.

Each composition, including the control AR composition, was administered to the mice in each group beginning with a tolerizing dose of adalimumab at age 1 week, and followed by additional weekly dosages of 1 mg/kg for 10 weeks. From weeks 2.5 through weeks 13.5, weekly measurements of weight and arthritic scores were taken and weekly serum collection was made. In addition, at the end of the study, tissue samples from perfused mice were obtained and analyzed. The following tissues were harvested for testing drug levels, anti-drug antibodies (ADA), and complexed and free TNF levels: front paws, inguinal, popliteal and mesenteric lymph nodes, spleen, tail (for skin sample), knees. The femur and spine tissues were harvested for micro-CT scanning.

Results

Figure 101A:
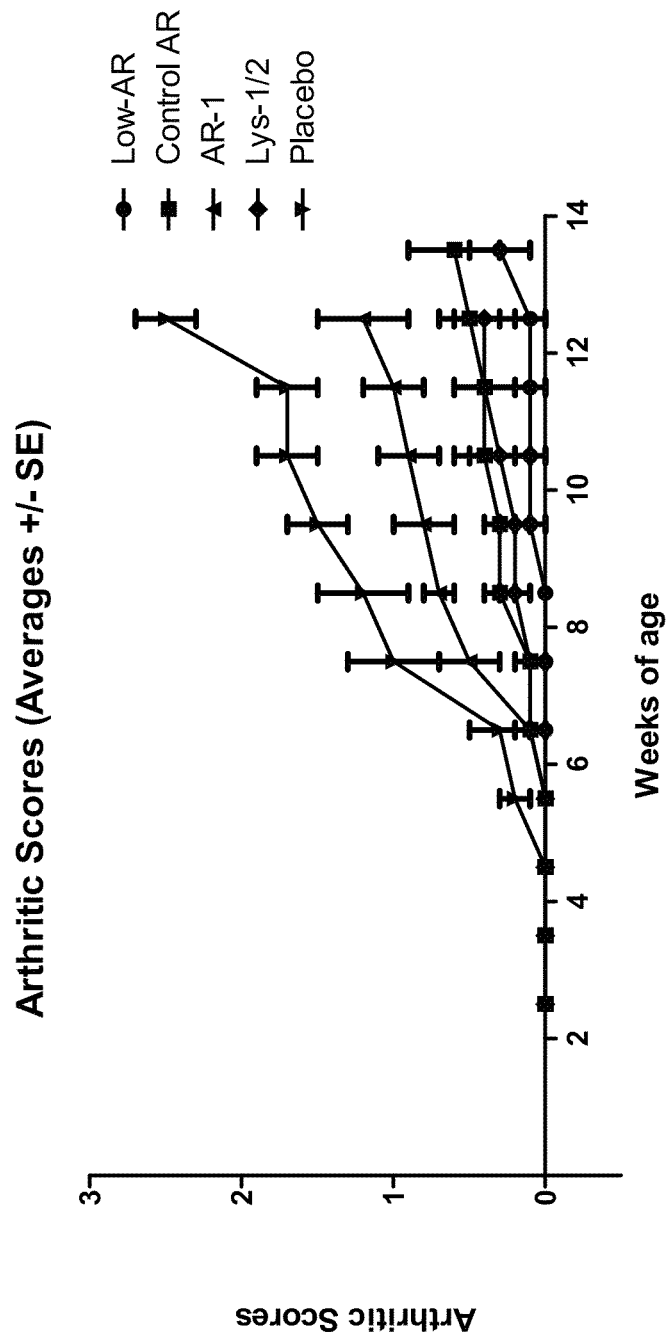
FIGS. 101A-B depict the (A) average arthritic scores and (B) growth related weight gain of mice administered low AR composition, control AR composition, AR1 composition, modulated lysine variant species composition (Lys-1/2), and placebo.
Figure 101B:
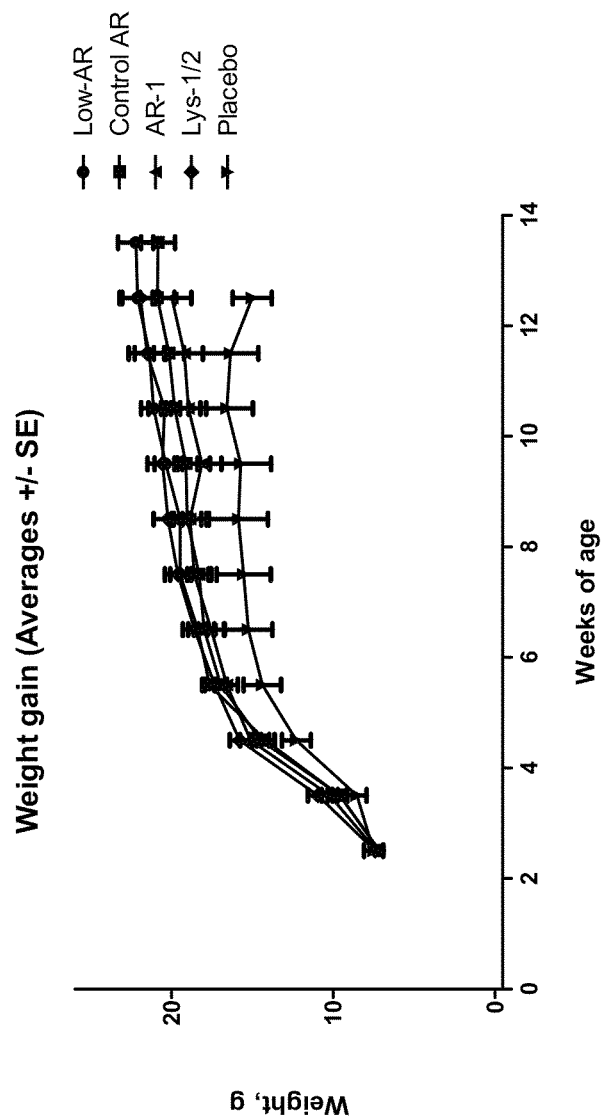

As shown in FIG. 101A, the animals receiving the modulated lysine variant species composition (Lys-1/2) had arthritic scores similar to the control AR composition. Furthermore, as shown in FIG. 101B, the mice administered the modulated lysine variant species composition exhibited an average weight gain that was comparable to the control AR composition, indicating safety of the modulated lysine variant species composition, and a lack of adverse effects that impact weight gain and growth of the mice.

Figure 102:
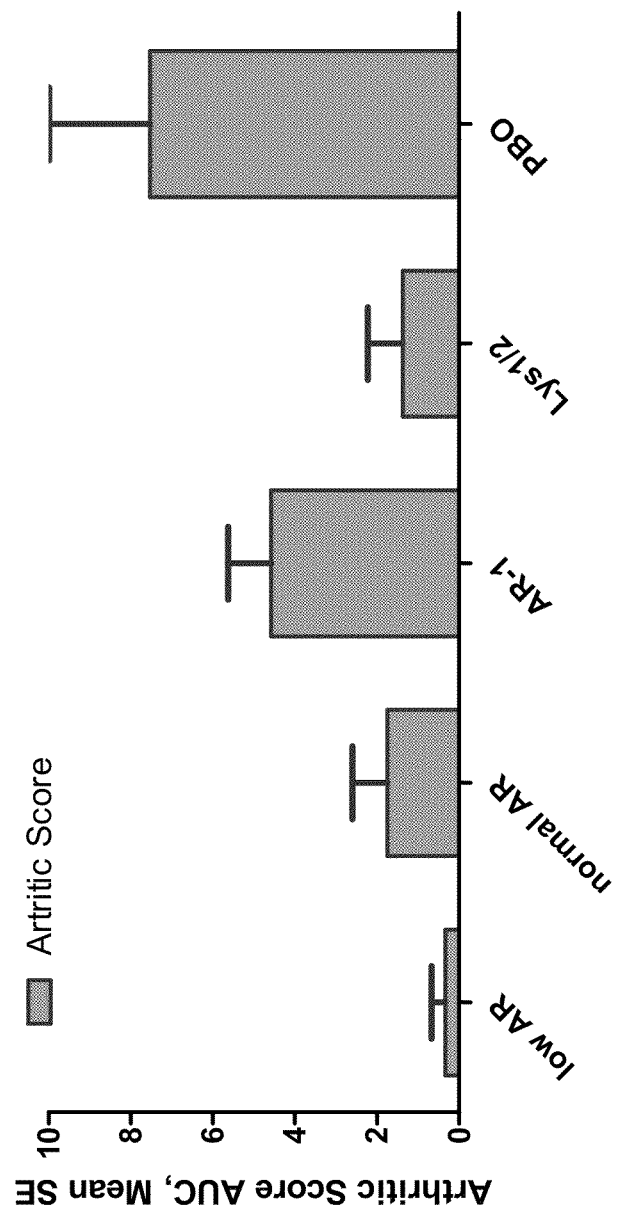
FIG. 102 depicts the average arthritic scores (area under the curve) of mice administered low AR composition, control (normal) AR composition, AR1 composition, modulated lysine variant species composition (Lys-1/2), and placebo (PBO).

As shown in FIG. 102, during the 12-13 week treatment period of the mice, the modulated lysine variant species composition (Lys-1/2) provided good protection against developing arthritic scores, as it was more effective than the control, or "normal," AR composition. The AR1 composition offered the least protection against development of arthritic scores, and it was less protective than the control AR composition.

Figure 103A:
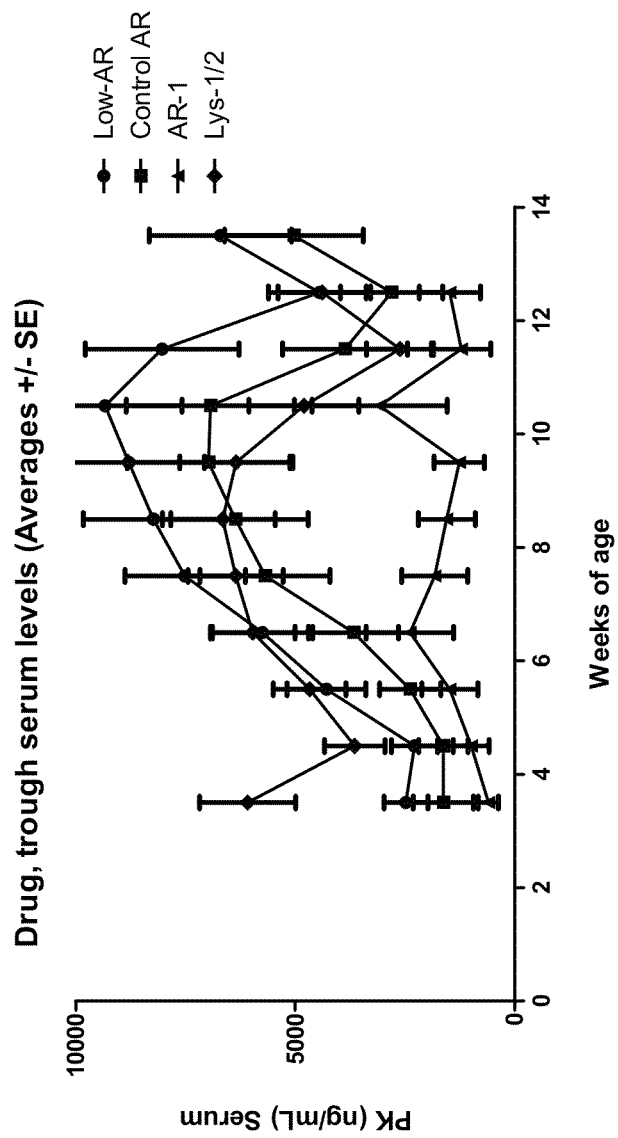
FIGS. 103A-B depict the (A) average trough serum drug levels and (B) average trough serum ADA levels for mice administered low AR composition, control AR composition, AR1 composition, and modulated lysine variant species composition.
Figure 103B:
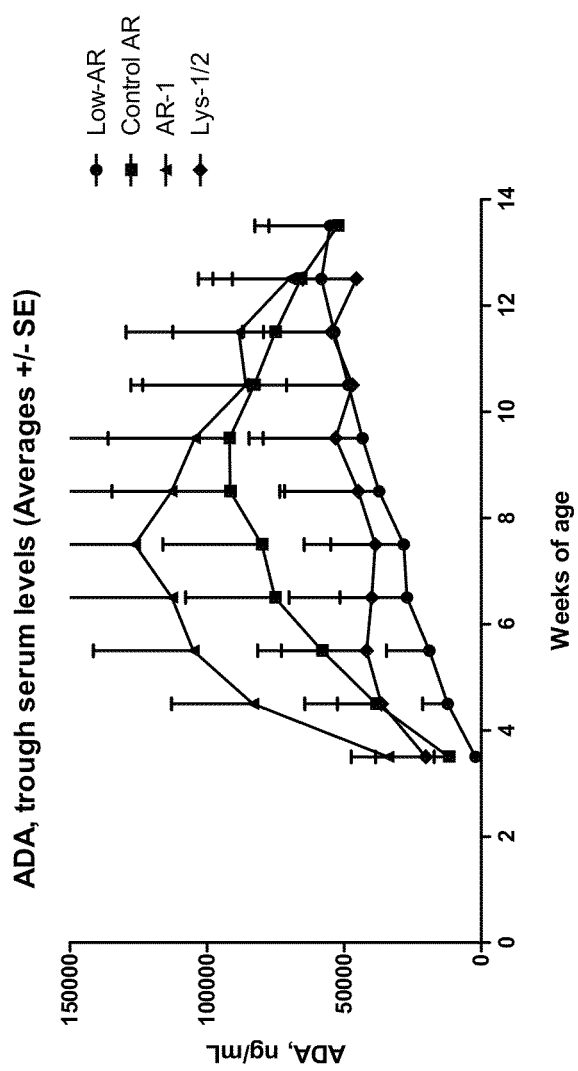

Serum levels of ADA and drug levels were measured from 3 to 14 weeks of age. As shown in FIG. 103B, the modulated lysine variant species composition (Lys-1/2) exhibited low average levels of ADA across the time frame measured. In addition, the modulated lysine variant species composition (Lys-1/2) composition exhibited drug levels comparable to the control AR composition (FIG. 103A), indicating that a lack of presence of the drug in the serum was not responsible for the low levels of serum ADA.

Figure 104:
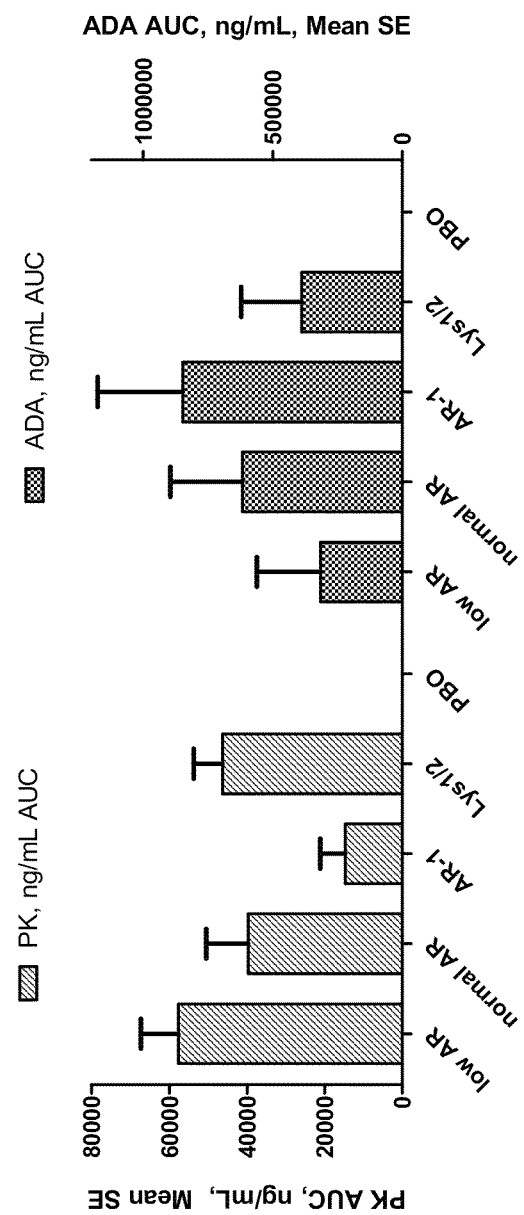
FIG. 104 depicts the average pK and ADA profiles (area under the curve) for mice administered low AR composition, control (normal) AR composition, AR1 composition, modulated lysine variant species composition (Lys-1/2), and placebo (PBO).

As set forth in FIG. 104, cumulative serum concentration values (PK) during the ten week treatment period was high in the treated mice for the modulated lysine variant species composition (Lys-1/2). As also shown in FIG. 104, the highest ADA titers were observed for animals administered the AR1 composition and the lowest for animals administered the modulated lysine variant species composition and the low AR composition.

Figure 105:
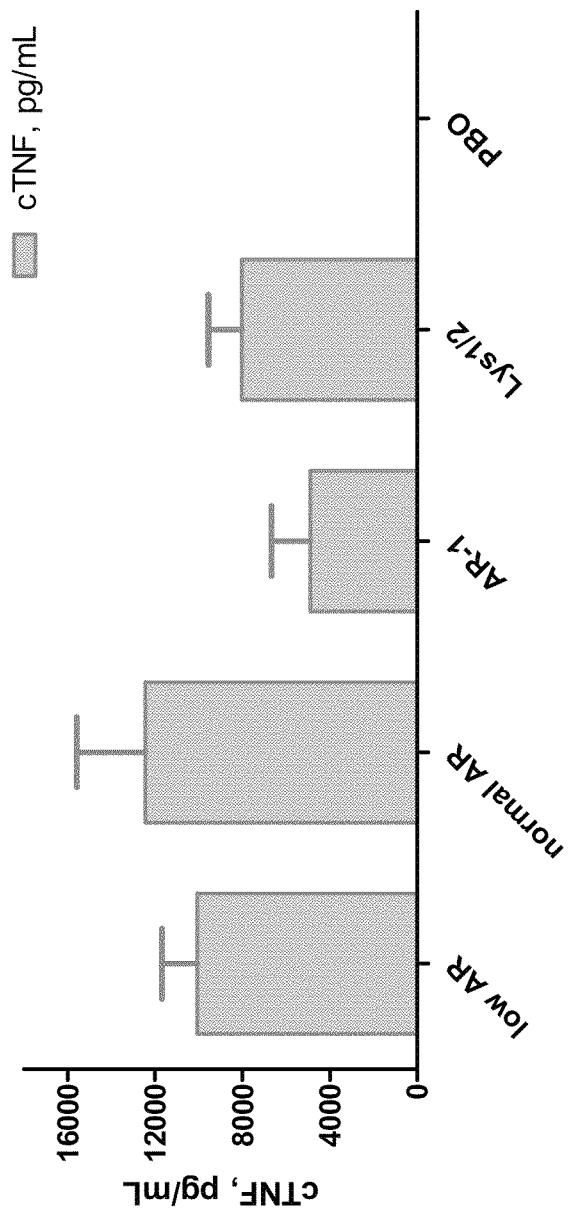
FIG. 105 depicts complexed TNF levels (area under the curve) and shows that the cumulative serum concentration values of adalimumab for mice administered low AR composition, control (normal) AR composition, AR1 composition, modulated lysine variant species composition (Lys-1/2), and placebo (PBO) during the ten week treatment period was highest for the modulated lysine variant species composition, the low AR composition, and the control AR composition, and lowest for the AR1 composition.

Furthermore, complexed TNF levels show that cumulative serum concentration values during the ten week treatment period were highest for the animals administered the control (normal) AR composition and lowest for the AR1 fraction (FIG. 105). Cumulative serum concentration values for the modulated lysine variant species composition (Lys-1/2) were lower than the control AR composition, but higher than the AR1 fraction.

Figure 106:
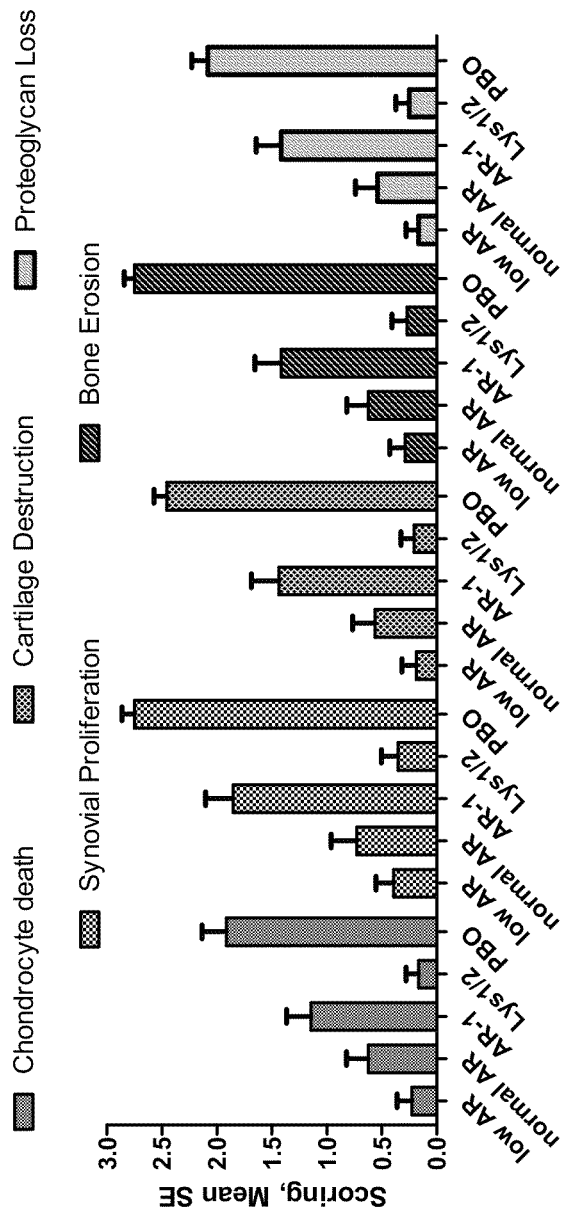
FIG. 106 depicts the chondrocyte death, synovial proliferation, proteoglycan loss, cartilage destruction, and bone erosion of mice administered low AR composition, control (normal) AR composition, AR1 composition, modulated lysine variant species composition (Lys-1/2), and placebo (PBO).

A histopathology evaluation of the joints of the mice indicated that good protection was afforded by the modulated lysine variant species composition (Lys-1/2), indicating that the modulated lysine variant species composition protects against the formation of arthritis in the joint in vivo. As shown in FIG. 106, the modulated lysine variant species composition (Lys-1/2) protected against chondrocyte death, synovial proliferation, proteoglycan loss, cartilage destruction, and bone erosion more effectively than the control AR formulation.

Figure 107:
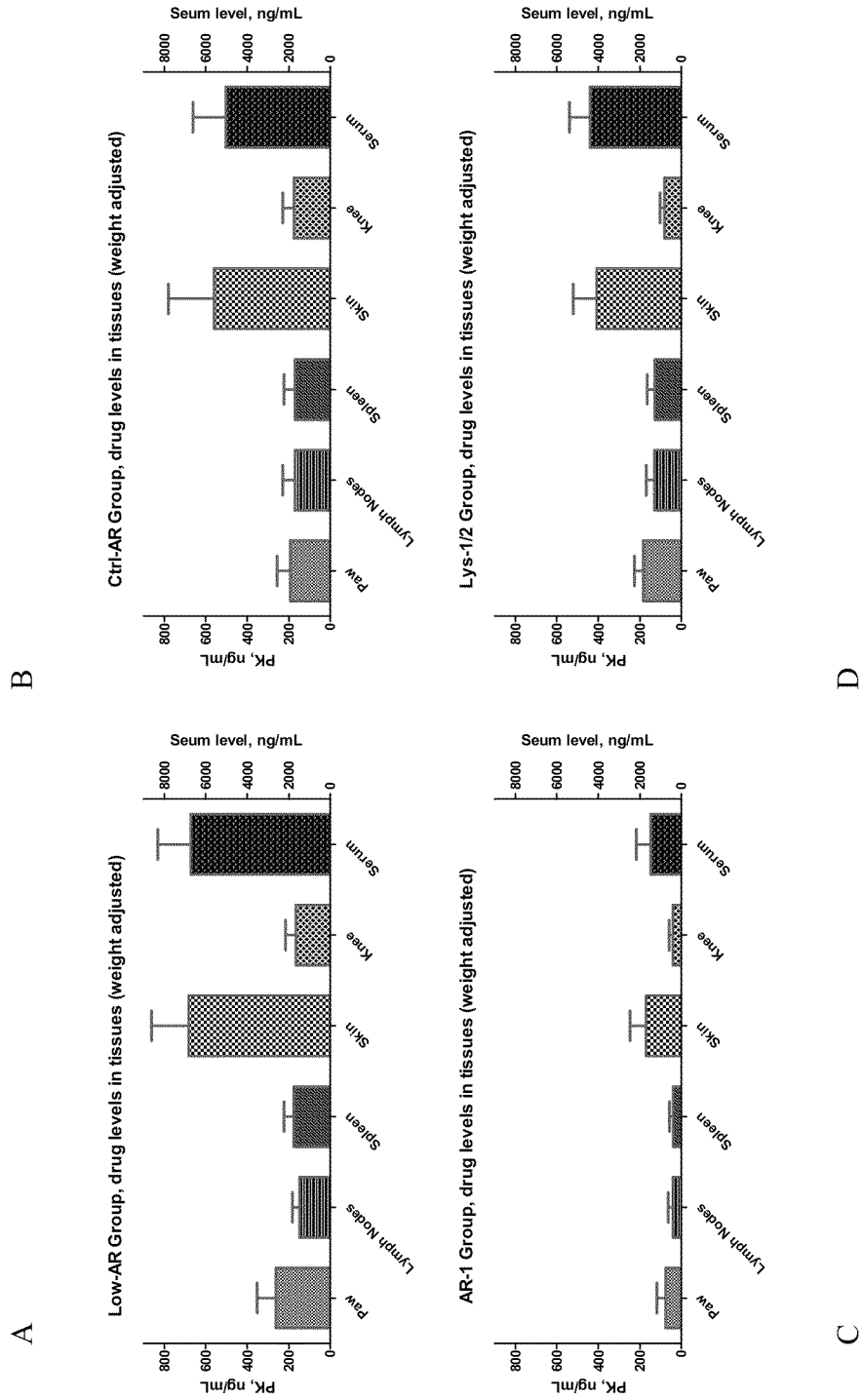
FIGS. 107A-D illustrate the average drug levels for various tissues (paw, lymph node, spleen, skin, knee and serum) for mice administered (A) low AR composition; (B) control AR composition; (C) AR1 composition; and (D) modulated lysine variant species composition (Lys-1/2).

FIG. 107 illustrates the average drug levels for various tissues (paw, lymph node, spleen, skin, knee and serum) for the low AR composition, the control AR composition, the AR1 composition, and the Lys-1/2 composition. As shown therein, animals administered the modulated lysine variant species composition (Lys-1/2) has drug levels comparable to the other compositions tested, including the AR control.

Figure 108:
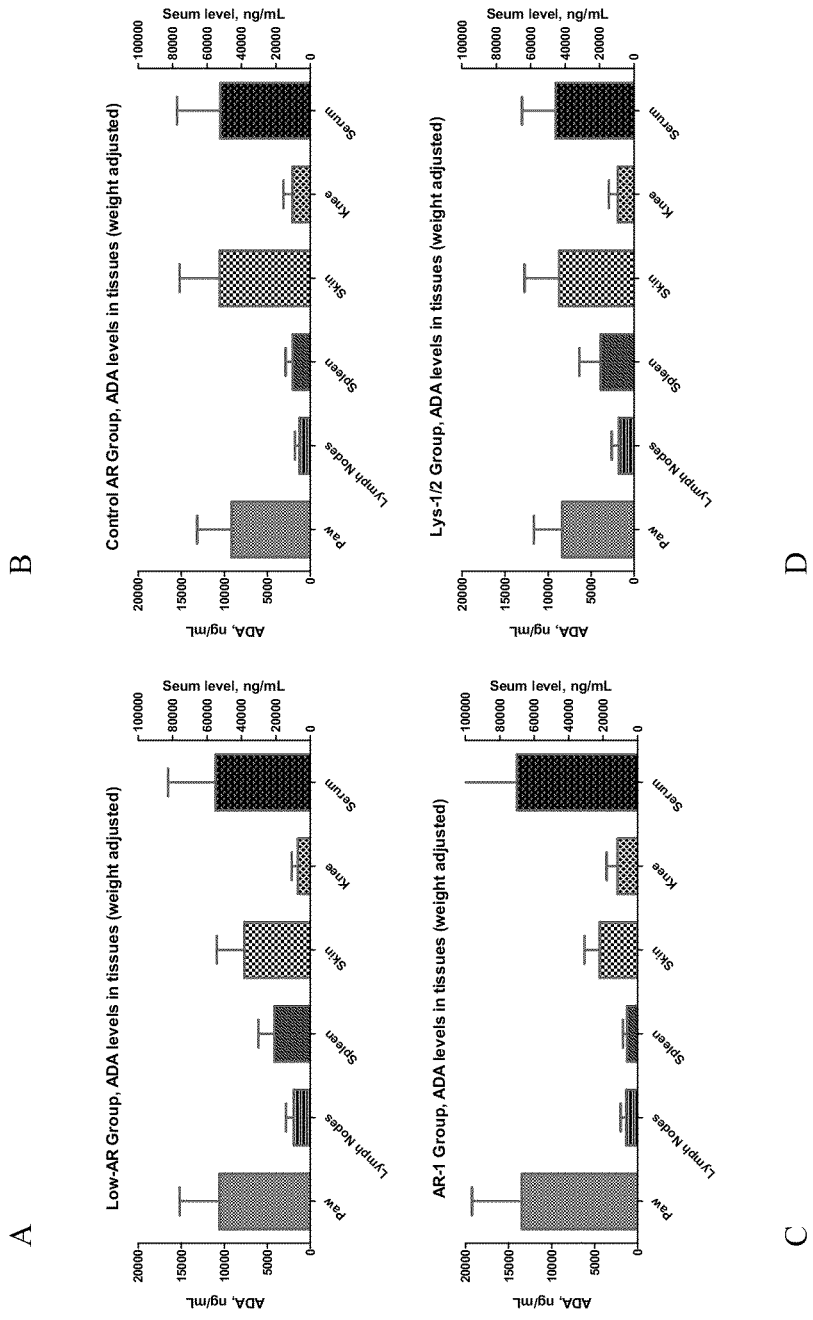
FIGS. 108A-D illustrate the average ADA levels for various tissues (paw, lymph node, spleen, skin, knee and serum) for mice administered (A) low AR composition; (B) control AR composition; (C) AR1 composition; and (D) modulated lysine variant species composition (Lys-1/2).

FIG. 108 illustrates average ADA levels in the same tissues for the same compositions (the low AR composition, the control AR composition, the AR1 composition, and the Lys- 1/2 composition). As shown there, the modulated lysine variant species composition, the highest ADA concentrations are present in the paws (which corresponds to the location of the highest levels of inflammation in the animals), and the serum.

Figure 109:
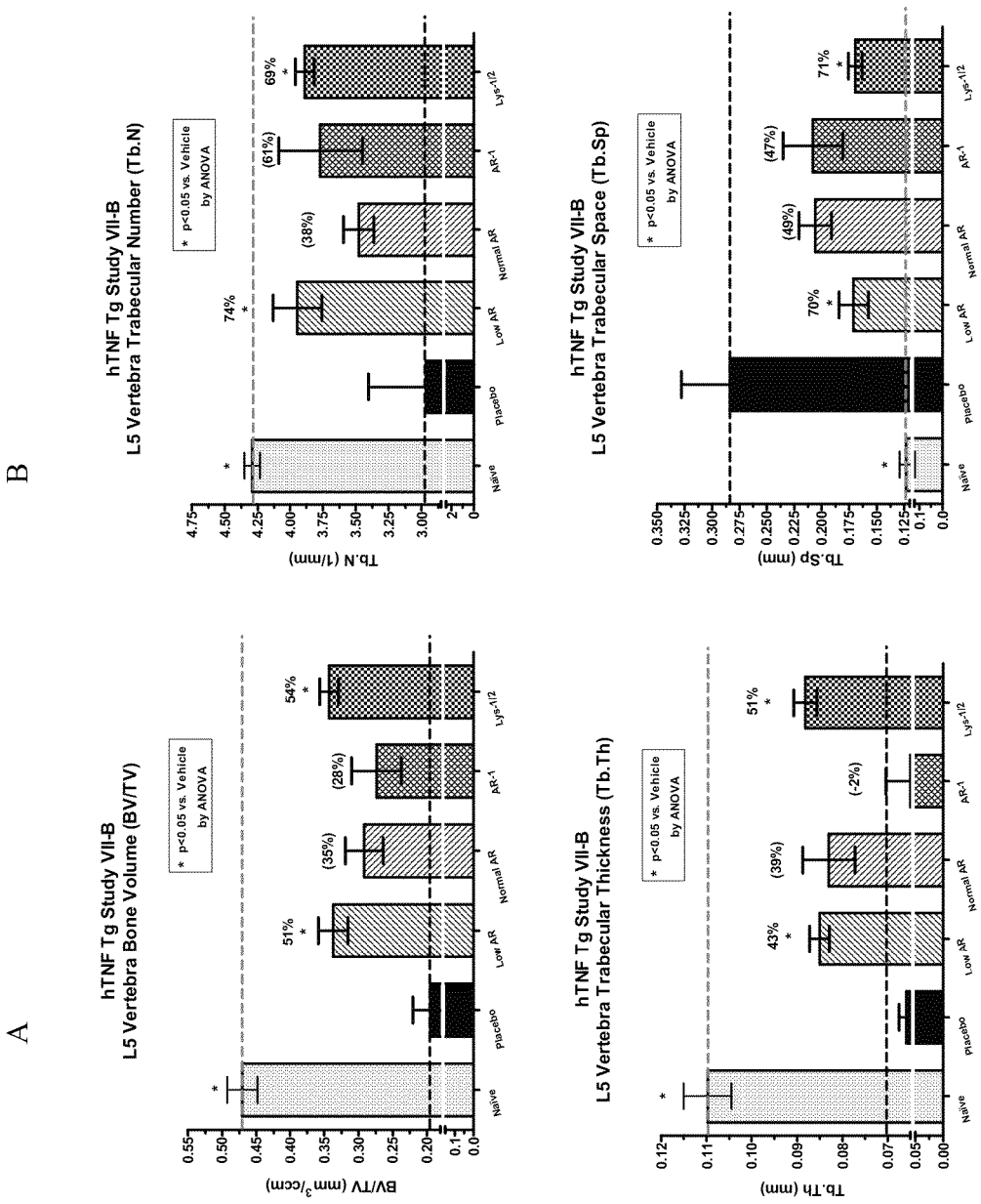
FIGS. 109A-D show the results of a micro CT analysis of spines and femurs obtained from TNF-Tg197 transgenic mice which were administered placebo, low AR composition, control (normal) AR composition, AR1 composition, and modulated lysine variant species composition (Lys-1/2). The graphs depict the effect of the administered compositions on (A) vertebra bone volume; (B) vertebra trabecular number; (C) vertebra trabecular thickness; and (D) vertebra trabecular space.
Figure 110:
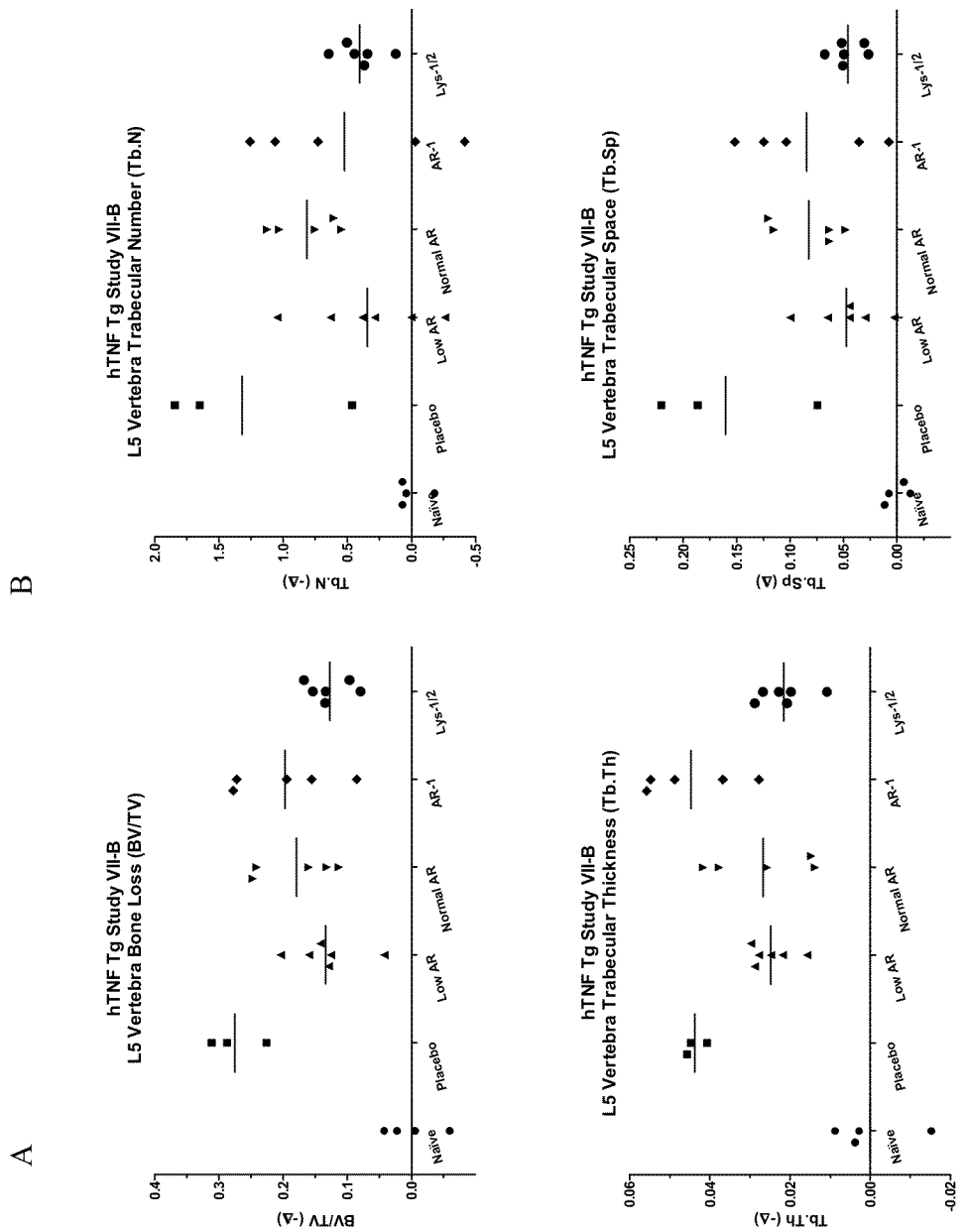
FIGS. 110A-D show the results of a micro CT analysis of spines and femurs obtained from TNF-Tg197 transgenic mice which were administered placebo, low AR composition, control (normal) AR composition, AR1 composition, and modulated lysine variant species composition (Lys-1/2). The graphs depict the effect of the administered compositions on (A) vertebra bone loss; (B) vertebra trabecular number; (C) vertebra trabecular thickness; and (D) vertebra trabecular space.

FIGS. 109 and 110 show the results of a micro CT analysis of spines and femurs obtained from the transgenic mice at the end of the study that were administered low AR composition, control AR composition, AR1 composition, modulated lysine variant species composition, as well as naïve, (control) and placebo. Samples were analyzed for L5 vertebra bone volume, L5 vertebra trabecular number, L5 vertebra trabecular thickness, and L5 vertebra trabecular space. As shown in the Figures, the modulated lysine variant species composition (Lys-1/2) resulted in greater bone volume, trabecular number, trabecular thickness and trabecular space, as compared to the vehicle alone.

Figure 111:
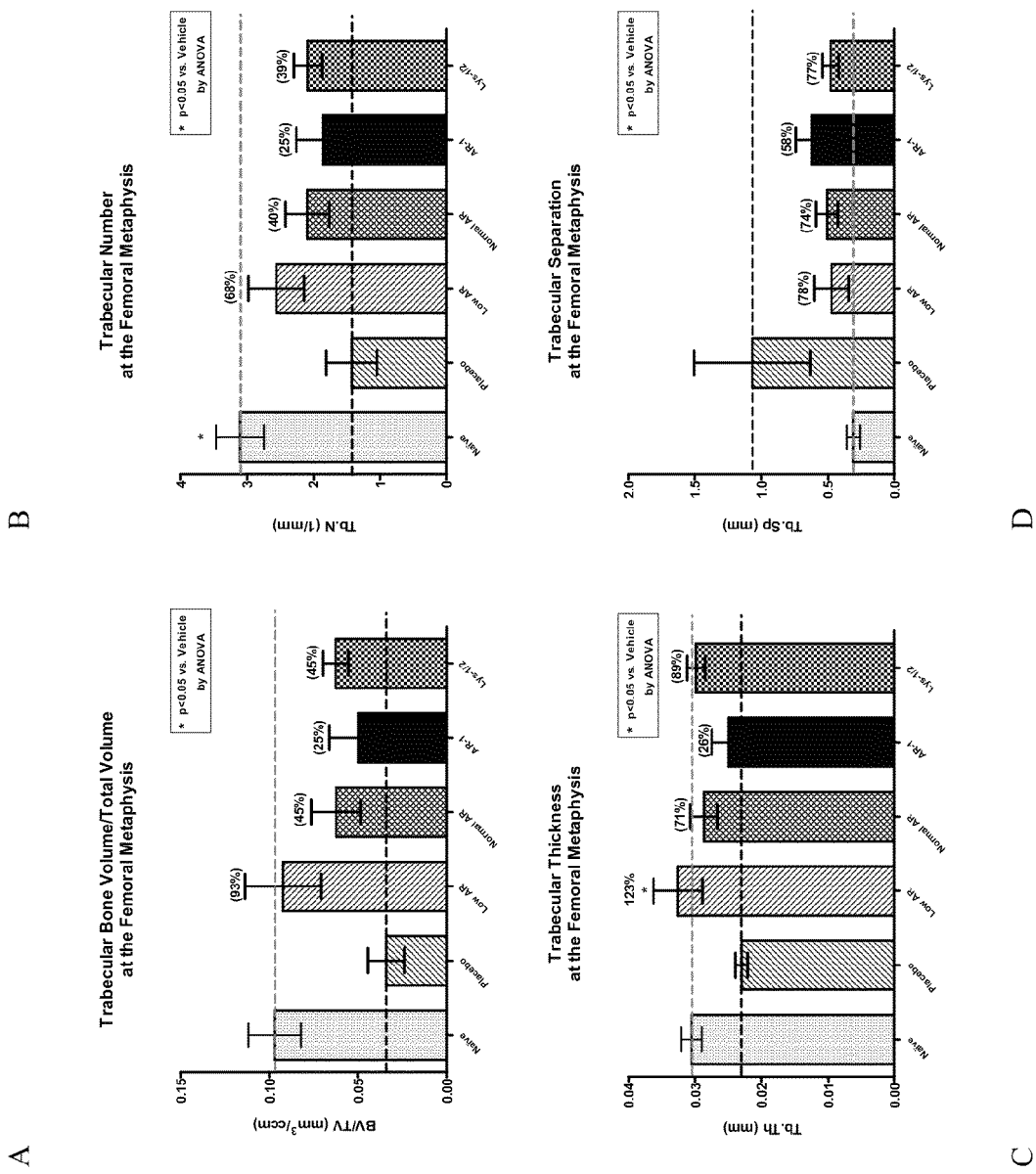
FIGS. 111A-D show results of a micro CT analysis of spines and femurs obtained from TNF-Tg197 transgenic mice which were administered placebo, low AR composition, control (normal) AR composition, AR1 composition, and modulated lysine variant species composition (Lys-1/2). The graphs depict the effect of the administered compositions on (A) trabecular bone volume/total volume at the femoral metaphysis; (B) trabecular number at the femoral metaphysis; (C) trabecular thickness at the femoral metaphysis; and (D) trabecular separation at the femoral metaphysis.

FIG. 111 shows additional results of a micro CT analysis of spines and femurs obtained from the transgenic mice. Samples were analyzed for trabecula bone volume at the femoral metaphysis, trabecular number at the femoral metaphysis, trabecular thickness at the femoral metaphysis, and trabecular separation at the femoral metaphysis. As shown in FIG. 111, the modulated lysine variant species composition (Lys-1/2) resulted in similar trabecula bone volume at the femoral metaphysis, trabecular number at the femoral metaphysis, and trabecular thickness at the femoral metaphysis, as compared to the control (normal) AR composition.

Figure 113:
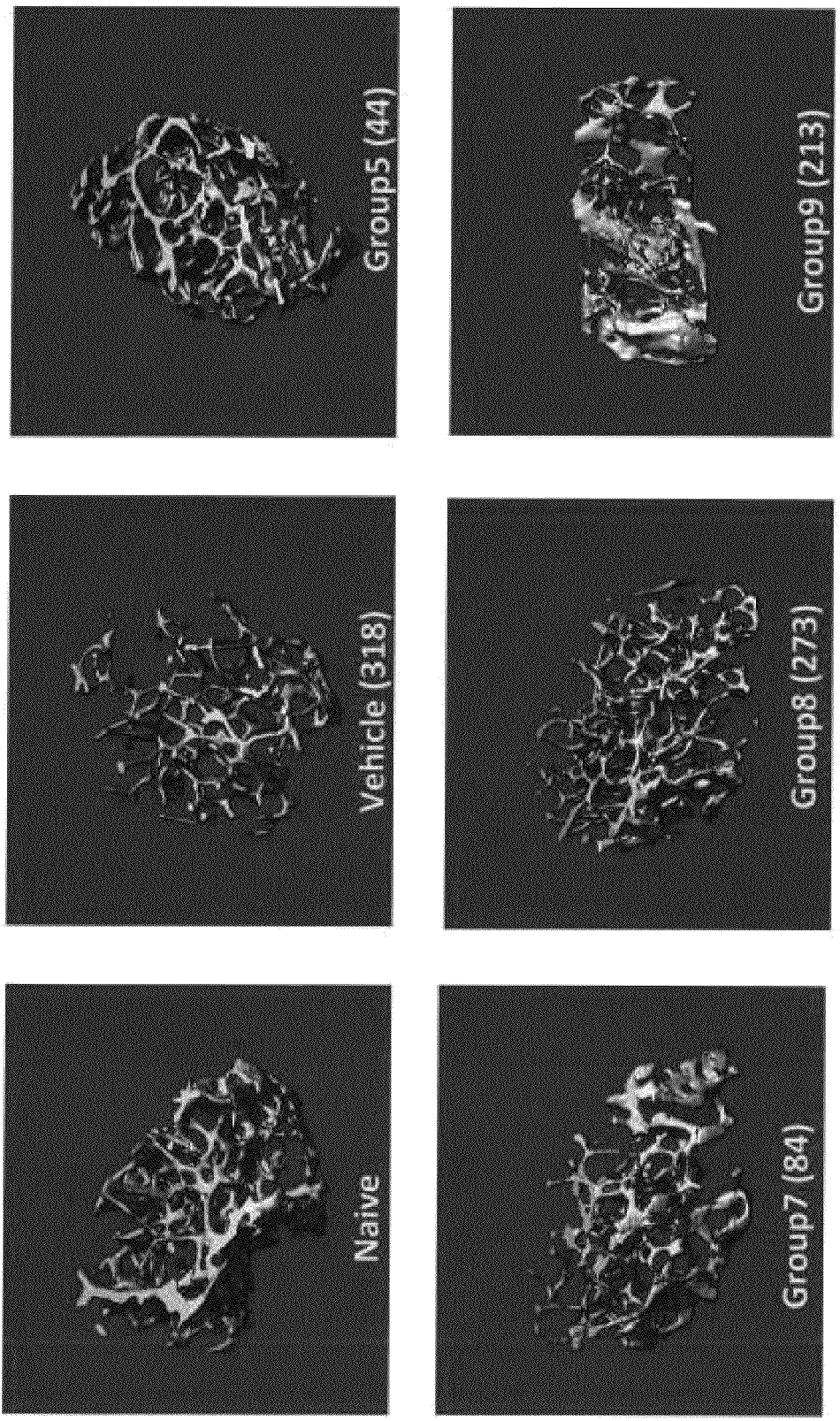
FIG. 113 depicts micro CT images of the femur from each of six groups of mice administered the following compositions: naïve, vehicle (control), low AR composition (group 5), low host cell protein (HCP) composition (group 7), AR1 composition (containing only AR1 acidic variants) (group 8), and modulated lysine variant species composition (Lys-1/2) (containing only Lys 1 and Lys 2 variants) (group 9).

Furthermore, FIGS. 112 and 113 show actual micro CT images of the spine and femur, respectively, from each of six groups of mice administered the following compositions: naïve, vehicle (control), low AR composition (group 5), low host cell protein (HCP) composition (group 7), AR1 composition (containing only AR1 acidic variants) (group 8), and Lys 1 and Lys 2 composition (containing only Lys 1 and Lys 2 variants and referred to as the modulated lysine variant species composition) (group 9). As seen in both the spine and the femur, the Lys 1/2 composition (group 9), provided protection from bone erosion, as compared to the vehicle, as there is less bone erosion visible in the "group 9" image as compared to the vehicle.

The results of these experiments demonstrate that a weekly dose of 1 mg/kg adalimumab in TNF-Tg197 mice provides protection from arthritis development as measured by arthritic scores and histopathology scores (radiologic damage involving cartilage and bone as well as local inflammation) in the TNF-Tg197 mouse model. Thus, the control AR group with unmodified Lys variant levels and normal AR levels was efficacious.

Furthermore, formulations containing the modulated lysine variant species composition (Lys-1/2) and the low AR composition provided greatest protection, as compared to the control AR group, from development of arthritic and histopathology scores and showed increased efficacy as compared to the control AR group in all parameters tested including cell infiltration, synovial proliferation, proteoglycan loss, cartilage destruction, and bone erosion.

Accordingly, the modulated lysine variant species composition (Lys-1/2) and the low AR compositions have increased efficacy in the treatment and prevention of arthritis as compared to the control adalimumab formulation.

* * *

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The contents of all cited references, including literature references, issued patents, and published patent applications, as cited throughout this application are hereby expressly incorporated herein by reference. It should further be understood that the contents of all the figures and tables attached hereto are expressly incorporated herein by reference. The entire contents of the following applications are also expressly incorporated herein by reference: U.S. Provisional Patent Application 61/893,123, entitled "STABLE SOLID PROTEIN COMPOSITIONS AND METHODS OF MAKING SAME", filed on Oct. 18, 2013; U.S. Provisional Application Ser. No. 61/892,833, entitled "LOW ACIDIC SPECIES COMPOSITIONS AND METHODS FOR PRODUCING THE SAME USING DISPLACEMENT CHROMATOGRAPHY", filed on Oct. 18, 2013; U.S. Provisional Patent Application 61/892,710, entitled "MUTATED ANTI-TNFa ANTIBODIES AND METHODS OF THEIR USE", filed on Oct. 18, 2013; U.S. Provisional Patent Application 61/893,068, entitled "LOW ACIDIC SPECIES COMPOSITIONS AND METHODS FOR PRODUCING THE SAME", filed on Oct. 18, 2013; and U.S. Provisional Patent Application 61/893,131, entitled "PURIFICATION OF PROTEINS USING HYDROPHOBIC INTERACTION CHROMATOGRAPHY", filed on Oct. 18, 2013.

The invention claimed is:

1. A composition comprising a human anti-TNFα antibody, wherein less than 65% of the lysine variant species in said composition have zero C-terminal lysines (Lys 0),
   wherein the lysine variant species include the main peak and peaks that elute at a relative residence time later than the main peak, as detected using weak cation-exchange chromatography, and
   wherein the human anti-TNFα antibody comprises a light chain variable region (LCVR) having a CDR1 domain comprising the amino acid sequence of SEQ ID NO:7, a CDR2 domain comprising the amino acid sequence of SEQ ID NO:5, and a CDR3 domain comprising the amino acid sequence of SEQ ID NO:3; and a heavy chain variable region (HCVR) having a CDR1 domain comprising the amino acid sequence of SEQ ID NO:8, a CDR2 domain comprising the amino acid sequence of SEQ ID NO:6, and a CDR3 domain comprising the amino acid sequence of SEQ ID NO:4.

2. The composition of claim 1, wherein said human anti-TNFα antibody is adalimumab.

3. The composition of claim 2, wherein less than 60% of the lysine variant species in said composition have zero C-terminal lysines (Lys 0).

4. The composition of claim 2, wherein 50-60% of the lysine variant species in said composition have zero C-terminal lysines (Lys 0).

5. The composition of claim 2, wherein less than 55% of the lysine variant species in said composition have zero C-terminal lysines (Lys 0).

6. The composition of claim 1, wherein said composition is lyophilized.

7. A composition comprising a human anti-TNFα antibody, wherein the sum of the lysine variant species having one C-terminal lysine (Lys 1) and the lysine variant species having two C-terminal lysines (Lys 2) in said composition is greater than 35%,
   wherein the lysine variant species include the main peak and peaks that elute at a relative residence time later than the main peak, as detected using weak cation-exchange chromatography,
   and wherein the human anti-TNFα antibody comprises a light chain variable region (LCVR) having a CDR1 domain comprising the amino acid sequence of SEQ ID NO:7, a CDR2 domain comprising the amino acid sequence of SEQ ID NO:5, and a CDR3 domain comprising the amino acid sequence of SEQ ID NO:3; and a heavy chain variable region (HCVR) having a CDR1 domain comprising the amino acid sequence of SEQ ID NO:8, a CDR2 domain comprising the amino acid sequence of SEQ ID NO:6, and a CDR3 domain comprising the amino acid sequence of SEQ ID NO:4.

8. The composition of claim 7, wherein said human anti-TNFα antibody is adalimumab.

9. The composition of claim 8, wherein the sum of the lysine variant species having one C-terminal lysine (Lys 1) and the lysine variant species having two C-terminal lysines (Lys 2) in said composition is greater than 40%.

10. The composition of claim 8, wherein the sum of the lysine variant species having one C-terminal lysine (Lys 1) and the lysine variant species having two C-terminal lysines (Lys 2) in said composition is 40-50%.

11. The composition of claim 8, wherein the sum of the lysine variant species having one C-terminal lysine (Lys 1) and the lysine variant species having two C-terminal lysines (Lys 2) in said composition is greater than 50%.

12. The composition of claim 8, wherein greater than 25% of the lysine variant species in said composition have one C-terminal lysine (Lys 1).

13. The composition of claim 8, wherein greater than 30% of the lysine variant species in said composition have one C-terminal lysine (Lys 1).

14. The composition of claim 7, wherein said composition is lyophilized.

15. A pharmaceutical formulation comprising the composition of claim 1 and a pharmaceutically acceptable carrier.

16. A pharmaceutical formulation comprising the composition of claim 7 and a pharmaceutically acceptable carrier.

17. A pharmaceutical formulation comprising
    a composition comprising a human anti-TNFα antibody, wherein less than 65% of the lysine variant species in said composition have zero C-terminal lysines (Lys 0),
    wherein the lysine variant species include the main peak and peaks that elute at a relative residence time later than the main peak, as detected using weak cation-exchange chromatography, and
    wherein the human anti-TNFα antibody comprises a light chain variable region (LCVR) having a CDR1 domain comprising the amino acid sequence of SEQ ID NO:7, a CDR2 domain comprising the amino acid sequence of SEQ ID NO:5, and a CDR3 domain comprising the amino acid sequence of SEQ ID NO:3; and a heavy chain variable region (HCVR) having a CDR1 domain comprising the amino acid sequence of SEQ ID NO:8, a CDR2 domain comprising the amino acid sequence of SEQ ID NO:6, and a CDR3 domain comprising the amino acid sequence of SEQ ID NO:4; and
    a pharmaceutically acceptable carrier.

18. A pharmaceutical formulation comprising a composition comprising a human anti-TNFα antibody, wherein the sum of the lysine variant species having one C-terminal lysine (Lys 1) and the lysine variant species having two C-terminal lysines (Lys 2) in said composition is greater than 35%,
wherein the lysine variant species include the main peak and peaks that elute at a relative residence time later than the main peak, as detected using weak cation-exchange chromatography,
and wherein the human anti-TNFα antibody comprises a light chain variable region (LCVR) having a CDR1 domain comprising the amino acid sequence of SEQ ID NO:7, a CDR2 domain comprising the amino acid sequence of SEQ ID NO:5, and a CDR3 domain comprising the amino acid sequence of SEQ ID NO:3; and a heavy chain variable region (HCVR) having a CDR1 domain comprising the amino acid sequence of SEQ ID NO:8, a CDR2 domain comprising the amino acid sequence of SEQ ID NO:6, and a CDR3 domain comprising the amino acid sequence of SEQ ID NO:4; and a pharmaceutically acceptable carrier.

19. The composition of claim 2, wherein said adalimumab is produced in a mammalian host cell grown in cell culture.

20. The composition of claim 19, wherein the mammalian host cell is selected from the group consisting of a CHO cell, an NSO cell, a COS cell, and an SP2 cell.

21. The composition of claim 8, wherein said adalimumab is produced in a mammalian host cell grown in cell culture.

22. The composition of claim 21, wherein the mammalian host cell is selected from the group consisting of a CHO cell, an NSO cell, a COS cell, and an SP2 cell.

23. The pharmaceutical composition of claim 17, wherein said human anti-TNFα antibody is adalimumab.

24. The pharmaceutical composition of claim 23, wherein less than 60% of the lysine variant species in said composition have zero C-terminal lysines (Lys 0).

25. The pharmaceutical composition of claim 23, wherein adalimumab is present in said pharmaceutical composition at a concentration of 25-100 mg/ml.

26. The pharmaceutical composition of claim 23, wherein said pharmaceutical composition comprises one or more excipient selected from the group consisting of a buffering agent, a surfactant and a polyol, or a combination thereof.

27. The pharmaceutical composition of claim 18, wherein said human anti-TNFα antibody is adalimumab.

28. The pharmaceutical composition of claim 27, wherein the sum of the lysine variant species having one C-terminal lysine (Lys 1) and the lysine variant species having two C-terminal lysines (Lys 2) in said composition is greater than 40%.

29. The pharmaceutical composition of claim 27, wherein the sum of the lysine variant species having one C-terminal lysine (Lys 1) and the lysine variant species having two C-terminal lysines (Lys 2) in said composition is 40-50%.

30. The pharmaceutical composition of claim 27, wherein the sum of the lysine variant species having one C-terminal lysine (Lys 1) and the lysine variant species having two C-terminal lysines (Lys 2) in said composition is greater than 50%.

\* \* \* \* \*